(12) United States Patent
Yue et al.

(10) Patent No.: US 9,918,990 B2
(45) Date of Patent: *Mar. 20, 2018

(54) SUBSTITUTED PYRROLO[2,3-C]PYRIDINES AND PYRAZOLO[3,4-C]PYRIDINES AS BET PROTEIN INHIBITORS

(71) Applicant: Incyte Corporation, Wilmington, DE (US)

(72) Inventors: Eddy W. Yue, Landenberg, PA (US); Andrew P. Combs, Kennett Square, PA (US); Brent Douty, Fallowfield, PA (US)

(73) Assignee: Incyte Corporation, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/186,697

(22) Filed: Jun. 20, 2016

(65) Prior Publication Data

US 2017/0014418 A1  Jan. 19, 2017

Related U.S. Application Data

(63) Continuation of application No. 14/554,306, filed on Nov. 26, 2014, now Pat. No. 9,399,640.

(60) Provisional application No. 61/908,968, filed on Nov. 26, 2013.

(51) Int. Cl.
```
C07D 471/04      (2006.01)
A61K 31/538      (2006.01)
A61K 31/437      (2006.01)
A61K 31/4545     (2006.01)
A61K 31/496      (2006.01)
A61K 31/498      (2006.01)
A61K 31/519      (2006.01)
A61K 31/5377     (2006.01)
```

(52) U.S. Cl.
CPC .......... *A61K 31/538* (2013.01); *A61K 31/437* (2013.01); *A61K 31/4545* (2013.01); *A61K 31/496* (2013.01); *A61K 31/498* (2013.01); *A61K 31/519* (2013.01); *A61K 31/5377* (2013.01); *C07D 471/04* (2013.01)

(58) Field of Classification Search
CPC .................................................... C07D 471/04
USPC .................................................. 546/113, 119
See application file for complete search history.

(56) References Cited

U.S. PATENT DOCUMENTS

| | | | |
|---|---|---|---|
| 5,589,476 A | 12/1996 | Jegham et al. |
| 8,633,186 B2 | 1/2014 | Tachdjian et al. |
| 8,669,249 B2 | 3/2014 | Brown et al. |
| 9,012,642 B2 | 4/2015 | Haydar et al. |
| 9,227,985 B2 | 1/2016 | Combs et al. |
| 9,290,514 B2 | 3/2016 | Combs et al. |
| 9,309,246 B2 | 4/2016 | Rodgers et al. |
| 9,315,501 B2 | 4/2016 | Yue et al. |
| 9,399,640 B2 | 7/2016 | Yue et al. |
| 9,527,864 B2 | 12/2016 | Combs et al. |
| 9,533,997 B2 | 1/2017 | Combs et al. |
| 9,540,368 B2 | 1/2017 | Combs et al. |
| 9,624,241 B2 | 4/2017 | Combs et al. |
| 9,737,516 B2 | 8/2017 | Yue et al. |
| 9,777,003 B2 | 10/2017 | Shepard et al. |
| 2002/0004510 A1 | 1/2002 | McCall et al. |
| 2007/0191447 A1 | 8/2007 | Kodo et al. |
| 2007/0244096 A1 | 10/2007 | Fox et al. |
| 2008/0306093 A1 | 12/2008 | Servant et al. |
| 2009/0306122 A1 | 12/2009 | Staehle et al. |
| 2013/0045229 A1 | 2/2013 | Iadonato et al. |
| 2013/0261109 A1 | 10/2013 | Miyoshi et al. |
| 2013/0281396 A1 | 10/2013 | McLure et al. |
| 2013/0281397 A1 | 10/2013 | McLure et al. |
| 2013/0281398 A1 | 10/2013 | McLure et al. |
| 2013/0281399 A1 | 10/2013 | McLure et al. |

(Continued)

FOREIGN PATENT DOCUMENTS

| | | |
|---|---|---|
| CA | 2171579 | 9/1996 |
| EP | 0646583 | 4/1995 |

(Continued)

OTHER PUBLICATIONS

Ai et al., "Signal-induced Brd4 release from chromatin is essential for its role transition from chromatin targeting to transcriptional regulation," Nucleic Acids Res., 2011, 1-13.

(Continued)

*Primary Examiner* — Douglas M Willis
(74) *Attorney, Agent, or Firm* — Fish & Richardson P.C.

(57) ABSTRACT

The present invention relates to compounds represented by the general Formula I which are inhibitors of BET proteins such as BRD2, BRD3, BRD4, and BRD-t and are useful in the treatment of diseases such as cancer.

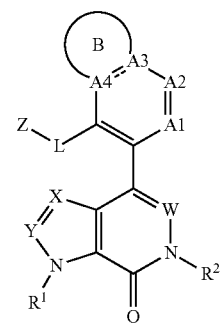

58 Claims, No Drawings

(56) References Cited

U.S. PATENT DOCUMENTS

| | | |
|---|---|---|
| 2014/0135316 A1 | 5/2014 | Albrecht et al. |
| 2014/0275030 A1 | 9/2014 | Combs et al. |
| 2015/0011540 A1 | 1/2015 | Combs et al. |
| 2015/0148342 A1 | 5/2015 | Yue et al. |
| 2015/0148372 A1 | 5/2015 | Yue et al. |
| 2015/0148375 A1 | 5/2015 | Yue et al. |
| 2015/0175604 A1 | 6/2015 | Rodgers et al. |
| 2015/0307493 A1 | 10/2015 | Combs et al. |
| 2016/0046650 A1 | 2/2016 | Combs et al. |
| 2016/0075721 A1 | 3/2016 | Combs et al. |
| 2016/0159817 A1 | 6/2016 | Combs et al. |
| 2016/0168148 A1 | 6/2016 | Shepard |
| 2016/0213654 A1 | 7/2016 | Yue et al. |
| 2016/0331749 A1 | 11/2016 | Bogdan et al. |
| 2017/0121347 A1 | 5/2017 | Chen et al. |
| 2017/0158689 A1 | 6/2017 | Combs et al. |
| 2017/0158710 A1 | 6/2017 | Combs et al. |
| 2017/0210754 A1 | 7/2017 | Combs et al. |
| 2017/0127985 A1 | 8/2017 | Combs et al. |

FOREIGN PATENT DOCUMENTS

| | | |
|---|---|---|
| EP | 0 732 334 | 9/1996 |
| EP | 1462103 | 9/2004 |
| EP | 2 239 264 | 10/2010 |
| EP | 2415767 | 2/2012 |
| EP | 2568287 | 3/2013 |
| EP | 2573559 | 3/2013 |
| FR | 2747678 | 10/1997 |
| JP | H 03014566 | 1/1991 |
| JP | H 05-097849 | 4/1993 |
| JP | 08-269058 | 10/1996 |
| JP | 2004-502650 | 1/2004 |
| JP | 2006-509764 | 3/2006 |
| JP | 2008-532954 | 8/2008 |
| JP | 2009-503069 | 1/2009 |
| JP | 2012-529536 | 11/2012 |
| JP | 2012-530053 | 11/2012 |
| JP | 2013/010719 | 1/2013 |
| KR | 20150037711 | 4/2015 |
| WO | WO 2002/000196 | 1/2002 |
| WO | WO 2004/024736 | 3/2004 |
| WO | WO 2005/080334 | 9/2005 |
| WO | WO 2005/099688 | 10/2005 |
| WO | WO 2006/124874 | 11/2006 |
| WO | WO 2007/018998 | 2/2007 |
| WO | WO 2008/154221 | 12/2008 |
| WO | WO 2009/020559 | 2/2009 |
| WO | WO 2009/020677 | 2/2009 |
| WO | WO 2009/084693 | 7/2009 |
| WO | WO 2010/046190 | 4/2010 |
| WO | WO 2010/144679 | 12/2010 |
| WO | WO 2010/144680 | 12/2010 |
| WO | WO 2011/024987 | 3/2011 |
| WO | WO 2011/054553 | 5/2011 |
| WO | WO 2011/054841 | 5/2011 |
| WO | WO 2011/054843 | 5/2011 |
| WO | WO 2011/054844 | 5/2011 |
| WO | WO 2011/054845 | 5/2011 |
| WO | WO 2011/054846 | 5/2011 |
| WO | WO 2011/054848 | 5/2011 |
| WO | WO 2011/054851 | 5/2011 |
| WO | WO 2011/133722 | 10/2011 |
| WO | WO 2011/143651 | 11/2011 |
| WO | WO 2011/143657 | 11/2011 |
| WO | WO 2011/143660 | 11/2011 |
| WO | WO 2011/143669 | 11/2011 |
| WO | WO 2011/161031 | 12/2011 |
| WO | WO 2012/075383 | 6/2012 |
| WO | WO 2012/075456 | 6/2012 |
| WO | WO 2012/107465 | 8/2012 |
| WO | WO 2012/116170 | 8/2012 |
| WO | WO 2012/143413 | 10/2012 |
| WO | WO 2012/143415 | 10/2012 |
| WO | WO 2012/143416 | 10/2012 |
| WO | WO 2012/150234 | 11/2012 |
| WO | WO 2012/151512 | 11/2012 |
| WO | WO 2012/174487 | 12/2012 |
| WO | WO 2012/178208 | 12/2012 |
| WO | WO 2013/019710 | 2/2013 |
| WO | WO 2013/024104 | 2/2013 |
| WO | WO 2013/027168 | 2/2013 |
| WO | WO 2013/029548 | 3/2013 |
| WO | WO 2013/030150 | 3/2013 |
| WO | WO 2013/033268 | 3/2013 |
| WO | WO 2013/033269 | 3/2013 |
| WO | WO 2013/033270 | 3/2013 |
| WO | WO 2013/043553 | 3/2013 |
| WO | WO 2013/044511 | 4/2013 |
| WO | WO 2013/064900 | 5/2013 |
| WO | WO 2013/097052 | 7/2013 |
| WO | WO 2013/097601 | 7/2013 |
| WO | WO 2013/148197 | 10/2013 |
| WO | WO 2013/155695 | 10/2013 |
| WO | WO 2013/156869 | 10/2013 |
| WO | WO 2013/158952 | 10/2013 |
| WO | WO 2013/175281 | 11/2013 |
| WO | WO 2013/184876 | 12/2013 |
| WO | WO 2013/184878 | 12/2013 |
| WO | WO 2013/185284 | 12/2013 |
| WO | WO 2013/186612 | 12/2013 |
| WO | WO 2013/188381 | 12/2013 |
| WO | WO 2014/001356 | 1/2014 |
| WO | WO 2014/015175 | 1/2014 |
| WO | WO 2014/026997 | 2/2014 |
| WO | WO 2014/028547 | 2/2014 |
| WO | WO 2014/048945 | 4/2014 |
| WO | WO 2014/068402 | 5/2014 |
| WO | WO 2014/076146 | 5/2014 |
| WO | WO 2014/078257 | 5/2014 |
| WO | WO 2014/080290 | 5/2014 |
| WO | WO 2014/080291 | 5/2014 |
| WO | WO 2014/095774 | 6/2014 |
| WO | WO 2014/095775 | 6/2014 |
| WO | WO 2014/096965 | 6/2014 |
| WO | WO 2014/128655 | 8/2014 |
| WO | WO 2014/134232 | 9/2014 |
| WO | WO 2014/134267 | 9/2014 |
| WO | WO 2014/139324 | 9/2014 |
| WO | WO 2014/140076 | 9/2014 |
| WO | WO 2014/140077 | 9/2014 |
| WO | WO 2014/143768 | 9/2014 |
| WO | WO 2014/145051 | 9/2014 |
| WO | WO 2014/152029 | 9/2014 |
| WO | WO 2014/154760 | 10/2014 |
| WO | WO 2014/154762 | 10/2014 |
| WO | WO 2014/159392 | 10/2014 |
| WO | WO 2014/159837 | 10/2014 |
| WO | WO 2014/160873 | 10/2014 |
| WO | WO 2014/164596 | 10/2014 |
| WO | WO 2014/164771 | 10/2014 |
| WO | WO 2014/164780 | 10/2014 |
| WO | WO 2014/165127 | 10/2014 |
| WO | WO 2014/165143 | 10/2014 |
| WO | WO 2014/170350 | 10/2014 |
| WO | WO 2014/173241 | 10/2014 |
| WO | WO 2014/182929 | 11/2014 |
| WO | WO 2014/191894 | 12/2014 |
| WO | WO 2014/191896 | 12/2014 |
| WO | WO 2014/191906 | 12/2014 |
| WO | WO 2014/191911 | 12/2014 |
| WO | WO 2014/202578 | 12/2014 |
| WO | WO 2014/206150 | 12/2014 |
| WO | WO 2014/206345 | 12/2014 |
| WO | WO 2014/210425 | 12/2014 |
| WO | WO 2015/002754 | 1/2015 |
| WO | WO 2015/004533 | 1/2015 |
| WO | WO 2015/004534 | 1/2015 |
| WO | WO 2015/006193 | 1/2015 |
| WO | WO 2015/013635 | 1/2015 |
| WO | WO 2015/081203 | 6/2015 |
| WO | WO 2015/164480 | 10/2015 |
| WO | WO 2015/168555 | 11/2015 |
| WO | WO 2015/168621 | 11/2015 |

(56) References Cited

FOREIGN PATENT DOCUMENTS

| WO | WO 2015/169951 | 11/2015 |
|---|---|---|
| WO | WO 2015/169953 | 11/2015 |
| WO | WO 2015/184257 | 12/2015 |
| WO | WO 2016/044130 | 3/2016 |
| WO | WO 2016/186453 | 11/2016 |
| WO | WO 2016/194806 | 12/2016 |
| WO | WO 2017/127930 | 8/2017 |
| WO | WO 2017/133681 | 8/2017 |

OTHER PUBLICATIONS

Bamborough et al., "Fragment-Based Discovery of Bromodomain Inhibitors Part 2: Optimization of Phenylisoxazole Sulfonamides," J Med Chem., 2012, 55:587-596.
Bartholomeeusen et al., "BET bromodomain inhibition activates transcription via a transient release of P-TEFb from 7SK snRNP," JBC, 2012, 16 pages.
Belkina and Denis, "BET domain co-regulators in obesity inflammation and cancer," Nat Rev Cancer, Jul. 2012, 12:465-477.
Belkina et al., "BET Protein Function is Required for Inflammation: Brd2 Genetic Disruption and BET Inhibitor JQ1 Impair Mouse Macrophage Inflammatory Responses," J Immunol., 2013, 190:3670-3678.
Berge et al., "Pharmaceutical Salts," J Pharm. Sci., 1977, 66(1):1-19.
Blom et al., "Optimizing Preparative LC-MS Configurations and Methods for Parallel Synthesis Purification," J Comb Chem., 2003, 5(5):670-683.
Blom et al., "Preparative LCMS Purification: Improved Compound Specific Method Optimization," J Comb Chem., 2004, 6(6):874-883.
Blom, "Two-pump at-column-dilution configuration for preparative liquid chromatography-mass spectrometry," J Comb Chem., 2002, 4(4):295-301.
Chiang, "Brd4 engagement from chromatin targeting to transcriptional regulation: selective contact with acetylated histone H3 and H4," Biology Reports, Dec. 2009, 1:98, 7 pages.
Chinese Office Action in Chinese Application No. 201480025137, dated May 17, 2016, 14 pages (English Translation).
Chung et al., "Discovery and Characterization of Small Molecule Inhibitors of the BET Family Bromodomains," J Med Chem., 2011, 54:3827-3838.
Chung et al., "Fragment-Based Discovery of Bromodomain Inhibitors Part 1: Inhibitor Binding Modes and Implications for Lead Discovery," J Med Chem., 2011, 11 pages.
Chung et al., "Fragment-based discovery of bromodomain inhibitors part 1: inhibitor binding modes and implications for lead discovery," Supporting Information, 2011, 6 pages.
Dawson et al., "Inhibition of BET recruitment to chromatin as an effective treatment for MLL-fusion leukaemia," Nature, 2011, 5 pages.
Dawson, "Supplementary Information: Inhibition of BET recruitment to chromatin as an effective treatment for MLL-fusion leukaemia," Nature, 2011, 50 pages.
Delmore et al., "BET bromodomain inhibition as a therapeutic strategy to target c-Myc," Cell, 2011, 146(6):904-917, Supplemental Information: S1-S11.
Delmore et al., "BET bromodomain inhibition as a therapeutic strategy to target c-Myc," Cell, Sep. 2011, 146(6):904-917.
Devaiah et al., "BRD4 is an atypical kinase that phosphorylates serine2 of the RNA polymerase II carboxy-terminal domain," Proc. Nat. Acad. Sci. USA., 2012, 109(18):6927-6932.
Draker et al., "A Combination of H2A.Z and H4 Acetylation Recruits Brd2 to Chromatin during Transcriptional Activation," PLoS Genet., Nov. 2012, 8(11):e1003047, 17 pages.
Dorwald, F. Zaragoza. Side Reactions in Organic Synthesis: A Guide to Successful Synthesis Design, Weinheim: Wiley-VCH Verlag GmbH & Co. KGaA, 2005, Preface.

Filippakopoulos and Knapp, "Targeting bromodomains: epigenetic readers of lysine acetylation," Nature Rev Drug Disc., May 2014, 13:337-356.
Filippakopoulos et al., "Benzodiazepines and benzotriazepines as protein interaction inhibitors targeting bromodomains of the BET family," Bioorg Med Chem., 2011, 9 pages.
Filippakopoulos et al., "Histone Recognition and Large-Scale Structural Analysis of the Human Bromodomain Family," Cell, Mar. 2012, 149:214-231.
Filippakopoulos et al., "Selective inhibition of BET bromodomains," Nature, 2010, 468:1067-1073.
Filippakopoulos et al., "Supplemental Information: Selective inhibition of BET bromodomains," Nature, 2010, 468:1067-1073.
Floyd et al., "Supplemental Information: The bromodomain protein Brd4 insulates chromatin from DNA damage signalling," Nature, 2013, 14 pages.
Floyd et al., "The bromodomain protein Brd4 insulates chromatin from DNA damage signalling," Nature, 2013, 498:246-250.
French et al., "BRD4-NUT fusion oncogene: a novel mechanism in aggressive carcinoma," Cancer Res., 2003, 63(2):304-307.
French et al., "BRD-NUT oncoproteins: a family of closely related nuclear proteins that block epithelial differentiation and maintain the growth of carcinoma cells," Oncogene, 2008, 27:2237-2242.
French et al., "Midline carcinoma of children and young adults with NUT rearrangement," J Clin. Oneal., 2004, 22(20):4135-4139.
French, "Demystified molecular pathology of NUT midline carcinomas," J Clin Pathol., 2010, 63:492-496.
French, "NUT midline carcinoma," Cancer Genet Cytogenetics, 2010, 203:16-20.
Frizzo et al., "Structural and thermodynamic properties of new pyrazolo [3,4-d] pyridazinones," Thermochimica Acta., Oct. 2013, 574:63-72.
Gallenkamp et al., "Bromodomains and their Pharmacological Inhibitors," Chem Med Chem., Mar. 2014, 9(3):438-464.
Garnier et al., "BET bromodoma in inhibitors: a patent review," Exp Opin Therapeutic Patents, Feb. 2014, 24(2):185-199.
Hackam et al., JAMA, 296(14), 2006, 1731-1732.
Hewings et al., "3,5-Dimethylisoxazoles Act as Acetyl-lysine-mimetic Bromodomain Ligands," J Med Chem., 2011, 54:6761-6770.
Hewings et al., "Progress in the Development and Applciation of Small Molecule Inhibitors of Bromodomain-Acetyl-lysine Interactions," J Med Chem., Nov. 2012, 104 pages (Author Manuscript).
Hewings et al., "Progress in the Development and Applciation of Small Molecule Inhibitors of Bromodomain-Acetyl-lysine Interactions," J Med Chem., Nov. 2012, 55(22):9393-9413.
Houzelstein et al., "Growth and Early Postimplantation Defects in Mice Deficient for the Bromodomain-Containing Protein Brd4," Mole Cell Biol., Jun. 2002, 22(11):3794-3802.
Huang et al., "Brd4 coactivates transcriptional activation of NF-κB via specific binding to acetylated RelA," Mol. Cell Biol., 2009, 29(5):1375-1387.
International Preliminary Report on Patentability in International Application No. PCT/US2014/045543, dated Jan. 21, 2016, 7 pages.
International Search Report and Written Opinion in International Application No. PCT/US2014/027872, dated Jun. 30, 2014, 12 pages.
International Search Report and Written Opinion in International Application No. PCT/US2014/045543, dated Sep. 10, 2014, 11 pages.
International Search Report and Written Opinion in International Application No. PCT/US2014/067598, dated Feb. 13, 2015, 9 pages.
International Search Report and Written Opinion in International Application No. PCT/US2014/067629, dated Feb. 16, 2015, 11 pages.
International Search Report and Written Opinion in International Application No. PCT/US2014/067691, dated Feb. 2, 2015, 10 pages.
International Search Report and Written Opinion in International Application No. PCT/US2014/071102, dated Feb. 13, 2015, 9 pages.

(56) References Cited

OTHER PUBLICATIONS

International Preliminary Report on Patentability in International Application No. PCT/US2014/027872, dated Sep. 24, 2015, 8 pages.
International Search Report and Written Opinion in International Application No. PCT/US2015/027047, dated Jul. 10, 2015, 14 pages.
International Search Report and Written Opinion in International Application No. PCT/US2015/049909, dated Dec. 7, 2015, 13 pages.
International Preliminary Report on Patentability in International Application No. PCT/US2014/067691, dated May 31, 2016, 7 pages.
International Preliminary Report on Patentability in International Application No. PCT/US2014/067629, dated May 31, 2016, 7 pages.
International Preliminary Report on Patentability in International Application No. PCT/US2014/067598, dated May 31, 2016, 7 pages.
International Preliminary Report on Patentability in International Application No. PCT/US2014/071102, dated Jun. 21, 2016, 7 pages.
Jang et al., "The bromodomain protein Brd4 is a positive regulatory component of P-TEFb and stimulates RNA polymerase II-dependent transcription," Mol. Cell, Aug. 2005, 19(4):523-534.
Jin et al., "c-Myb binds MLL through menin in human leukemia cells and is an important driver of MLL-associated leukemogenesis," J Clinc Invest., 2010, 120(2):593-606.
Jordan, V.C. Nature Reviews: Drug Discovery, 2, 2003, 205.
Jung et al., "Affinity Map of BRD4 Interactions with the Histone H4 Tail and the Small Molecule Inhibitor JQ1," J Biol Chem., 2014, 28 pages.
Lamonica et al., "Bromodomain protein Brd3 associates with acetylated GATA1 to promote its chromatin occupancy at erythroid target genes," Proc. Nat. Acad. Sci., USA, 2011, 108(22):E159-168.
Leroy et al., "The double bromodomain proteins Brd2 and Brd3 couple histone acetylation to transcription," Mol. Cell, Apr. 2008, 30(1):51-60.
Lockwood et al., "Sensitivity of human lung adenocarcinoma cell lines to targeted inhibition of BET epigenetic signaling proteins," PNAS Early Edition, 2012, 14 pages.
Martin et al., "Cyclin-Dependent Kinase Inhibitor Dinaciclib Interacts with the Acetyl-Lysine Recognition Site of Bromodomains," ACS Chem Biol., 2013, 8:2360-2365.
Maruyama et al., "A Mammalian Bromodomain Protein, Brd4, Interacts with Replication Factor C and Inhibits Progression to S Phase," Mol Cell Biol., 2002, 22(18):6509-6520.
Matzuk et al., "Small-Molecule Inhibition of BRDT for Male Contraception," Cell, Aug. 2012, 150:673-684.
McLure et al., "RVX-208, an Inducer of ApoA-I in Humans, Is a BET Bromodomain Antagonist," PLOS One, Dec. 2013, 8(12):e83190, 12 pages.
Mertz et al., "Targeting MYC dependence in cancer by inhibiting BET bromodomains," PNAS, 2011, 108(40):16669-16674.
Mirguet et al., "From ApoA1 upregulation to BET family bromodomain inhibition: Discovery of I-BET151," Bioorg Med Chem Lett., 2012, 22:2963-2967.
Mochizuki et al., "The bromodomain protein Brd4 stimulates G1 gene transcription and promotes progression to S phase," J Biol. Chem. 2008, 283(14):9040-9048.
Moriniere et al., "Cooperative binding of two acetylation marks on a histone tail by a single bromodomain," Nature, 2009, 461:664-669.
Muller et al., "Bromodomains as therapeutic targets," Expert Reviews, 2011, 13:e29, 21 pages.
Nicodeme et al., "Supplementary Information: Suppression of inflammation by a synthetic histone mimic," Nature, 2010, 40 pages.
Nicodeme et al., "Suppression of inflammation by a synthetic histone mimic," Nature, 2010, 468:1119-1123.

Nishiyama et al., "Brd4 is Required for Recovery from Antimicrotubule Drug-induced Mitotic Arrest Preservation of Acetylated Chromatin," Mol Biol Cell, Feb. 2006, 17:814-823.
Ott et al., "BET bromodomain inhibition targets both c-MYC and IL7R in high-risk acute lymphoblastic leukemia," Blood, published online 2012, 29 pages.
Peturssion et al., "Protecting Groups in Carbohydrate Chemistry," J Chem. Educ., 1997, 74(11):1297-1303.
Picaud et al., "RVX-208, an inhibitor of BET transcriptional regulators with selectivity for the second bromodomain," PNAS Early Edition, 2013, 6 pages.
Picaud et al., "Supplemental Information: RVX-208, an inhibitor of BET transcriptional regulators with selectivity for the second bromodomain," PNAS Early Edition, 2013, 9 pages.
Prinjhas et al., "Place your BETs: the therapeutic potential of bromodomains," Trends Pharmacol Sci., 2012, 33(3):146-153.
Rahman et al., "The Brd4 Extraterminal Domain Confers Transcription Activation Independent of pTEFb by Recruiting Multiple Proteins, Including NSD3," Mol Cell Biol., Jul. 2011, 31(13):2641-2652.
Ravin, "Preformulation," Remington's Pharmaceutical Sciences, 17th Ed., (Mack Publishing Company, Easton, 1985), pp. 1409-1423.
Sanchez and Zhou, "The role of human bromodomains in chromatin biology and gene transcription," Curr Opin Drug Discov Devel., Sep. 2009, 12(5):659-665 (Author Manuscript).
Schroder et al., "Two-pronged Binding with Bromodomain-containing Protein 4 Liberates Positive Transcription Elongation Factor b from Inactive Ribonucleoprotein Complexes," J Biol Chem., Jan. 6, 2012, 287(2):1000-1009.
Schwartz et al., "Differentiation of NUT Midline Carcinoma by Epigenomic Reprogramming," Cancer Res., 2011, 71:2686-2696.
Seal et al., "Identification of a novel series of BET family bromodomain inhibitors: Binding mode and profile of I-BET151 (GSK1210151A)," Bioorg Med Chem., 2012, 22:2968-2972.
Smith et al., "Genome-wide siRNA screen identifies SMCX, EP400, and Brd4 as E2-dependent regulators of human papillomavirus oncogene expression," PNAS, Feb. 23, 2010, 107(8):3752-3757.
Stenman et al., "New tricks from an old oncogene: Gene fusion and copy number alterations of MYB in human cancer," Cell Cyle, Aug. 2010, 9(15):2986-2955.
Vidler et al., "Druggability Analysis and Structural Classification of Bromodomain Acetyl-lysine Binding Sites," J Med Chem., 2012, 14 pages.
Wang et al., "Brd2 disruption in mice causes severe obesity without Type 2 diabetes," Biochem. J., 2010, 425(1):71-83.
Wang et al., "The Bromodomain Protein Brd4 Associated with Acetylated Chromatin is Important for Maintenance of Higher-Order Chromatin Structure," JBC, 2012, 22 pages.
Weidner-Glunde et al., "What do viruses BET on?" Frontiers Biosci., Jan. 2010, 15:537-549.
Wu and Chiang et al., "The Double Bromodomaincontaining Chromatin Adaptor Brd4 and Transcriptional Regulation," J Biol Chem., May 2007, 282(18):13141-13145.
Wu et al., "Brd4 links chromatin targeting to HPV transcriptional silencing," Genes Dev., 2006, 20:2383-2396.
Yan et al., "Perturbation of BRD4 Protein Function by BRD4-NUT Protein Abrogates Cellular Differentiation in NUT Midline Carcinoma," J Biol Chem., Aug. 2011, 286(31):27663-27675.
Yan et al., "Supplemental Data: Perturbation of BRD4 Protein Function by BRD4-NUT Protein Abrogates Cellular Differentiation in NUT Midline Carcinoma," J Biol Chem., Aug. 2011, 12 pages.
Yang et al., "Brd4 Recruits P-TEFb to Chromosomes at Late Mitosis to Promote G1 Gene Expression and Cell Cycle Progression," Mol Cell Biol., Feb. 2008, 28(3):967-976.
You et al., "Interaction of the bovine papillomavirus E2 protein with Brd4 tethers the viral DNA to host mitotic chromosomes," Cell, 2004, 117(3):349-60.
You et al., "Regulation of Aurora B Expression by the Bromodomain Protein Brd4," Mol Cell Biol., Sep. 2009, 29(18):5094-5103.

(56) References Cited

OTHER PUBLICATIONS

Zhang et al., "Bromodomain-Containing-Protein 4 (BRD4) Regulates RNA Polymerase II Serine 2 Phosphorylation in Human CD4+ T Cells," JBC, 2012, 30 pages.
Zhu et al., "Reactivation of latent HIV-1 by inhibition of BRD4," Cell Reports, 2012, 2(4):807-816.
Zuber et al., "An integrated approach to dissecting oncogene addiction implicates a Myb-coordinated self-renewal program as essential for leukemia maintenance," Genes Dev., 2011, 25:1628-1640.
Zuber et al., "RNAi screen identifies Brd4 as a therapeutic target in acute myeloid leukaemia," Nature, 2011, 478(7370):524-528.
Zuber et al., "Supplemental Information: RNAi screen identifies Brd4 as a therapeutic target in acute myeloid leukaemia," Nature, 2011, 33 pages.
Bauer, "Pharmaceutical Solids—The Amorphous Phase," Journal of Validation Technology, Jan. 2009, 15(3): 63-68.
Byrn et al., "Pharmaceutical Solids: A Strategic Approach to Regulatory Considerations," Pharmaceutical Research, Jul. 1995, 12(7): 945-954.
Cheng et al., "Inhibition of BET Bromodomain Targets Genetically Diverse Glioblastoma," Clin Cancer Res 19:1748-1759, Feb. 2013.
Chilean Office Action in Chilean Application No. 201502734, dated Jan. 18, 2017, 8 pages (English Translation).
Chinese Office Action in Chinese Application No. 201480025137, dated Feb. 16, 2017, 21 pages (w/ English Translation).
Greenwald et al., "Eμ-BRD2 transgenic mice develop B-cell lymphoma and leukemia," Blood 103(4):1475-1484, Feb. 2004.
International Preliminary Report on Patentability in International Application No. PCT/US2015/027047, dated Oct. 25, 2016, 10 pages.
International Search Report and Written Opinion in International Application No. PCT/US2016/059360, dated Feb. 13, 2017, 20 pages.
Japanese Office Action in Japanese Application No. 2016-502650, dated Jan. 10, 2017, 3 pages (English translation only).
Puissant et al., "Targeting MYCN in Neuroblastoma by BET Bromodomain Inhibition," Cancer Discovery, 16 pages, Mar. 2013.
Shimamura et al., "Efficacy of BET Bromodomain Inhibition in Kras-Mutant Non-Small Cell Lung Cancer," Clin Cancer Res, 10 pages, 2013.
Segura et al., "BRD4 Sustains Melanoma Proliferation and Represents a New Target for Epigenetic Therapy," Cancer Res 73:6264-6276, Aug. 2013.
Wyce et al., "Inhibition of BET bromodomain proteins as a therapeutic approach in prostate cancer," Oncotarget, 13 pages, Nov. 2013.

US 9,918,990 B2

SUBSTITUTED PYRROLO[2,3-C]PYRIDINES AND PYRAZOLO[3,4-C]PYRIDINES AS BET PROTEIN INHIBITORS

CLAIM OF PRIORITY

This application claims priority under 35 USC § 119(e) to U.S. Patent Application Ser. No. 61/908,968, filed on Nov. 26, 2013, the entire contents of which are hereby incorporated by reference.

TECHNICAL FIELD

The present invention relates to bicyclic heterocycles which are inhibitors of BET proteins such as BRD2, BRD3, BRD4, and BRD-t and are useful in the treatment of diseases such as cancer.

BACKGROUND

The genomes of eukaryotic organisms are highly organized within the nucleus of the cell. DNA is packaged into chromatin by wrapping around a core of histone proteins to form a nucleosome. These nucleosomes are further compacted by aggregation and folding to form a highly condensed chromatin structure. A range of different states of condensation are possible, and the tightness of this structure varies during the cell cycle, being most compact during the process of cell division. Chromatin structure plays a critical role in regulating gene transcription by regulating protein access to the DNA. The chromatin structure is controlled by a series of post translational modifications to histone proteins, mainly within the tails of histones H3 and H4 that extend beyond the core nucleosome structure. These reversible modifications include acetylation, methylation, phosphorylation, ubiquitination and SUMOylation. These epigenetic marks are written and erased by specific enzymes that modify specific residues within the histone tail, thereby forming an epigenetic code. Other nuclear proteins bind to these marks and effect outputs specified by this information through the regulation of chromatin structure and gene transcription. Increasing evidence links genetic changes to genes encoding epigenetic modifiers and regulators leading to aberrant histone marks in diseases such as neurodegenerative disorders, metabolic diseases, inflammation and cancer.

Histone acetylation is typically associated with the activation of gene transcription, as the modification weakens the interaction between the DNA and the histone proteins, permitting greater access to DNA by the transcriptional machinery. Specific proteins bind to acetylated lysine residues within histones to "read" the epigenetic code. A highly conserved protein module called the bromodomain binds to acetylated lysine residues on histone and other proteins. There are more than 60 bromodomain-containing proteins in the human genome.

The BET (Bromodomain and Extra-Terminal) family of bromodomain containing proteins comprises 4 proteins (BRD2, BRD3, BRD4 and BRD-t) that share a conserved structural organization containing tandem N-terminal bromodomains capable of binding to acetylated lysine residues of histones and other proteins. BRD2, BRD3 and BRD4 are ubiquitously expressed while BRDt is restricted to germ cells. BRD proteins play essential, but non-overlapping roles in regulating gene transcription and controlling cell growth. BET proteins are associated with large protein complexes including Mediator, PAFc and super elongation complex that regulate many aspects of gene transcription. BRD2 and BRD4 proteins have been shown to remain in complex with chromosomes during mitosis and are required to promote transcription of critical genes including cyclin D and c-Myc that initiate the cell cycle (Mochizuki J Biol. Chem. 2008 283:9040-9048). BRD4 is essential for recruiting the protein translational elongation factor B complex to the promoters of inducible genes resulting in the phosphorylation of RNA polymerase II and stimulating productive gene transcription and elongation (Jang et al. Mol. Cell 2005 19:523-534). In some instances, a kinase activity of BRD4 may directly phosphorylate and activate RNA polymerase II (Devaiah et al. PNAS 2012 109:6927-6932). Cells lacking BRD4 show impaired progression through cell cycle. BRD2 and BRD3 are reported to associate with histones along actively transcribed genes and may be involved in facilitating transcriptional elongation (Leroy et al, Mol. Cell. 2008 30:51-60). In addition to acetylated histones, BET proteins have been shown to bind selectively to acetylated transcription factors including the RelA subunit of NF-kB and GATA1 thereby directly regulating the transcriptional activity of these proteins to control expression of genes involved in inflammation and hematopoietic differentiation (Huang et al, Mol. Cell. Biol. 2009 29:1375-1387; Lamonica Proc. Nat. Acad. Sci. 2011 108:E159-168).

A recurrent translocation involving NUT (nuclear protein in testes) with BRD3 or BRD4 to form a novel fusion oncogene, BRD-NUT, is found in a highly malignant form of epithelial neoplasia (French et al, Cancer Research 2003 63:304-307; French et al, Journal of Clinical Oncology 2004 22:4135-4139). Selective ablation of this oncogene restores normal cellular differentiation and reverses the tumorigenic phenotype (Filippakopoulos et al, Nature 2010 468:1068-1073). Genetic knockdown of BRD2, BRD3 and BRD4 has been shown to impair the growth and viability of a wide range of hematological and solid tumor cells (Zuber et al, Nature 2011 478:524-528; Delmore et al, Cell 2011 146:904-917). Aside from a role in cancer, BET proteins regulate inflammatory responses to bacterial challenge, and a BRD2 hypomorph mouse model showed dramatically lower levels of inflammatory cytokines and protection from obesity induced diabetes (Wang et al Biochem J. 2009 425:71-83; Belkina et al. J. Immunol 2013). In addition, some viruses make use of these BET proteins to tether their genomes to the host cell chromatin, as part of the process of viral replication or use BET proteins to facilitate viral gene transcription and repression (You et al, Cell 2004 117:349-60; Zhu et al, Cell Reports 2012 2:807-816).

Accordingly, there is a need for compounds that modulate the activity of the BET family of proteins, including BRD2, BRD3, and BRD4, that can be used to treat BET protein-associated diseases such as cancer. The compounds of the invention help meet this need.

SUMMARY

The present invention provides, inter alia, a compound of Formula I:

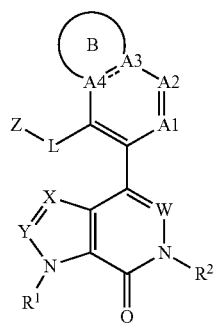

or a pharmaceutically acceptable salt thereof; wherein the variables are as defined below.

The present invention also provides a pharmaceutical composition comprising a compound of Formula I, or a pharmaceutically acceptable salt thereof, and at least one pharmaceutically acceptable carrier.

The present invention also provides a method of inhibiting a BET protein comprising contacting a compound of Formula I, or a pharmaceutically acceptable salt thereof, with the BET protein.

The present invention also provides a method of treating cancer and other diseases comprising administering to a patient a therapeutically effective amount of a compound of Formula I, or a pharmaceutically acceptable salt thereof.

The present invention also provides a compound of Formula I, or a pharmaceutically acceptable salt thereof, for use in therapy.

The present invention also provides use of a compound of Formula I, or a pharmaceutically acceptable salt thereof, in the preparation of a medicament for use in therapy.

DETAILED DESCRIPTION

The present invention provides, inter alia, a compound of Formula I:

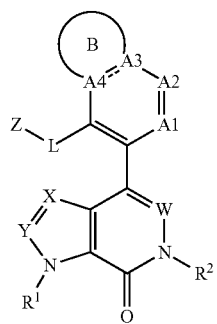

I or a pharmaceutically acceptable salt thereof, wherein:
====== represents a single or double bond;
Ring B is phenyl, 5-membered heteroaryl, 6-membered heteroaryl, $C_5$-cycloalkyl, $C_6$-cycloalkyl, 5-membered heterocycloalkyl, or 6-membered heterocycloalkyl, each optionally substituted by 1, 2, 3, or 4 $R^B$;
L is absent, $-(CR^aR^b)_p-$, $-(CR^aR^b)_n-O-(CR^aR^b)_m-$, $-(CR^aR^b)_n-S-(CR^aR^b)_m-$, $-(CR^aR^b)_n-S(=O)-(CR^aR^b)_m-$, $-(CR^aR^b)_n-S(=O)_2-(CR^aR^b)_m-$, $-(CR^aR^b)_n-C(=O)-(CR^aR^b)_m-$, $-(CR^aR^b)_n-C(=O)O-(CR^aR^b)_m-$, $-(CR^aR^b)_n-OC(=O)-(CR^aR^b)_m-$, $-(CR^aR^b)_n-NR^c-(CR^aR^b)_m-$, $-(CR^aR^b)_n-C(=O)NR^c-(CR^aR^b)_m-$, $-(CR^aR^b)_n-NR^cC(=O)-(CR^aR^b)_m-$, or $-(CR^aR^b)_n-NR^cC(=O)NR^d-(CR^aR^b)_m-$;
A1 is $CR^3$ or N;
A2 is $CR^4$ or N;
A3 is C or N;
A4 is C or N;
wherein when one of A3 and A4 is N, then the other of A3 and A4 is C;
W is $CR^5$ or N;
X is $CR^6$ or N;
Y is $CR^7$ or N;
Z is $C_{1-6}$ alkyl, $C_{6-10}$ aryl, $C_{3-10}$ cycloalkyl, or 5-10 membered heteroaryl, or 4-10 membered heterocycloalkyl, each of which is optionally substituted by 1, 2, 3, 4, or 5 $R^Z$;
$R^1$ is H or $C_{1-4}$ alkyl;
$R^2$ is H, $C_{1-4}$ alkyl, $C_{1-4}$ haloalkyl, $C_{1-4}$ hydroxyalkyl, $C_{1-4}$ cyanoalkyl, or $C_{6-10}$ aryl-$C_{1-6}$ alkyl;
$R^3$ and $R^4$ are each independently selected from H, halo, CN, $NO_2$, $C_{1-6}$ alkyl, $C_{1-6}$ haloalkyl, $C_{1-6}$ hydroxyalkyl, $C_{1-6}$ aminoalkyl, $C_{1-6}$ alkylamino-$C_{1-6}$ alkyl, di-$C_{1-6}$-alkylamino-$C_{1-6}$ alkyl, $C_{2-6}$ alkenyl, and $C_{2-6}$ alkynyl, wherein said $C_{1-6}$ alkylamino-$C_{1-6}$ alkyl, di-$C_{1-6}$-alkylamino-$C_{1-6}$ alkyl, are each optionally substituted with 1 or 2 substituents independently selected from $C_{6-10}$ aryl, $C_{3-10}$ cycloalkyl, 5-10 membered heteroaryl, and 4-10 membered heterocycloalkyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;
each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, and wherein said phenyl, $C_{3-7}$ cycloalkyl, 5-6 membered heteroaryl, and 4-7 membered heterocycloalkyl are each independently substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$ and $R^b$ is independently selected from H, halo, OH, methyl, and ethyl;

each $R^c$ and $R^d$ is independently selected from H, $C_{1-4}$ alkyl, $C_{1-4}$ haloalkyl, $C_{1-4}$ hydroxyalkyl, and cyclopropyl;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{e1}$, $R^{e2}$, $R^{e3}$, and $R^{e4}$ is independently selected from H, $C_{1-4}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group, including the heterocycloalkyl group of Ring B, is optionally substituted by 1 or 2 oxo groups.

The present invention further provides, inter alia, a compound of Formula I:

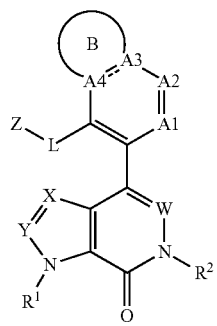

I or a pharmaceutically acceptable salt thereof; wherein
‑ ‑ ‑ ‑ ‑ ‑ represents a single or double bond;

Ring B is phenyl, 5-membered heteroaryl, 6-membered heteroaryl, $C_5$-cycloalkyl, $C_6$-cycloalkyl, 5-membered heterocycloalkyl, or 6-membered heterocycloalkyl, each optionally substituted by 1, 2, 3, or 4 $R^B$;

L is absent, $-(CR^aR^b)_p-$, $-(CR^aR^b)_n-O-(CR^aR^b)_m-$, $-(CR^aR^b)_n-S-(CR^aR^b)_m-$, $-(CR^aR^b)_n-S(=O)-(CR^aR^b)_m-$, $-(CR^aR^b)_n-S(=O)_2-(CR^aR^b)_m-$, $-(CR^aR^b)_n-C(=O)-(CR^aR^b)_m-$, $-(CR^aR^b)_n-C(=O)O-(CR^aR^b)_m-$, $-(CR^aR^b)_n-OC(=O)-(CR^aR^b)_m-$, $-(CR^aR^b)_n-NR^c-(CR^aR^b)_m-$, $-(CR^aR^b)_n-C(=O)NR^c-(CR^aR^b)_m-$, $-(CR^aR^b)_n-NR^cC(=O)-(CR^aR^b)_m-$, or $-(CR^aR^b)_n-NR^cC(=O)NR^d-(CR^aR^b)_m-$;

A1 is $CR^3$ or N;
A2 is $CR^4$ or N;
A3 is C or N;
A4 is C or N;
wherein when one of A3 and A4 is N, then the other of A3 and A4 is C;

W is $CR^5$ or N;
X is $CR^6$ or N;
Y is $CR^7$ or N;
Z is $C_{6-10}$ aryl, $C_{3-10}$ cycloalkyl, or 5-10 membered heteroaryl, or 4-10 membered heterocycloalkyl, each of which is optionally substituted by 1, 2, 3, 4, or 5 $R^Z$;

$R^1$ is H or $C_{1-4}$ alkyl;
$R^2$ is $C_{1-4}$ alkyl, $C_{1-4}$ haloalkyl, or $C_{1-4}$ hydroxyalkyl;
$R^3$ and $R^4$ are each independently selected from H, halo, CN, $NO_2$, $C_{1-6}$ alkyl, $C_{1-6}$ haloalkyl, $C_{2-6}$ alkenyl, and $C_{2-6}$ alkynyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^a$ and $R^b$ is independently selected from H, halo, OH, methyl, and ethyl;

each $R^c$ and $R^d$ is independently selected from H, $C_{1-4}$ alkyl, $C_{1-4}$ haloalkyl, $C_{1-4}$ hydroxyalkyl, and cyclopropyl;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{e1}$, $R^{e2}$, $R^{e3}$, and $R^{e4}$ is independently selected from H, $C_{1-4}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group, including the heterocycloalkyl group of Ring B, is optionally substituted by 1 or 2 oxo groups.

When both A3 and A4 are C, then the symbol ====== represents a double bond, and when one of A3 and A4 is N and the other is C, then the symbol ====== represents a single bond.

In some embodiments, $R^1$ is H.

In some embodiments, $R^2$ is $C_{1-4}$ alkyl, $C_{1-4}$ cyanoalkyl, or $C_{6-10}$ aryl-$C_{1-6}$ alkyl.

In some embodiments, $R^2$ is methyl, cyanomethyl, or benzyl.

In some embodiments, $R^2$ is $C_{1-4}$ alkyl.

In some embodiments, $R^2$ is methyl.

In some embodiments, W is $CR^5$.

In some embodiments, X is $CR^6$.

In some embodiments, Y is $CR^7$.

In some embodiments, Y is N.

In some embodiments, the bicyclic ring containing W, X, and Y is selected from:

In some embodiments, the bicyclic ring containing W, X, and Y is selected from:

In some embodiments, L is —$(CR^aR^b)_p$—, —$(CR^aR^b)_n$—O—$(CR^aR^b)_m$—, —$(CR^aR^b)_n$—S—$(CR^aR^b)_m$—, or —$(CR^aR^b)_n$—S(=O)$_2$—$(CR^aR^b)_m$—.

In some embodiments, L is —$(CR^aR^b)_n$—O—$(CR^aR^b)_m$—.

In some embodiments, L is —CH$_2$—O—.

In some embodiments, L is O, S, or S(=O)$_2$.

In some embodiments, L is O.

In some embodiments, Z is $C_{1-4}$ alkyl, $C_{6-10}$ aryl, $C_{3-10}$ cycloalkyl, or 4-10 membered heterocycloalkyl, each of which is optionally substituted by 1, 2, 3, 4, or 5 $R^Z$.

In some embodiments, Z is $C_{6-10}$ aryl or $C_{3-10}$ cycloalkyl, each of which is optionally substituted by 1, 2, 3, 4, or 5 $R^Z$.

In some embodiments, Z is phenyl optionally substituted by 1, 2, 3, 4, or 5 $R^Z$.

In some embodiments, Z is

In some embodiments, Z is $C_{1-4}$ alkyl.

In some embodiments, Z is $C_{3-7}$ cycloalkyl optionally substituted by 1, 2, 3, 4, or 5 $R^Z$.

In some embodiments, Z is cyclopropyl, cyclobutyl, cyclopentyl, or cyclohexyl, each of which is optionally substituted by 1, 2, 3, 4, or 5 $R^Z$.

In some embodiments, Z is 4-10 membered heterocycloalkyl optionally substituted by 1, 2, 3, 4, or 5 $R^Z$.

In some embodiments, Z is tetrahydropyranyl.

In some embodiments, Z is cyclopropyl.

In some embodiments, each $R^Z$ is independently selected from halo, $C_{1-6}$ alkyl, $C_{2-6}$ alkenyl, $C_{2-6}$ alkynyl, $C_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$.

In some embodiments, each $R^Z$ is independently selected from F, Cl, and Br.

In some embodiments, A1 is $CR^3$.

In some embodiments, A2 is $CR^4$.

In some embodiments, A2 is N.

In some embodiments, A3 is C.

In some embodiments, A4 is C.

In some embodiments, A4 is N.

In some embodiments, $R^3$ is H or $C_{1-6}$ alkyl.

In some embodiments, $R^3$ is H or methyl.

In some embodiments, $R^3$ is H.

In some embodiments, $R^4$ is H, $C_{1-6}$ hydroxyalkyl, or $C_{1-6}$ alkylamino-$C_{1-6}$ alkyl, wherein said $C_{1-6}$ alkylamino-$C_{1-6}$ alkyl is optionally substituted with 1 or 2 substituents independently selected from $C_{6-10}$ aryl, $C_{3-10}$ cycloalkyl, 5-10 membered heteroaryl, and 4-10 membered heterocycloalkyl.

In some embodiments, $R^4$ is H.

In some embodiments, $R^4$ is 1-hydroxyethyl.

In some embodiments, $R^4$ is $C_{1-6}$ alkylamino-$C_{1-6}$ alkyl substituted with 2-(morpholin-N-yl)ethyl, benzyl, or cyclopropylmethyl.

In some embodiments, $R^5$ is H.

In some embodiments, $R^6$ is H.

In some embodiments, $R^7$ is H.

In some embodiments, each $R^B$ is independently selected from $C_{1-6}$ alkyl, $C_{6-10}$ aryl, or $NR^{c3}R^{d3}$; wherein said $C_{1-6}$ alkyl is optionally substituted with 1, 2, or 3 substituents independently selected from phenyl, 4-7 membered heterocycloalkyl, CN, $C(O)NR^{c3}R^{d3}$, $NR^{c3}R^{d3}$, and $NR^{c3}C(O)R^{b3}$, and wherein said phenyl and 4-7 membered heterocycloalkyl are each optionally substituted by 1, 2, or 3 substituents independently selected from $C_{1-6}$ alkyl, $C(O)R^{b3}$, and $S(O)_2R^{b3}$.

In some embodiments, each $R^B$ is $C_{1-6}$ alkyl optionally substituted with 1, 2, or 3 substituents independently selected from phenyl, 4-7 membered heterocycloalkyl, CN, $C(O)NR^{c3}R^{d3}$, $NR^{c3}R^{d3}$, and $NR^{c3}C(O)R^{b3}$, and wherein said phenyl and 4-7 membered heterocycloalkyl are each optionally substituted by 1, 2, or 3 substituents independently selected from $C_{1-6}$ alkyl, $C(O)R^{b3}$, and $S(O)_2R^{b3}$.

In some embodiments, each $R^B$ is $C_{1-6}$ alkyl.

In some embodiments, Ring B is substituted by 1 or 2 oxo groups.

In some embodiments, Ring B is substituted by 1 oxo group.

In some embodiments, the compounds of the invention have Formula II:

II wherein:

the 5-membered ring formed by A3, A4, B1, B2, and B3 is (1) 5-membered heteroaryl wherein B1, B2, and B3 are each independently selected from CH, N, NH, O, and S, (2) $C_5$-cycloalkyl wherein B1, B2, and B3 are each independently selected from CH, $CH_2$, and C(O), or (3) 5-membered heterocycloalkyl wherein B1, B2, and B3 are each independently selected from CH, $CH_2$, C(O), N, NH, O, S, S(O), and $S(O)_2$; and q is 0, 1, 2 or 3.

The floating substituent —$(R^B)_q$ depicted in Formula II and other formulae is meant to indicate that there can be q number of $R^B$ groups substituted on any of the B1, B2, and B3 components of the A3, A4, B1, B2, and B3 5-membered ring. For example, when B1 is selected as CH, the hydrogen of the CH can be replaced by $R^B$ when it is substituted.

In some embodiments, B1, B2, and B3 are each independently selected from CH, C(O), N, O, and NH.

In some embodiments, B1, B2, and B3 are each independently selected from CH, C(O), N, and NH.

In some embodiments, B1 is N, NH, CH, or O.

In some embodiments, B1 is NH.

In some embodiments, B2 is N, C(O), C or CH.

In some embodiments, B2 is N, C(O), or CH.

In some embodiments, B3 is N, NH, or CH.

In some embodiments, B3 is N or NH.

In some embodiments, the compounds of the invention have Formula IIa:

IIa

In some embodiments, the compounds of the invention have Formula IIa-1:

IIa-1

In some embodiments, the compounds of the invention have Formula IIb:

IIb

In some embodiments, the compounds of the invention have Formula IIb-1, IIb-2, IIb-3, IIb-4, or IIb-5:

IIb-1

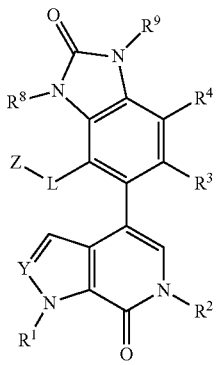

IIb-2

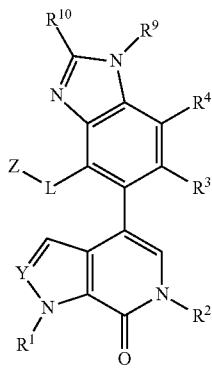

IIb-3

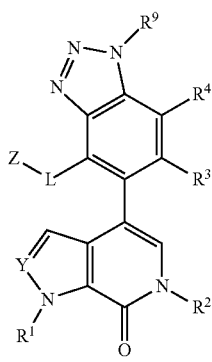

IIb-4

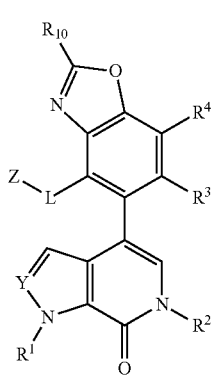

-continued

IIb-5

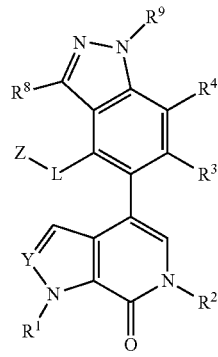

wherein:

$R^8$, $R^9$, and $R^{10}$ are each independently selected from H, halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, and wherein said phenyl, $C_{3-7}$ cycloalkyl, 5-6 membered heteroaryl, and 4-7 membered heterocycloalkyl are each independently substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, the compounds of the invention have Formula IIc:

IIc

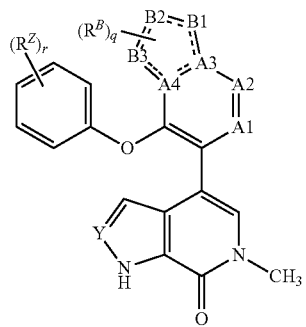

wherein r is 0, 1, 2, 3, 4, or 5.

The floating substituent —(R$^Z$)$_r$ depicted in the phenyl ring of Formula IIc and in other formulae herein is meant to indicate that there can be r number of R$^Z$ groups substituted on the phenyl ring.

In some embodiments, the compounds of the invention have Formula IId, IIe, IIf, or IIf-1:

IId
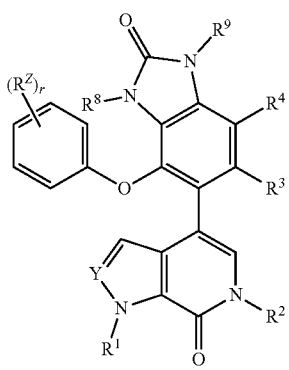

IIe
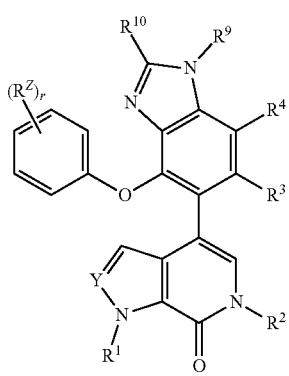

IIf
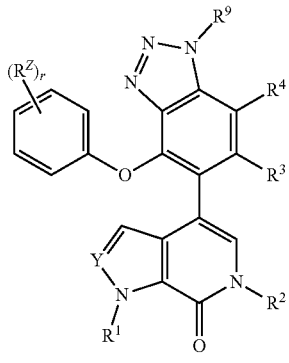

IIf-1
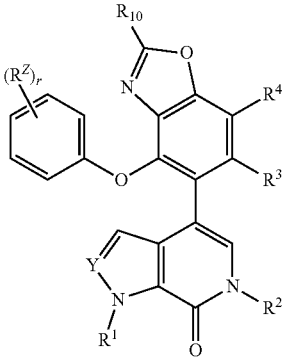

wherein:

r is 0, 1, 2, 3, 4, or 5; and

R$^8$, R$^9$, and R$^{10}$ are each independently selected from H, halo, C$_{1-6}$ alkyl, C$_{2-6}$ alkenyl, C$_{2-6}$ alkynyl, C$_{1-6}$ haloalkyl, C$_{6-10}$ aryl, C$_{3-10}$ cycloalkyl, 5-10 membered heteroaryl, 4-10 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, phenyl, C$_{3-7}$ cycloalkyl, 5-6 membered heteroaryl, 4-7 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$, and wherein said phenyl, C$_{3-7}$ cycloalkyl, 5-6 membered heteroaryl, and 4-7 membered heterocycloalkyl are each independently substituted by 1, 2, or 3 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$.

In some embodiments, the compounds of the invention have Formula IId, IIe, or IIf:

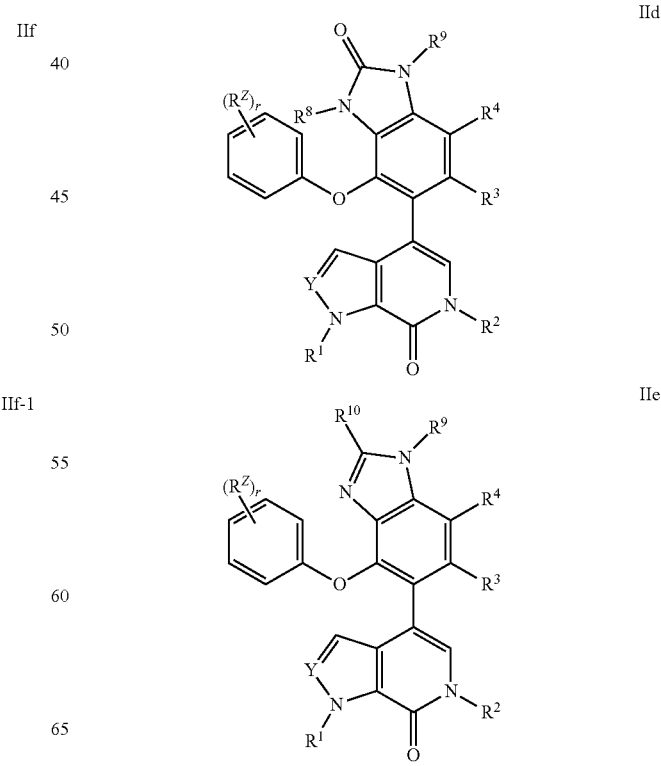

-continued

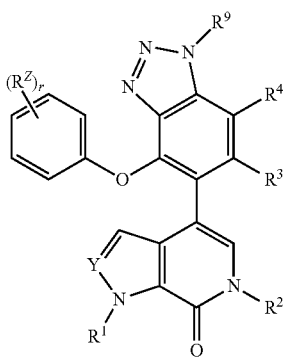

IIf wherein:
r is 0, 1, 2, 3, 4, or 5; and
$R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently) selected from halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

In some embodiments, r is 0, 1, 2, or 3.
In some embodiments, r is 0, 1, or 2.
In some embodiments, the compounds of the invention have Formula IIg:

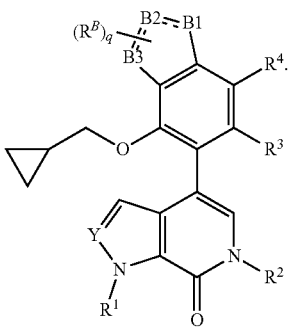

IIg

In some embodiments, the compounds of the invention have Formula III:

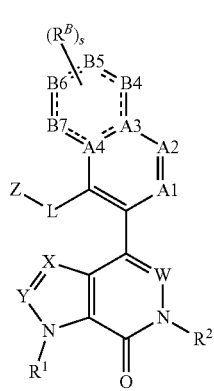

III wherein:
the 6-membered ring formed by A3, A4, B4, B5, B6, and B7 is (1) phenyl, (2) 6-membered heteroaryl wherein B4, B5, B6, and B7 are each independently selected from CH and N, (3) $C_6$-cycloalkyl wherein B4, B5, B6, and B7 are each independently selected from CH, $CH_2$, and C(O), or (4) 6-membered heterocycloalkyl wherein B4, B5, B6, and B7 are each independently selected from CH, $CH_2$, C(O), N, NH, O, S, S(O), and $S(O)_2$; and s is 0, 1, 2, 3, or 4.

The floating substituent —$(R^B)_s$ depicted in Formula III and other formulae herein is meant to indicate that there can be s number of $R^B$ groups substituted on any of the B4, B5, B6, and B7 components of the A3, A4, B4, B5, B6, and B7 6-membered ring. For example, when B4 is selected as CH, the hydrogen of the CH can be replaced by $R^B$ when it is substituted.

In some embodiments, the 6-membered ring formed by A3, A4, B4, B5, B6, and B7 is 6-membered heterocycloalkyl wherein B4, B5, B6, and B7 are each independently selected from CH, $CH_2$, C(O), N, NH, O, S, S(O), and $S(O)_2$.

In some embodiments, B4 is selected from O or N.
In some embodiments, B5 is selected from C, CH, or $CH_2$.
In some embodiments, B6 is selected from CH or C(=O).
In some embodiments, B7 is selected from N or NH.
In some embodiments, the compounds of the invention have Formula IIIa:

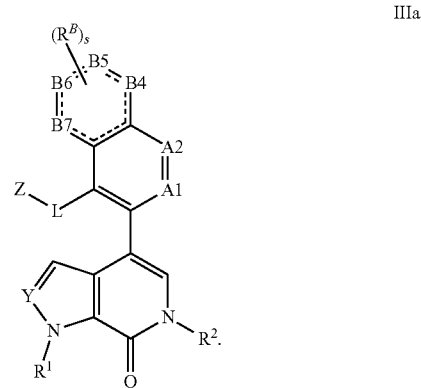

IIIa

In some embodiments, the compounds of the invention have Formula IIIa-1, IIIa-2, or IIIa-3:

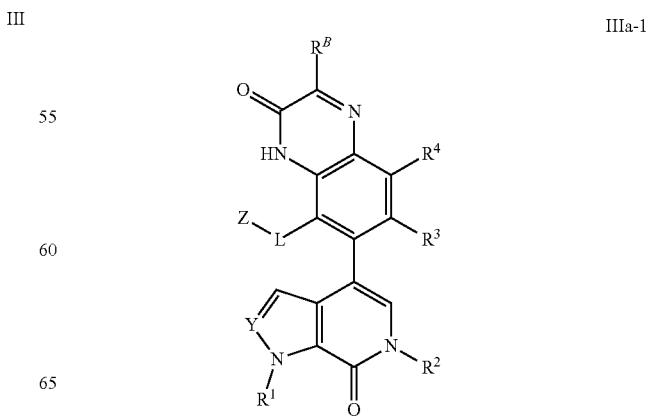

IIIa-1

-continued

IIIa-2

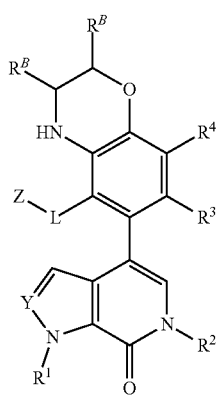

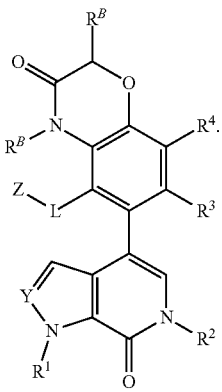

IIIa-3

In some embodiments, the bicyclic moiety containing Ring B has the formula:

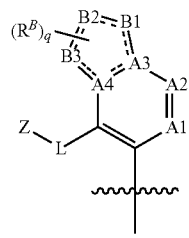

wherein q is 0, 1, 2 or 3.

In some embodiments, the bicyclic moiety containing Ring B has the formula:

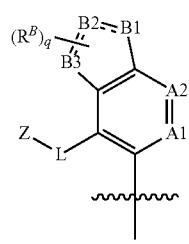

wherein q is 0, 1, 2 or 3.

In some embodiments, the bicyclic moiety containing Ring B has the formula:

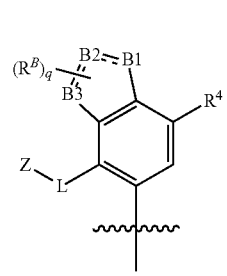

wherein q is 0, 1, 2 or 3.

In some embodiments, the bicyclic moiety containing Ring B has the formula:

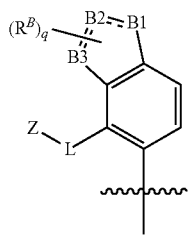

wherein q is 0, 1, 2 or 3.

In some embodiments, the bicyclic moiety containing Ring B has the formula:

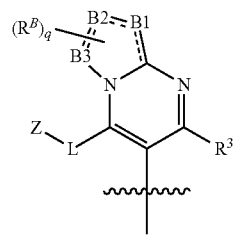

wherein q is 0, 1, 2 or 3.

In some embodiments, the bicyclic moiety containing Ring B has the formula:

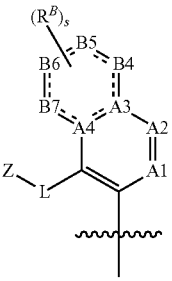

wherein s is 0, 1, 2, 3, or 4.

In some embodiments, the bicyclic moiety containing Ring B has the formula:

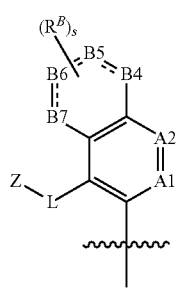
wherein s is 0, 1, 2, 3, or 4.
In some embodiments, the bicyclic moiety containing Ring B has the formula:
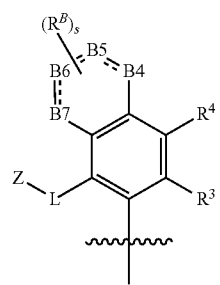
wherein s is 0, 1, 2, 3, or 4.
In some embodiments, the bicyclic moiety containing Ring B has the formula:
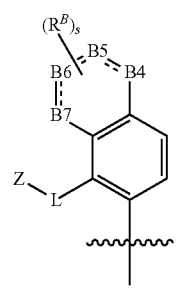
wherein s is 0, 1, 2, 3, or 4.
In some embodiments, the bicyclic moiety containing Ring B is selected from:
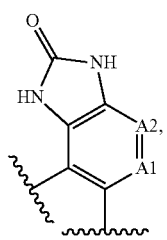 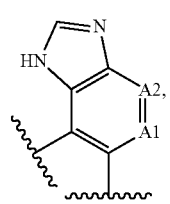 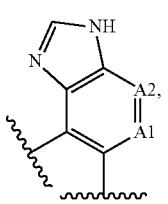
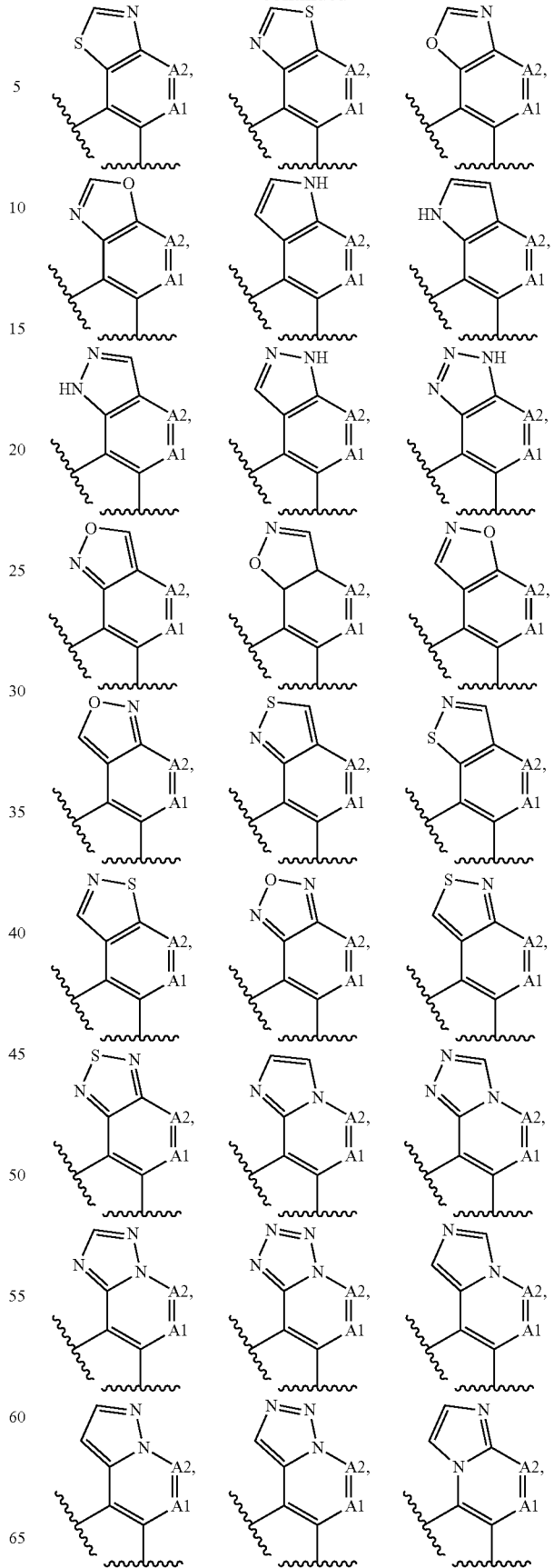

-continued
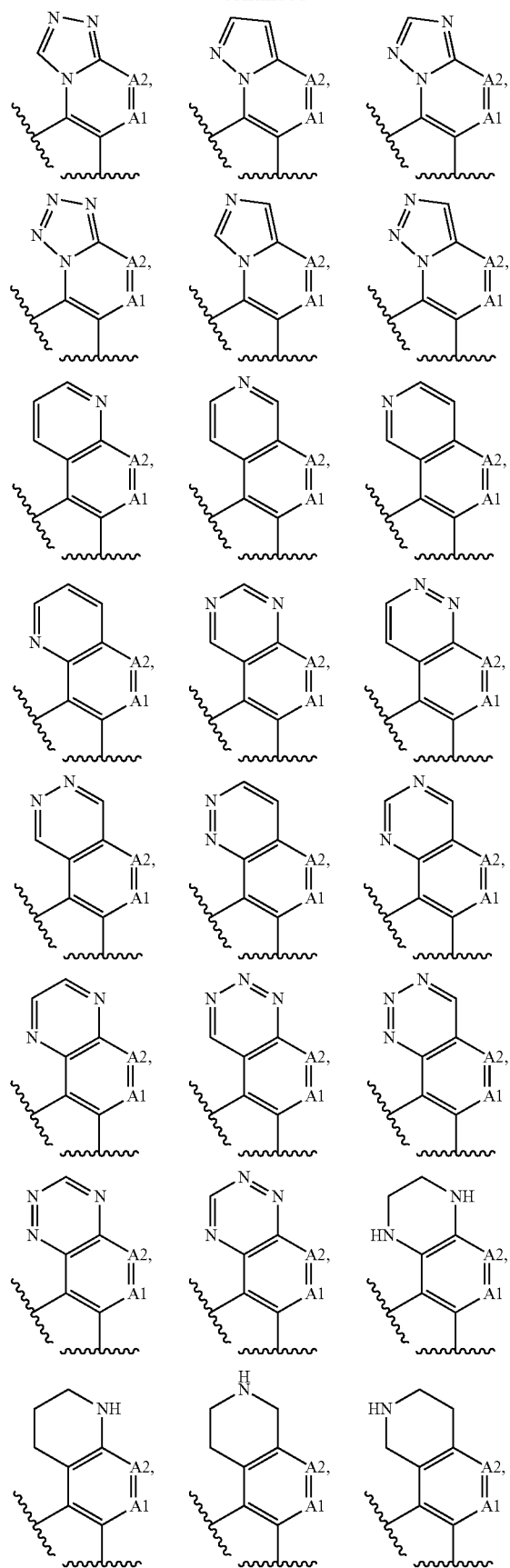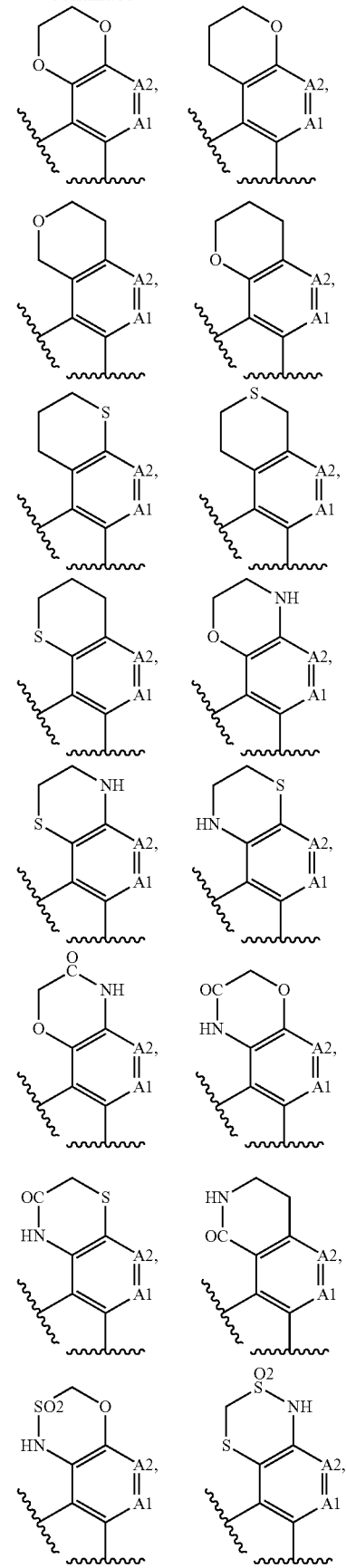

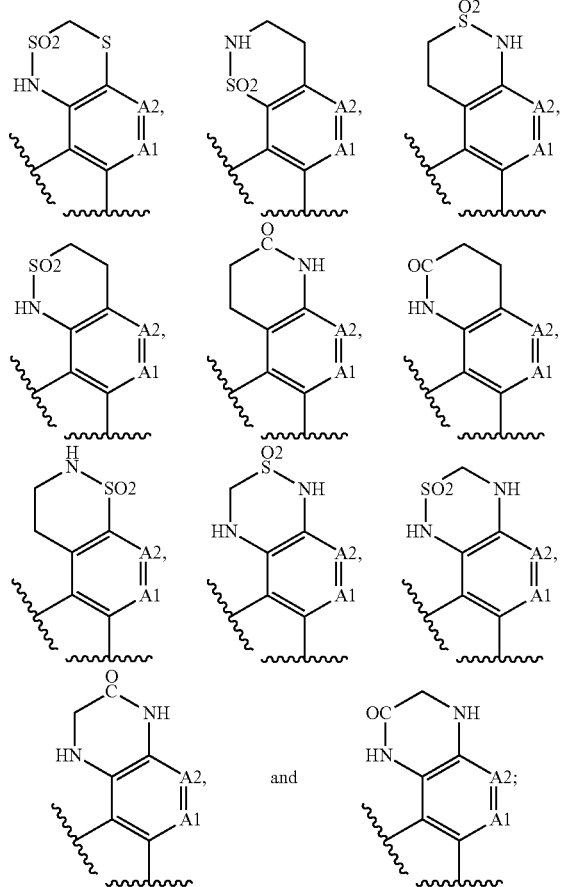

wherein each of the above formulas can be optionally substituted by one or more $R^B$ on the 5- or 6-membered ring corresponding to Ring B by up to 5 substituents or up to the available substitutable valencies, whichever is less.

In some embodiments, the bicyclic moiety containing Ring B is selected from:

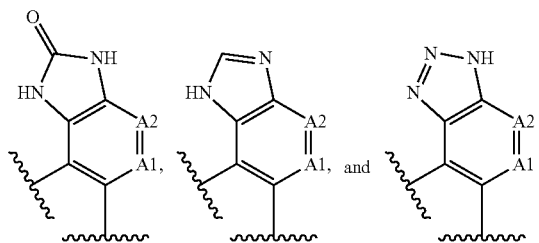

wherein each of the above formulas can be optionally substituted as valency allows by one or two $R^B$ on the 5-membered ring corresponding to Ring B. In some embodiments, A1 and A2 are each CH.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "sub- stituted" means that a hydrogen atom is removed and replaced by a monovalent non-hydrogen substituent or two hydrogen atoms are removed and replaced by a divalent substituent, like oxo. It is to be understood that substitution at a given atom is limited by valency. Throughout the definitions, the term "$C_{i\text{-}j}$" indicates a range which includes the endpoints, wherein i and j are integers and indicate the number of carbons. Examples include $C_{1\text{-}4}$, $C_{1\text{-}6}$, and the like.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

As used herein, the term "$C_{i\text{-}j}$ alkyl," employed alone or in combination with other terms, refers to a saturated hydrocarbon group that may be straight-chain or branched, having i to j carbons. In some embodiments, the alkyl group contains from 1 to 6 carbon atoms or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl.

As used herein, the term "$C_{i\text{-}j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i\text{-}j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i\text{-}j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i\text{-}j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms.

As used herein, the term "di-$C_{i\text{-}j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms.

As used herein, the term "$C_{i\text{-}j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms.

As used herein, the term "amino," employed alone or in combination with other terms, refers to a group of formula —NH$_2$.

As used herein, the term "oxo," employed alone or in combination with other terms, refers to a group of formula =O.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, the aryl group is a naphthalene ring or phenyl ring. In some embodiments, the aryl group is phenyl.

As used herein, the term "carbonyl", employed alone or in combination with other terms, refers to a —C(O)— group.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic (e.g., having 2, 3 or 4 fused rings) ring systems. Also included in the definition of cycloalkyl are moieties that have one or more aromatic rings fused (i.e., having a bond in common with) to the cycloalkyl ring, for example, benzo derivatives of cyclopentane, cyclopentene, cyclohexane, and the like. One or more ring-forming carbon atoms of a cycloalkyl group can be oxidized to form carbonyl linkages. In some embodiments, cycloalkyl is $C_{3-7}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like.

As used herein, "$C_{i-j}$ haloalkoxy," employed alone or in combination with other terms, refers to a group of formula —O-haloalkyl having i to j carbon atoms. An example haloalkoxy group is $OCF_3$. An additional example haloalkoxy group is $OCHF_2$. In some embodiments, the haloalkoxy group is fluorinated only. In some embodiments, the alkyl group has 1 to 6 or 1 to 4 carbon atoms.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the alkyl group has 1 to 6 or 1 to 4 carbon atoms.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridine, pyrimidine, pyrazine, pyridazine, pyrrole, pyrazole, azolyl, oxazole, isoxazole, thiazole, isothiazole, imidazole, furan, thiophene, triazole, tetrazole, thiadiazole, quinoline, isoquinoline, indole, benzothiophene, benzofuran, benzisoxazole, imidazo[1,2-b]thiazole, purine, triazine. and the like.

A 5-membered heteroaryl is a heteroaryl group having five ring-forming atoms comprising wherein one or more of the ring-forming atoms are independently selected from N, O, and S. In some embodiments, the 5-membered heteroaryl group has 1, 2, or 3 heteroatom ring members. In some embodiments, the 5-membered heteroaryl group has 1 or 2 heteroatom ring members. In some embodiments, the 5-membered heteroaryl group has 1 heteroatom ring member. Example ring-forming members include CH, N, NH, O, and S. Example five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl.

A 6-membered heteroaryl is a heteroaryl group having six ring-forming atoms wherein one or more of the ring-forming atoms is N. In some embodiments, the 6-membered heteroaryl group has 1, 2, or 3 heteroatom ring members. In some embodiments, the 6-membered heteroaryl group has 1 or 2 heteroatom ring members. In some embodiments, the 6-membered heteroaryl group has 1 heteroatom ring member. Example ring-forming members include CH and N. Example six-membered ring heteroaryls are pyridyl, pyrazinyl, pyrimidinyl, triazinyl, and pyridazinyl.

As used herein, the term "heterocycloalkyl," employed alone or in combination with other terms, refers to non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems, including spiro systems. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered. Examples of heterocycloalkyl groups include 1, 2, 3, 4-tetrahydro-quinoline, dihydrobenzofuran, azetidine, azepane, pyrrolidine, piperidine, piperazine, morpholine, thiomorpholine, and pyran.

The compounds described herein can be asymmetric (e.g., having one or more stereocenters). All stereoisomers, such as enantiomers and diastereoisomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, are substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. Methods for isolating compounds and their salts are routine in the art.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.*, 1977, 66(1), 1-19, and in Stahl et al., *Handbook of Pharmaceutical Salts: Properties, Selection, and Use*, (Wiley, 2002). In some embodiments, the compounds described herein include the N-oxide forms.

The following abbreviations may be used herein: AcOH (acetic acid); Ac$_2$O (acetic anhydride); aq. (aqueous); atm. (atmosphere(s)); Boc (t-butoxycarbonyl); br (broad); Cbz (carboxybenzyl); calc. (calculated); d (doublet); dd (doublet of doublets); DCM (dichloromethane); DIAD (N, N'-diisopropyl azidodicarboxylate); DIPEA (N, N-diisopropylethylamine); DMF (N, N-dimethylformamide); Et (ethyl); EtOAc (ethyl acetate); g (gram(s)); h (hour(s)); HATU (N,N,N',N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); m (multiplet); M (molar); mCPBA (3-chloroperoxybenzoic acid); MgSO$_4$ (magnesium sulfate); MS (Mass spectrometry); Me (methyl); MeCN (acetonitrile); MeOH (methanol); mg (milligram(s)); min. (minutes(s)); mL (milliliter(s)); mmol (millimole(s)); N (normal); NaHCO$_3$ (sodium bicarbonate); NaOH (sodium hydroxide); Na$_2$SO$_4$ (sodium sulfate); NH$_4$Cl (ammonium chloride); NH$_4$OH (ammonium hydroxide); nM (nanomolar); NMR (nuclear magnetic resonance spectroscopy); OTf (trifluoromethanesulfonate); Pd (palladium); Ph (phenyl); pM (picomolar); POCl$_3$ (phosphoryl chloride); RP-HPLC (reverse phase high performance liquid chromatography); s (singlet); t (triplet or tertiary); TBS (tert-butyldimethylsilyl); tert (tertiary); tt (triplet of triplets); t-Bu (tert-butyl); TFA (trifluoroacetic acid); THF (tetrahydrofuran); μg (microgram(s)); μL (microliter(s)); μM (micromolar); wt % (weight percent).

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety. Protecting groups in the synthetic schemes are typically represented by "PG."

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("*Preparative LC-MS Purification: Improved Compound Specific Method Optimization*" Karl F. Blom, Brian Glass, Richard Sparks, Andrew P. Combs *J. Combi. Chem.* 2004, 6(6), 874-883, which is incorporated herein by reference in its entirety) and normal phase silica chromatography.

Compounds of Formula I can be formed as shown in Scheme I. The heterocyclic halide (i) (Hal=Cl, Br, or I) can be coupled to M-Het, where M is a boronic acid, boronic ester or an appropriately substituted metal (e.g., Het-M is Het-B(OH)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine)palladium(0)), to give a derivative of Formula I (iii).

Alternatively, heterocyclic halide (i) can be converted to a boronic acid or boronate ester (iv) under standard transmetalation conditions (e.g., pinacol boronate, in the presence of a palladium(0) catalyst, such as tetrakis(triphenylphosphine)palladium(0)). The heterocyclic boronate (iv) can be coupled to halo substituted heterocycles (v), (e.g., Hal-Het, where Hal=Cl, Br, or I), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine) palladium(0)) to give a compound of Formula I (iii).

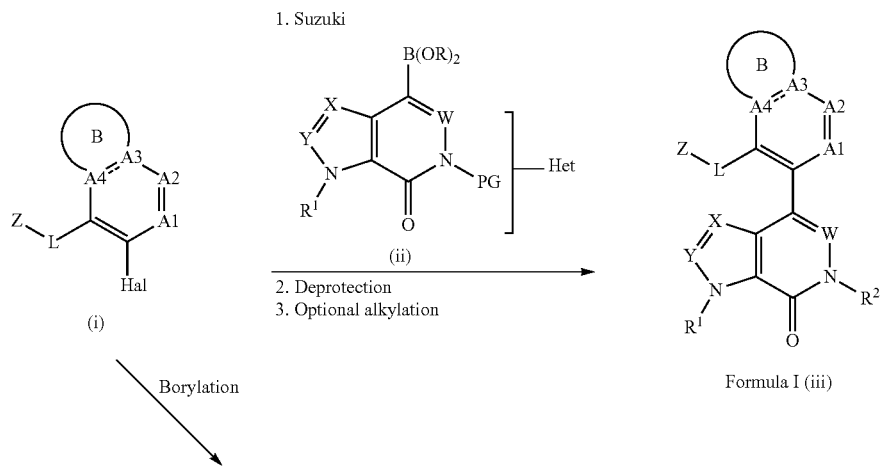

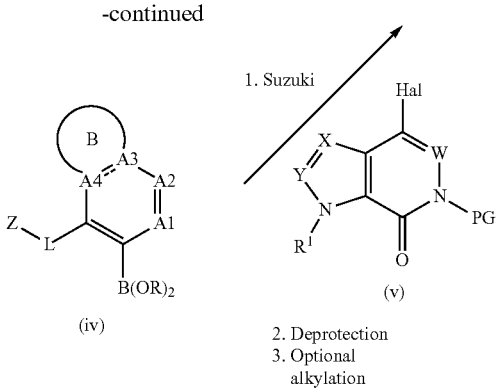

(iv)

(v)

2. Deprotection
3. Optional alkylation

Synthesis of heterocyclic intermediates useful in the preparation of compounds of Formula I can be formed as shown in Scheme II. The heterocycle (i) can be alkylated (e.g., Z-Hal, where Hal=Br, Cl, or I) with a base (e.g., triethylamine, NaH or $Na_2CO_3$) or under Mitsunobu conditions to afford the heterocycle (ii). Alternatively, heterocycle (i) can be arylated either under Evans' conditions with an aryl-boronic acid (e.g., Z—$B(OR)_2$, in the presence of a palladium(0) catalyst) or Ullman conditions with an aryl halide (e.g., Z-Hal, in the presence of palladium(0)) to afford the heterocycle (ii). Halogenation of heterocycle (ii) under standard conditions ($Br_2$, AcOH or N-chlorosuccinamide, N-bromosuccinamide or N-iodosuccinamide) can give halide (iii) where Hal=Cl, Br or I.

Scheme II

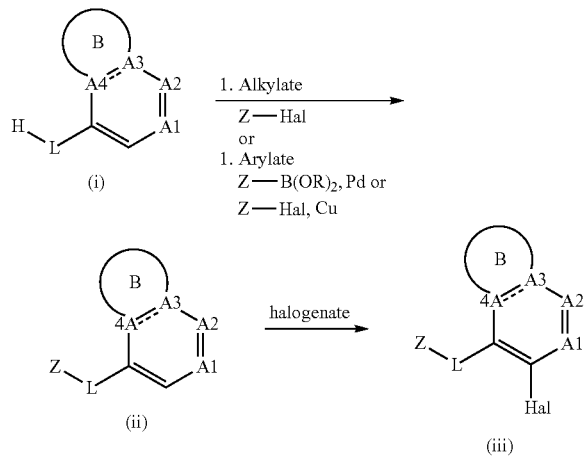

Synthesis of heterocyclic intermediates useful in the preparation of compounds of Formula I can be formed as shown in Scheme III. Halogenation of heterocycle (i) under standard conditions (e.g., $Br_2$, AcOH or N-chlorosuccinamide, N-bromosuccinamide or N-iodosuccinamide) can give halide (ii) where Hal=Cl, Br or I. The heterocycle (ii) can be alkylated (e.g., Z-Hal, where Hal=Br, Cl, or I) with a base, (e.g. triethylamine, NaH or $Na_2CO_3$) or under Mitsunobu conditions to afford the heterocycle (iii). Alternatively, heterocycle (ii) can be arylated either under Evans' conditions with an aryl-boronic acid (e.g., Z—$B(OR)_2$, in the presence of a palladium(0) catalyst) or Ullmann conditions with an aryl halide (e.g., Z-Hal, in the presence of copper) to afford the heterocycle (iii).

Scheme III

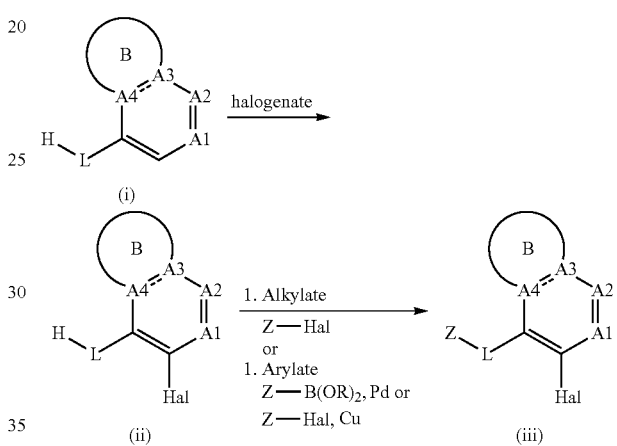

Compounds of Formula I can be formed as shown in Scheme IV. The heterocyclic fluoride (i) can be coupled to Het-M (ii), where M is a boronic acid, boronic ester or an appropriately substituted metal (e.g., Het-M is Het-$B(OH)_2$, Het-$B(OR)_2$, Het-$Sn(Bu)_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)), to give a compound of formula (iii).

Alternatively, heterocyclic halide (i) can be converted to a boronic acid or boronate acid (iv) under standard transmetalation conditions (e.g., pinacol boronate, in the presence of a palladium(0) catalyst, such as tetrakis(triphenylphosphine)palladium(0)). The heterocyclic boronate (iv) can be coupled to halo substituted heterocycle (v) (e.g., Hal-Het, where Hal is a halide (e.g., Hal=Cl, Br, or I)), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give the compounds of formula (iii). Thiols, amines, and alcohols of formula H-L-Z can displace the fluoro group of compounds (iii) using standard conditions (e.g., $Cs_2CO_3$/DMSO) to give thioethers, arylamines, and ethers of Formula I (vi) after deprotection of the nitrogen protecting group and optional alkylation with Hal-$R^2$.

Scheme IV

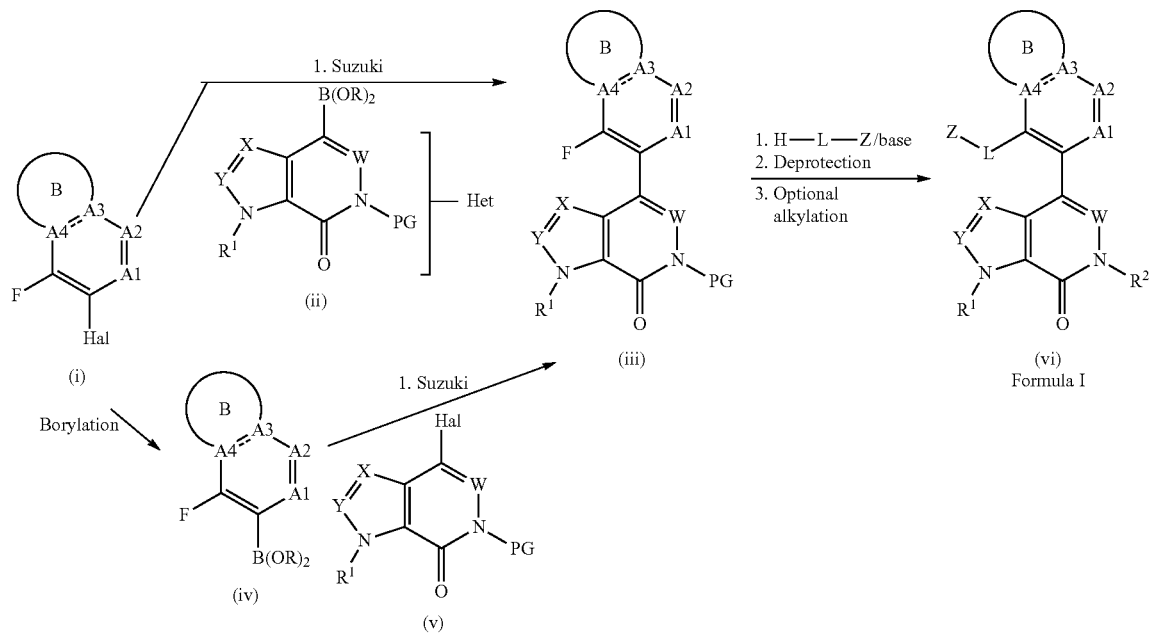

Synthesis of heterocyclic intermediates useful in the preparation of compounds of Formula I can be formed as shown in Scheme V. Conversion of Hal derivative (i) wherein Hal=Br, Cl, or I, with 1,1-dimethoxy-N,N-dimethylmethanamine in the absence or presence of a base can provide enamines (ii). Catalytic hydrogenation of (ii) in the presence of a catalyst (e.g., Raney-Nickel under hydrogen atmosphere) can provide amines that cyclize to form a heterocycle. Protection of the heterocyclic nitrogen atom with a protecting group such as, but not limited to, benzyl, tosyl, and (trimethylsilyl)ethoxy)methyl group can provide heterocycle (iii). Hydrolysis of the methoxy substituent with an acid such as, but not limited to, hydrochloric acid or hydrobromic acid to provides heterocycles (iv). Compound (iv) can be alkylated (e.g., $R^2$-Hal and a base (e.g., triethylamine, NaH or $Na_2CO_3$) or under Mitsunobu conditions) to afford the heterocycle (v). The conversion of halide (v) to the boronate (vi) or boronic acid (vi) can be performed under standard conditions (e.g., pinacol boronate, in the presence of a palladium(0) catalyst, such as tetrakis(triphenylphosphine)palladium(0)).

Scheme V

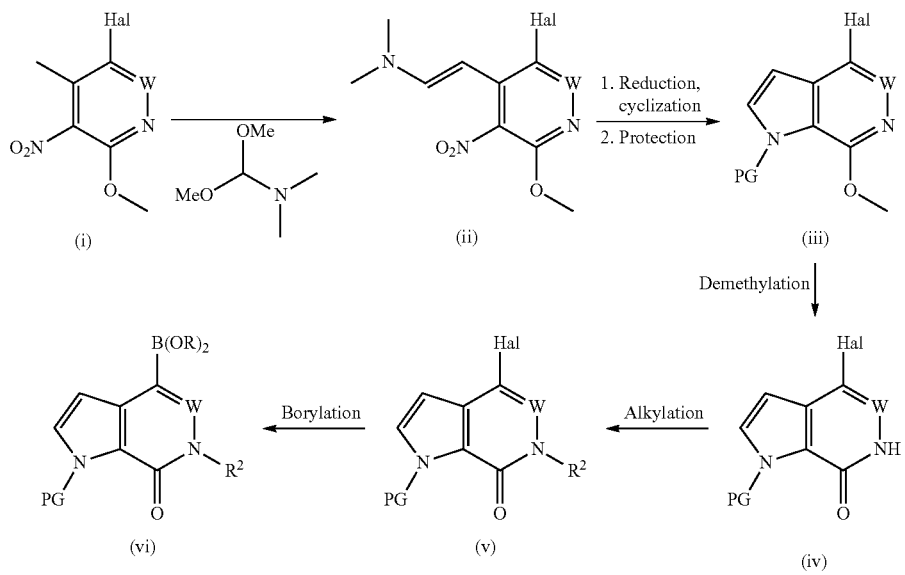

Synthesis of heterocyclic intermediates useful in the preparation of compounds of Formula I can be formed as shown in Scheme VI. Conversion of halo heterocycle (i) with ammonium hydroxide can afford amines (ii). Iodination of amine (ii) with N-iodosuccinimide can afford iodo derivatives (iii). Coupling with (E)-2-(2-ethoxyvinyl)-4,4,S,S-tetramethyl-1,3,2-dioxaborolane utilizing Suzuki coupling reaction conditions (e.g., in the presence of a palladium(0) catalyst, such as tetrakis(triphenylphosphine)palladium(0) and a base (e.g., bicarbonate or carbonate base)) can provide heterocycles (iv). Cyclization of (iv) in the presence of an acid such as, but not limited to, acetic acid or hydrochloric acid, followed by protection of the nitrogen atom can afford heterocycles (v). The conversion of halide (v) to the boronate ester (vi) or boronic acid (vi) can be performed under standard conditions (e.g., pinacol boronate, in the presence of a palladium(0) catalyst, such as tetrakis(triphenylphosphine)palladium(0)).

shown in Scheme VII. Conversion of iodo derivative (i) to heterocyclic acid (ii) can be performed by reacting with pyruvic acid in the presence of a palladium catalyst (e.g., palladium(II)acetate, and a base such as DBU). Esterification of the acid (ii) can be performed by standard reaction conditions such as treatment with an alcohol under acidic condition. Protection of the nitrogen of the heterocycle (iii) can be performed under standard conditions to give N-protected heterocycle (iv). Hydrolysis of the ester to the acid and formation of the amide (v) can be performed under standard peptide coupling conditions, (e.g., amine HNRR in the presence of a coupling reagent, such as, 1,1'-carbonyldiimidazole (CDI) or N,N,N',N'-tetramethyluronium hexafluorophosphate (HATU)). The conversion of halide (v) to the boronate ester (vi) or boronic acid (vi) can be performed under standard condition (e.g., pinacol boronate, in the presence of a palladium(0) catalyst, such as tetrakis(triphenylphosphine)palladium(0)).

Scheme VI

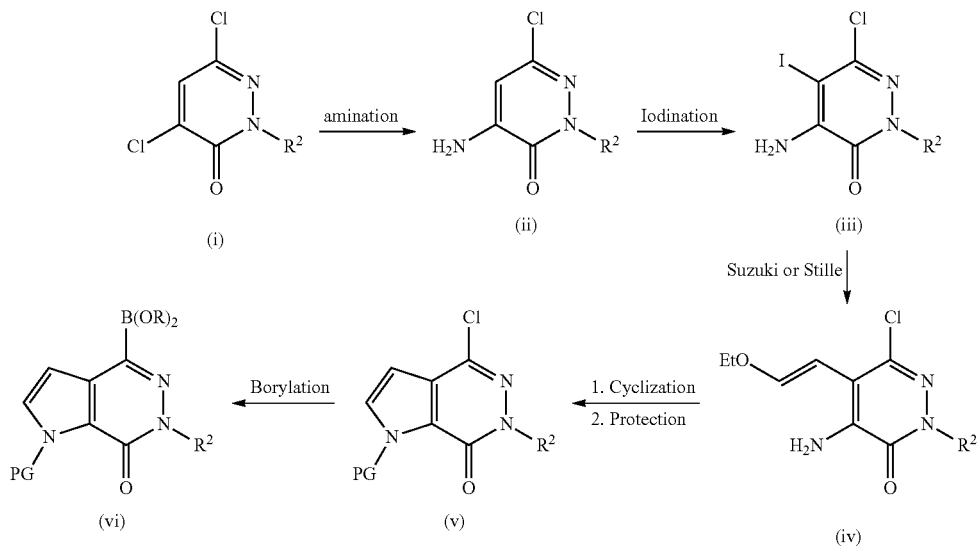

Synthesis of heterocyclic intermediates useful in the preparation of compounds of Formula I can be formed as Scheme VII

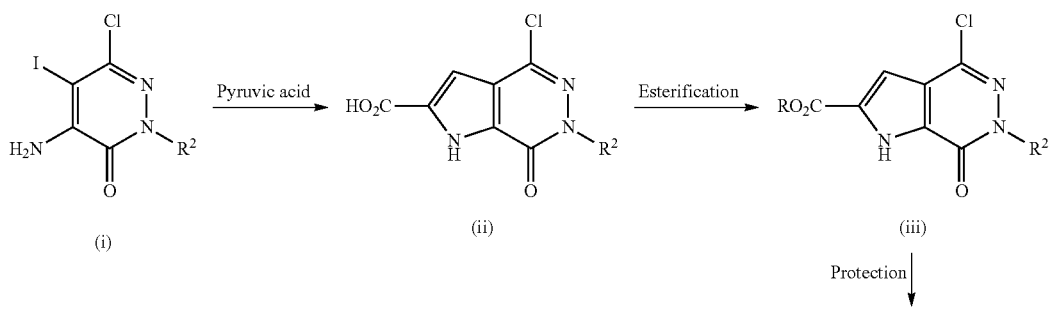

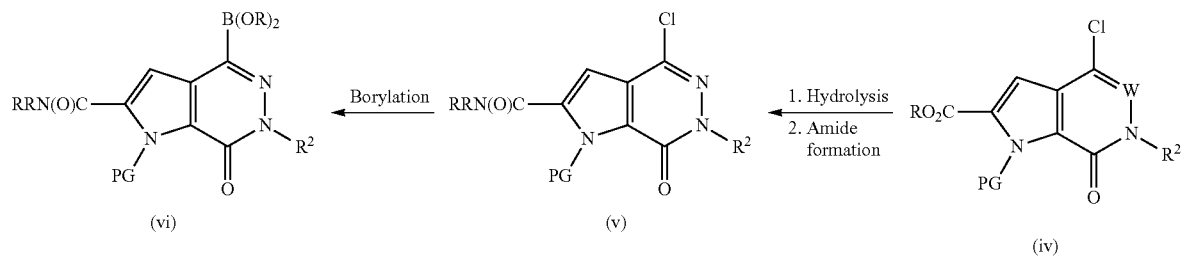

Synthesis of heterocyclic intermediates useful in the preparation of compounds of Formula I can be formed as shown in Scheme VIII. Reaction of heterocycle (i) with an oxalate ester in the presence of a base (e.g., potassium ethoxide) and reduction followed by cyclization of the resulting ester (ii) upon heating and protection of the heterocyclic nitrogen can afford heterocycle (iii). Cleavage of the methyl ether under acidic conditions can afford heterocycle (iv). Compounds of formula (iv) can be alkylated (e.g., $R^2$-Hal, where Hal=Br, Cl, or I) with a base, such as triethylamine, NaH or $Na_2CO_3$ or under Mitsunobu conditions to afford the heterocycle (v). The conversion of halide (v) to the boronate ester (vi) or boronic acid (vi) can be performed under standard condition (e.g., pinacol boronate, in the presence of a palladium(0) catalyst, such as tetrakis(triphenylphosphine)palladium(0)).

Synthesis of heterocyclic intermediates useful in the preparation of compounds of Formula I can be formed as shown in Scheme IX. Heterocycle (i) can be alkylated with $R^2$-Hal (Hal=Cl, Br, I, or other leaving group, e.g., MeI) and a suitable base (e.g., NaH) to give compound (ii). Selective reduction of the nitro heterocycle (ii) (e.g., Hal=Cl, Br or I using iron with AcOH or HCl) can give the amine (iii). Cyclization of (iii) to (iv) can be accomplished by isoamylnitrite. Protection of the nitrogen of (iv) can be accomplished using standard conditions (e.g., tosylchloride and NaH) to give (v). The conversion of halide (v) to the boronate ester (vi) or boronic acid (vi) can be performed under standard condition (e.g., pinacol boronate, in the presence of a palladium(0) catalyst, such as tetrakis(triphenylphosphine)palladium(0)).

Scheme VIII

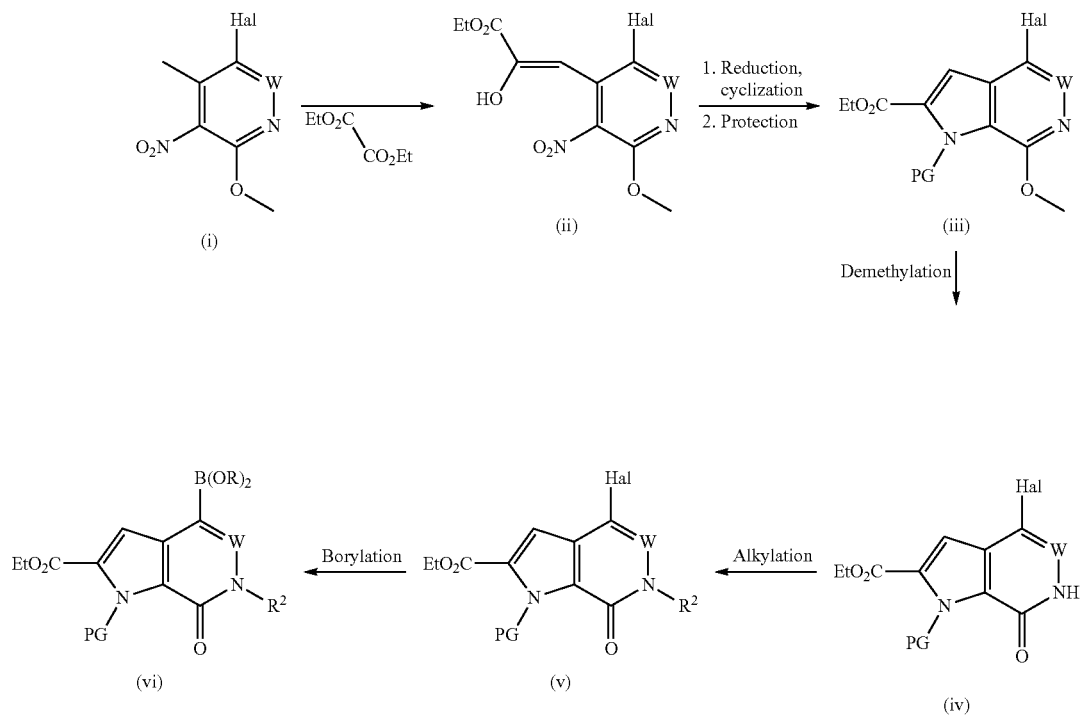

Scheme IX

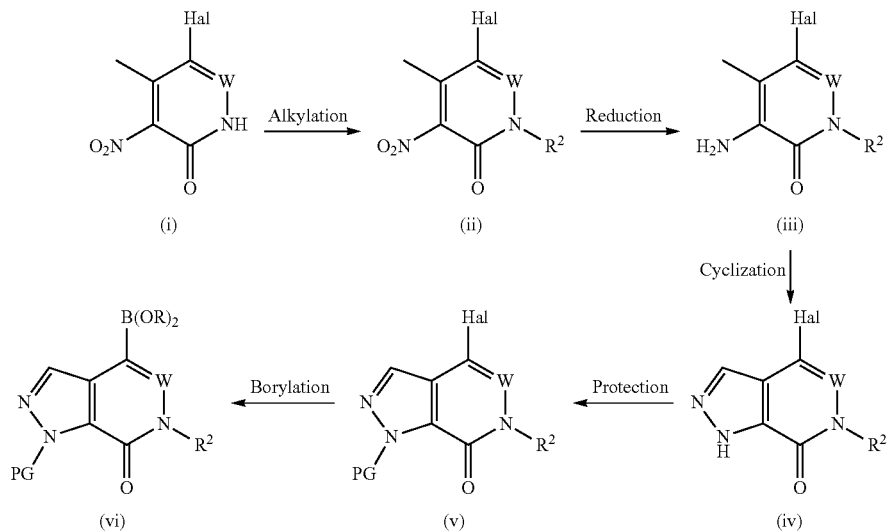

Synthesis of compounds of Formula I can be formed as shown in Scheme X. Thiols, amines, and alcohols of formula H-L-Z can displace the fluoro group of compounds (i) using standard conditions (e.g., $Cs_2CO_3$/DMSO) to give thioethers, arylamines, and ethers of formula (ii) where L=S, NR, and O, respectively. Selective reduction of the nitro benzene (ii) (when Hal=Cl, Br or I) using iron/AcOH can give the bis-aniline (iii). Conversion of bis-aniline to urea can occur under standard conditions (e.g., carbonyl diimidazole or triphosgene) to give (iv). The heterocyclic halide (iv) can be coupled to Het-M (v), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0)) and a base (e.g., bicarbonate or carbonate base) or standard Negishi conditions (e.g., in the presence of a palladium(0) catalyst, such as tetrakis(triphenylphosphine)palladium(0)) to give compounds (vi). Deprotection of (vi) can give compounds of Formula I (vii).

Scheme X

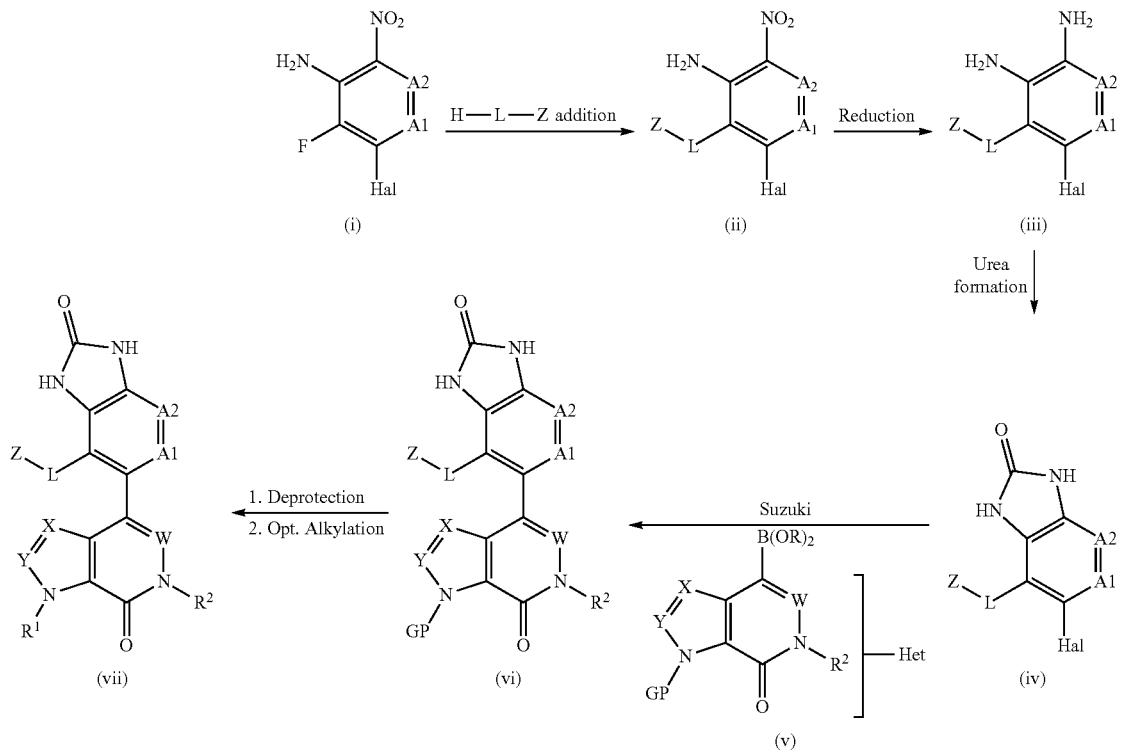

Compounds of Formula I can be formed as shown in Scheme XI. Aniline (i) (from Scheme X) can be converted to the trifluoroacetamide using standard conditions (e.g., trifluoroacetic anhydride) and then alkylated with $R^B$-Hal (e.g., Hal=Cl, Br, I, or other leaving group, e.g., MeI) and a suitable base (e.g., NaH) to give compound (ii). Removal of the trifluoroacetamide followed by selective reduction of the nitro (when Hal=Cl, Br or I) using iron/AcOH can give the bis-aniline (iii). Conversion of bis-aniline to urea can occur under standard conditions (e.g., carbonyl diimidazole or triphosgene) to give (iv). The heterocyclic halide (iv) can be coupled to Het-M (v), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (vi). Deprotection of (vi) can give compounds of the invention (vii).

substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iii). The nitro group of (iii) can be reduced to give the bis-aniline which can be converted to the urea under standard conditions (e.g., carbonyl diimidazole or triphosgene) to give (vii). Deprotection of (vii) can give compounds of the invention (vi).

Alternatively, the aniline of compound (iii) can be converted to the trifluoroacetamide using standard conditions (e.g., trifluoroacetic anhydride) and then alkylated with $R^B$-Hal (Hal=Cl, Br, I, or other leaving group, e.g. MeI) and a suitable base (e.g., NaH) to give compound (iv). Removal of the trifluoroacetamide followed by reduction of the nitro under standard conditions (e.g., hydrogenation with palladium, iron/AcOH, or zinc) can give the bis-aniline which can be converted to the urea under standard conditions (e.g., Scheme XI

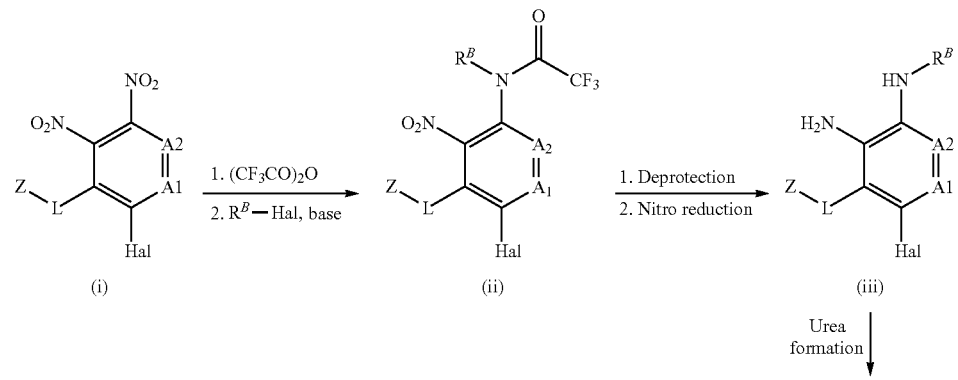

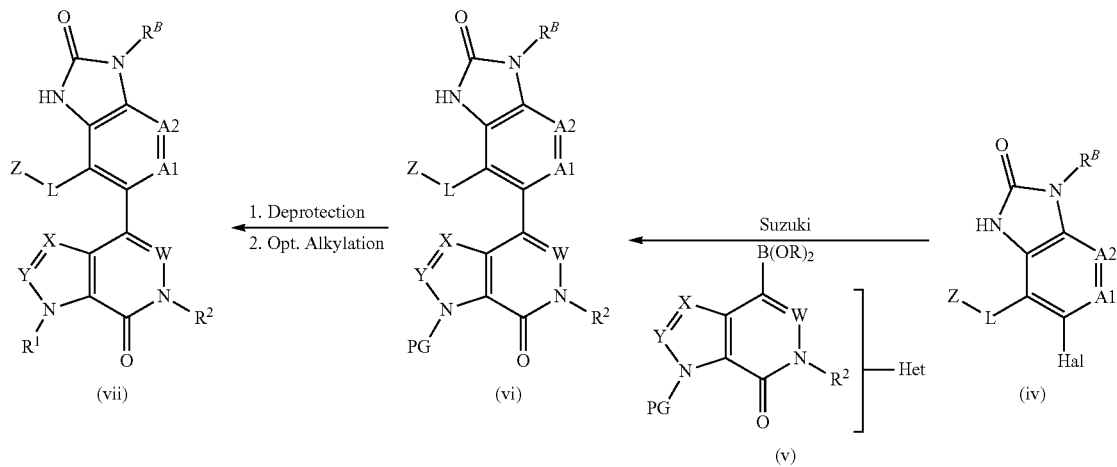

Compounds of Formula I can be formed as shown in Scheme XII. The aniline (i) can be coupled to Het-M (ii), where M is a boronic acid, boronic ester or an appropriately carbonyl diimidazole or triphosgene) to give (v). Finally deprotection of (v) can give compounds of the invention (vi).

Scheme XII

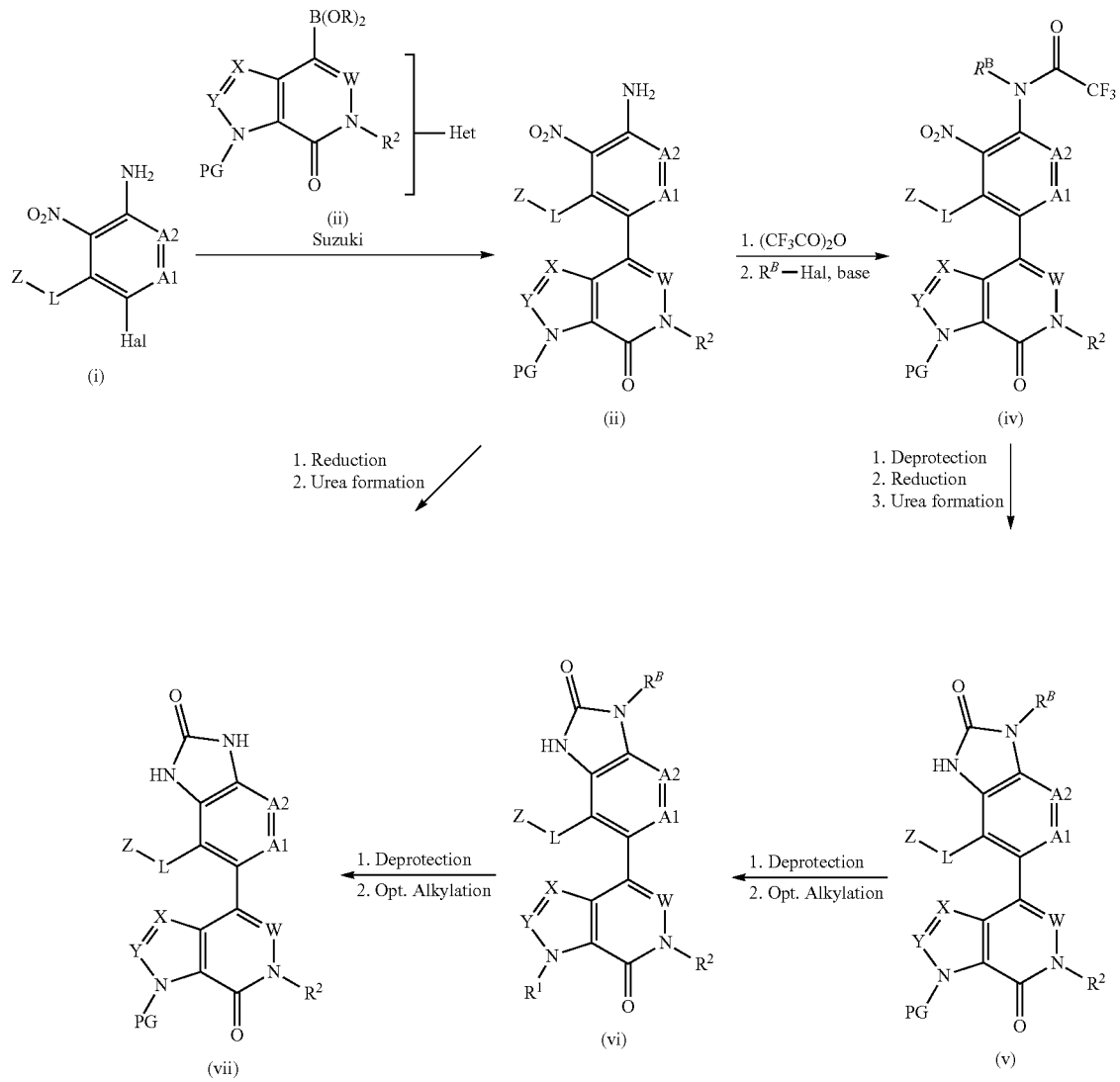

Compounds of Formula I can be formed as shown in Scheme XIII Selective reduction of the nitro benzene (i) (when Hal=Cl, Br or I) using iron/AcOH can give the bis-aniline which can be converted under standard conditions (e.g., $(EtO)_3CR^B$ with p-TsOH, $R^BCHO$ with TMSCl or peroxide/HCL or copper catalyzed, or $R^BCO_2H$ with borane) to give benzimidazole (ii). The benzimidazole (ii) can be coupled to Het-M (iii), where M is a boronic acid, boronate ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iv). Finally deprotection of (iv) can give compounds of the invention (v).

Alternatively, aniline (i) can be converted to the trifluoroacetamide using standard conditions (e.g., trifluoroacetic anhydride) and then alkylated with $R^B$-Hal (Hal=Cl, Br, I, or other leaving group, e.g. MeI) and a suitable base (e.g., NaH) to give compound (vi). Removal of the trifluoroacetamide followed by selective reduction of the nitro (when Hal=Cl, Br or I) using iron/AcOH can give the bis-aniline which can be converted under standard conditions (e.g., $(EtO)_3CR^B$ with p-TsOH, $R^BCHO$ with TMSCl or peroxide/HCL or copper catalyzed, or $R^BCO_2H$ with borane) to give benzimidazole (vii). The benzimidazole (vii) can be coupled to Het-M (iii), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds of the invention (v) after deprotection and optional alkylation.

Scheme XIII

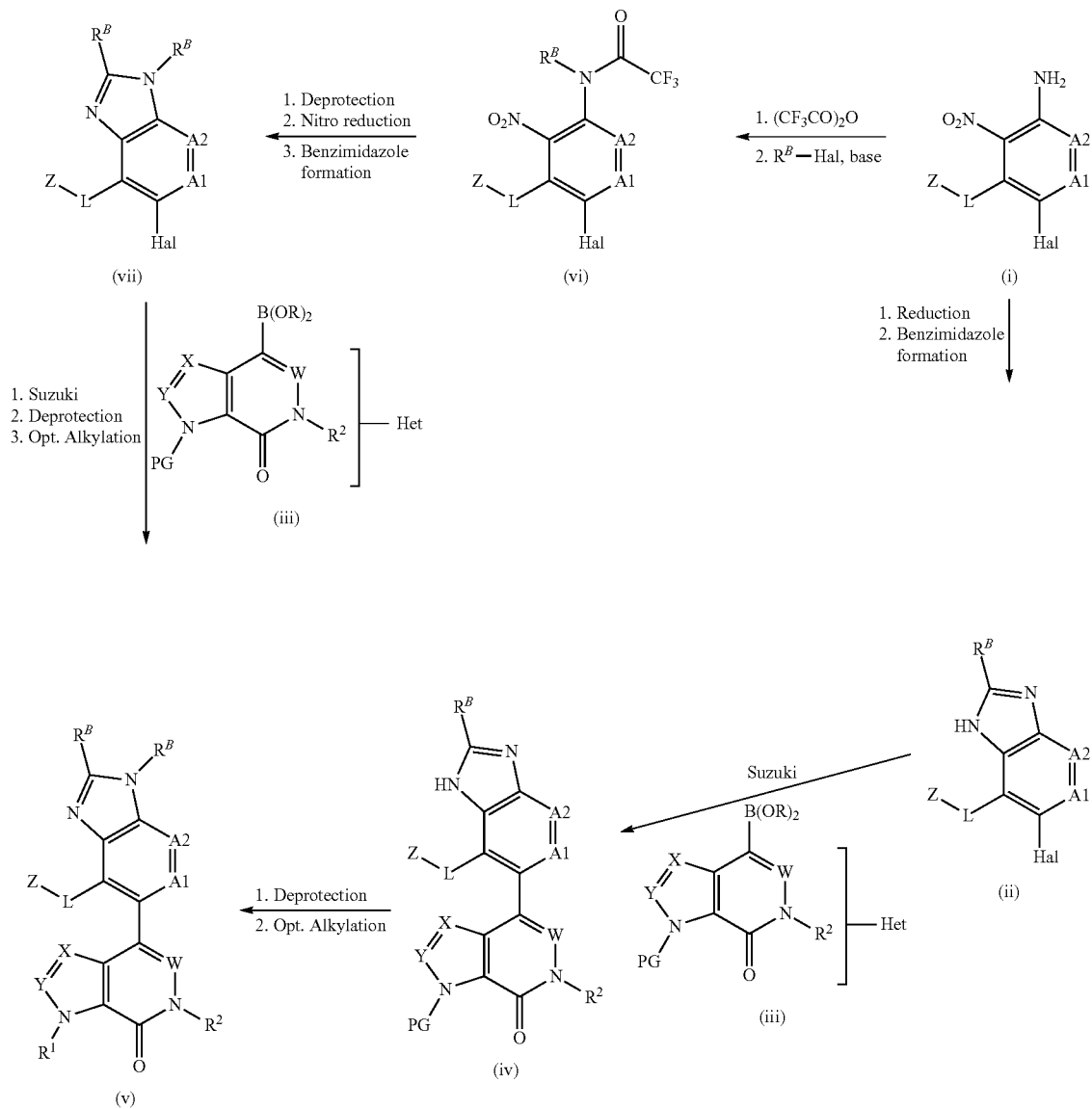

Compounds of Formula I can be formed as shown in Scheme XIV. Selective reduction of the nitro benzene (i) (when Hal=Cl, Br or I) using iron/AcOH can give the bis-aniline which can be converted (e.g., sodium nitrite/acetic acid) to benzotriazole (ii). The benzotriazole (ii) can be coupled to Het-M (iii), where M is a boronic acid, boronate ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds (iv). Finally deprotection of (iv) can give compounds of the invention (v).

Alternatively, aniline (i) can be converted to the trifluoroacetamide using standard conditions (e.g., trifluoroacetic anhydride) and then alkylated with $R^B$-Hal (Hal=Cl, Br, I, or other leaving group, e.g. MeI) and a suitable base (e.g., NaH) to give compound (vi). Removal of the trifluoroacetamide followed by selective reduction of the nitro (when Hal=Cl, Br or I) using iron/AcOH can give the bis-aniline which can be converted (e.g., sodium nitrite with acetic acid) to benzotriazole (vii). The benzotriazole (vii) can be coupled to Het-M (iii), where M is a boronic acid, boronic ester or an appropriately substituted metal (e.g., Het-M is Het-B(OH)$_2$, Het-B(OR)$_2$, Het-Sn(Bu)$_4$, or Zn-Het), under standard Suzuki conditions or standard Stille conditions (e.g., in the presence of a palladium(0) catalyst, such as tetrakis(triphenylphosphine)palladium(0) and a base (e.g., bicarbonate or carbonate base)) or standard Negishi conditions (e.g., in the presence of a palladium(0) catalyst, such as tetrakis(triphenylphosphine)palladium(0)) to give compounds of the invention (v) after deprotection and optional alkylation.

Scheme XIV

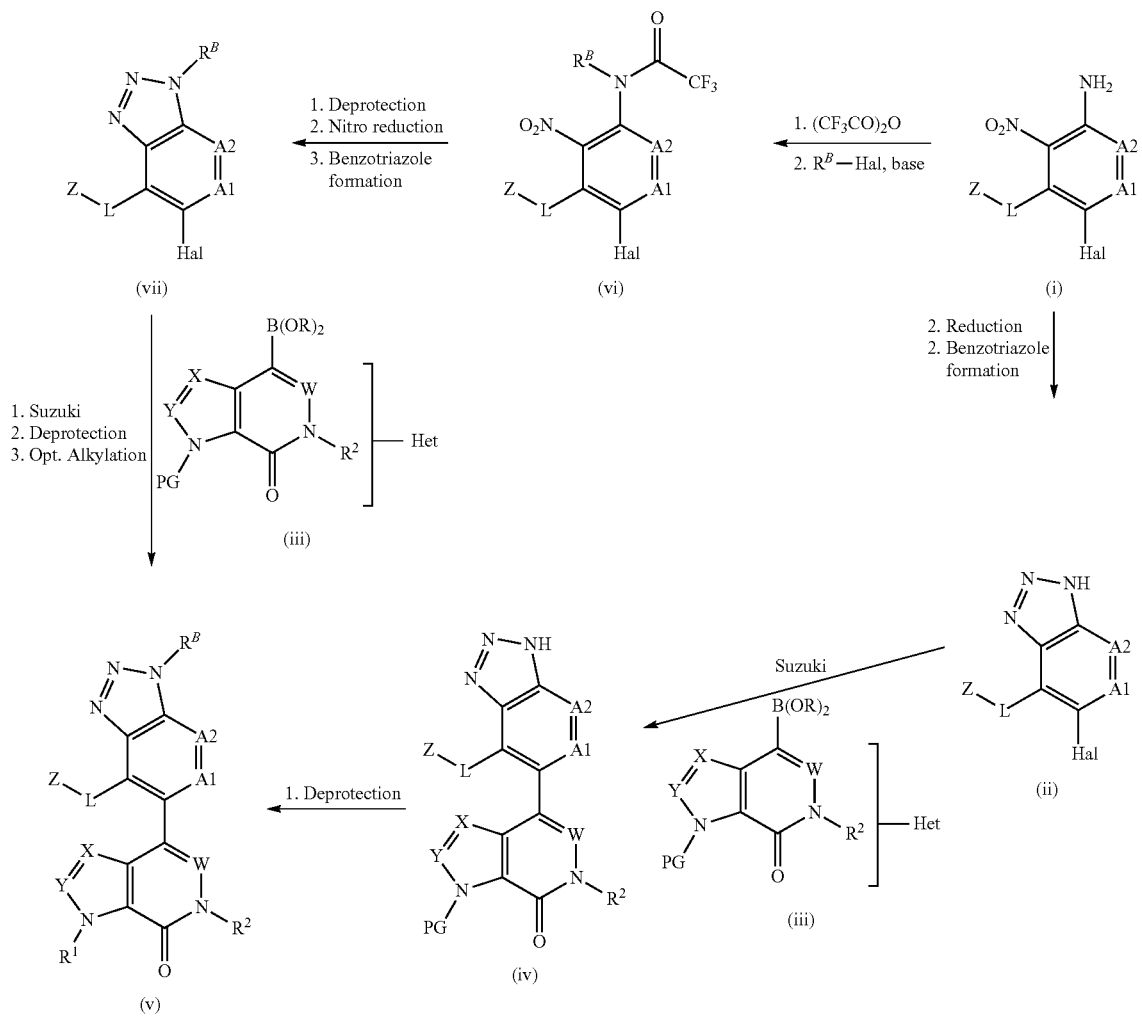

Methods of Use

Compounds of the invention are BET protein inhibitors and, thus, are useful in treating diseases and disorders associated with activity of BET proteins. For the uses described herein, any of the compounds of the invention, including any of the embodiments thereof, may be used.

The compounds of the invention can inhibit one or more of BET proteins BRD2, BRD3, BRD4, and BRD-t. In some embodiments, the BET protein is BRD2. In some embodiments, the BET protein is BRD3. In some embodiments, the BET protein is BRD4. In some embodiments, the BET protein is BRD-t. In some embodiments, the compounds of the invention selectively inhibit one or more BET proteins over another. "Selective" means that the compound binds to or inhibits a BET protein with greater affinity or potency, respectively, compared to a reference, such as another BET protein. For example, the compounds can be selective for BRD2 over BRD3, BRD4 and BRD-t, selective for BRD3 over BRD2, BRD4 and BRD-t, selective for BRD4 over BRD2, BRD3 and BRD-t, or selective for BRD-t over BRD2, BRD3 and BRD4. In some embodiments, the compounds inhibit two or more of the BET proteins, or all of the BET proteins. In general, selectivity can be at least about 5-fold, at least about 10-fold, at least about 20-fold, at least about 50-fold, at least about 100-fold, at least about 200-fold, at least about 500-fold or at least about 1000-fold.

In some embodiments, the present invention is directed to a method of inhibiting BRD2 comprising contacting a compound of the invention with BRD2. In some embodiments, the present invention is directed to a method of inhibiting BRD3 comprising contacting a compound of the invention with BRD3. In some embodiments, the present invention is directed to a method of inhibiting BRD4 comprising contacting a compound of the invention with BRD4. In some embodiments, the present invention is directed to a method of inhibiting BRD-t comprising contacting a compound of the invention with BRD-t.

The compounds of the invention are therefore useful for treating BET protein mediated disorders. The term "BET-mediated" refers to any disease or condition in which one or more of the BET proteins, such as BRD2, BRD3, BRD4 and/or BRD-t, or a mutant thereof, plays a role, or where the disease or condition is associated with expression or activity of one or more of the BET proteins. The compounds of the invention can therefore be used to treat or lessen the severity of diseases and conditions where BET proteins, such as BRD2, BRD3, BRD4, and/or BRD-t, or a mutant thereof, are known to play a role.

Diseases and conditions treatable using the compounds of the invention include, but are not limited to, cancer and other proliferative disorders, autoimmune disease, chronic inflammatory diseases, sepsis, and acute inflammatory diseases, sepsis, and viral infection. The diseases can be treated by administering to an individual (e.g., a patient) in need of the treatment a therapeutically effective amount or dose of a compound of the invention, or any of the embodiments thereof, or a pharmaceutical composition thereof. The present disclosure also provides a compound of the invention, or any of the embodiments thereof, or a pharmaceutical composition thereof, for use in treating a BET-mediated disease or disorder. Also provided is the use of a compound of the invention, or any of the embodiments thereof, or a pharmaceutical composition thereof, in the manufacture of a medicament for treating a BET-mediated disease or disorder.

Diseases that can be treated with the compounds of the invention include cancers. The cancers can include, but are not limited to, adrenal cancer, acinic cell carcinoma, acoustic neuroma, acral lentiginous melanoma, acrospiroma, acute eosinophilic leukemia, acute erythroid leukemia, acute lymphoblastic leukemia, acute megakaryoblastic leukemia, acute monocytic leukemia, acute promyelocytic leukemia, adenocarcinoma, adenoid cystic carcinoma, adenoma, adenomatoid odontogenic tumor, adenosquamous carcinoma, adipose tissue neoplasm, adrenocortical carcinoma, adult T-cell leukemia/lymphoma, aggressive NK-cell leukemia, AIDS-related lymphoma, alveolar rhabdomyosarcoma, alveolar soft part sarcoma, ameloblastic fibroma, anaplastic large cell lymphoma, anaplastic thyroid cancer, angioimmunoblastic T-cell lymphoma, angiomyolipoma, angiosarcoma, astrocytoma, atypical teratoid rhabdoid tumor, B-cell chronic lymphocytic leukemia, B-cell prolymphocytic leukemia, B-cell lymphoma, basal cell carcinoma, biliary tract cancer, bladder cancer, blastoma, bone cancer, Brenner tumor, Brown tumor, Burkitt's lymphoma, breast cancer, brain cancer, carcinoma, carcinoma in situ, carcinosarcoma, cartilage tumor, cementoma, myeloid sarcoma, chondroma, chordoma, choriocarcinoma, choroid plexus papilloma, clear-cell sarcoma of the kidney, craniopharyngioma, cutaneous T-cell lymphoma, cervical cancer, colorectal cancer, Degos disease, desmoplastic small round cell tumor, diffuse large B-cell lymphoma, dysembryoplastic neuroepithelial tumor, dysgerminoma, embryonal carcinoma, endocrine gland neoplasm, endodermal sinus tumor, enteropathy-associated T-cell lymphoma, esophageal cancer, fetus in fetu, fibroma, fibrosarcoma, follicular lymphoma, follicular thyroid cancer, ganglioneuroma, gastrointestinal cancer, germ cell tumor, gestational choriocarcinoma, giant cell fibroblastoma, giant cell tumor of the bone, glial tumor, glioblastoma multiforme, glioma, gliomatosis cerebri, glucagonoma, gonadoblastoma, granulosa cell tumor, gynandroblastoma, gallbladder cancer, gastric cancer, hairy cell leukemia, hemangioblastoma, head and neck cancer, hemangiopericytoma, hematological malignancy, hepatoblastoma, hepatosplenic T-cell lymphoma, Hodgkin's lymphoma, non-Hodgkin's lymphoma, invasive lobular carcinoma, intestinal cancer, kidney cancer, laryngeal cancer, lentigo maligna, lethal midline carcinoma, leukemia, leydig cell tumor, liposarcoma, lung cancer, lymphangioma, lymphangiosarcoma, lymphoepithelioma, lymphoma, acute lymphocytic leukemia, acute myelogenous leukemia, chronic lymphocytic leukemia, liver cancer, small cell lung cancer, non-small cell lung cancer, MALT lymphoma, malignant fibrous histiocytoma, malignant peripheral nerve sheath tumor, malignant triton tumor, mantle cell lymphoma, marginal zone B-cell lymphoma, mast cell leukemia, mediastinal germ cell tumor, medullary carcinoma of the breast, medullary thyroid cancer, medulloblastoma, melanoma, meningioma, merkel cell cancer, mesothelioma, metastatic urothelial carcinoma, mixed Mullerian tumor, mucinous tumor, multiple myeloma, muscle tissue neoplasm, mycosis fungoides, myxoid liposarcoma, myxoma, myxosarcoma, nasopharyngeal carcinoma, neurinoma, neuroblastoma, neurofibroma, neuroma, nodular melanoma, ocular cancer, oligoastrocytoma, oligodendroglioma, oncocytoma, optic nerve sheath meningioma, optic nerve tumor, oral cancer, osteosarcoma, ovarian cancer, Pancoast tumor, papillary thyroid cancer, paraganglioma, pinealoblastoma, pineocytoma, pituicytoma, pituitary adenoma, pituitary tumor, plasmacytoma, polyembryoma, precursor T-lymphoblastic lymphoma, primary central nervous system lymphoma, primary effusion lymphoma, primary peritoneal cancer, prostate cancer, pancreatic cancer, pharyngeal cancer, pseudomyxoma peritonei, renal cell carcinoma, renal medullary carcinoma, retinoblastoma, rhabdomyoma, rhabdomyosarcoma, Richter's transformation, rectal cancer, sarcoma, Schwannomatosis, seminoma, Sertoli cell tumor, sex cord-gonadal stromal tumor, signet ring cell carcinoma, skin cancer, small blue round cell tumors, small cell carcinoma, soft tissue sarcoma, somatostatinoma, soot wart, spinal tumor, splenic marginal zone lymphoma, squamous cell carcinoma, synovial sarcoma, Sezary's disease, small intestine cancer, squamous carcinoma, stomach cancer, T-cell lymphoma, testicular cancer, thecoma, thyroid cancer, transitional cell carcinoma, throat cancer, urachal cancer, urogenital cancer, urothelial carcinoma, uveal melanoma, uterine cancer, verrucous carcinoma, visual pathway glioma, vulvar cancer, vaginal cancer, Waldenstrom's macroglobulinemia, Warthin's tumor, and Wilms' tumor. In some embodiments, the cancer can be adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

The diseases treatable using the compounds of the invention also include MYC dependent cancers wherein the cancer is associated with at least one of myc RNA expression or MYC protein expression. A patient can be identified for such treatment by determining myc RNA expression or MYC protein expression in the cancerous tissue or cells.

Diseases that can be treated with compounds of the invention also include non-cancerous proliferative disorders. Examples of proliferative disorders that can be treated include, but are not limited to, benign soft tissue tumors, bone tumors, brain and spinal tumors, eyelid and orbital tumors, granuloma, lipoma, meningioma, multiple endocrine neoplasia, nasal polyps, pituitary tumors, prolactinoma, pseudotumor cerebri, seborrheic keratoses, stomach polyps, thyroid nodules, cystic neoplasms of the pancreas, hemangiomas, vocal cord nodules, polyps, and cysts, Castleman disease, chronic pilonidal disease, dermatofibroma, pilar cyst, pyogenic granuloma, and juvenile polyposis syndrome.

The diseases and conditions that can be treated with the compounds of the invention also include chronic autoimmune and inflammatory conditions. Examples of autoimmune and inflammatory conditions that can be treated include acute, hyperacute or chronic rejection of transplanted organs, acute gout, acute inflammatory responses (such as acute respiratory distress syndrome and ischemia/reperfusion injury), Addison's disease, agammaglobulinemia, allergic rhinitis, allergy, alopecia, Alzheimer's disease, appendicitis, atherosclerosis, asthma, osteoarthritis, juvenile arthritis, psoriatic arthritis, rheumatoid arthriti, satopic dermatitis, autoimmune alopecia, autoimmune hemolytic and thrombocytopenic states, autoimmune hypopituitarism, autoimmune polyglandular disease, Behcet's disease, bullous skin diseases, cholecystitis, chronic idiopathic thrombocytopenic purpura, chronic obstructive pulmonary disease (COPD), cirrhosis, degenerative joint disease, depression, dermatitis, dermatomyositis, eczema, enteritis, encephalitis, gastritis glomerulonephritis, giant cell arteritis, Goodpasture's syndrome, Guillain-Barre syndrome, gingivitis, Graves' disease, Hashimoto's thyroiditis, hepatitis, hypophysitis, inflammatory bowel disease (Crohn's disease and ulcerative colitis), inflammatory pelvic disease, irritable bowel syndrome, Kawasaki disease, LPS-induced endotoxic shock, meningitis, multiple sclerosis, myocarditis, myasthenia gravis, mycosis fungoides, myositis, nephritis, osteomyelitis, pancreatitis, Parkinson's disease, pericarditis, pernicious anemia, pneumonitis, primary biliary sclerosing cholangitis, polyarteritis nodosa, psoriasis, retinitis, scleritis, scleracierma, scleroderma, sinusitis, Sjogren's disease, sepsis, septic shock, sunburn, systemic lupus erythematosus, tissue graft rejection, thyroiditis, type I diabetes, Takayasu's arteritis, urethritis, uveitis, vasculitis, vasculitis including giant cell arteritis, vasculitis with organ involvement such as glomerulonephritis, vitiligo, Waldenstrom macroglobulinemia and Wegener's granulomatosis.

The diseases and conditions that can be treated with the compounds of the invention also include diseases and conditions which involve inflammatory responses to infections with bacteria, viruses, fungi, parasites or their toxins, such as sepsis, sepsis syndrome, septic shock, endotoxaemia, systemic inflammatory response syndrome (SIRS), multi-organ dysfunction syndrome, toxic shock syndrome, acute lung injury, ARDS (adult respiratory distress syndrome), acute renal failure, fulminant hepatitis, burns, acute pancreatitis, post-surgical syndromes, sarcoidosis, Herxheimer reactions, encephalitis, myelitis, meningitis, malaria, SIRS associated with viral infections such as influenza, herpes zoster, herpes simplex and coronavirus.

Other diseases that can be treated with the compounds of the invention include viral infections. Examples of viral infections that can be treated include Epstein-Barr virus, hepatitis B virus, hepatitis C virus, herpes virus, human immunodeficiency virus, human papilloma virus, adenovirus, poxvirus and other episome-based DNA viruses. The compounds can therefore be used to treat disease and conditions such as herpes simplex infections and reactivations, cold sores, herpes zoster infections and reactivations, chickenpox, shingles, human papilloma virus, cervical neoplasia, adenovirus infections, including acute respiratory disease, and poxvirus infections such as cowpox and smallpox and African swine fever virus. In one particular embodiment, the compounds of the invention are indicated for the treatment of human papilloma virus infections of skin or cervical epithelia.

The diseases and conditions that can be treated with the compounds of the invention also include conditions that are associated with ischaemia-reperfusion injury. Examples of such conditions include, but are not limited to conditions such as myocardial infarction, cerebrovascular ischaemia (stroke), acute coronary syndromes, renal reperfusion injury, organ transplantation, coronary artery bypass grafting, cardio-pulmonary bypass procedures and pulmonary, renal, hepatic, gastro-intestinal or peripheral limb embolism.

The compounds of the invention are also useful in the treatment of disorders of lipid metabolism via the regulation of APO-A1 such as hypercholesterolemia, atherosclerosis and Alzheimer's disease.

The compounds of the invention are also useful in the treatment of fibrotic conditions such as idiopathic pulmonary fibrosis, renal fibrosis, post-operative stricture, keloid formation, scleroderma and cardiac fibrosis.

The compounds of the invention can also be used to treat ophthamological indications such as dry eye.

The compounds of the invention can also be used to treat heart disease such as heart failure.

As used herein, the term "contacting" refers to the bringing together of indicated moieties in an in vitro system or an in vivo system. For example, "contacting" a BET protein with a compound of the invention includes the administration of a compound of the present invention to an individual or patient, such as a human, having a BET protein, as well as, for example, introducing a compound of the invention into a sample containing a cellular or purified preparation containing the BET protein.

As used herein, the term "individual" or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent that elicits the biological or medicinal response that is being sought in a tissue, system, animal, individual or human by a researcher, veterinarian, medical doctor or other clinician.

As used herein, the term "treating" or "treatment" refers to inhibiting the disease; for example, inhibiting a disease, condition or disorder in an individual who is experiencing or displaying the pathology or symptomatology of the disease, condition or disorder (i.e. arresting further development of the pathology and/or symptomatology) or ameliorating the disease; for example, ameliorating a disease, condition or disorder in an individual who is experiencing or displaying the pathology or symptomatology of the disease, condition or disorder (i.e. reversing the pathology and/or symptomatology) such as decreasing the severity of disease.

As used herein, the term "preventing" or "prevention" refers to preventing the disease; for example, preventing a disease, condition or disorder in an individual who may be predisposed to the disease, condition or disorder but does not yet experience or display the pathology or symptomatology of the disease.

Combination Therapies

The compounds of the invention can be used in combination treatments where the compound of the invention is administered in conjunction with other treatments such as the administration of one or more additional therapeutic agents. The additional therapeutic agents are typically those which are normally used to treat the particular condition to be treated. The additional therapeutic agents can include, e.g., chemotherapeutics, anti-inflammatory agents, steroids, immunosuppressants, as well as Bcr-Abl, Flt-3, RAF, FAK, and JAK kinase inhibitors for treatment of BET protein-associated diseases, disorders or conditions. The one or more additional pharmaceutical agents can be administered to a patient simultaneously or sequentially.

In some embodiments, the compounds of the invention can be used in combination with a therapeutic agent that targets an epigenetic regulator. Examples of epigenetic regulators include the histone lysine methyltransferases, histone arginine methyl transferases, histone demethylases, histone deacetylases, histone acetylases, and DNA methyltransferases. Histone deacetylase inhibitors include, e.g., vorinostat.

For treating cancer and other proliferative diseases, the compounds of the invention can be used in combination with chemotherapeutic agents, or other anti-proliferative agents. The compounds of the invention can also be used in combination with medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

For treating cancer and other proliferative diseases, the compounds of the invention can be used in combination with ruxolitinib.

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

For treating autoimmune or inflammatory conditions, the compound of the invention can be administered in combination with one or more additional agents selected from Dehydrex™ (Holles Labs), Civamide (Opko), sodium hyaluronate (Vismed, Lantibio/TRB Chemedia), cyclosporine (ST-603, Sirion Therapeutics), ARG101(T) (testosterone, Argentis), AGR1012(P) (Argentis), ecabet sodium (Senju-Ista), gefarnate (Santen), 15-(s)-hydroxyeicosatetraenoic acid (15(S)-HETE), cevilemine, doxycycline (ALTY-0501, Alacrity), minocycline, iDestrin™ (NP50301, Nascent Pharmaceuticals), cyclosporine A (Nova22007, Novagali), oxytetracycline (Duramycin, MOLI1901, Lantibio), CF101 (2S,3S,4R,5R)-3,4-dihydroxy-5-[6-[(3-iodophenyl)methylamino]purin-9-yl]-N-methyl-oxolane-2-carbamyl, Can-Fite Biopharma), voclosporin (LX212 or LX214, Lux Biosciences), ARG103 (Agentis), RX-10045 (synthetic resolvin analog, Resolvyx), DYN15 (Dyanmis Therapeutics), rivoglitazone (DE011, Daiichi Sanko), TB4 (RegeneRx), OPH-01 (Ophtalmis Monaco), PCS101 (Pericor Science), REV1-31 (Evolutec), Lacritin (Senju), rebamipide (Otsuka-Novartis), OT-551 (Othera), PAI-2 (University of Pennsylvania and Temple University), pilocarpine, tacrolimus, pimecrolimus (AMS981, Novartis), loteprednol etabonate, rituximab, diquafosol tetrasodium (INS365, Inspire), KLS-0611 (Kissei Pharmaceuticals), dehydroepiandrosterone, anakinra, efalizumab, mycophenolate sodium, etanercept (Embrel®), hydroxychloroquine, NGX267 (TorreyPines Therapeutics), or thalidomide.

In some embodiments, the compound of the invention can be administered in combination with one or more agents selected from an antibiotic, antiviral, antifungal, anesthetic, anti-inflammatory agents including steroidal and non-steroidal anti-inflammatories, and anti-allergic agents. Examples of suitable medicaments include aminoglycosides such as amikacin, gentamycin, tobramycin, streptomycin, netilmycin, and kanamycin; fluoroquinolones such as ciprofloxacin, norfloxacin, ofloxacin, trovafloxacin, lomefloxacin, levofloxacin, and enoxacin; naphthyridine; sulfonamides; polymyxin; chloramphenicol; neomycin; paromomycin; colistimethate; bacitracin; vancomycin; tetracyclines; rifampin and its derivatives ("rifampins"); cycloserine; beta-lactams; cephalosporins; amphotericins; fluconazole; flucytosine; natamycin; miconazole; ketoconazole; corticosteroids; diclofenac; flurbiprofen; ketorolac; suprofen; cromolyn; lodoxamide; levocabastin; naphazoline; antazoline; pheniramine; or azalide antibiotic.

Other examples of agents, one or more of which a provided compound may also be combined with include: a treatment for Alzheimer's Disease such as donepezil and rivastigmine; a treatment for Parkinson's Disease such as L-DOPA/carbidopa, entacapone, ropinirole, pramipexole, bromocriptine, pergolide, trihexyphenidyl, and amantadine; an agent for treating multiple sclerosis (MS) such as beta interferon (e.g., Avonex® and Rebif®), glatiramer acetate, and mitoxantrone; a treatment for asthma such as albuterol and montelukast; an agent for treating schizophrenia such as zyprexa, risperdal, seroquel, and haloperidol; an anti-inflammatory agent such as a corticosteroid, such as dexamethasone or prednisone, a TNF blocker, IL-1 RA, azathioprine, cyclophosphamide, and sulfasalazine; an immunomodulatory agent, including immunosuppressive agents, such as cyclosporin, tacrolimus, rapamycin, mycophenolate mofetil, an interferon, a corticosteroid, cyclophosphamide, azathioprine, and sulfasalazine; a neurotrophic factor such as an acetylcholinesterase inhibitor, an MAO inhibitor, an interferon, an anti-convulsant, an ion channel blocker, riluzole, or an anti-Parkinson's agent; an agent for treating cardiovascular disease such as a beta-blocker, an ACE inhibitor, a diuretic, a nitrate, a calcium channel blocker, or a statin; an agent for treating liver disease such as a corticosteroid, cholestyramine, an interferon, and an anti-viral agent; an agent for treating blood disorders such as a corticosteroid, an anti-leukemic agent, or a growth factor; or an agent for treating immunodeficiency disorders such as gamma globulin.

Formulation, Dosage Forms and Administration

When employed as pharmaceuticals, the compounds of the invention can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the invention or a pharmaceutically acceptable salt thereof, in combination with one or more pharmaceutically acceptable carriers (excipients). In some embodiments, the composition is suitable for topical administration. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art, e.g., see International App. No. WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions can be formulated in a unit dosage form, each dosage containing from about 5 to about 1,000 mg (1 g), more usually about 100 mg to about 500 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, for example, about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders.

The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, for example, liquid paraffin, polyoxyethylene alkyl ether, propylene glycol, white vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, for example, glycerol, hydroxyethyl cellulose, and the like. In some embodiments, topical formulations contain at least about 0.1, at least about 0.25, at least about 0.5, at least about 1, at least about 2, or at least about 5 wt % of the compound of the invention. The topical formulations can be suitably packaged in tubes of, for example, 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration, and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of a compound of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µs/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

The compositions of the invention can further include one or more additional pharmaceutical agents such as a chemotherapeutic, steroid, anti-inflammatory compound, or immunosuppressant, examples of which are listed hereinabove.

The compounds of the invention can be provided with or used in combination with a companion diagnostic. As used herein, the term "companion diagnostic" refers to a diagnostic device useful for determining the safe and effective use of a therapeutic agent. For example, a companion diagnostic may be used to customize dosage of a therapeutic agent for a given subject, identify appropriate subpopulations for treatment, or identify populations who should not receive a particular treatment because of an increased risk of a serious side effect.

In some embodiments, the companion diagnostic is used to monitor treatment response in a patient. In some embodiments, the companion diagnostic is used to identify a subject that is likely to benefit from a given compound or therapeutic agent. In some embodiments, the companion diagnostic is used to identify a subject having an increased risk of adverse side effects from administration of a therapeutic agent, compared to a reference standard. In some embodiments, the companion diagnostic is an in-vitro diagnostic or imaging tool selected from the list of FDA cleared or approved companion diagnostic devices. In some embodiments, the companion diagnostic is selected from the list of tests that have been cleared or approved by the Center for Devices and Radiological Health.

Labeled Compounds and Assay Methods

Another aspect of the present invention relates to labeled compounds of the invention (radio-labeled, fluorescent-labeled, etc.) that would be useful not only in imaging techniques but also in assays, both in vitro and in vivo, for localizing and quantitating BET proteins in tissue samples, including human, and for identifying BET protein ligands by inhibition binding of a labeled compound. Accordingly, the present invention includes BET protein assays that contain such labeled compounds.

The present invention further includes isotopically-labeled compounds of the invention. An "isotopically" or "radio-labeled" compound is a compound of the invention where one or more atoms are replaced or substituted by an atom having an atomic mass or mass number different from the atomic mass or mass number typically found in nature (i.e., naturally occurring). Suitable radionuclides that may be incorporated in compounds of the present invention include but are not limited to $^{3}$H (also written as T for tritium) $^{11}$C, $^{13}$C, $^{14}$C, $^{13}$N, $^{15}$N, $^{15}$O, $^{17}$O, $^{18}$O, $^{18}$F, $^{35}$S, $^{36}$Cl, $^{82}$Br, $^{75}$Br, $^{76}$Br, $^{77}$Br, $^{123}$I, $^{124}$I, $^{125}$I and $^{131}$I. The radionuclide that is incorporated in the instant radio-labeled compounds will depend on the specific application of that radio-labeled compound. For example, for in vitro BET protein labeling and competition assays, compounds that incorporate $^{3}$H, $^{14}$C, $^{125}$I, $^{131}$I, or $^{35}$S will generally be most useful. For radio-imaging applications $^{11}$C, $^{18}$F, $^{125}$I, $^{123}$I, $^{124}$I, $^{131}$I, $^{75}$Br, $^{76}$Br or $^{77}$Br will generally be most useful.

It is to be understood that a "radio-labeled" or "labeled compound" is a compound that has incorporated at least one radionuclide. In some embodiments the radionuclide is selected from the group consisting of $^{3}H$, $^{14}C$, $^{125}I$, $^{35}S$ and $^{82}Br$. In some embodiments, the compound incorporates 1, 2, or 3 deuterium atoms.

The present invention can further include synthetic methods for incorporating radio-isotopes into compounds of the invention. Synthetic methods for incorporating radio-isotopes into organic compounds are well known in the art, and an ordinary skill in the art will readily recognize the methods applicable for the compounds of invention.

A labeled compound of the invention can be used in a screening assay to identify/evaluate compounds. For example, a newly synthesized or identified compound (i.e., test compound) which is labeled can be evaluated for its ability to bind a BET protein by monitoring its concentration variation when contacting with the BET protein, through tracking of the labeling. For example, a test compound (labeled) can be evaluated for its ability to reduce binding of another compound which is known to bind to a BET protein (i.e., standard compound). Accordingly, the ability of a test compound to compete with the standard compound for binding to the BET protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples were found to be inhibitors of one or more BET proteins as described below.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, J. Combi. Chem., 4, 295 (2002); "Optimizing Preparative LC-MS Configurations and Methods for Parallel Synthesis Purification", K. Blom, R. Sparks, J. Doughty, G. Everlof, T. Hague, A. Combs, J. Combi. Chem., 5, 670 (2003); and "Preparative LC-MS Purification: Improved Compound Specific Method Optimization", K. Blom, B. Glass, R. Sparks, A. Combs, J. Combi. Chem., 6, 874-883 (2004). The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 µm, 2.1×5.0 mm, Buffers: mobile phase A: 0.025% TFA in water and mobile phase B: 0.025% TFA in acetonitrile; gradient 2% to 80% of B in 3 minutes with flow rate 1.5 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 µm, 19×100 mm column, eluting with mobile phase A: 0.1% TFA (trifluoroacetic acid) in water and mobile phase B: 0.1% TFA in acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters) (Bridge $C_{18}$ 5 µm, 19×100 mm column, eluting with mobile phase A: 0.15% $NH_4OH$ in water and mobile phase B: 0.15% $NH_4OH$ in acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute.

Example 1. 4-(2,4-Difluorophenoxy)-5-(6-methyl-7-oxo-6,7-dihydro-1H-pyrrolo[2,3-c]pyridin-4-yl)-1,3-dihydro-2H-benzimidazol-2-one

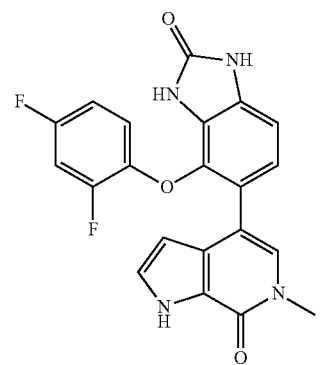 [SMILES: Cn1cc(-c2ccc3[nH]c(=O)[nH]c3c2Oc2ccc(F)cc2F)c2cc[nH]c2c1=O]

Step 1.
4-Bromo-3-(2,4-difluorophenoxy)-2-nitroaniline

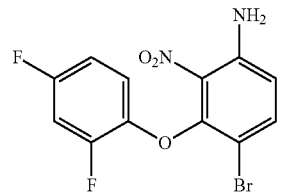 [SMILES: Nc1ccc(Br)c(Oc2ccc(F)cc2F)c1[N+](=O)[O-]]

A solution of 4-bromo-3-fluoro-2-nitroaniline (0.100 g, 0.426 mmol) [Combi-Blocks, AN-2785] and cesium carbonate (0.167 g, 0.511 mmol) in dimethyl sulfoxide (0.47 mL) was treated with 2,4-difluorophenol (0.083 mL, 0.512 mmol) and stirred at 20° C. for 30 min and heated at 110° C. for 30 min. The reaction mixture was diluted with ethyl acetate and water. The organic layer was separated and washed with water and brine, dried with magnesium sulfate, filtered, and concentrated to give a crude residue. Purification by flash column chromatography (100% hexanes to 40% EtOAc/hexanes) gave the desired product (140 mg, 95%) as an orange/brown oil. LCMS calculated for $C_{12}H_8BrF_2N_2O_3$ (M+H)$^+$: m/z=345.0, 347.0; found: 344.9, 346.9.

Step 2. 4-[4-amino-2-(2,4-difluorophenoxy)-3-nitrophenyl]-6-methyl-1-[(4-methylphenyl)sulfonyl]-1,6-dihydro-7H-pyrrolo[2,3-c]pyridin-7-one

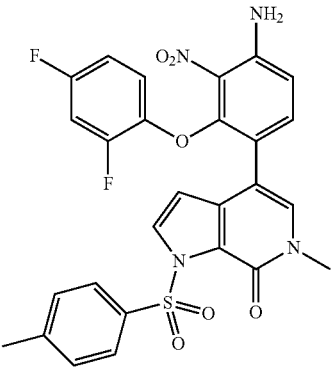

A suspension of 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (0.17 g, 0.40 mmol), 4-bromo-3-(2,4-difluorophenoxy)-2-nitroaniline (0.14 g, 0.40 mmol), potassium phosphate (0.22 g, 1.0 mmol), tris(dibenzylideneacetone)dipalladium (0) (0.01 g, 0.01 mmol), and 1,3,5,7-tetramethyl-8-phenyl-2,4,6-trioxa-8-phosphatricyclo[3.3.1.13,7]decane (0.0139 g, 0.0475 mmol) in 1,4-dioxane (4 mL) and water (0.9 mL) was degassed with nitrogen for 5 min and stirred at 80° C. for 2 h. The reaction mixture was diluted with ethyl acetate and water. The organic layer was separated, washed with brine, dried with magnesium sulfate, filtered, and concentrated to give a crude residue. Purification by flash column chromatography (100% hexanes to 40% EtOAc/hexanes) gave the desired product (108 mg, 23%) as a brown oil. LCMS calculated for $C_{27}H_{21}F_2N_4O_6S$ (M+H)$^+$: m/z=567.1; found: 567.1.

Step 3. 4-[3,4-Diamino-2-(2,4-difluorophenoxy)phenyl]-6-methyl-1-[(4-methylphenyl)sulfonyl]-1,6-dihydro-7H-pyrrolo[2,3-c]pyridin-7-one

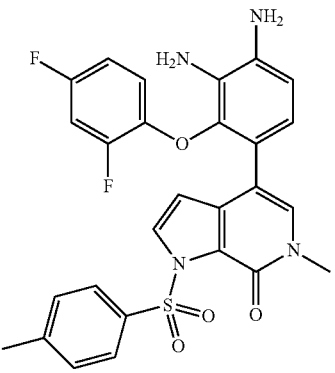

A solution of 4-[4-amino-2-(2,4-difluorophenoxy)-3-nitrophenyl]-6-methyl-1-[(4-methylphenyl)sulfonyl]-1,6-dihydro-7H-pyrrolo[2,3-c]pyridin-7-one (108 mg, 0.191 mmol) in ethyl acetate (0.46 mL) was treated with methanol (0.46 mL) and saturated aqueous ammonium chloride solution (0.166 mL, 2.48 mmol) and cooled to 0° C. The reaction mixture was treated with zinc (99.7 mg, 1.52 mmol) and stirred at room temperature overnight. The reaction mixture was diluted with ethyl acetate, filtered through a pad of Celite, and the solids were washed with ethyl acetate. The filtrate was washed with saturated sodium bicarbonate solution (40 mL). The aqueous layer was separated and re-extracted with ethyl acetate (40 mL). The combined organic layers were washed with brine, dried with sodium sulfate, filtered, and concentrated to give a crude residue. Purification by flash column chromatography (40% EtOAc/hexanes to 100% EtOAc) gave the desired product (100 mg, 93%) as a brown oil. LCMS calculated for $C_{27}H_{23}F_2N_4O_4S$ (M+H)$^+$: m/z=537.1; found: 537.1.

Step 4. 4-(2,4-Difluorophenoxy)-5-(6-methyl-7-oxo-6,7-dihydro-1H-pyrrolo[2,3-c]pyridin-4-yl)-1,3-dihydro-2H-benzimidazol-2-one A solution of 4-[3,4-diamino-2-(2,4-difluorophenoxy)phenyl]-6-methyl-1-[(4-methylphenyl)sulfonyl]-1,6-dihydro-7H-pyrrolo[2,3-c]pyridin-7-one (35.0 mg, 0.065 mmol) in ethyl acetate (0.289 mL) was heated to 50° C., treated with N,N-carbonyldiimidazole (21 mg, 0.13 mmol), and stirred at 50° C. for 1 h. The reaction mixture was concentrated to give the crude intermediate urea which was used immediately without further purification. The intermediate urea was dissolved in ethanol (1.0 mL), treated with 1.0 M sodium hydroxide in water (326 µL, 0.326 mmol), and heated at 60° C. overnight. The reaction mixture was diluted with ethyl acetate and water. The organic layer was separated and washed with brine, dried with sodium sulfate, filtered, and concentrated to give a crude residue. This material was purified via preparative LCMS (XBridge C18 column, eluting with a gradient of methanol/water containing 0.1% trifluoroacetic acid, at flow rate of 60 mL/min) to give the desired product (7.3 mg, 19%) as a white solid. $^1$H NMR (300 MHz, DMSO-d$_6$) δ 11.93 (br s, 1H), 11.01 (s, 1H), 10.91 (s, 1H), 7.23-7.11 (m, 2H), 7.11-7.03 (m, 2H), 6.98-6.92 (m, 1H), 6.76-6.64 (m, 1H), 6.52-6.37 (m, 1H), 6.14-6.05 (m, 1H), 3.43 (s, 3H); LCMS calculated for $C_{21}H_{15}F_2N_4O_3$ (M+H)$^+$: m/z=409.1; found: 409.1.

Example 2. 4-[4-(2,4-Difluorophenoxy)-1H-benzimidazol-5-yl]-6-methyl-1,6-dihydro-7H-pyrrolo[2,3-c]pyridin-7-one trifluoroacetate

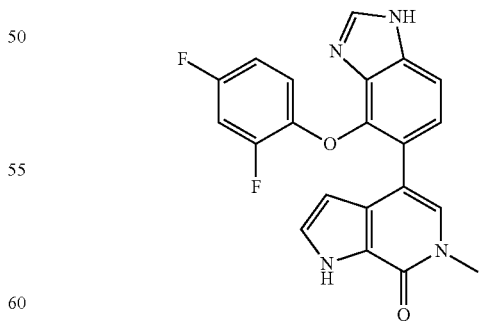

A solution of 4-[3,4-diamino-2-(2,4-difluorophenoxy)phenyl]-6-methyl-1-[(4-methylphenyl)sulfonyl]-1,6-dihydro-7H-pyrrolo[2,3-c]pyridin-7-one (31.0 mg, 0.058 mmol) in tetrahydrofuran (0.50 mL) was treated with ethyl orthoformate (28.8 µL, 0.173 mmol) followed by p-toluenesulfonic acid monohydrate (1.1 mg, 5.8 µmol) and stirred at 50° C. for 1 h. The reaction mixture was concentrated to give the intermediate benzimidazole which was used immediately without further purification. The intermediate benzimidazole was dissolved in ethanol (1.0 mL), treated with 1.0 M sodium hydroxide in water (300 μL, 0.90 mmol), and heated at 60° C. overnight. The reaction mixture was purified via preparative LCMS (XBridge C18 column, eluting with a gradient of methanol/water containing 0.1% trifluoroacetic acid, at flow rate of 60 mL/min) to give the desired product (6 mg, 26%) as a white solid. $^1$H NMR (300 MHz, DMSO-$d_6$) δ 12.01 (s, 1H), 8.72 (br s, 1H), 7.65 (d, J=8.4 Hz, 1H), 7.44 (d, J=8.3 Hz, 1H), 7.32-7.15 (m, 3H), 6.80-6.65 (m, 1H), 6.63-6.48 (m, 1H), 6.20-6.03 (m, 1H), 3.48 (s, 3H); LCMS calculated for $C_{21}H_{15}F_2N_4O_2$ (M+H)$^+$: m/z=393.1; found: 393.1.

Example 3. 4-[4-(2,4-Difluorophenoxy)-2-methyl-1H-benzimidazol-5-yl]-6-methyl-1,6-dihydro-7H-pyrrolo[2,3-c]pyridin-7-one trifluoroacetate

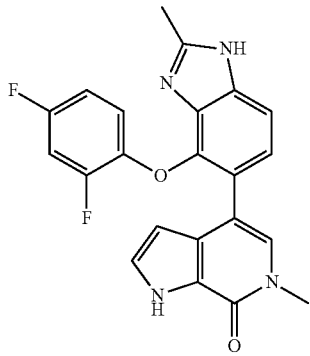

This compound was synthesized according to the procedure of Example 2 using triethyl orthoacetate instead of ethyl orthoformate. $^1$H NMR (300 MHz, DMSO-$d_6$) δ 12.01 (s, 1H), 7.68 (d, J=8.4 Hz, 1H), 7.50 (d, J=8.4 Hz, 1H), 7.31-7.10 (m, 3H), 6.78-6.63 (m, 1H), 6.60-6.43 (m, 1H), 6.14-6.02 (m, 1H), 3.46 (s, 3H), 2.69 (s, 3H); LCMS calculated for $C_{22}H_{17}F_2N_4O_2$ (M+H)$^+$: m/z=407.1; found: 407.1.

Example 4. 4-[4-(2,4-Difluorophenoxy)-1-methyl-1H-benzimidazol-5-yl]-6-methyl-1,6-dihydro-7H-pyrrolo[2,3-c]pyridin-7-one trifluoroacetate

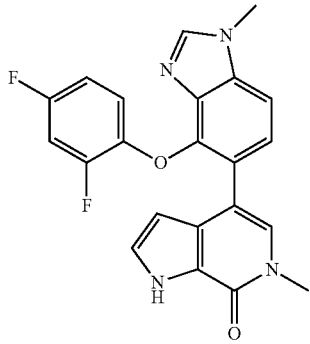

Step 1. N-(3-(2,4-Difluorophenoxy)-4-{6-methyl-1-[(4-methylphenyl)sulfonyl]-7-oxo-6,7-dihydro-1H-pyrrolo[2,3-c]pyridin-4-yl}-2-nitrophenyl)-2,2,2-trifluoroacetamide

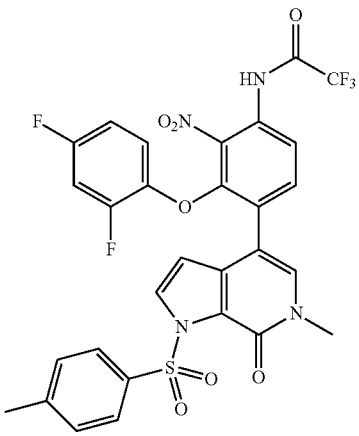 [SMILES: Cc1ccc(S(=O)(=O)n2ccc3c(-c4ccc(NC(=O)C(F)(F)F)c([N+](=O)[O-])c4Oc4ccc(F)cc4F)cn(C)c(=O)c32)cc1]

A solution of 4-[4-amino-2-(2,4-difluorophenoxy)-3-nitrophenyl]-6-methyl-1-[(4-methylphenyl)sulfonyl]-1,6-dihydro-7H-pyrrolo[2,3-c]pyridin-7-one (250 mg, 0.441 mmol) in methylene chloride (2.1 mL) was treated with triethylamine (123 μL, 0.882 mmol), cooled to 0° C., treated with trifluoroacetic anhydride (125 μL, 0.882 mmol) dropwise, and stirred at ambient temperature for 1.5 h. The above reaction mixture was diluted with dichloromethane (50 mL) and brine (50 mL). The aqueous layer was separated and extracted with dichloromethane (2×40 mL). The combined organic layers were washed with brine, dried with sodium sulfate, filtered, and concentrated to give a crude residue. Purification by flash column chromatography (40% EtOAc/hexanes to 80% EtOAc/hexanes) gave the desired product (293 mg, quantitative) as a solid. LCMS calculated for $C_{29}H_{20}F_5N_4O_7S$ (M+H)$^+$: m/z=663.1; found: 663.0.

Step 2. 4-[2-(2,4-Difluorophenoxy)-4-(methylamino)-3-nitrophenyl]-6-methyl-1-[(4-methylphenyl)sulfonyl]-1,6-dihydro-7H-pyrrolo[2,3-c]pyridin-7-one

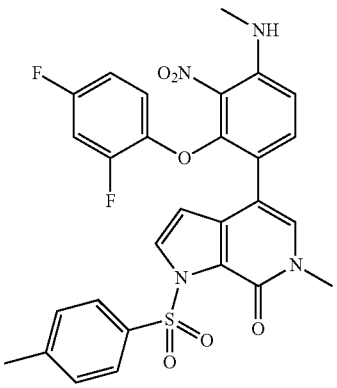

A solution of N-(3-(2,4-difluorophenoxy)-4-{6-methyl-1-[(4-methylphenyl)sulfonyl]-7-oxo-6,7-dihydro-1H-pyrrolo

[2,3-c]pyridin-4-yl}-2-nitrophenyl)-2,2,2-trifluoroacetamide (80.0 mg, 0.121 mmol) in N,N-dimethylformamide (1.4 mL) was treated with cesium carbonate (78.7 mg, 0.241 mmol) followed by methyl iodide (37.6 µL, 0.604 mmol) and stirred at 50° C. for 2 h. The reaction mixture was diluted with ethyl acetate (200 mL), washed with water (3×50 mL) and brine, dried with magnesium sulfate, filtered, and concentrated to give the desired methylated amide that was used immediately without further purification. The intermediate methyl trifluoroacetamide was dissolved in methanol (1.4 mL, 33.7 mmol) and water (0.27 mL), treated with potassium carbonate (83.4 mg, 0.604 mmol), and stirred at 60° C. for 3 h. The reaction mixture was diluted with ethyl acetate (~100 mL), washed with water & brine, dried with magnesium sulfate, filtered, and concentrated to give the desired product (69 mg, 98%) that was used without further purification. LCMS calculated for $C_{28}H_{23}F_2N_4O_6S$ $(M+H)^+$: m/z=581.1; found: 581.1.

Step 3. 4-[3-Amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one

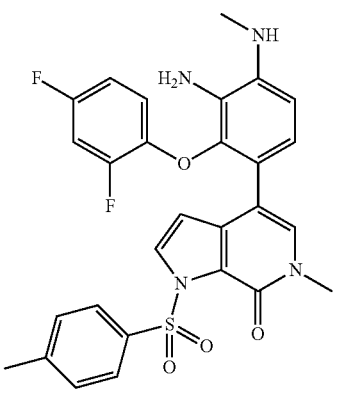

This compound was synthesized according to the procedure of Example 1, Step 3, using 4-[2-(2,4-difluorophenoxy)-4-(methylamino)-3-nitrophenyl]-6-methyl-1-[(4-methylphenyl)sulfonyl]-1,6-dihydro-7H-pyrrolo[2,3-c]pyridin-7-one instead of 4-[4-amino-2-(2,4-difluorophenoxy)-3-nitrophenyl]-6-methyl-1-[(4-methylphenyl)sulfonyl]-1,6-dihydro-7H-pyrrolo[2,3-c]pyridin-7-one. LCMS calculated for $C_{28}H_{25}F_2N_4O_4S$ $(M+H)^+$: m/z=551.2; found: 551.2.

Step 4. 4-[4-(2,4-Difluorophenoxy)-1-methyl-1H-benzimidazol-5-yl]-6-methyl-1,6-dihydro-7H-pyrrolo[2,3-c]pyridin-7-one trifluoroacetate This compound was synthesized according to the procedure of Example 2 using 4-[3-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one instead of 4-[3,4-diamino-2-(2,4-difluorophenoxy)phenyl]-6-methyl-1-[(4-methylphenyl)sulfonyl]-1,6-dihydro-7H-pyrrolo[2,3-c]pyridin-7-one. $^1$H NMR (500 MHz, DMSO-$d_6$) δ 11.98 (s, 1H), 8.50 (br s, 1H), 7.65 (d, J=8.4 Hz, 1H), 7.46 (d, J=8.4 Hz, 1H), 7.31-7.12 (m, 3H), 6.78-6.66 (m, 1H), 6.63-6.53 (m, 1H), 6.10 (dd, J=2.3, 2.3 Hz, 1H), 3.93 (s, 3H), 3.49 (s, 3H); LCMS calculated for $C_{22}H_{17}F_2N_4O_2$ $(M+H)^+$: m/z=407.1; found: 407.1.

Example 5. 4-[4-(2,4-Difluorophenoxy)-1,2-dimethyl-1H-benzimidazol-5-yl]-6-methyl-1,6-dihydro-7H-pyrrolo[2,3-c]pyridin-7-one trifluoroacetate

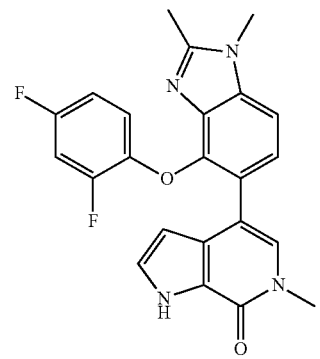 [SMILES: Cc1nc2c(Oc3ccc(F)cc3F)c(-c3cn(C)c(=O)c4[nH]ccc34)ccc2n1C]

This compound was synthesized according to the procedure of Example 2 using 4-[3-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one instead of 4-[3,4-diamino-2-(2,4-difluorophenoxy)phenyl]-6-methyl-1-[(4-methylphenyl)sulfonyl]-1,6-dihydro-7H-pyrrolo[2,3-c]pyridin-7-one and triethyl orthoacetate instead of ethyl orthoformate. $^1$H NMR (500 MHz, DMSO-$d_6$) δ 11.99 (s, 1H), 7.77 (d, J=8.3 Hz, 1H), 7.54 (d, J=8.4 Hz, 1H), 7.27-7.15 (m, 3H), 6.75-6.64 (m, 1H), 6.55-6.47 (m, 1H), 6.07 (dd, J=2.3, 2.3 Hz, 1H), 3.92 (s, 3H), 3.47 (s, 3H), 2.69 (s, 3H); LCMS calculated for $C_{23}H_{19}F_2N_4O_2$ $(M+H)^+$: m/z=421.1; found: 421.1.

Example 6. 4-(2,4-Difluorophenoxy)-1-methyl-5-(6-methyl-7-oxo-6,7-dihydro-1H-pyrrolo[2,3-c]pyridin-4-yl)-1,3-dihydro-2H-benzimidazol-2-one

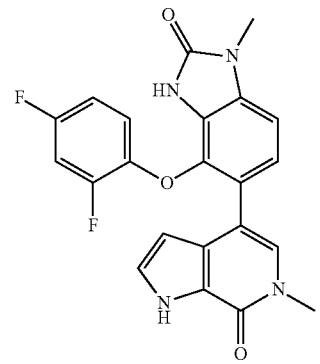 [SMILES: Cn1cc(-c2ccc3c([nH]c(=O)n3C)c2Oc2ccc(F)cc2F)c2cc[nH]c2c1=O]

Step 1. 4-(2,4-difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one

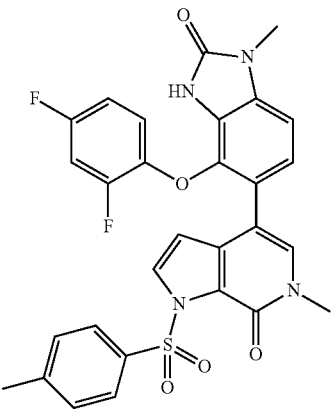

A solution of 4-[3-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one (98.0 mg, 0.178 mmol) in tetrahydrofuran (1.0 mL) was treated with N,N-carbonyldiimidazole (57.7 mg, 0.356 mmol) and stirred at 50° C. for 1 h. The reaction mixture was purified via preparative LCMS (XBridge C18 column, eluting with a gradient of acetonitrile/water 0.1% ammonium hydroxide, at flow rate of 60 mL/min) to give the desired product (77 mg, 75%). LCMS calculated for $C_{29}H_{23}F_2N_4O_5S$ (M+H)$^+$: m/z=577.1; found: 577.1.

Step 2. 4-(2,4-Difluorophenoxy)-1-methyl-5-(6-methyl-7-oxo-6,7-dihydro-1H-pyrrolo[2,3-c]pyridin-4-yl)-1,3-dihydro-2H-benzimidazol-2-one

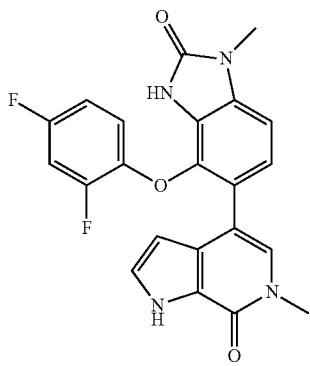

A solution of 4-(2,4-difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one (20.0 mg, 0.0347 mmol) in ethanol (2.0 mL) was treated with 3.0 M Sodium hydroxide in water (116 µL, 0.347 mmol) and stirred at RT overnight. The reaction mixture was purified via preparative LCMS (XBridge C18 column, eluting with a gradient of acetonitrile/water containing 0.1% trifluoroacetic acid, at flow rate of 60 mL/min) to give the desired product (14.5 mg, 99%). $^1$H NMR (400 MHz, DMSO-d$_6$) δ 11.94 (s, 1H), 11.25 (s, 1H), 7.25-7.06 (m, 5H), 6.74-6.62 (m, 1H), 6.51-6.38 (m, 1H), 6.14-6.05 (m, 1H), 3.44 (s, 3H), 3.34 (s, 3H); LCMS calculated for $C_{22}H_{17}F_2N_4O_3$ (M+H)$^+$: m/z=423.1; found: 423.1.

Example 7. 4-(2,4-Difluorophenoxy)-1,3-dimethyl-5-(6-methyl-7-oxo-6,7-dihydro-1H-pyrrolo[2,3-c]pyridin-4-yl)-1,3-dihydro-2H-benzimidazol-2-one

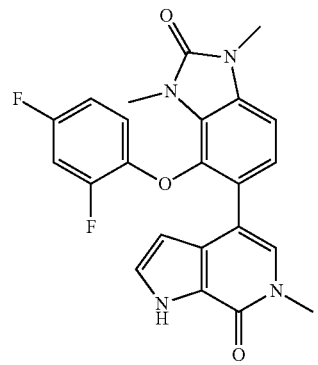 [SMILES: Cn1cc(-c2ccc3c(c2Oc2ccc(F)cc2F)n(C)c(=O)n3C)c2cc[nH]c2c1=O]

A solution of 4-(2,4-difluorophenoxy)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one (30.0 mg, 0.0520 mmol) in N,N-dimethylformamide (0.25 mL) was treated with sodium hydride (4.2 mg, 0.104 mmol) and stirred at RT for 30 min. The reaction mixture was treated with methyl iodide (4.9 µL, 0.0780 mmol) and stirred at RT for 1 h. Analytical LCMS indicated the reaction was complete. The reaction mixture was diluted with ethanol (3.0 mL), treated with 3.0 M sodium hydroxide in water (0.175 mL, 0.525 mmol), and stirred at RT overnight. The reaction was quenched with acetic acid (0.044 mL, 0.780 mmol) and purified via preparative LCMS (XBridge C18 column, eluting with a gradient of acetonitrile/water containing 0.1% trifluoroacetic acid, at flow rate of 60 mL/min) to give the desired product (14.5 mg, 64%). $^1$H NMR (400 MHz, DMSO-d$_6$) δ 11.93 (s, 1H), 7.25-7.10 (m, 5H), 6.74-6.62 (m, 1H), 6.56-6.42 (m, 1H), 6.16-6.05 (m, 1H), 3.44 (s, 3H), 3.39 (s, 3H), 3.32 (s, 3H); LCMS calculated for $C_{23}H_{19}F_2N_4O_3$ (M+H)$^+$: m/z=437.1; found: 437.1.

Example 8. 4-[4-(2,4-Difluorophenoxy)-1H-1,2,3-benzotriazol-5-yl]-6-methyl-1,6-dihydro-7H-pyrrolo[2,3-c]pyridin-7-one

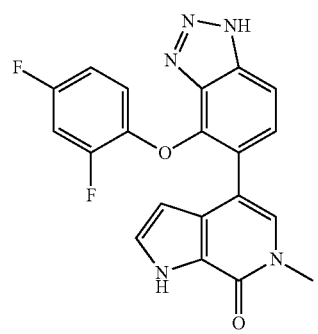 [SMILES: Cn1cc(-c2ccc3[nH]nnc3c2Oc2ccc(F)cc2F)c2cc[nH]c2c1=O]

Step 1. 4-[4-(2,4-Difluorophenoxy)-1H-1,2,3-benzo-triazol-5-yl]-6-methyl-1-[(4-methylphenyl)sulfonyl]-1,6-dihydro-7H-pyrrolo[2,3-c]pyridin-7-one

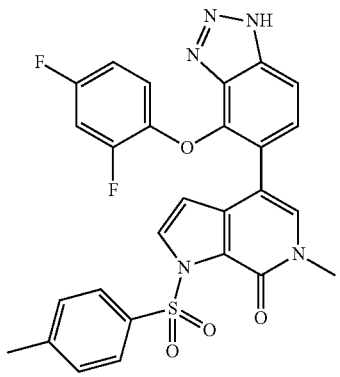

A solution of 4-[3,4-diamino-2-(2,4-difluorophenoxy)phenyl]-6-methyl-1-[(4-methylphenyl)sulfonyl]-1,6-dihydro-7H-pyrrolo[2,3-c]pyridin-7-one (0.040 g, 0.074 mmol) in acetic acid (0.1 mL, 3 mmol) was treated with water (0.37 mL, 21 mmol) followed by sodium nitrite (0.026 g, 0.37 mmol) and stirred at 20° C. for 30 min. The reaction mixture was diluted with ethyl acetate and water. The organic layer was washed with saturated sodium bicarbonate (2×) and brine, dried with magnesium sulfate, filtered, and concentrated to give the desired product (32 mg, 78%) as a crude brown residue that was used immediately without further purification. LCMS calculated for $C_{27}H_{20}F_2N_5O_4S$ $(M+H)^+$: m/z=548.1; found: 548.1.

Step 2. 4-[4-(2,4-Difluorophenoxy)-1H-1,2,3-benzo-triazol-5-yl]-6-methyl-1,6-dihydro-7H-pyrrolo[2,3-c]pyridin-7-one

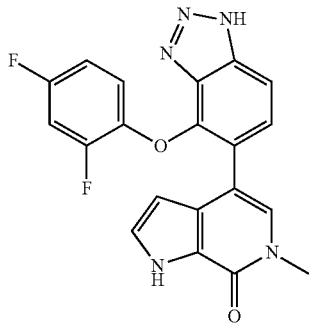

A solution of 4-[4-(2,4-difluorophenoxy)-1H-1,2,3-benzotriazol-5-yl]-6-methyl-1-[(4-methylphenyl)sulfonyl]-1,6-dihydro-7H-pyrrolo[2,3-c]pyridin-7-one (32 mg, 0.058 mmol) in ethanol (3.4 mL) was treated with 3.0 M sodium hydroxide in water (195 μL, 0.584 mmol) and stirred at 20° C. for 15 h. The reaction mixture was purified via preparative LCMS (XBridge C18 column, eluting with a gradient of acetonitrile/water 0.1% ammonium hydroxide, at flow rate of 60 mL/min) to give the desired product (13 mg, 56%). $^1$H NMR (400 MHz, DMSO-$d_6$) δ 12.05 (s, 1H), 7.77 (br s, 1H), 7.53 (d, J=8.5 Hz, 1H), 7.37-7.19 (m, 3H), 6.77 (br s, 2H), 6.23-6.07 (m, 1H), 3.50 (s, 3H); LCMS calculated for $C_{20}H_{14}F_2N_5O_2$ $(M+H)^+$: m/z=394.1; found: 394.0.

Example 9. 4-[4-(2,4-Difluorophenoxy)-1-methyl-1H-1,2,3-benzotriazol-5-yl]-6-methyl-1,6-dihydro-7H-pyrrolo[2,3-c]pyridin-7-one

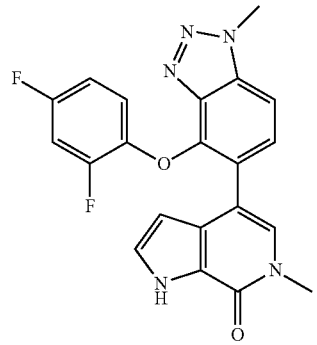 [SMILES: Cn1cc(-c2ccc3c(nnn3C)c2Oc2ccc(F)cc2F)c2cc[nH]c2c1=O]

This compound was synthesized according to the procedure of Example 8 using 4-[3-amino-2-(2,4-difluorophenoxy)-4-(methylamino)phenyl]-6-methyl-1-[(4-methylphenyl)sulfonyl]-1,6-dihydro-7H-pyrrolo[2,3-c]pyridin-7-one as the starting material. $^1$H NMR (400 MHz, DMSO-$d_6$) δ 12.08 (s, 1H), 7.77 (d, J=8.6 Hz, 1H), 7.64 (d, J=8.5 Hz, 1H), 7.37-7.21 (m, 3H), 6.91-6.77 (m, 2H), 6.13 (s, 1H), 4.33 (s, 3H), 3.52 (s, 3H); LCMS calculated for $C_{21}H_{16}F_2N_5O_2$ $(M+H)^+$: m/z=408.1; found: 408.1.

Example 10. 4-[4-(2,4-Difluorophenoxy)-1H-1,2,3-benzotriazol-5-yl]-6-methyl-1,6-dihydro-7H-pyrazolo[3,4-c]pyridin-7-one

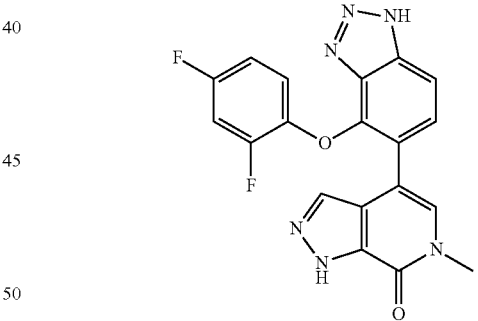

Step 1.
5-Bromo-1,4-dimethyl-3-nitropyridin-2(1H)-one

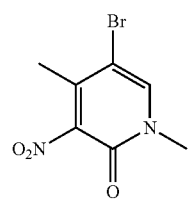

A solution of 5-bromo-4-methyl-3-nitropyridin-2-ol (15.00 g, 64.37 mmol) [Combi-Blocks, AN-1086] in N,N-dimethylformamide (250 mL) was treated with sodium hydride (3.09 g, 77.3 mmol) (60% dispersion on mineral oil) slowly and portionwise, and stirred at RT for 30 min. The reaction mixture was treated with methyl iodide (4.81 mL, 77.2 mmol) dropwise and stirred at RT for 3 h. LCMS indicated a clean peak for methylated product. The reaction mixture was poured over water/ice (~400 mL) and allowed to stir while the ice melted. The aqueous mixture was extracted with ethyl acetate. The organic layer was washed with water (3×) and brine, dried with magnesium sulfate, filtered, and concentrated to give the desired product (14.9 g, 93%) that was used without further purification. LCMS calculated for $C_7H_8BrN_2O_3$ $(M+H)^+$: m/z=247.0, 249.0; found: 247.0, 248.9.

Step 2. 4-Bromo-6-methyl-1,6-dihydro-7H-pyrazolo[3,4-c]pyridin-7-one

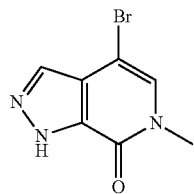

A solution of 3-amino-5-bromo-1,4-dimethylpyridin-2(1H)-one (12.1 g, 55.9 mmol) in toluene (300 mL) was treated with acetic anhydride (15.8 mL, 168 mmol) followed by potassium acetate (6.58 g, 67.1 mmol) and stirred at RT overnight. The reaction mixture was treated with amyl nitrite (11.3 mL, 83.8 mmol) and heated at 80° C. overnight. The reaction mixture was diluted with ethyl acetate, washed with water and brine, dried with magnesium sulfate, filtered, and concentrated to give a mixture of the desired product along with the acetylated desired product. This mixture was diluted with methanol (490 mL) and treated with 1.0 M sodium hydroxide in water (280 mL) and stirred at RT for 1 h. The reaction mixture was diluted with ethyl acetate, washed with water and brine, dried with magnesium sulfate, filtered, and concentrated to give crude product. Purification by flash column chromatography (100% hexanes to 100% EtOAc) gave the desired product (8.4 g, 66%). LCMS calculated for $C_7H_7BrN_3O$ $(M+H)^+$: m/z=228.0, 230.0; found: 227.9, 229.9.

Step 3. 4-Bromo-6-methyl-1-{[(trimethylsilyl)ethoxy]methyl}-1,6-dihydro-7H-pyrazolo[3,4-c]pyridin-7-one and 4-bromo-6-methyl-2-{[2-(trimethylsilyl)ethoxy]methyl}-2,6-dihydro-7H-pyrazolo[3,4-c]pyridin-7-one

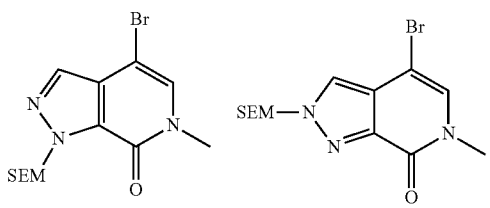 [SMILES: Cn1cc(Br)c2cnn(COCC[Si](C)(C)C)c2c1=O ; Cn1cc(Br)c2cn(COCC[Si](C)(C)C)nc2c1=O]

A solution of 4-bromo-6-methyl-1,6-dihydro-7H-pyrazolo[3,4-c]pyridin-7-one (5.40 g, 23.7 mmol) in N,N-dimethylformamide (170 mL) at 0° C. was treated with sodium hydride (1.42 g, 35.5 mmol) and stirred at 0° C. for 30 min. The reaction mixture was treated with [β-(trimethylsilyl)ethoxy]methyl chloride (7.90 g, 47.4 mmol) and stirred at 0° C. for 1 h. The reaction mixture was poured into ethyl acetate (200 mL) and washed with saturated sodium bicarbonate solution. The aqueous layer was extracted with ethyl acetate (2×100 mL). The combined organic layers were washed with water (3×) and brine, dried with magnesium sulfate, filtered, and concentrated to give the crude product. Purification by flash column chromatography (100% hexanes to 100% EtOAc) gave a major product and a minor product (8.5 g total yield, quantitative) as an ~4:1 mixture of SEM-protected isomers. 41 NMR analysis of the individual products revealed the major isomer was consistent with the SEM group at the 1-position and the minor isomer was consistent with the SEM group at the 2-position. In practice, the isomers were not separated at this step and used as a mixture of isomers in the next step. LCMS calculated for $C_{13}H_{21}BrN_3O_2Si$ $(M+H)^+$: m/z=358.1, 360.1; found: 358.0, 360.0.

Step 4. 6-Methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one and 6-methyl-4-(4,4,5,5-tetramethyl-1,3,2-dioxaborolan-2-yl)-2-{[2-(trimethylsilyl)ethoxy]methyl}-2,6-dihydro-7H-pyrazolo[3,4-c]pyridin-7-one

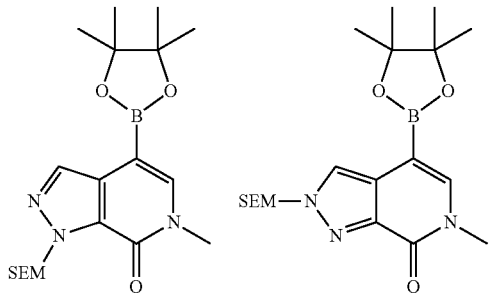 [SMILES: Cn1cc(B2OC(C)(C)C(C)(C)O2)c2cnn(COCC[Si](C)(C)C)c2c1=O ; Cn1cc(B2OC(C)(C)C(C)(C)O2)c2cn(COCC[Si](C)(C)C)nc2c1=O]

A suspension of 4-bromo-6-methyl-1-{[2-(trimethylsilyl)ethoxy]methyl}-1,6-dihydro-7H-pyrazolo[3,4-c]pyridin-7-one and 4-bromo-6-methyl-2-{[2-(trimethylsilyl)ethoxy]methyl}-2,6-dihydro-7H-pyrazolo[3,4-c]pyridin-7-one (8.50 g, 23.7 mmol) (~4:1 mixture of isomers), 4,4,5,5,4',4',5',5'-cetamethyl-[2,2']bi[[1,3,2]dioxaborolanyl] (12.0 g, 47.5 mmol), dicyclohexyl(2',4',6'-triisopropylbiphenyl-2-yl)phosphine (1.23 g, 2.58 mmol), potassium acetate (5.12 g, 52.2 mmol), and tris(dibenzylideneacetone)dipalladium(0) (543 mg, 0.592 mmol) in 1,4-dioxane (120 mL) was degassed with nitrogen for 10 min and stirred at 80° C. for 3 h. The reaction mixture was diluted with ethyl acetate (100 mL) and saturated sodium bicarbonate solution (100 mL), filtered over Celite, and washed with ethyl acetate. The aqueous layer was separated and re-extracted with ethyl acetate (100 mL). The combined organic layers were washed with brine, dried with magnesium sulfate, filtered, and concentrated to give a crude residue. Purification by flash column chromatography (100% hexanes to 60% EtOAc/hexanes) gave the individual isomers of the desired product (major isomer: 5.23 g, 54%; minor isomer: 1.28 g, 13%).

Major isomer (SEM at 1-position): LCMS calculated for C₁₉H₃₃BN₃O₄Si (M+H)⁺: m/z=406.2; found: 406.2; minor isomer (SEM at 2-position): LCMS calculated for C₁₉H₃₃BN₃O₄Si (M+H)⁺: m/z=406.2; found: 406.2.

Step 5. 4-[4-Amino-2-(2,4-difluorophenoxy)-3-nitrophenyl]-6-methyl-2-{[2-(trimethylsilyl)ethoxy]methyl}-2,6-dihydro-7H-pyrazolo[3,4-c]pyridin-7-one

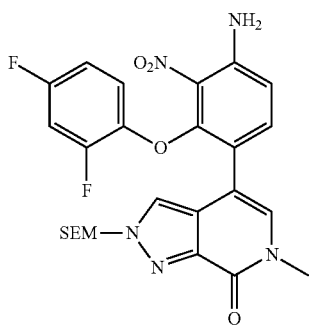 [SMILES: Cn1cc(-c2ccc(N)c([N+](=O)[O-])c2Oc2ccc(F)cc2F)c2cn(COCC[Si](C)(C)C)nc2c1=O]

A solution of 4-(di-tert-butylphosphino)-N,N-dimethylaniline-dichloropalladium (2:1) (22.3 mg, 0.0314 mmol), cesium fluoride (1.11 g, 7.34 mmol), 4-bromo-3-(2,4-difluorophenoxy)-2-nitroaniline (724 mg, 2.10 mmol), and 6-methyl-4-(4,4,5,5-tetramethyl-1,3,2-dioxaborolan-2-yl)-2-{[2-(trimethylsilyl)ethoxy]methyl}-2,6-dihydro-7H-pyrazolo[3,4-c]pyridin-7-one (850 mg, 2.097 mmol) in 1-butanol (9.5 mL) and water (2.2 mL) was degassed with nitrogen for 5 min and heated at 100° C. for 2 h. The reaction mixture was diluted with ethyl acetate and water. The organic layer was separated and washed with brine, dried with magnesium sulfate, filtered, and concentrated to give the crude product. Purification by flash column chromatography (50% EtOAc/hexanes to 100% EtOAc) gave the desired product (0.57 g, 50%). LCMS calculated for C₂₅H₂₈F₂N₅O₅Si (M+H)⁺: m/z=544.2; found: 544.1.

Step 6. 4-[3,4-Diamino-2-(2,4-difluorophenoxy)phenyl]-6-methyl-2-{[2-(trimethylsilyl)ethoxy]methyl}-2,6-dihydro-7H-pyrazolo[3,4-c]pyridin-7-one

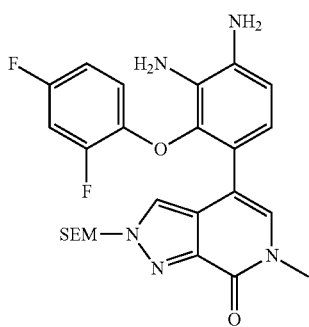

This compound was synthesized according to the procedure of Example 1, Step 3, using 4-[4-amino-2-(2,4-difluorophenoxy)-3-nitrophenyl]-6-methyl-2-{[2-(trimethylsilyl)ethoxy]methyl}-2,6-dihydro-7H-pyrazolo[3,4-c]pyridin-7-one as the starting material. LCMS calculated for C₂₅H₃₀F₂N₅O₃Si (M+H)⁺: m/z=514.2; found: 514.2.

Step 7. 4-[4-(2,4-Difluorophenoxy)-1H-1,2,3-benzotriazol-5-yl]-6-methyl-1,6-dihydro-7H-pyrazolo[3,4-c]pyridin-7-one A solution of 4-[3,4-diamino-2-(2,4-difluorophenoxy)phenyl]-6-methyl-2-{[2-(trimethylsilyl)ethoxy]methyl}-2,6-dihydro-7H-pyrazolo[3,4-c]pyridin-7-one (103 mg, 0.200 mmol) in acetic acid (0.40 mL) was treated with water (1.0 mL) followed by sodium nitrite (69.0 mg, 1.00 mmol) and stirred at 20° C. for 30 min. The reaction mixture was diluted with ethyl acetate and water. The organic layer was separated, washed with saturated sodium bicarbonate (2×) and brine, dried with magnesium sulfate, filtered, and concentrated to give the SEM-protected intermediate which was used without further purification. The crude intermediate was diluted with methylene chloride (4.00 mL) and trifluoroacetic acid (4.00 mL) and stirred at 40° C. for 3 h. The reaction mixture was concentrated, diluted with acetonitrile, adjusted to pH ~7 with 1 M NaOH, and purified via preparative LCMS (XBridge C18 column, eluting with a gradient of acetonitrile/water 0.1% ammonium hydroxide, at flow rate of 60 mL/min) to give the desired product (16 mg, 20%). ¹H NMR (500 MHz, DMSO-d₆) δ 14.05 (br s, 1H), 7.86-7.72 (m, 2H), 7.57 (d, J=8.4 Hz, 1H), 7.35 (s, 1H), 7.31-7.22 (m, 1H), 6.85-6.73 (m, 2H), 3.53 (s, 3H); LCMS calculated for C₁₉H₁₃F₂N₆O₂ (M+H)⁺: m/z=395.1; found: 395.1.

Example 11. 4-(Cyclopropylmethoxy)-5-(6-methyl-7-oxo-6,7-dihydro-1H-pyrrolo[2,3-c]pyridin-4-yl)-1,3-dihydro-2H-benzimidazol-2-one

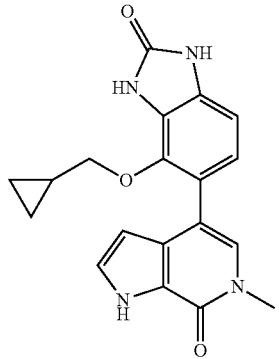 [SMILES: Cn1cc(-c2ccc3[nH]c(=O)[nH]c3c2OCC2CC2)c2cc[nH]c2c1=O]

Step 1.
4-Bromo-3-(cyclopropylmethoxy)-2-nitroaniline

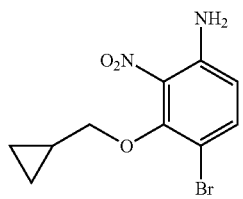 [SMILES: Nc1ccc(Br)c(OCC2CC2)c1[N+](=O)[O-]]

A solution of cyclopropyl carbinol (0.269 mL, 3.40 mmol) in tetrahydrofuran (6.9 mL) at 0° C. was treated with sodium hydride (0.0860 g, 3.40 mmol) and stirred at RT for 30 min. The reaction mixture was cooled to 0° C., treated with 4-bromo-3-fluoro-2-nitroaniline (0.400 g, 1.70 mmol) [Combi-Blocks, AN-2785] and stirred at RT for 15 h. The reaction mixture was cooled to 0° C. and quenched with saturated ammonium chloride solution. The reaction mixture was diluted with ethyl acetate (50 mL) and water (40 mL). The organic layer was washed with brine, dried with sodium sulfate, filtered, and concentrated to give crude oil. Purification by flash column chromatography (100% hexanes to 40% EtOAc/hexanes) gave the desired product (0.365 g, 75%). LCMS calculated for $C_{10}H_{12}BrN_2O_3$ (M+H)$^+$: m/z=287.1; found: 286.8.

Step 2. 4-(4-Amino-2-(cyclopropylmethoxy)-3-nitrophenyl)-6-methyl-1-tosyl-1H-pyrrolo[2,3-c]pyridin-7(6H)-one

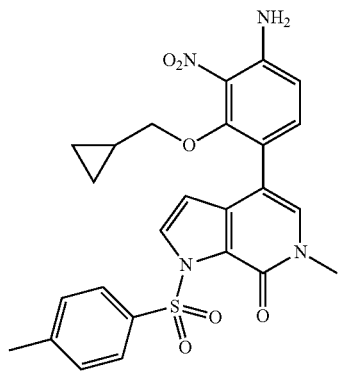

This compound was synthesized according to the procedure of Example 10, Step 5, using 4-bromo-3-(cyclopropylmethoxy)-2-nitroaniline and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{25}H_{25}N_4O_6S$ (M+H)$^+$: m/z=509.1; found: 509.1.

Step 3. 4-[3,4-Diamino-2-(cyclopropylmethoxy) phenyl]-6-methyl-1-[(4-methylphenyl)sulfonyl]-1,6-dihydro-7H-pyrrolo[2,3-c]pyridin-7-one

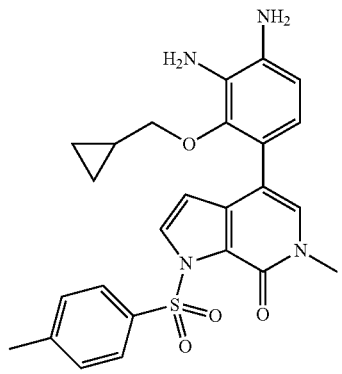

A suspension of 4-[4-amino-2-(cyclopropylmethoxy)-3-nitrophenyl]-6-methyl-1-[(4-methylphenyl)sulfonyl]-1,6-dihydro-7H-pyrrolo[2,3-c]pyridin-7-one (0.119 g, 0.234 mmol) in ethyl acetate (1.2 mL) and methanol (1.2 mL) was treated with saturated aqueous ammonium chloride solution (0.274 mL, 4.09 mmol). The mixture was cooled to 0° C., treated with zinc (0.122 g, 1.87 mmol) in two portions over 5 min, stirred at RT for 30 min and heated at 55° C. for 1 h. The reaction mixture was diluted with dichloromethane, filtered through a Celite pad, and the solids were washed with dichloromethane. The filtrate was concentrated to give a residue. The residue was dissolved in dichloromethane (30 mL), washed with saturated sodium bicarbonate solution (20 mL), dried with sodium sulfate, filtered, and concentrated to give the desired product that was used without further purification. LCMS calculated for $C_{25}H_{27}N_4O_4S$ (M+H)$^+$: m/z=479.2; found: 479.1.

Step 4. 4-(Cyclopropylmethoxy)-5-(6-methyl-7-oxo-6,7-dihydro-1H-pyrrolo[2,3-c]pyridin-4-yl)-1,3-dihydro-2H-benzimidazol-2-one

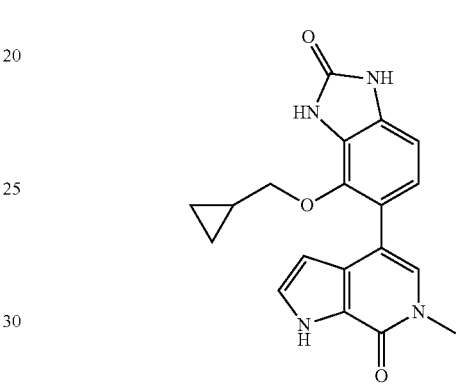

This compound was synthesized according to the procedure of Example 1, Step 4, using 4-[3,4-diamino-2-(cyclopropylmethoxy)phenyl]-6-methyl-1-[(4-methylphenyl)sulfonyl]-1,6-dihydro-7H-pyrrolo[2,3-c]pyridin-7-one as the starting material. $^1$H NMR (400 MHz, DMSO-d$_6$) δ 11.98 (s, 1H), 10.84 (s, 1H), 10.69 (s, 1H), 7.24 (dd, J=2.7, 2.7 Hz, 1H), 7.20 (s, 1H), 6.93 (d, J=8.0 Hz, 1H), 6.74 (d, J=8.0 Hz, 1H), 6.13 (dd, J=2.3, 2.3 Hz, 1H), 3.55 (s, 3H), 3.45 (d, J=7.0 Hz, 2H), 0.98-0.83 (m, 1H), 0.30-0.20 (m, 2H), −0.06-−0.14 (m, 2H); LCMS calculated for $C_{19}H_{19}N_4O_3$ (M+H)$^+$: m/z=351.1; found: 351.1.

Example 12. 4-[4-(Cyclopropylmethoxy)-1H-benzimidazol-5-yl]-6-methyl-1,6-dihydro-7H-pyrrolo[2,3-c]pyridin-7-one

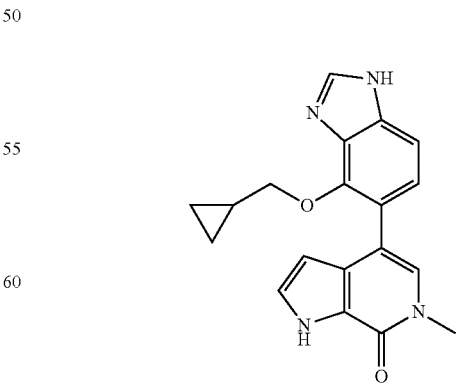

This compound was synthesized according to the procedure of Example 2 using 4-[3,4-diamino-2-(cyclopropylmethoxy)phenyl]-6-methyl-1-[(4-methylphenyl)sulfonyl]-1,6-dihydro-7H-pyrrolo[2,3-c]pyridin-7-one as the starting material. $^1$H NMR (400 MHz, DMSO-d$_6$) δ 12.64 (s, 0.25H), 12.50 (s, 0.75H), 12.01 (s, 0.25H), 11.95 (s, 0.75H), 8.21 (s, 0.25H), 8.16 (s, 0.75H), 7.49-7.38 (m, 0.25H), 7.31-7.08 (m, 3.75H), 6.13 (s, 0.25H), 6.08 (s, 0.75H), 4.43 (d, J=6.8 Hz, 2H), 3.56 (s, 3H), 1.09-0.90 (m, 1H), 0.40-0.32 (m, 1.5H), 0.31-0.22 (m, 0.5H), 0.16-0.08 (m, 1.5H), −0.01−−0.12 (m, 0.5H); LCMS calculated for C$_{19}$H$_{19}$N$_4$O$_2$ (M+H)$^+$: m/z=335.1; found: 335.1.

Example 13. 4-[4-(Cyclopropylmethoxy)-2-methyl-1H-benzimidazol-5-yl]-6-methyl-1,6-dihydro-7H-pyrrolo[2,3-c]pyridin-7-one

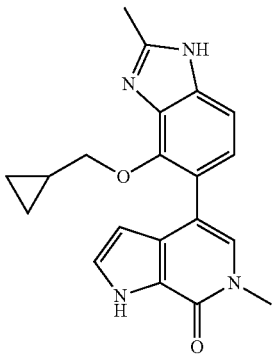 [SMILES: Cc1nc2c(OCC3CC3)c(-c3cn(C)c(=O)c4[nH]ccc34)ccc2[nH]1]

This compound was synthesized according to the procedure of Example 2 using 4-[3,4-diamino-2-(cyclopropylmethoxy)phenyl]-6-methyl-1-[(4-methylphenyl)sulfonyl]-1,6-dihydro-7H-pyrrolo[2,3-c]pyridin-7-one as the starting material and triethyl orthoacetate instead of ethyl orthoformate. $^1$H NMR (300 MHz, DMSO-d$_6$) δ 12.23 (s, 1H), 11.99 (s, 0.3H), 11.93 (s, 0.7H), 7.33-7.19 (m, 1.2H), 7.18-7.00 (m, 2.8H), 6.17-6.10 (m, 0.3H), 6.10-6.02 (m, 0.7H), 4.37 (d, J=6.8 Hz, 2H), 3.62-3.51 (m, 3H), 1.09-0.89 (m, 1H), 0.41-0.25 (m, 2H), 0.17-0.06 (m, 1.4H), −0.01−−0.12 (m, 0.6H); LCMS calculated for C$_{20}$H$_{21}$N$_4$O$_2$ (M+H)$^+$: m/z=349.2; found: 349.1.

Example 14. 4-[4-(2,4-Difluorophenoxy)-1H-benzimidazol-5-yl]-6-methyl-1,6-dihydro-7H-pyrazolo[3,4-c]pyridin-7-one

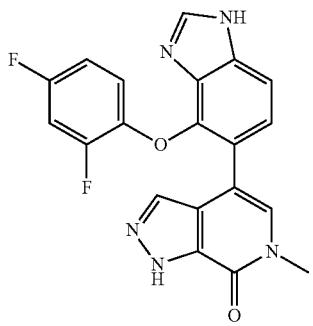 [SMILES: Cn1cc(-c2ccc3[nH]cnc3c2Oc2ccc(F)cc2F)c2cn[nH]c2c1=O]

A solution of 4-[3,4-diamino-2-(2,4-difluorophenoxy)phenyl]-6-methyl-2-{[2-(trimethylsilyl)ethoxy]methyl}-2,6-dihydro-7H-pyrazolo[3,4-c]pyridin-7-one (50.0 mg, 0.0973 mmol) in tetrahydrofuran (0.842 mL) was treated with ethyl orthoformate (48.6 μL, 0.292 mmol) followed by p-toluenesulfonic acid monohydrate (1.85 mg, 0.00973 mmol) and stirred at 50° C. for 1 h. The reaction mixture was diluted with methylene chloride (4.0 mL), treated with trifluoroacetic acid (4.0 mL), and heated at 40° C. for 2 h. The reaction mixture was purified via preparative LCMS (XBridge C18 column, eluting with a gradient of acetonitrile/water 0.1% ammonium hydroxide, at flow rate of 60 mL/min) to give the desired product (23 mg, 60%). $^1$H NMR (500 MHz, DMSO-d$_6$) δ 14.02 (s, 1H), 12.79 (br s, 1H), 8.22 (s, 1H), 7.72 (s, 1H), 7.56 (d, J=8.2 Hz, 1H), 7.35 (d, J=8.3 Hz, 1H), 7.30-7.14 (m, 2H), 6.73 (dd, J=8.0, 8.0 Hz, 1H), 6.66-6.49 (m, 1H), 3.52 (s, 3H); LCMS calculated for C$_{20}$H$_{14}$F$_2$N$_5$O$_2$ (M+H)$^+$: m/z=394.1; found: 394.1.

Example 15. 4-[4-(2,4-Difluorophenoxy)-2-methyl-1H-benzimidazol-5-yl]-6-methyl-1,6-dihydro-7H-pyrazolo[3,4-c]pyridin-7-one

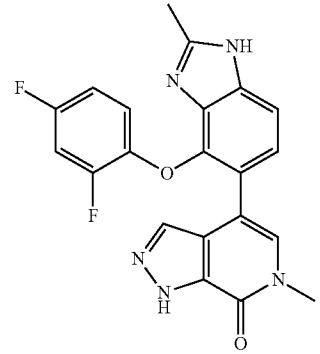 [SMILES: Cc1nc2c(Oc3ccc(F)cc3F)c(-c3cn(C)c(=O)c4[nH]ncc34)ccc2[nH]1]

This compound was synthesized according to the procedure of Example 14 using triethyl orthoacetate instead of ethyl orthoformate. $^1$H NMR (500 MHz, DMSO-d$_6$) δ 14.00 (s, 1H), 12.59 (br s, 1H), 7.69 (s, 1H), 7.46 (d, J=8.2, 8.2 Hz, 1H), 7.31-7.14 (m, 3H), 6.71 (dd, J=8.1, 8.1 Hz, 1H), 6.56-6.40 (m, 1H), 3.50 (s, 3H), 2.46 (s, 3H); LCMS calculated for C$_{11}$H$_{16}$F$_2$N$_5$O$_2$ (M+H)$^+$: m/z=408.1; found: 408.1.

Example 16. 4-[4-(2,4-Difluorophenoxy)-2-oxo-2,3-dihydro-1H-benzimidazol-5-yl]-6-methyl-1,6-dihydro-7H-pyrazolo[3,4-c]pyridin-7-one

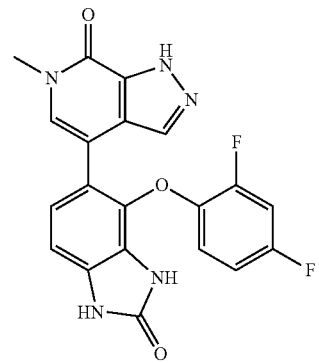 [SMILES: Cn1cc(-c2ccc3[nH]c(=O)[nH]c3c2Oc2ccc(F)cc2F)c2cn[nH]c2c1=O]

Step 1. 4-[4-Amino-2-(2,4-difluorophenoxy)-3-nitrophenyl]-6-methyl-1-{[2-(trimethylsilyl)ethoxy]methyl}-1,6-dihydro-7H-pyrazolo[3,4-c]pyridin-7-one

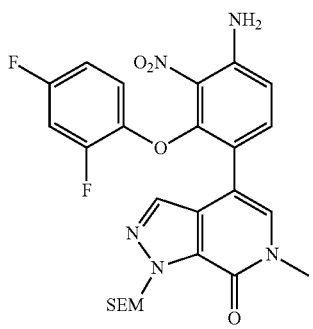

This compound was synthesized according to the procedure of Example 10, Step 5, using 6-methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one instead of 4-bromo-6-methyl-2-{[2-(trimethylsilyl)ethoxy]methyl}-2,6-dihydro-7H-pyrazolo[3,4-c]pyridin-7-one. LCMS calculated for $C_{25}H_{28}F_2N_5O_5Si$ (M+H)+: m/z=544.2; found: 544.1.

Step 2. 4-[3,4-Diamino-2-(2,4-difluorophenoxy)phenyl]-6-methyl-1-{[2-(trimethylsilyl)ethoxy]methyl}-1,6-dihydro-7H-pyrazolo[3,4-c]pyridin-7-one

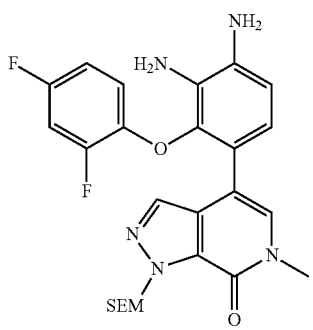 [SMILES: Cn1cc(-c2ccc(N)c([N+](=O)[O-])c2Oc2ccc(F)cc2F)c2cnn(COCC[Si](C)(C)C)c2c1=O]

This compound was synthesized according to the procedure of Example 1, Step 3, using 4-[4-amino-2-(2,4-difluorophenoxy)-3-nitrophenyl]-6-methyl-1-{[2-(trimethylsilyl)ethoxy]methyl}-1,6-dihydro-7H-pyrazolo[3,4-c]pyridin-7-one as the starting material.

Step 3. 4-[4-(2,4-Difluorophenoxy)-2-oxo-2,3-dihydro-1H-benzimidazol-5-yl]-6-methyl-1,6-dihydro-7H-pyrazolo[3,4-c]pyridin-7-one

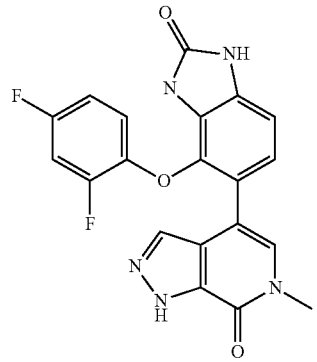 [SMILES: Cn1cc(-c2ccc3[nH]c(=O)[nH]c3c2Oc2ccc(F)cc2F)c2cn[nH]c2c1=O]

A solution of 4-[3,4-diamino-2-(2,4-difluorophenoxy)phenyl]-6-methyl-1-{[2-(trimethylsilyl)ethoxy]methyl}-1,6-dihydro-7H-pyrazolo[3,4-c]pyridin-7-one (80.0 mg, 0.156 mmol) in tetrahydrofuran (3.0 mL) was treated with N,N-carbonyldiimidazole (50.0 mg, 0.31 mmol) and stirred at 50° C. for 1 h. The reaction mixture was diluted with ethyl acetate and water. The organic layer was separated and washed with water and brine, dried with magnesium sulfate, filtered, and concentrated in vacuo to give the SEM-protected intermediate which was used without further purification. The crude intermediate was diluted with methylene chloride (4.0 mL) and trifluoroacetic acid (4.0 mL) and stirred at 40° C. for 2 h. The reaction mixture was concentrated, diluted with acetonitrile, adjusted to pH 7 with 1 M NaOH, and purified via preparative LCMS (XBridge C18 column, eluting with a gradient of acetonitrile/water 0.1% ammonium hydroxide, at flow rate of 60 mL/min) to give the desired product (16 mg, 20%). $^1$H NMR (500 MHz, DMSO-$d_6$) δ 13.96 (br s, 1H), 11.03 (br s, 1H), 10.91 (br s, 1H), 7.68 (br s, 1H), 7.22-7.05 (m, 3H), 6.97 (d, J=8.0 Hz, 1H), 6.70 (dd, J=8.6, 8.6 Hz, 1H), 6.53-6.39 (m, 1H), 3.46 (s, 3H); LCMS calculated for $C_{20}H_{14}F_2N_5O_3$ (M+H)+: m/z=410.1; found: 410.1.

Example 17. 4-[4-(2,4-Difluorophenoxy)-1-(2-morpholin-4-ylethyl)-1H-benzimidazol-5-yl]-6-methyl-1,6-dihydro-7H-pyrazolo[3,4-c]pyridin-7-one

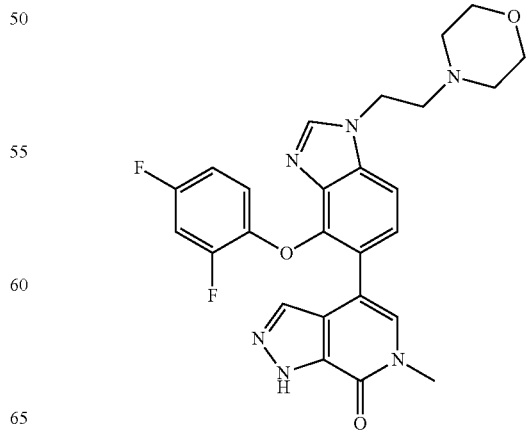

Step 1. N-[3-(2,4-Difluorophenoxy)-4-(6-methyl-7-oxo-1-{[2-(trimethylsilyl)ethoxy]methyl}-6,7-dihydro-1H-pyrazolo[3,4-c]pyridin-4-yl)-2-nitrophenyl]-2,2,2-trifluoroacetamide

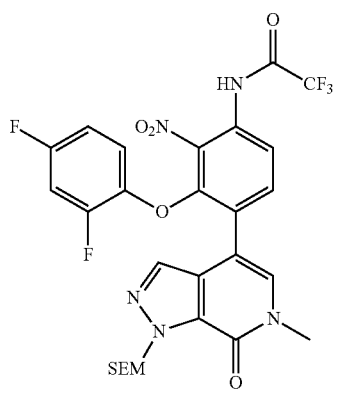 [SMILES: Cn1cc(-c2ccc(NC(=O)C(F)(F)F)c([N+](=O)[O-])c2Oc2ccc(F)cc2F)c2cnn(COCC[Si](C)(C)C)c2c1=O]

This compound was synthesized according to the procedure of Example 4, Step 1, using 4-[4-amino-2-(2,4-difluorophenoxy)-3-nitrophenyl]-6-methyl-1-{[2-(trimethylsilyl)ethoxy]methyl}-1,6-dihydro-7H-pyrazolo[3,4-c]pyridin-7-one as the starting material. LCMS calculated for $C_{27}H_{26}F_5N_5O_6SiNa$ (M+Na)$^+$: m/z=662.2; found: 662.0.

Step 2. 4-{2-(2,4-Difluorophenoxy)-4-[(2-morpholin-4-ylethyl)amino]-3-nitrophenyl}-6-methyl-1-{[2-(trimethylsilyl)ethoxy]methyl}-1,6-dihydro-7H-pyrazolo[3,4-c]pyridin-7-one

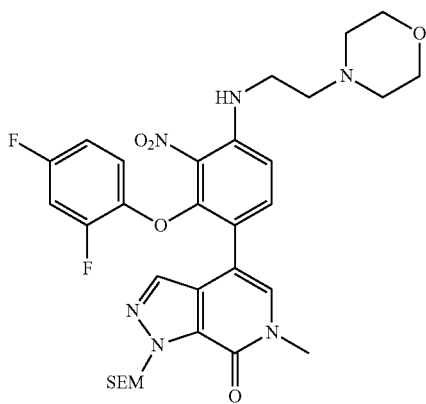

A solution of 4-morpholineethanol (43.0 μL, 0.352 mmol) and triphenylphosphine (92.3 mg, 0.352 mmol) in tetrahydrofuran (1.9 mL) was treated with diisopropyl azodicarboxylate (73.9 μL, 0.375 mmol) and stirred at 20° C. for 5 min. The reaction mixture was treated with a solution of N-[3-(2,4-difluorophenoxy)-4-(6-methyl-7-oxo-1-{[2-(trimethylsilyl)ethoxy]methyl}-6,7-dihydro-1H-pyrazolo[3,4-c]pyridin-4-yl)-2-nitrophenyl]-2,2,2-trifluoroacetamide (150 mg, 0.235 mmol) in THF and stirred overnight at RT. The reaction mixture was diluted with ethyl acetate and water. Layers were separated and the organic layer was washed with water and brine, dried with magnesium sulfate, filtered, and concentrated in vacuo to give the crude trifluoroacetamide which was used without further purification.

The crude intermediate was diluted with methylene chloride (2.0 mL) and ammonium hydroxide (1.0 mL) and stirred at RT for 30 min. The reaction mixture was diluted with methanol and purified via preparative LCMS (XBridge C18 column, eluting with a gradient of acetonitrile/water 0.1% ammonium hydroxide, at flow rate of 60 mL/min) to give the desired product (44 mg, 29%). LCMS calculated for $C_{31}H_{39}F_2N_6O_6Si$ (M+H)$^+$: m/z=657.3; found: 657.3.

Step 3. 4-{3-Amino-2-(2,4-difluorophenoxy)-4-[(2-morpholin-4-ylethyl)amino]phenyl}-6-methyl-1-{[2-(trimethylsilyl)ethoxy]methyl}-1,6-dihydro-7H-pyrazolo[3,4-c]pyridin-7-one

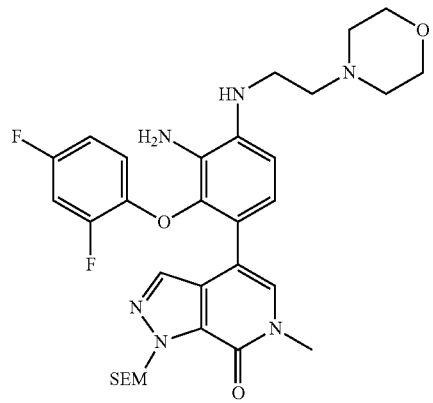 [SMILES: Cn1cc(-c2ccc(NCCN3CCOCC3)c([N+](=O)[O-])c2Oc2ccc(F)cc2F)c2cnn(COCC[Si](C)(C)C)c2c1=O]

This compound was synthesized according to the procedure of Example 1, Step 3, using 4-{2-(2,4-difluoro phenoxy)-4-[(2-morpholin-4-ylethyl)amino]-3-nitrophenyl}-6-methyl-1-{[2-(trimethylsilyl)ethoxy]methyl}-1,6-dihydro-7H-pyrazolo[3,4-c]pyridin-7-one as the starting material. LCMS calculated for $C_{31}H_{41}F_2N_6O_4Si$ (M+H)$^+$: m/z=627.3; found: 627.3.

Step 4. 4-[4-(2,4-Difluorophenoxy)-1-(2-morpholin-4-ylethyl)-1H-benzimidazol-5-yl]-6-methyl-1,6-dihydro-7H-pyrazolo[3,4-e]pyridin-7-one

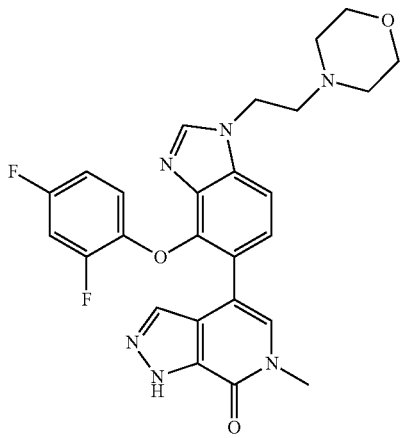 [SMILES: Cn1cc(-c2ccc3c(ncn3CCN3CCOCC3)c2Oc2ccc(F)cc2F)c2cn[nH]c2c1=O]

This compound was synthesized according to the procedure of Example 14 using 4-{3-amino-2-(2,4-difluorophenoxy)-4-[(2-morpholin-4-ylethyl)amino]phenyl}-6-methyl- 1-{[2-(trimethylsilyl)ethoxy]methyl}-1,6-dihydro-7H-pyrazolo[3,4-c]pyridin-7-one as the starting material. ¹H NMR (500 MHz, DMSO-d₆) δ 14.02 (br s, 1H), 8.19 (s, 1H), 7.73 (s, 1H), 7.62 (d, J=8.4 Hz, 1H), 7.39 (d, J=8.3 Hz, 1H), 7.25 (s, 1H), 7.21 (ddd, J=11.6, 8.8, 3.0 Hz, 1H), 6.80-6.71 (m, 1H), 6.64 (ddd, J=9.3, 9.3, 5.5 Hz, 1H), 4.39 (t, J=6.2 Hz, 2H), 3.61-3.45 (m, 6H), 2.72 (t, J=6.2 Hz, 2H), 2.47-2.38 (m, 4H); LCMS calculated for C₂₆H₂₅F₂N₆O₃ (M+H)⁺: m/z=507.2; found: 507.1.

Example 18. 4-[4-(2,4-Difluorophenoxy)-1-methyl-1H-benzimidazol-5-yl]-6-methyl-1,6-dihydro-7H-pyrazolo[3,4-c]pyridin-7-one

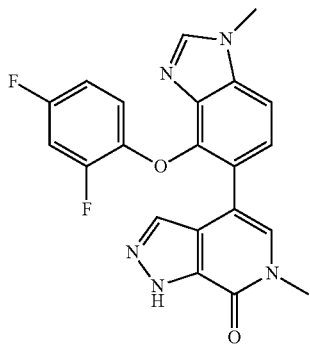

Step 1. 4-[2-(2,4-Difluorophenoxy)-4-(methylamino)-3-nitrophenyl]-6-methyl-1-{[2-(trimethylsilyl)ethoxy]methyl}-1,6-dihydro-7H-pyrazolo[3,4-c]pyridin-7-one

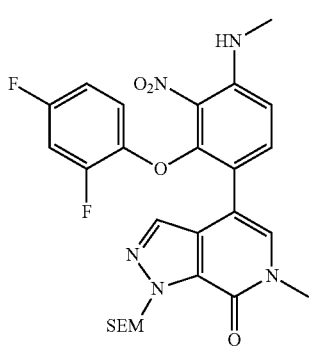

This compound was synthesized according to the procedure of Example 4, Step 2, using N-[3-(2,4-difluorophenoxy)-4-(6-methyl-7-oxo-1-{[2-(trimethylsilyl)ethoxy]methyl}-6,7-dihydro-1H-pyrazolo[3,4-c]pyridin-4-yl)-2-nitrophenyl]-2,2,2-trifluoroacetamide as the starting material. LCMS calculated for C₂₆H₃₀F₂N₅O₅Si (M+H)⁺: m/z=558.2; found: 558.2.

Step 2. 4-[3-Amino-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one

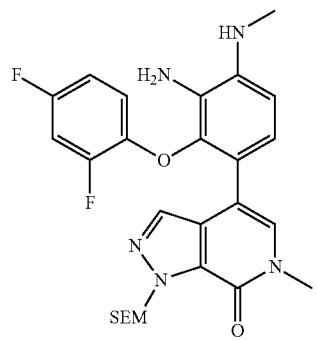 [SMILES: CNc1ccc(-c2cn(C)c(=O)c3c2cnn3COCC[Si](C)(C)C)c(Oc2ccc(F)cc2F)c1N]

This compound was synthesized according to the procedure of Example 1, Step 3, using 4-[2-(2,4-difluorophenoxy)-4-(methylamino)-3-nitrophenyl]-6-methyl-1-{[2-(trimethylsilyl)ethoxy]methyl}-1,6-dihydro-7H-pyrazolo[3,4-c]pyridin-7-one as the starting material. LCMS calculated for C₂₆H₃₂F₂N₅O₃Si (M+H)⁺: m/z=528.2; found: 528.2.

Step 3. 4-[4-(2,4-Difluorophenoxy)-1-methyl-1H-benzimidazol-5-yl]-6-methyl-1,6-dihydro-7H-pyrazolo[3,4-c]pyridin-7-one This compound was synthesized according to the procedure of Example 14 using 4-[3-amino-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one as the starting material. ¹H NMR (400 MHz, DMSO-d₆) δ 8.15 (s, 1H), 7.71 (br s, 1H), 7.64-7.50 (m, 1H), 7.49-7.34 (m, 1H), 7.33-7.13 (m, 2H), 6.87-6.69 (m, 1H), 6.69-6.51 (m, 1H), 3.88 (s, 3H), 3.53 (s, 3H); LCMS calculated for C₂₁H₁₆F₂N₅O₂ (M+H)⁺: m/z=408.1; found: 408.1.

Example 19. 4-[4-(2,4-Difluorophenoxy)-1,2-dimethyl-1H-benzimidazol-5-yl]-6-methyl-1,6-dihydro-7H-pyrazolo[3,4-c]pyridin-7-one

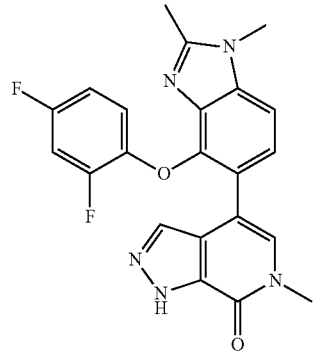 [SMILES: Cc1nc2c(Oc3ccc(F)cc3F)c(-c3cn(C)c(=O)c4[nH]ncc34)ccc2n1C]

This compound was synthesized according to the procedure of Example 18 using triethyl orthoacetate instead of ethyl orthoformate. ¹H NMR (400 MHz, DMSO-d₆) δ 7.70

(s, 1H), 7.51 (d, J=8.3 Hz, 1H), 7.34 (d, J=8.3 Hz, 1H), 7.29-7.14 (m, 2H), 6.79-6.67 (m, 1H), 6.55-6.44 (m, 1H), 3.77 (s, 3H), 3.51 (s, 3H), 2.48 (s, 3H); LCMS calculated for $C_{22}H_{18}F_2N_5O_2$ (M+H)$^+$: m/z=422.1; found: 422.1.

Example 20. 4-[4-(2,4-Difluorophenoxy)-1-methyl-1H-1,2,3-benzotriazol-5-yl]-6-methyl-1,6-dihydro-7H-pyrazolo[3,4-c]pyridin-7-one

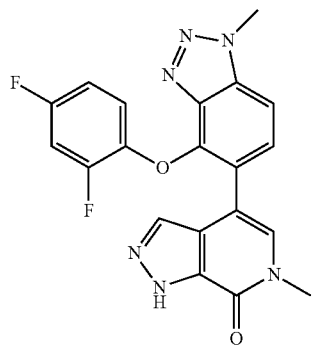

This compound was synthesized according to the procedure of Example 10, Step 7, using 4-[3-amino-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one as the starting material. $^1$H NMR (400 MHz, DMSO-d$_6$) δ 7.80 (d, J=8.6 Hz, 1H), 7.75 (br s, 1H), 7.69 (d, J=8.6 Hz, 1H), 7.39 (br s, 1H), 7.36-7.24 (m, 1H), 6.99-6.77 (m, 2H), 4.33 (s, 3H), 3.56 (s, 3H); LCMS calculated for $C_{20}H_{15}F_2N_6O_2$ (M+H)$^+$: m/z=409.1; found: 409.1.

Example 21. 4-[4-(2,4-Difluorophenoxy)-1-methyl-2-oxo-2,3-dihydro-1H-benzimidazol-5-yl]-6-methyl-1,6-dihydro-7H-pyrazolo[3,4-c]pyridin-7-one

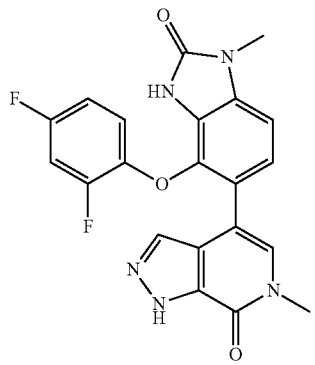 [SMILES: Cn1cc(-c2ccc3c([nH]c(=O)n3C)c2Oc2ccc(F)cc2F)c2cn[nH]c2c1=O]

This compound was synthesized according to the procedure of Example 16, Step 3, using 4-[3-amino-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one as the starting material. $^1$H NMR (400 MHz, DMSO-d6) δ 11.31 (br s, 1H), 7.69 (s, 1H), 7.26-7.07 (m, 4H), 6.76-6.63 (m, 1H), 6.53-6.38 (m, 1H), 3.47 (s, 3H), 3.35 (s, 3H); LCMS calculated for $C_{11}H_{16}F_2N_5O_3$ (M+H)$^+$: m/z=424.1; found: 424.1.

The examples in Table 1 were synthesized according to procedure of Examples 1 or 11 using the appropriate phenols or alcohols

TABLE 1

| Ex. No. | Compound Name | R | Ref. Ex. | MS [M + H]$^+$ |
|---|---|---|---|---|
| 22 | 5-(6-Methyl-7-oxo-6,7-dihydro-1H-pyrrolo[2,3-c]pyridin-4-yl)-4-phenoxy-1,3-dihydro-2H-benzimidazol-2-one | phenyl | 1 | 373.1 |
| 23 | 4-[(4,4-Difluorocyclohexyl)oxy]-5-(6-methyl-7-oxo-6,7-dihydro-1H-pyrrolo[2,3-c]pyridin-4-yl)-1,3-dihydro-2H-benzimidazol-2-one | 4,4-difluorocyclohexyl | 11 | 415.1 |

TABLE 1-continued

| | | | | |
|---|---|---|---|---|
| 24 | 4-(4-Fluorophenoxy)-5-(6-methyl-7-oxo-6,7-dihydro-1H-pyrrolo[2,3-c]pyridin-4-yl)-1,3-dihydro-2H-benzimidazol-2-one | 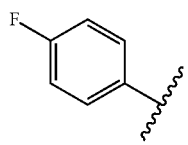 | 1 | 391.1 |
| 25 | 4-(3-Fluorophenoxy)-5-(6-methyl-7-oxo-6,7-dihydro-1H-pyrrolo[2,3-c]pyridin-4-yl)-1,3-dihydro-2H-benzimidazol-2-one | 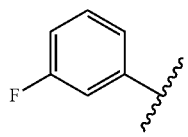 [SMILES: *c1cccc(F)c1] | 1 | 391.1 |
| 26 | 5-(6-Methyl-7-oxo-6,7-dihydro-1H-pyrrolo[2,3-c]pyridin-4-yl)-4-(tetrahydro-2H-pyran-3-yloxy)-1,3-dihydro-2H-benzimidazol-2-one | 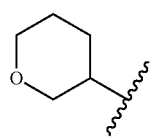 [SMILES: *C1CCCOC1] | 11 | 381.1 |

$^1$H NMR data for examples 22-26

| Ex. No. | $^1$H NMR |
|---|---|
| 22 | (300 MHz, DMSO-$d_6$) δ 11.91 (br s, 1H), 10.77 (br s, 2H), 7.22 (d, J = 2.7 Hz, 1H), 7.15-7.03 (m, 4H), 6.93 (d, J = 8.0 Hz, 1H), 6.83 (dd, J = 7.3, 7.3 Hz, 1H), 6.58 (d, J = 7.9 Hz, 2H), 6.19 (d, J = 2.7 Hz, 1H), 3.40 (s, 3H) |
| 23 | (400 MHz, DMSO-$d_6$) δ 11.98 (br s, 1H), 10.80 (br s, 2H), 7.25 (d, J = 2.8 Hz, 1H), 7.20 (s, 1H), 6.94 (d, J = 8.0 Hz, 1H), 6.76 (d, J = 8.0 Hz, 1H), 6.14 (d, J = 2.8 Hz, 1H), 4.04 (br s, 1H), 3.54 (s, 3H), 1.81-1.36 (m, 8H) |
| 24 | (400 MHz, DMSO-$d_6$) δ 11.94 (br s, 1H), 10.88 (br s, 2H), 7.23 (d, J = 2.8 Hz, 1H), 7.10-7.02 (m, 2H), 6.97-6.87 (m, 3H), 6.62-6.53 (m, 2H), 6.16 (d, J = 2.8 Hz, 1H), 3.42 (s, 3H) |
| 25 | (400 MHz, DMSO-$d_6$) δ 11.95 (br s, 1H), 10.96 (br s, 2H), 7.23 (d, J = 2.7 Hz, 1H), 7.18-7.05 (m, 3H), 6.95 (d, J = 8.0 Hz, 1H), 6.72-6.64 (m, 1H), 6.46-6.37 (m, 2H), 6.17 (d, J = 2.7 Hz, 1H), 3.42 (s, 3H) |
| 26 | (400 MHz, DMSO-$d_6$) δ 11.99 (br s, 1H), 10.73 (br s, 2H), 7.25 (dd, J = 2.6, 2.6 Hz, 1H), 7.21 (s, 1H), 6.94 (d, J = 8.0 Hz, 1H), 6.76 (d, J = 8.0 Hz, 1H), 6.18-6.09 (m, 1H), 3.66-3.57 (m, 1H), 3.55 (s, 3H), 3.49-3.39 (m, 1H), 3.20-3.07 (m, 2H), 1.67-1.59 (m, 1H), 1.56-1.46 (m, 1H), 1.45-1.36 (m, 1H), 1.20-1.04 (m, 1H), 0.91-0.79 (m, 1H) |

Example 27. 4-(Benzyloxy)-1-methyl-5-(6-methyl-7-oxo-6,7-dihydro-1H-pyrrolo[2,3-c]pyridin-4-yl)-1,3-dihydro-2H-benzimidazol-2-one

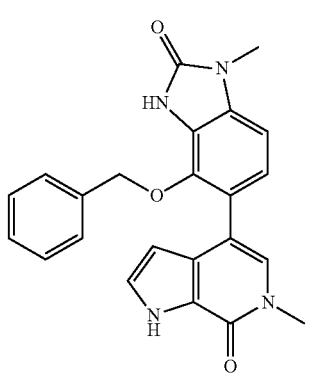 [SMILES: Cn1cc(-c2ccc3c([nH]c(=O)n3C)c2OCc2ccccc2)c2cc[nH]c2c1=O]

Step 1. 3-(Benzyloxy)-4-bromo-2-nitroaniline

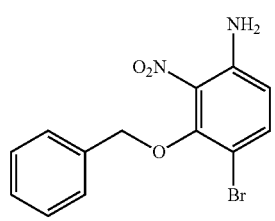 [SMILES: Nc1ccc(Br)c(OCc2ccccc2)c1[N+](=O)[O-]]

This compound was synthesized according to the procedure of Example 11, Step 1, using benzyl alcohol instead of cyclopropyl carbinol. LCMS calculated for $C_{13}H_{12}BrN_2O_3$ (M+H)$^+$: m/z=323.0, 325.0; found: 323.0, 325.0.

Step 2. 4-[4-Amino-2-(benzyloxy)-3-nitrophenyl]-6-methyl-1-[(4-methylphenyl)sulfonyl]-1,6-dihydro-7H-pyrrolo[2,3-c]pyridin-7-one

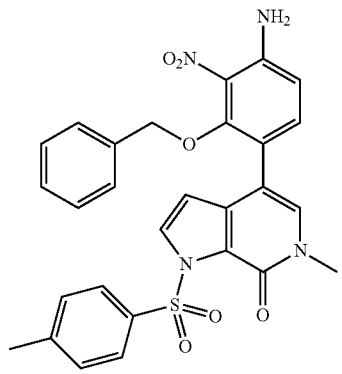

This compound was synthesized according to the procedure of Example 10, Step 5, using 3-(benzyloxy)-4-bromo-2-nitroaniline and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{28}H_{25}N_4O_6S$ $(M+H)^+$: m/z=545.1; found: 545.2.

Step 3. N-(3-(Benzyloxy)-4-{6-methyl-1-[(4-methylphenyl)sulfonyl]-7-oxo-6,7-dihydro-1H-pyrrolo[2,3-c]pyridin-4-yl}-2-nitrophenyl)-2,2,2-trifluoroacetamide

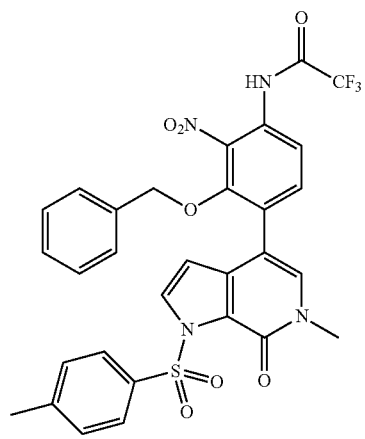 [SMILES: Cc1ccc(S(=O)(=O)n2ccc3c(-c4ccc(NC(=O)C(F)(F)F)c([N+](=O)[O-])c4OCc4ccccc4)cn(C)c(=O)c32)cc1]

This compound was synthesized according to the procedure of Example 4, Step 1, using 4-[4-amino-2-(benzyloxy)-3-nitrophenyl]-6-methyl-1-[(4-methylphenyl)sulfonyl]-1,6-dihydro-7H-pyrrolo[2,3-c]pyridin-7-one as the starting material. LCMS calculated for $C_{30}H_{24}F_3N_4O_7S$ $(M+H)^+$: m/z=641.1; found: 641.2.

Step 4. 4-[2-(Benzyloxy)-4-(methylamino)-3-nitrophenyl]-6-methyl-1-[(4-methylphenyl)sulfonyl]-1,6-dihydro-7H-pyrrolo[2,3-c]pyridin-7-one

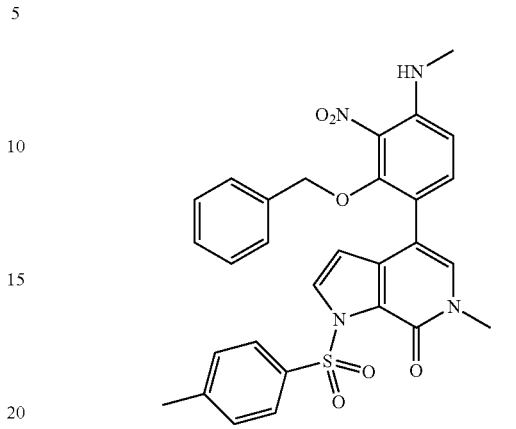

This compound was synthesized according to the procedure of Example 4, Step 2, using N-(3-(benzyloxy)-4-{6-methyl-1-[(4-methylphenyl)sulfonyl]-7-oxo-6,7-dihydro-1H-pyrrolo[2,3-c]pyridin-4-yl}-2-nitrophenyl)-2,2,2-trifluoroacetamide as the starting material. LCMS calculated for $C_{29}H_{27}N_4O_6S$ $(M+H)^+$: m/z=559.2; found: 559.1.

Step 5. 4-[3-Amino-2-(benzyloxy)-4-(methylamino)phenyl]-6-methyl-1-[(4-methylphenyl)sulfonyl]-1,6-dihydro-7H-pyrrolo[2,3-c]pyridin-7-one

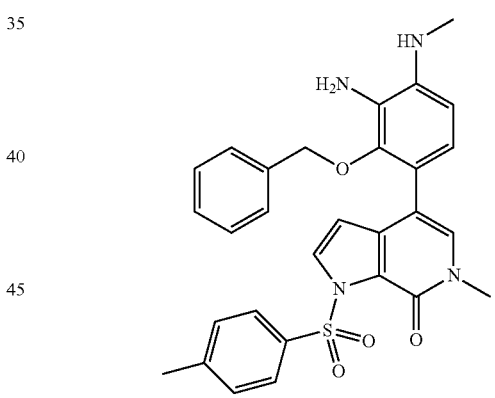

This compound was synthesized according to the procedure of Example 1, Step 3, using 4-[2-(benzyloxy)-4-(methylamino)-3-nitrophenyl]-6-methyl-1-[(4-methylphenyl)sulfonyl]-1,6-dihydro-7H-pyrrolo[2,3-c]pyridin-7-one as the starting material. LCMS calculated for $C_{29}H_{29}N_4O_4S$ $(M+H)^+$: m/z=529.2; found: 529.2.

Step 6. 4-(Benzyloxy)-1-methyl-5-(6-methyl-7-oxo-6,7-dihydro-1H-pyrrolo[2,3-c]pyridin-4-yl)-1,3-dihydro-2H-benzimidazol-2-one This compound was synthesized according to the procedure of Example 1, Step 4, using 4-[3-amino-2-(benzyloxy)-4-(methylamino)phenyl]-6-methyl-1-[(4-methylphenyl)sulfonyl]-1,6-dihydro-7H-pyrrolo[2,3-c]pyridin-7-one as the starting material. LCMS calculated for $C_{23}H_{21}N_4O_3$ $(M+H)^+$: m/z=401.2; found: 401.1.

The examples in Table 2 were synthesized according to procedure of examples 6, 27, or 88 using the appropriate phenols or alcohols.

TABLE 2

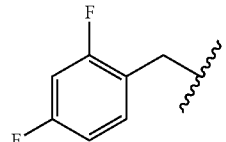

| Ex. No. | Compound Name | R | Ref. Ex. | MS [M + H]+ |
|---|---|---|---|---|
| 28 | 4-[(2,4-Difluorobenzyl)oxy]-1-methyl-5-(6-methyl-7-oxo-6,7-dihydro-1H-pyrrolo[2,3-c]pyridin-4-yl)-1,3-dihydro-2H-benzimidazol-2-one | 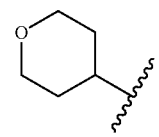 [SMILES: *C1CCOCC1] | 27 | 437.1 |
| 29 | 1-Methyl-5-(6-methyl-7-oxo-6,7-dihydro-1H-pyrrolo[2,3-c]pyridin-4-yl)-4-(tetrahydro-2H-pyran-4-yloxy)-1,3-dihydro-2H-benzimidazol-2-one | 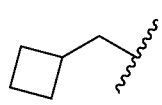 [SMILES: *CC1CCC1] | 27 | 395.1 |
| 37 | 4-(Cyclobutylmethoxy)-1-methyl-5-(6-methyl-7-oxo-6,7-dihydro-1H-pyrrolo[2,3-c]pyridin-4-yl)-1,3-dihydro-2H-benzimidazol-2-one | 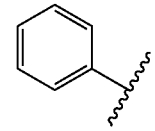 [SMILES: *c1ccccc1] | 27 | 379.1 |
| 38 | 1-Methyl-5-(6-methyl-7-oxo-6,7-dihydro-1H-pyrrolo[2,3-c]pyridin-4-yl)-4-phenoxy-1,3-dihydro-2H-benzimidazol-2-one | 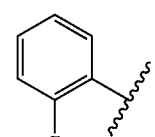 | 6 | 387.1 |
| 39 | 4-(2-Fluorophenoxy)-1-methyl-5-(6-methyl-7-oxo-6,7-dihydro-1H-pyrrolo[2,3-c]pyridin-4-yl)-1,3-dihydro-2H-benzimidazol-2-one | 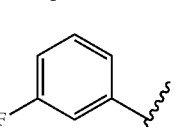 | 6 | 405.1 |
| 40 | 4-(3-Fluorophenoxy)-1-methyl-5-(6-methyl-7-oxo-6,7-dihydro-1H-pyrrolo[2,3-c]pyridin-4-yl)-1,3-dihydro-2H-benzimidazol-2-one | 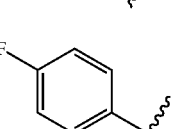 | 6 | 405.1 |
| 41 | 4-(4-Fluorophenoxy)-1-methyl-5-(6-methyl-7-oxo-6,7-dihydro-1H-pyrrolo[2,3-c]pyridin-4-yl)-1,3-dihydro-2H-benzimidazol-2-one | 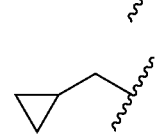 | 6 | 405.1 |
| 74 | 4-(Cyclopropylmethoxy)-1-methyl-5-(6-methyl-7-oxo-6,7-dihydro-1H-pyrrolo[2,3-c]pyridin-4-yl)-1,3-dihydro-2H-benzimidazol-2-one | | 27 | 365.1 |

TABLE 2-continued

| | | | | |
|---|---|---|---|---|
| 89 | 4-(Cyclobutyloxy)-1-methyl-5-(6-methyl-7-oxo-6,7-dihydro-1H-pyrrolo[2,3-c]pyridin-4-yl)-1,3-dihydro-2H-benzimidazol-2-one | 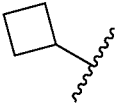 | 88 | 365.1 |
| 90 | 4-(Cyclohexyloxy)-1-methyl-5-(6-methyl-7-oxo-6,7-dihydro-1H-pyrrolo[2,3-c]pyridin-4-yl)-1,3-dihydro-2H-benzimidazol-2-one | 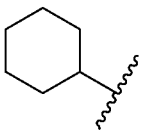 [SMILES: *C1CCCCC1] | 88 | 393.1 |
| 91 | 1-Methyl-5-(6-methyl-7-oxo-6,7-dihydro-1H-pyrrolo[2,3-c]pyridin-4-yl)-4-(tetrahydro-2H-pyran-3-yloxy)-1,3-dihydro-2H-benzimidazol-2-one | 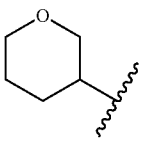 [SMILES: *C1CCCOC1] | 88 | 395.1 |
| 92 | 4-(Cyclopentylmethoxy)-1-methyl-5-(6-methyl-7-oxo-6,7-dihydro-1H-pyrrolo[2,3-c]pyridin-4-yl)-1,3-dihydro-2H-benzimidazol-2-one | 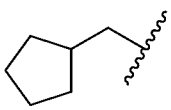 | 88 | 393.1 |
| 93 | 4-(Cyclopentyloxy)-1-methyl-5-(6-methyl-7-oxo-6,7-dihydro-1H-pyrrolo[2,3-c]pyridin-4-yl)-1,3-dihydro-2H-benzimidazol-2-one | 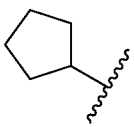 [SMILES: *C1CCCC1] | 88 | 379.1 |

$^{1}$H NMR data for examples 28, 29, 37-41, 74, 89-93

| Ex. No. | $^{1}$H NMR |
|---|---|
| 28 | N/A |
| 29 | (300 MHz, DMSO-d$_6$) δ 11.99 (s, 1H), 11.06 (s, 1H), 7.30-7.17 (m, 2H), 7.04 (d, J = 8.0 Hz, 1H), 6.92 (d, J = 8.1 Hz, 1H), 6.14 (s, 1H), 4.01-3.82 (m, 1H), 3.66-3.44 (m, 5H), 3.32 (s, 1H), 3.10-2.95 (m, 2H), 1.63-1.26 (m, 6H) |
| 37 | (300 MHz, DMSO-d$_6$) δ 11.97 (br s, 1H), 11.05 (br s, 1H), 7.25 (d, J = 2.7 Hz, 1H), 7.19 (s, 1H), 7.02 (d, J = 8.0 Hz, 1H), 6.91 (d, J = 8.1 Hz, 1H), 6.12 (d, J = 2.7 Hz, 1H), 3.63 (d, J = 6.6 Hz, 2H), 3.54 (s, 3H), 3.29 (s, 3H), 2.47-2.32 (m, 1H), 1.74-1.60 (m, 3H), 1.60-1.47 (m, 1H), 1.47-1.30 (m, 2H) |
| 38 | (300 MHz, DMSO-d$_6$) δ 11.94 (br s, 1H), 11.17 (br s, 1H), 7.23 (d, J = 2.7 Hz, 1H), 7.20-7.01 (m, 5H), 6.83 (dd, J = 7.3, 7.3 Hz, 1H), 6.58 (d, J = 7.8 Hz, 2H), 6.19 (d, J = 2.7 Hz, 1H), 3.40 (s, 3H), 3.33 (s, 3H) |
| 39 | (300 MHz, DMSO-d$_6$) δ 11.94 (br s, 1H), 11.27 (br s, 1H), 7.27-7.01 (m, 5H), 6.90-6.74 (m, 2H), 6.49-6.35 (m, 1H), 6.13 (d, J = 2.5 Hz, 1H), 3.42 (s, 3H), 3.34 (s, 3H) |
| 40 | (300 MHz, DMSO-d$_6$) δ 11.96 (br s, 1H), 11.22 (br s, 1H), 7.29-7.21 (m, 1H), 7.20-7.04 (m, 4H), 6.76-6.59 (m, 1H), 6.47-6.33 (m, 2H), 6.22-6.12 (m, 1H), 3.43 (s, 3H), 3.33 (s, 3H) |
| 41 | (300 MHz, DMSO-d$_6$) δ 11.96 (br s, 1H), 11.20 (br s, 1H), 7.24 (s, 1H), 7.19-7.05 (m, 3H), 6.99-6.86 (m, 2H), 6.65-6.53 (m, 2H), 6.23-6.11 (m, 1H), 3.43 (s, 3H), 3.33 (s, 3H) |
| 74 | (500 MHz, DMSO-d$_6$) δ 11.96 (br s, 1H), 11.04 (br s, 1H), 7.24 (d, J = 2.8 Hz, 1H), 7.21 (s, 1H), 7.02 (d, J = 8.0 Hz, 1H), 6.90 (d, J = 8.1 Hz, 1H), 6.13 (d, J = 2.8 Hz, 1H), 3.55 (s, 3H), 3.47 (d, J = 7.0 Hz, 2H), 3.29 (s, 3H), 1.01-0.80 (m, 1H), 0.34-0.15 (m, 2H), 0.05--0.19 (m, 2H) |
| 89 | (400 MHz, DMSO-d$_6$) δ 12.01 (br s, 1H), 11.08 (s, 1H), 7.25 (dd, J = 2.6, 2.6 Hz, 1H), 7.20 (s, 1H), 7.01 (d, J = 8.0 Hz, 1H), 6.90 (d, J = 8.1 Hz, 1H), 6.29-5.95 (m, 1H), 4.36-3.96 (m, 1H), 3.55 (s, 3H), 3.28 (s, 3H), 1.97-1.64 (m, 4H), 1.59-1.30 (m, 1H), 1.27-0.99 (m, 1H) |
| 90 | (400 MHz, DMSO-d$_6$) δ 11.98 (br s, 1H), 10.97 (s, 1H), 7.25 (dd, J = 2.4, 2.4 Hz, 1H), 7.21 (s, 1H), 7.02 (d, J = 8.0 Hz, 1H), 6.90 (d, J = 8.1 Hz, 1H), 6.14 (s, 1H), 3.77-3.60 (m, 1H), 3.55 (s, 3H), 3.28 (s, 3H), 1.58-1.38 (m, 4H), 1.37-1.09 (m, 3H), 1.08-0.56 (m, 3H) |
| 91 | (400 MHz, DMSO-d$_6$) δ 12.01 (br s, 1H), 10.97 (br s, 1H), 7.25 (s, 1H), 7.23 (s, 1H), 7.03 (d, J = 8.0 Hz, 1H), 6.93 (d, J = 8.1 Hz, 1H), 6.13 (d, J = 2.1 Hz, 1H), 3.71-3.59 (m, 1H), 3.56 (s, 3H), 3.50-3.36 (m, 2H), 3.29 (s, 3H), 3.25-3.07 (m, 2H), 1.68-1.56 (m, 1H), 1.56-1.45 (m, 1H), 1.46-1.27 (m, 1H), 1.27-1.01 (m, 1H) |
| 92 | (400 MHz, DMSO-d$_6$) δ 11.98 (br s, 1H), 11.06 (br s, 1H), 7.24 (dd, J = 2.4, 2.4 Hz, 1H), 7.19 (s, 1H), 7.01 (d, J = 8.0 Hz, 1H), 6.90 (d, J = 8.1 Hz, 1H), |

TABLE 2-continued

| | |
|---|---|
| | 6.09 (s, 1H), 3.54 (s, 3H), 3.50 (d, J = 6.9 Hz, 2H), 3.29 (s, 3H), 2.14-1.83 (m, 1H), 1.48-1.33 (m, 2H), 1.33-1.17 (m, 4H), 1.05-0.81 (m, 2H) |
| 93 | (400 MHz, DMSO-$d_6$) δ 11.97 (br s, 1H), 7.24 (s, 1H), 7.16 (s, 1H), 7.00 (d, J = 7.6 Hz, 1H), 6.87 (d, J = 8.1 Hz, 1H), 6.15 (s, 1H), 4.60-4.29 (m, 1H), 3.54 (s, 3H), 3.16 (s, 3H), 1.64-1.39 (m, 2H), 1.26 (s, 6H) |

Examples 30 and 31

4-[7-(2,4-Difluorophenoxy)-1-(2-morpholin-4-yl-2-oxoethyl)-1H-benzimidazol-6-yl]-6-methyl-1,6-dihydro-7H-pyrrolo[2,3-c]pyridin-7-one and 4-[4-(2,4-difluorophenoxy)-1-(2-morpholin-4-yl-2-oxoethyl)-1H-benzimidazol-5-yl]-6-methyl-1,6-dihydro-7H-pyrrolo[2,3-c]pyridin-7-one

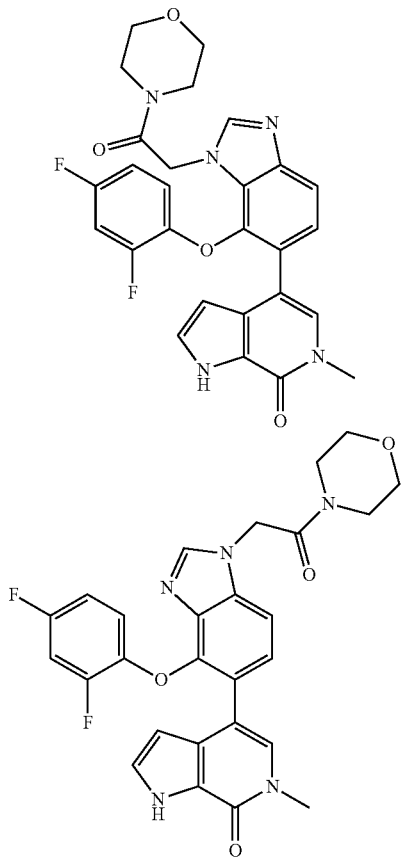

Step 1. 4-Bromo-6-methyl-1,6-dihydro-7H-pyrrolo[2,3-c]pyridin-7-one

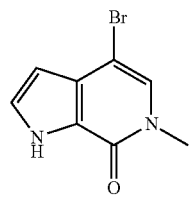

A solution of 4-bromo-6-methyl-1-[(4-methylphenyl)sulfonyl]-1,6-dihydro-7H-pyrrolo[2,3-c]pyridin-7-one (5.81 g, 15.2 mmol) in ethanol (100 mL) was treated with 3.0 M sodium hydroxide in water (50.8 mL, 152 mmol) and stirred at 20° C. for 16 h. The reaction mixture was concentrated in vacuo to remove most of the ethanol. The remaining aqueous layer was neutralized with concentrated HCl to pH 7 and extracted with ethyl acetate (2×). The combined organic layers were dried with magnesium sulfate, filtered, and concentrated to give the desired product (3.74 g, quantitative) which was used without further purification. LCMS calculated for $C_8H_8BrN_2O$ (M+H)$^+$: m/z=227.0, 229.0; found: 227.0, 228.9.

Step 2. 4-Bromo-6-methyl-1-{[2-(trimethylsilyl)ethoxy]methyl}-1,6-dihydro-7H-pyrrolo[2,3-c]pyridin-7-one

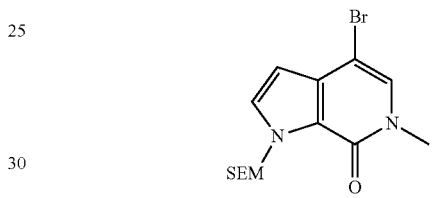

A solution of 4-bromo-6-methyl-1,6-dihydro-7H-pyrrolo[2,3-c]pyridin-7-one (0.967 g, 4.26 mmol) in N,N-dimethylformamide (30.6 mL) at 0° C. was treated with sodium hydride (0.255 g, 6.38 mmol) and stirred at 0° C. for 30 min. After this time the reaction mixture was treated with [β-(trimethylsilyl)ethoxy]methyl chloride (1.13 mL, 6.39 mmol) and subsequently stirred at 20° C. for 1 h. The reaction mixture was diluted with ethyl acetate and water. Layers were separated and the organic layer was washed with water (3×), dried with magnesium sulfate, filtered, and concentrated to give a crude residue. Purification by flash column chromatography (100% hexanes to 30% EtOAc/hexanes) gave the desired product (1.03 g, 68%) as a white solid. LCMS calculated for $C_{14}H_{22}BrN_2O_2Si$ (M+H)$^+$: m/z=357.1, 359.1; found: 357.0, 359.0.

Step 3. 6-Methyl-4-(4,4,5,5-tetramethyl-1,3,2-dioxaborolan-2-yl)-1-{[2-(trimethylsilyl)ethoxy]methyl}-1,6-dihydro-7H-pyrrolo[2,3-c]pyridin-7-one

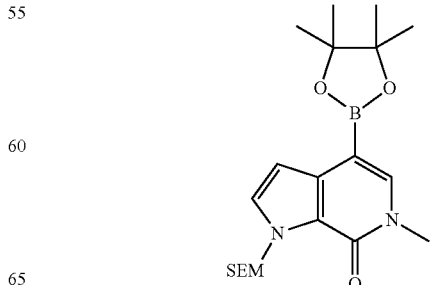

This compound was synthesized according to the procedure of Example 10, Step 4, using 4-bromo-6-methyl-1-{[2-(trimethylsilyl)ethoxy]methyl}-1,6-dihydro-7H-pyrrolo[2,3-c]pyridin-7-one as the starting material. LCMS calculated for $C_{20}H_{34}BN_2O_4Si$ (M+H)$^+$: m/z=405.2; found: 405.2.

Step 4. 4-[4-Amino-2-(2,4-difluorophenoxy)-3-nitrophenyl]-6-methyl-1-{[2-(trimethylsilyl)ethoxy]methyl}-1,6-dihydro-7H-pyrrolo[2,3-c]pyridin-7-one

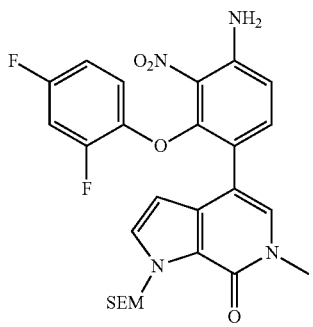 [SMILES: Cn1cc(-c2ccc(N)c([N+](=O)[O-])c2Oc2ccc(F)cc2F)c2ccn(COCC[Si](C)(C)C)c2c1=O]

This compound was synthesized according to the procedure of Example 10, Step 5, using 4-bromo-3-(2,4-difluorophenoxy)-2-nitroaniline and 6-methyl-4-(4,4,5,5-tetramethyl-1,3,2-dioxaborolan-2-yl)-1-{[2-(trimethylsilyl)ethoxy]methyl}-1,6-dihydro-7H-pyrrolo[2,3-c]pyridin-7-one as the starting materials. LCMS calculated for $C_{26}H_{29}F_2N_4O_5Si$ (M+H)$^+$: m/z=543.2; found: 543.2.

Step 5. 4-[3,4-Diamino-2-(2,4-difluorophenoxy)phenyl]-6-methyl-1-{[2-(trimethylsilyl)ethoxy]methyl}-1,6-dihydro-7H-pyrrolo[2,3-c]pyridin-7-one

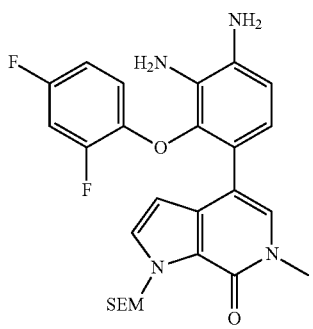

This compound was synthesized according to the procedure of Example 1, Step 3, using 4-[4-amino-2-(2,4-difluorophenoxy)-3-nitrophenyl]-6-methyl-1-{[2-(trimethylsilyl)ethoxy]methyl}-1,6-dihydro-7H-pyrrolo[2,3-c]pyridin-7-one as the starting material. LCMS calculated for $C_{26}H_{31}F_2N_4O_3Si$ (M+H)$^+$: m/z=513.2; found: 513.2.

Step 6. 4-[4-(2,4-Difluorophenoxy)-1H-benzimidazol-5-yl]-6-methyl-1-{[2-(trimethylsilyl)ethoxy]methyl}-1,6-dihydro-7H-pyrrolo[2,3-c]pyridin-7-one

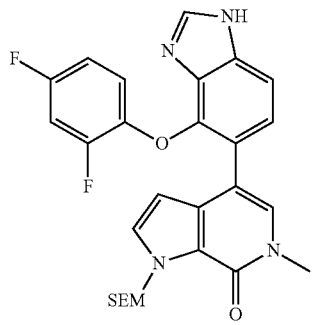 [SMILES: Cn1cc(-c2ccc3[nH]cnc3c2Oc2ccc(F)cc2F)c2ccn(COCC[Si](C)(C)C)c2c1=O]

A solution of 4-[3,4-diamino-2-(2,4-difluorophenoxy)phenyl]-6-methyl-1-{[2-(trimethylsilyl)ethoxy]methyl}-1,6-dihydro-7H-pyrrolo[2,3-c]pyridin-7-one (460 mg, 0.897 mmol) in tetrahydrofuran (7.76 mL) was treated with ethyl orthoformate (448 μL, 2.69 mmol) followed by addition of p-toluenesulfonic acid monohydrate (17.1 mg, 0.0897 mmol). The resultant reaction mixture was stirred at 50° C. for 1 h, after which time the reaction mixture was diluted with ethyl acetate and water. Layers were separated and the organic layer was washed with brine, dried with magnesium sulfate, filtered, and concentrated in vacuo to give the crude product. Purification by gradient flash column chromatography (50% EtOAc/hexanes to 100% EtOAc) gave the desired product (0.378 g, 81%). LCMS calculated for $C_{27}H_{29}F_2N_4O_3Si$ (M+H)$^+$: m/z=523.2; found: 523.2.

Step 7. Ethyl [4-(2,4-difluorophenoxy)-5-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetate and ethyl [7-(2,4-difluorophenoxy)-6-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetate

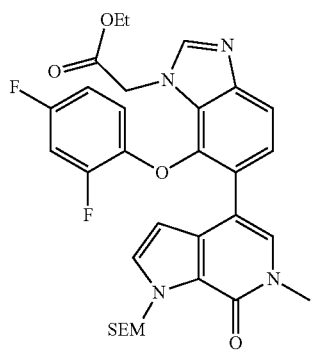

103
-continued

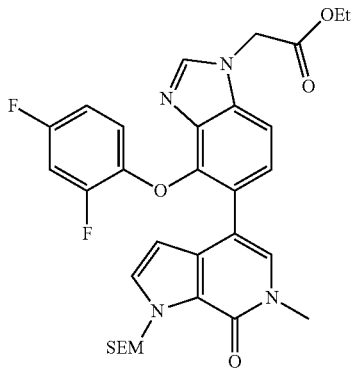

A solution of 4-[4-(2,4-difluorophenoxy)-1H-benzimidazol-5-yl]-6-methyl-1-{[2-(trimethylsilyl)ethoxy]methyl}-1,6-dihydro-7H-pyrrolo[2,3-c]pyridin-7-one (150 mg, 0.287 mmol) in N,N-dimethylformamide (2.84 mL) was treated with cesium carbonate (280 mg, 0.861 mmol) and ethyl bromoacetate (63.6 µL, 0.574 mmol) and the resultant reaction mixture was stirred at 60° C. overnight, after which time the reaction mixture was diluted with ethyl acetate and water. Layers were separated and the organic layer was washed with brine, dried with magnesium sulfate, filtered, and concentrated to give the crude product as a mixture of isomers (~3:1) which was used without further purification. LCMS calculated for $C_{31}H_{35}F_2N_4O_5Si$ (M+H)$^+$: m/z=609.2; found: 609.1.

Step 8. [4-(2,4-Difluorophenoxy)-5-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetic acid and [7-(2,4-difluorophenoxy)-6-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetic acid

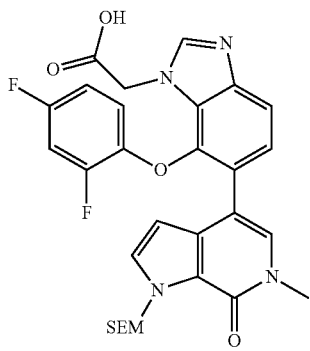

104
-continued

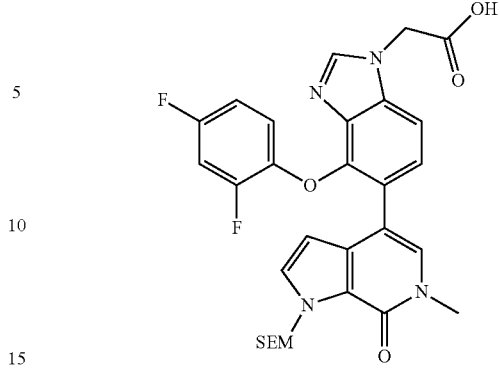

A solution of ethyl [4-(2,4-difluorophenoxy)-5-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetate and ethyl [7-(2,4-difluorophenoxy)-6-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl] acetate (169.0 mg, 0.2776 mmol, mixture of isomers) in methanol (1.42 mL) and tetrahydrofuran (2.84 mL) was treated with 4.0 M lithium hydroxide in water (350 µL, 1.40 mmol) and stirred at RT for 2 h. The reaction mixture was quenched with acetic acid to pH~6, filtered, and purified via preparative LCMS (XBridge C18 column, eluting with a gradient of acetonitrile/water 0.1% ammonium hydroxide, at flow rate of 60 mL/min) to give the desired product (105 mg, 65%) as a mixture of isomers. LCMS calculated for $C_{29}H_{31}F_2N_4O_5Si$ (M+H)$^+$: m/z=581.2; found: 581.2.

Step 9. 4-[7-(2,4-Difluorophenoxy)-1-(2-morpholin-4-yl-2-oxoethyl)-1H-benzimidazol-6-yl]-6-methyl-1,6-dihydro-7H-pyrrolo[2,3-c]pyridin-7-one and 4-[4-(2,4-difluorophenoxy)-1-(2-morpholin-4-yl-2-oxoethyl)-1H-benzimidazol-5-yl]-6-methyl-1,6-dihydro-7H-pyrrolo[2,3-c]pyridin-7-one A solution of [4-(2,4-difluorophenoxy)-5-(6-methyl-7-oxo-1-{[2-(trimethylsilyl)ethoxy]methyl}-6,7-dihydro-1H-pyrrolo[2,3-c]pyridin-4-yl)-1H-benzimidazol-1-yl]acetic acid (30.0 mg, 0.0517 mmol, mixture of isomers) in N,N-dimethylformamide (1.01 mL) was treated with morpholine (11.3 µL, 0.129 mmol) followed by N,N-diisopropylethylamine (45.0 µL, 0.258 mmol). The reaction mixture was stirred for several minutes and treated with benzotriazol-1-yloxytris(dimethylamino)phosphonium hexafluorophosphate (34.3 mg, 0.0775 mmol) and the resultant mixture was stirred at RT for 1 h, after which time the reaction mixture was diluted with ethyl acetate and water. Layers were separated and the organic layer was washed with brine, dried with magnesium sulfate, filtered, and concentrated to give the crude intermediate amide as a mixture of isomers which was used without further purification. The crude mixture of intermediate amides was diluted with methylene chloride (2.00 mL) and trifluoroacetic acid (1.00 mL) and stirred at RT for 2 h, after which time the reaction mixture was concentrated in vacuo and the resultant residue was reconcentrated from toluene. This crude residue was diluted with methanol (2.00 mL), treated with ethylenediamine (27.6 µL, 0.413 mmol), and stirred at RT overnight. The reaction mixture was concentrated in vacuo and purified via preparative LCMS (XBridge C18 column, eluting with a gradient of acetonitrile/water 0.1% ammonium hydroxide, at flow rate of 60 mL/min) to give the desired product 4-[7-(2,4-Difluorophenoxy)-1-(2-morpholin-4-yl-2-oxoethyl)-1H-benzimidazol-6-yl]-6-methyl-1,6-dihydro-7H-pyrrolo[2,3-c]pyridin-7-one (Example 30) as peak 1 (5 mg, 19%) and the desired product 4-[4-(2,4-difluorophenoxy)-1-(2-morpholin-4-yl-2-oxoethyl)-1H-benzimidazol-5-yl]-6-methyl-1,6-dihydro-7H-pyrrolo[2,3-c]pyridin-7-one (Example 31) as peak 2 (12 mg, 45%). Example 30: $^1$H NMR (500 MHz, DMSO-$d_6$) δ 11.84 (br s, 1H), 8.15 (s, 1H), 7.65 (d, J=8.3 Hz, 1H), 7.28 (d, J=8.3 Hz, 1H), 7.24-7.11 (m, 2H), 7.08 (s, 1H), 6.59-6.48 (m, 1H), 6.40-6.27 (m, 1H), 6.09 (d, J=2.8 Hz, 1H), 5.26 (s, 2H), 3.49-3.39 (m, 5H), 3.39-3.32 (m, 2H), 3.26-3.19 (m, 2H), 3.06-2.98 (m, 2H); LCMS calculated for $C_{27}H_{24}F_2N_5O_4$ (M+H)$^+$: m/z=520.2; found: 520.3. Example 31: $^1$H NMR (500 MHz, DMSO-$d_6$) δ 11.97 (s, 1H), 8.05 (s, 1H), 7.48 (d, J=8.4 Hz, 1H), 7.35 (d, J=8.3 Hz, 1H), 7.29-7.15 (m, 3H), 6.81-6.71 (m, 1H), 6.69-6.58 (m, 1H), 6.14 (d, J=2.8 Hz, 1H), 5.34 (s, 2H), 3.76-3.67 (m, 2H), 3.66-3.55 (m, 4H), 3.54-3.42 (m, 5H); LCMS calculated for $C_{27}H_{24}F_2N_5O_4$ (M+H)$^+$: m/z=520.2; found: 520.3.

Example 32. 4-Methoxy-1-methyl-5-(6-methyl-7-oxo-6,7-dihydro-1H-pyrrolo[2,3-c]pyridin-4-yl)-1,3-dihydro-2H-benzimidazol-2-one

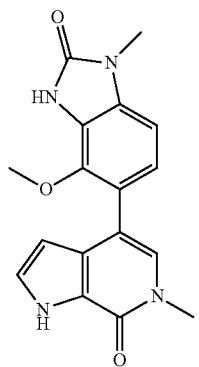

Step 1. N-(4-Bromo-3-fluoro-2-nitrophenyl)-2,2,2-trifluoroacetamide

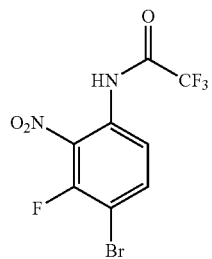 [SMILES: O=C(Nc1ccc(Br)c(F)c1[N+](=O)[O-])C(F)(F)F]

A solution of 4-bromo-3-fluoro-2-nitroaniline (0.955 g, 4.06 mmol) and triethylamine (1.13 mL, 8.13 mmol) in methylene chloride (21.0 mL) was cooled to 0° C., followed by dropwise addition of trifluoroacetic anhydride (1.15 mL, 8.13 mmol). The reaction mixture was stirred at 0° C. for 30 min, then warmed to 20° C. and stirred at that temperature for 1 h. The reaction mixture was diluted with brine. Layers were separated and the aqueous layer was extracted with dichloromethane. The combined organic layers were washed with brine, dried with magnesium sulfate, filtered, and concentrated in vacuo to give a crude oil. Purification by flash column chromatography (100% hexanes to 30% EtOAc/hexanes) gave the desired product (1.27 g, 94%) as a yellow solid.

Step 2.
4-Bromo-3-methoxy-N-methyl-2-nitroaniline

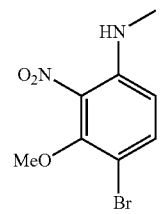

A solution of N-(4-bromo-3-fluoro-2-nitrophenyl)-2,2,2-trifluoroacetamide (1.27 g, 3.84 mmol) in N,N-dimethylformamide (43.4 mL) was treated with cesium carbonate (2.50 g, 7.67 mmol) followed by the addition of methyl iodide (1.19 mL, 19.2 mmol). The reaction mixture was stirred at 20° C. for 1 h, then warmed to 50° C. and stirred at that temperature for 16 h, after which time additional methyl iodide (0.5 eq) was added to the reaction mixture and the reaction mixture was heated at 50° C. for 4 h. The reaction mixture was diluted with ethyl acetate and water. Layers were separated and the organic layer was washed with water (3×) and brine, dried with magnesium sulfate, filtered, and concentrated in vacuo to give the crude methylated amide which was used without further purification. The crude intermediate methylated amide was dissolved in methanol (43.4 mL) and water (8.68 mL, 482 mmol), treated with potassium carbonate (2.65 g, 19.2 mmol), and the resultant mixture was stirred at 60° C. for 15 h, after which time the reaction mixture was concentrated to remove most of the methanol and the aqueous residue was extracted with ethyl acetate (2×). The combined organic layers were washed with brine, dried with magnesium sulfate, filtered, and concentrated to give the desired product (906 mg, 90%) as a yellow solid. LCMS calculated for $C_8H_{10}BrN_2O_3$ (M+H)$^+$: m/z=261.0, 263.0; found: 260.9, 262.8.

Step 3. 4-[2-Methoxy-4-(methylamino)-3-nitrophenyl]-6-methyl-1-[(4-methylphenyl)sulfonyl]1,6-dihydro-7H-pyrrolo[2,3-c]pyridin-7-one

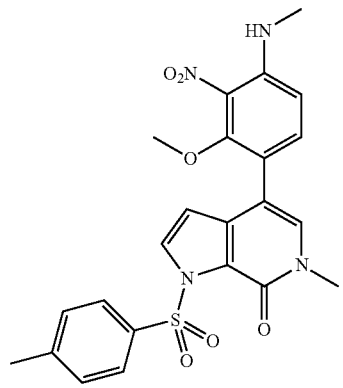

This compound was synthesized according to the procedure of Example 10, Step 5, using 4-bromo-3-methoxy-N-methyl-2-nitro aniline and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{23}H_{23}N_4O_6S$ $(M+H)^+$: m/z=483.1; found: 483.1.

Step 4. 4-[3-Amino-2-methoxy-4-(methylamino)phenyl]6-methyl-1-[(4-methylphenyl)sulfonyl]-1,6-dihydro-7H-pyrrolo[2,3-c]pyridin-7-one

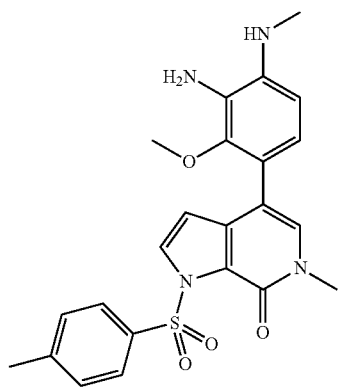

This compound was synthesized according to the procedure of Example 1, Step 3, using 4-[2-methoxy-4-(methylamino)-3-nitrophenyl]-6-methyl-1-[(4-methylphenyl)sulfonyl]-1,6-dihydro-7H-pyrrolo[2,3-c]pyridin-7-one as the starting material. LCMS calculated for $C_{23}H_{25}N_4O_4S$ $(M+H)^+$: m/z=453.2; found: 453.1.

Step 5. 4-Methoxy-1-methyl-5-(6-methyl-7-oxo-6,7-dihydro-1H-pyrrolo[2,3-c]pyridin-4-yl)-1,3-dihydro-2H-benzimidazol-2-one

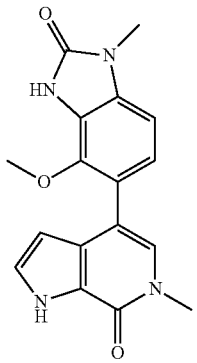

This compound was synthesized according to the procedure of Example 1, Step 4, using 4-[3-amino-2-methoxy-4-(methylamino)phenyl]-6-methyl-1-[(4-methylphenyl)sulfonyl]-1,6-dihydro-7H-pyrrolo[2,3-c]pyridin-7-one as the starting material. $^1$H NMR (300 MHz, DMSO-d$_6$) δ 12.01 (br s, 1H), 11.11 (br s, 1H), 7.29-7.21 (m, 1H), 7.17 (s, 1H), 6.99 (d, J=8.0 Hz, 1H), 6.91 (d, J=8.0 Hz, 1H), 6.08 (s, 1H), 3.55 (s, 3H), 3.52 (s, 3H), 3.29 (s, 3H); LCMS calculated for $C_{17}H_{17}N_4O_3$ $(M+H)^+$: m/z=325.1; found: 325.2.

Examples 33 and 34. 2-[7-(2,4-Difluorophenoxy)-6-(6-methyl-7-oxo-6,7-dihydro-1H-pyrrolo[2,3-c]pyridin-4-yl)-1H-benzimidazol-1-yl]-N,N-dimethylacetamide and 2-[4-(2,4-difluorophenoxy)-5-(6-methyl-7-oxo-6,7-dihydro-1H-pyrrolo[2,3-c]pyridin-4-yl)-1H-benzimidazol-1-yl]-N,N-dimethylacetamide

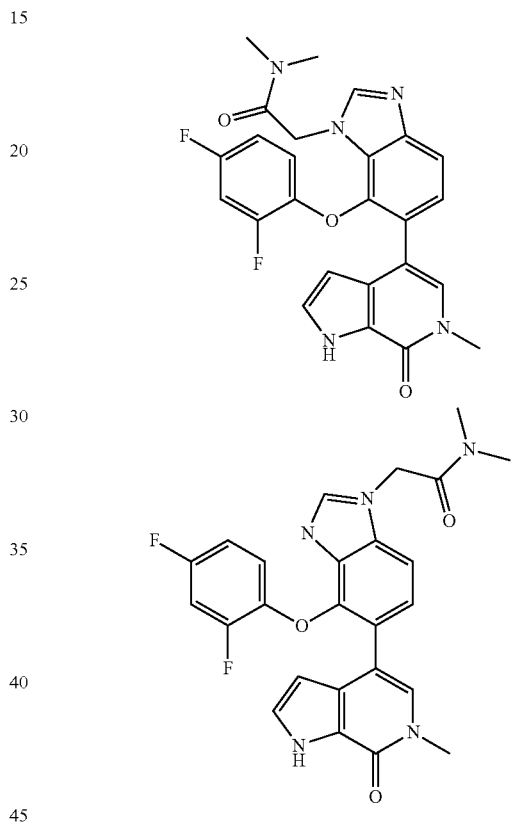

These compounds were synthesized according to the procedure of Examples 30 and 31, Step 9, using dimethylamine instead of morpholine. 2-[7-(2,4-Difluorophenoxy)-6-(6-methyl-7-oxo-6,7-dihydro-1H-pyrrolo[2,3-c]pyridin-4-yl)-1H-benzimidazol-1-yl]-N,N-dimethylacetamide (Example 33): $^1$H NMR (300 MHz, DMSO-d$_6$) δ 11.90 (br s, 1H), 8.15 (s, 1H), 7.66 (d, J=8.3 Hz, 1H), 7.29 (d, J=8.3 Hz, 1H), 7.24-7.04 (m, 3H), 6.67-6.48 (m, 1H), 6.37-6.24 (m, 1H), 6.13 (d, J=2.7 Hz, 1H), 5.21 (s, 2H), 3.43 (s, 3H), 2.85 (s, 3H), 2.39 (s, 3H); LCMS calculated for $C_{25}H_{22}F_2N_5O_3$ $(M+H)^+$: m/z=478.2; found: 478.3. 2-[4-(2,4-difluorophenoxy)-5-(6-methyl-7-oxo-6,7-dihydro-1H-pyrrolo[2,3-c]pyridin-4-yl)-1H-benzimidazol-1-yl]-N,N-dimethylacetamide (Example 34): $^1$H NMR (300 MHz, DMSO-d$_6$) δ 11.99 (br s, 1H), 8.04 (s, 1H), 7.47 (d, J=8.4 Hz, 1H), 7.33 (d, J=8.3 Hz, 1H), 7.30-7.12 (m, 3H), 6.84-6.71 (m, 1H), 6.69-6.55 (m, 1H), 6.14 (d, J=2.7 Hz, 1H), 5.30 (s, 2H), 3.49 (s, 3H), 3.12 (s, 3H), 2.88 (s, 3H); LCMS calculated for $C_{25}H_{22}F_2N_5O_3$ $(M+H)^+$: m/z=478.2; found: 478.2.

Examples 35 and 36. 2-[7-(2,4-Difluorophenoxy)-6-(6-methyl-7-oxo-6,7-dihydro-1H-pyrrolo[2,3-c]pyridin-4-yl)-1H-benzimidazol-1-yl]-N-methylacetamide and 2-[4-(2,4-difluorophenoxy)-5-(6-methyl-7-oxo-6,7-dihydro-1H-pyrrolo[2,3-c]pyridin-4-yl)-1H-benzimidazol-1-yl]-N-methylacetamide

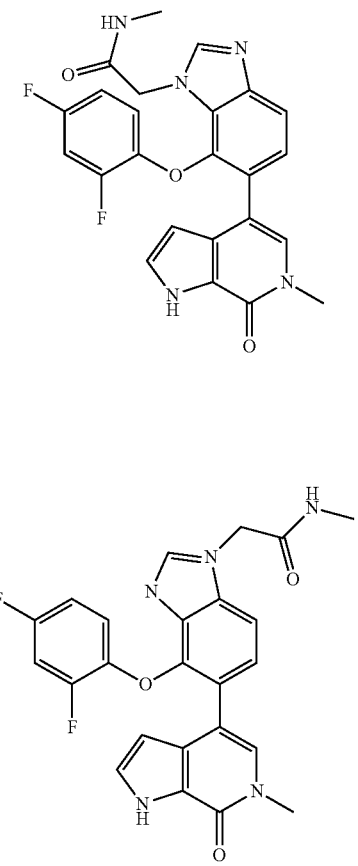

These compounds were synthesized according to the procedure of Examples 30 and 31, Step 9, using methylamine instead of morpholine. 2-[7-(2,4-Difluorophenoxy)-6-(6-methyl-7-oxo-6,7-dihydro-1H-pyrrolo[2,3-c]pyridin-4-yl)-1H-benzimidazol-1-yl]-N-methylacetamide (Example 35): $^1$H NMR (300 MHz, DMSO-d$_6$) δ 11.91 (s, 1H), 8.55 (s, 1H), 8.06-7.91 (m, 1H), 7.70 (d, J=8.4 Hz, 1H), 7.37 (d, J=8.3 Hz, 1H), 7.22-7.16 (m, 1H), 7.16-7.02 (m, 2H), 6.62-6.48 (m, 1H), 6.40-6.26 (m, 1H), 6.06 (s, 1H), 5.00 (s, 2H), 3.43 (s, 3H), 2.23 (d, J=4.4 Hz, 3H); LCMS calculated for C$_{24}$H$_{20}$F$_2$N$_5$O$_3$ (M+H)$^+$: m/z=464.2; found: 464.2. 2-[4-(2,4-difluorophenoxy)-5-(6-methyl-7-oxo-6,7-dihydro-1H-pyrrolo[2,3-c]pyridin-4-yl)-1H-benzimidazol-1-yl]-N-methylacetamide (Example 36): $^1$H NMR (300 MHz, DMSO-d$_6$) δ 12.00 (br s, 1H), 8.36-8.20 (m, 1H), 8.12 (s, 1H), 7.43 (d, J=8.4 Hz, 1H), 7.35 (d, J=8.3 Hz, 1H), 7.29-7.13 (m, 3H), 6.84-6.70 (m, 1H), 6.70-6.55 (m, 1H), 6.13 (d, J=2.7 Hz, 1H), 4.95 (s, 2H), 3.49 (s, 3H), 2.65 (d, J=4.5 Hz, 3H); LCMS calculated for C$_{24}$H$_{20}$F$_2$N$_5$O$_3$ (M+H)$^+$: m/z=464.2; found: 464.2.

Examples 42 and 43. 6-Methyl-4-[1-(2-morpholin-4-ylethyl)-7-phenoxy-1H-benzimidazol-6-yl]-1,6-dihydro-7H-pyrrolo[2,3-c]pyridin-7-one and 6-methyl-4-[1-(2-morpholin-4-ylethyl)-4-phenoxy-1H-benzimidazol-5-yl]-1,6-dihydro-7H-pyrrolo[2,3-c]pyridin-7-one

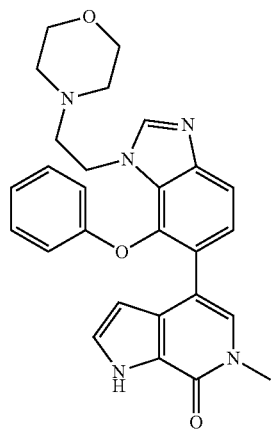

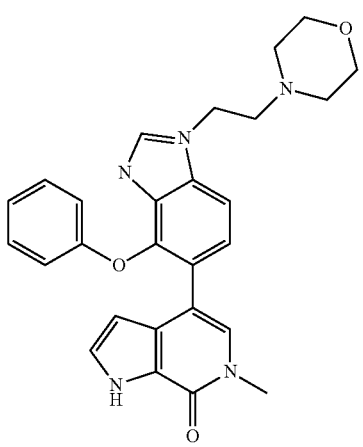

A solution of 6-methyl-4-(4-phenoxy-1H-benzimidazol-5-yl)-1-{[2-(trimethylsilyl)ethoxy]methyl}-1,6-dihydro-7H-pyrrolo[2,3-c]pyridin-7-one (50.0 mg, 0.103 mmol) in N,N-dimethylformamide (1.02 mL) was treated with cesium carbonate (167 mg, 0.514 mmol) followed by the addition of 4-(2-bromoethyl)morpholine hydrochloride (59.2 mg, 0.257 mmol). The resultant reaction mixture was warmed to 60° C. and stirred at that temperature for for 1 h. The reaction mixture was diluted with ethyl acetate and water. Layers were separated and the organic layer was washed with brine, dried with magnesium sulfate, filtered, and concentrated to give the crude intermediate amides as a mixture of isomers which was used without further purification. The crude mixture of intermediate amides was diluted with methylene chloride (1.0 mL) and trifluoroacetic acid (0.5 mL) and stirred at RT for 30 min. The reaction mixture was concentrated in vacuo and the resultant residue was reconcentrated from toluene. This crude residue was diluted with methanol (1.0 mL), treated with ethylenediamine (0.25 mL), and stirred at RT for 2 h. The reaction mixture was concentrated and purified via preparative LCMS (XBridge C18 column, eluting with a gradient of acetonitrile/water 0.1% ammonium hydroxide, at flow rate of 60 mL/min) to give the desired compound 6-Methyl-4-[1-(2-morpholin-4-ylethyl)-7-phenoxy-1H-benzimidazol-6-yl]-1,6-dihydro-7H-pyrrolo[2,3-c]pyridin-7-one (Example 42) as peak 1 (6 mg, 12%) and the desired compound 6-methyl-4-[1-(2-morpholin-4-ylethyl)-4-phenoxy-1H-benzimidazol-5-yl]-1,6-dihydro-7H-pyrrolo[2,3-c]pyridin-7-one (Example 43) as peak 2 (18 mg, 37%). Example 42: $^1$H NMR (300 MHz, DMSO-$d_6$) δ 11.98 (br s, 1H), 8.17 (s, 1H), 7.61 (d, J=8.4 Hz, 1H), 7.37 (d, J=8.4 Hz, 1H), 7.24 (d, J=2.8 Hz, 1H), 7.21-7.03 (m, 2H), 6.84 (dd, J=7.3, 7.3 Hz, 1H), 6.72-6.56 (m, 2H), 6.17 (d, J=2.8 Hz, 1H), 4.39 (dd, J=6.2, 6.2 Hz, 2H), 3.62-3.50 (m, 4H), 3.33 (s, 3H), 2.72 (dd, J=6.2, 6.2 Hz, 2H), 2.47-2.41 (m, 4H); LCMS calculated for $C_{27}H_{28}N_5O_3$ (M+H)$^+$: m/z=470.2; found: 470.2. Example 43: $^1$H NMR (300 MHz, DMSO-$d_6$) δ 11.93 (br s, 1H), 8.21 (s, 1H), 7.65 (d, J=8.3 Hz, 1H), 7.32 (d, J=8.3 Hz, 1H), 7.25 (dd, J=2.7, 2.7 Hz, 1H), 7.15 (s, 1H), 7.13-7.04 (m, 2H), 6.83 (dd, J=7.3, 7.3 Hz, 1H), 6.55 (d, J=7.8 Hz, 2H), 6.32-6.14 (m, 1H), 4.21 (dd, J=6.2, 6.2 Hz, 2H), 3.50-3.43 (m, 4H), 3.33 (s, 3H), 2.53 (d, J=6.2 Hz, 2H), 2.30-2.19 (m, 4H); LCMS calculated for $C_{27}H_{28}N_5O_3$ (M+H)$^+$: m/z=470.2; found: 470.2.

Example 44. 3-Benzyl-4-methoxy-1-methyl-5-(6-methyl-7-oxo-6,7-dihydro-1H-pyrrolo[2,3-c]pyridin-4-yl)-1,3-dihydro-2H-benzimidazol-2-one

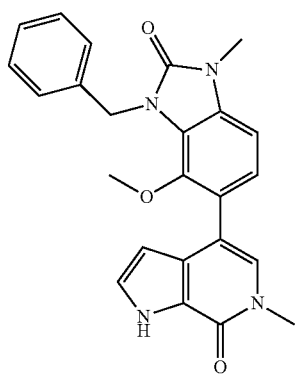 [SMILES: COc1c(-c2cn(C)c(=O)c3[nH]ccc23)ccc2c1n(Cc1ccccc1)c(=O)n2C]

Step 1. 5-Bromo-4-methoxy-1-methyl-1,3-dihydro-2H-benzimidazol-2-one

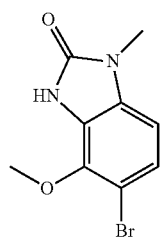

A 1.0 M solution of hydrogen chloride in water (2.3 mL, 2.3 mmol) was added to a suspension of iron (1.28 g, 23.0 mmol) (<10 μm) in ethanol (25.1 mL) and the resultant suspension was stirred at 60° C. for 2 h. The reaction mixture was then cooled to 55-60° C. and treated with a 5.0 M solution of ammonium chloride in water (3950 μL, 19.8 mmol), followed by the addition of 4-bromo-3-methoxy-N-methyl-2-nitroaniline (1.20 g, 4.60 mmol) as a solid. The flask containing 4-bromo-3-methoxy-N-methyl-2-nitroaniline was rinsed with ethanol (3.75 mL) and the solution was added to the reaction mixture. The resultant reaction mixture was stirred at 60-65° C. for 2 h, after which time the reaction mixture was diluted with ethyl acetate (100 mL), treated with anhydrous magnesium sulfate, stirred for 10 min and then filtered through a pad of Celite. The filtrate was concentrated to dryness in vacuo and the resulting solid was used immediately without further purification. The crude bis-aniline was dissolved in tetrahydrofuran (32.0 mL), treated with N,N-carbonyldiimidazole (1.86 g, 11.5 mmol) and stirred at RT overnight. The reaction mixture was diluted with ethyl acetate and water. Layers were separated and the organic layer was washed with brine, dried with magnesium sulfate, filtered, and concentrated in vacuo to give the crude product. Purification by flash column chromatography (100% hexanes to 30% EtOAc/hexanes to 100% EtOAc) gave the desired product (1.05 g, 89%) as a solid. LCMS calculated for $C_9H_{10}BrN_2O_2$ (M+H)$^+$: m/z=257.0, 259.0; found: 257.1, 259.1.

Step 2. 3-Benzyl-5-bromo-4-methoxy-1-methyl-1,3-dihydro-2H-benzimidazol-2-one

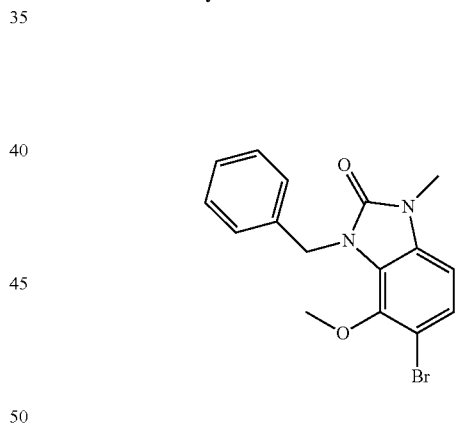

A solution of 5-bromo-4-methoxy-1-methyl-1,3-dihydro-2H-benzimidazol-2-one (60.0 mg, 0.233 mmol) in N,N-dimethylformamide (2.31 mL) was treated with cesium carbonate (380 mg, 1.17 mmol) and benzyl bromide (99.8 mg, 0.583 mmol) and stirred at 60° C. for 30 min. The reaction mixture was diluted with ethyl acetate and water. Layers were separated and the organic layer was washed with brine, dried with magnesium sulfate, filtered, and concentrated in vacuo to give the crude product. Purification by flash column chromatography (15% EtOAc/hexanes to 40% EtOAc/hexanes) gave the desired product (73 mg, 90%). LCMS calculated for $C_{16}H_{16}BrN_2O_2$ (M+H)$^+$: m/z=347.1, 349.1; found: 347.0, 349.0.

Step 3. 3-Benzyl-4-methoxy-1-methyl-5-(6-methyl-7-oxo-6,7-dihydro-1H-pyrrolo[2,3-c]pyridin-4-yl)-1,3-dihydro-2H-benzimidazol-2-one

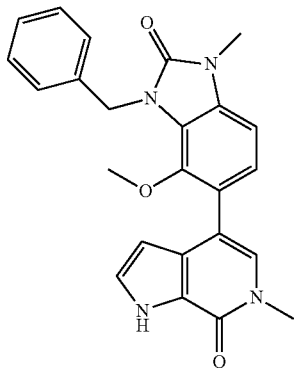 [SMILES: COc1c(-c2cn(C)c(=O)c3[nH]ccc23)ccc2c1n(Cc1ccccc1)c(=O)n2C]

A solution of 4-(di-tert-butylphosphino)-N,N-dimethylaniline-dichloropalladium (2:1) (2.20 mg, 0.00311 mmol), cesium fluoride (110 mg, 0.726 mmol), 3-benzyl-5-bromo-4-methoxy-1-methyl-1,3-dihydro-2H-benzimidazol-2-one (72.0 mg, 0.207 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (88.8 mg, 0.207 mmol) in 1-butanol (0.944 mL) and water (0.22 mL) was degassed with nitrogen for 5 minutes and the resultant reaction mixture was stirred at 100° C. for 1 h. The reaction mixture was diluted with ethyl acetate and water. Layers were separated and the organic layer was washed with brine, dried with magnesium sulfate, filtered, and concentrated to give the crude intermediate urea which was used without further purification. The intermediate urea was dissolved in methanol (1.0 mL), treated with 3.0 M sodium hydroxide in water (0.5 mL, 1.5 mmol), and heated at 60° C. for 3 h. The reaction mixture was purified via preparative LCMS (XBridge C18 column, eluting with a gradient of acetonitrile/water containing 0.1% trifluoroacetic acid, at flow rate of 60 mL/min) to give the desired product (40 mg, 47%). $^1$H NMR (300 MHz, DMSO-$d_6$) δ 12.02 (br s, 1H), 7.38-7.28 (m, 2H), 7.28-7.15 (m, 5H), 7.04 (s, 2H), 6.07-5.97 (m, 1H), 5.20 (s, 2H), 3.53 (s, 3H), 3.39 (s, 3H), 3.04 (s, 3H); LCMS calculated for $C_{24}H_{23}N_4O_3$ (M+H)$^+$: m/z=415.2; found: 415.1.

The examples in Table 3 were synthesized according to procedure of Examples 42 and 43 using the appropriate electrophiles.

TABLE 3

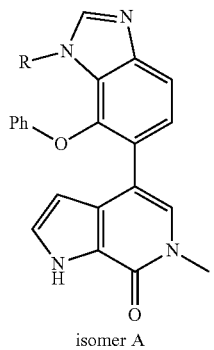

isomer A

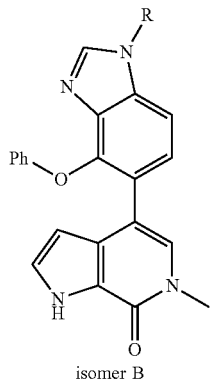

isomer B

| Ex. No. | Compound Name | R | Isomer | MS [M + H]$^+$ |
|---|---|---|---|---|
| 45 | 4-(1-Benzyl-7-phenoxy-1H-benzimidazol-6-yl)-6-methyl-1,6-dihydro-7H-pyrrolo[2,3-c]pyridin-7-one | benzyl | A | 447.1 |

TABLE 3-continued

| # | Name | Structure | | Mass |
|---|---|---|---|---|
| 46 | 4-(1-Benzyl-4-phenoxy-1H-benzimidazol-5-yl)-6-methyl-1,6-dihydro-7H-pyrrolo[2,3-c]pyridin-7-one | benzyl | B | 447.1 |
| 47 | 6-Methyl-4-[7-phenoxy-1-(2-phenylethyl)-1H-benzimidazol-6-yl]-1,6-dihydro-7H-pyrrolo[2,3-c]pyridin-7-one | phenylethyl | A | 461.1 |
| 48 | 6-Methyl-4-[4-phenoxy-1-(2-phenylethyl)-1H-benzimidazol-5-yl]-1,6-dihydro-7H-pyrrolo[2,3-c]pyridin-7-one | phenylethyl | B | 461.1 |
| 51 | 4-[6-(6-Methyl-7-oxo-6,7-dihydro-1H-pyrrolo[2,3-c]pyridin-4-yl)-7-phenoxy-1H-benzimidazol-1-yl]butanenitrile | NC-(CH2)3- | A | 424.1 |
| 52 | 4-[5-(6-Methyl-7-oxo-6,7-dihydro-1H-pyrrolo[2,3-c]pyridin-4-yl)-4-phenoxy-1H-benzimidazol-1-yl]butanenitrile | NC-(CH2)3- | B | 424.1 |
| 55 | 3-[6-(6-Methyl-7-oxo-6,7-dihydro-1H-pyrrolo[2,3-c]pyridin-4-yl)-7-phenoxy-1H-benzimidazol-1-yl]propanenitrile | NC-(CH2)2- | A | 410.1 |
| 113 | 3-[5-(6-Methyl-7-oxo-6,7-dihydro-1H-pyrrolo[2,3-c]pyridin-4-yl)-4-phenoxy-1H-benzimidazol-1-yl]propanenitrile | NC-(CH2)2- | B | 410.1 |

$^1$H NMR data for examples 45-48, 51, 52, 55, 113

| Ex. No. | $^1$H NMR |
|---|---|
| 45 | (500 MHz, DMSO-$d_6$) δ 11.85 (br s, 1H), 8.40 (s, 1H), 7.67 (d, J = 8.3 Hz, 1H), 7.33 (d, J = 8.3 Hz, 1H), 7.30-7.19 (m, 4H), 7.12-6.99 (m, 5H), 6.80 (dd, J = 7.3, 7.3 Hz, 1H), 6.46 (d, J = 7.9 Hz, 2H), 6.07 (d, J = 2.8 Hz, 1H), 5.32 (s, 2H), 3.38 (s, 3H) |
| 46 | NA |
| 47 | (400 MHz, DMSO-$d_6$) δ 11.99 (br s, 1H), 7.99 (s, 1H), 7.62 (d, J = 8.4 Hz, 1H), 7.37 (d, J = 8.3 Hz, 1H), 7.32-7.02 (m, 9H), 6.84 (dd, J = 7.3, 7.3 Hz, 1H), 6.60 (d, J = 7.9 Hz, 2H), 6.17 (d, J = 2.7 Hz, 1H), 4.52 (dd, J = 7.3, 7.3 Hz, 2H), 3.44 (s, 3H), 3.15 (dd, J = 7.2, 7.2 Hz, 2H) |
| 48 | (400 MHz, DMSO-$d_6$) δ 11.95 (br s, 1H), 8.06 (s, 1H), 7.64 (d, J = 8.3 Hz, 1H), 7.34 (d, J = 8.3 Hz, 1H), 7.29-7.07 (m, 7H), 6.97 (d, J = 6.7 Hz, 2H), 6.84 (dd, J = 7.3, 7.3 Hz, 1H), 6.60 (d, J = 7.9 Hz, 2H), 6.24 (d, J = 2.8 Hz, 1H), 4.31 (dd, J = 7.5, 7.5 Hz, 2H), 3.43 (s, 3H), 2.99 (dd, J = 7.5, 7.5 Hz, 2H) |
| 51 | (500 MHz, DMSO-$d_6$) δ 11.94 (br s, 1H), 8.19 (s, 1H), 7.61 (d, J = 8.3 Hz, 1H), 7.40 (d, J = 8.3 Hz, 1H), 7.23 (d, J = 2.5 Hz, 1H), 7.18-6.99 (m, 3H), 6.84 (dd, J = 7.3, 7.3 Hz, 1H), 6.65 (d, J = 8.0 Hz, 2H), 6.18 (d, J = 2.5 Hz, 1H), 4.36 (dd, J = 7.0, 7.0 Hz, 2H), 3.44 (s, 3H), 2.57 (dd, J = 7.1, 7.1 Hz, 2H), 2.31-2.07 (m, 2H) |
| 52 | (500 MHz, DMSO-$d_6$) δ 11.94 (br s, 1H), 8.94 (s, 1H), 7.77 (d, J = 8.4 Hz, 1H), 7.54 (d, J = 8.4 Hz, 1H), 7.26 (dd, J = 2.6, 2.6 Hz, 1H), 7.19 (s, 1H), 7.14-6.99 (m, 2H), 6.85 (dd, J = 7.3, 7.3 Hz, 1H), 6.61 (d, J = 8.1 Hz, 2H), 6.22 (s, 1H), 4.29 (dd, J = 6.9, 6.9 Hz, 2H), 3.42 (s, 3H), 2.23-1.97 (m, 2H) |
| 55 | NA |
| 113 | (500 MHz, DMSO-$d_6$) δ 11.95 (br s, 1H), 8.25 (s, 1H), 7.71 (d, J = 8.4 Hz, 1H), 7.42 (d, J = 8.4 Hz, 1H), 7.24 (dd, J = 2.7, 2.7 Hz, 1H), 7.20-7.03 (m, 3H), 6.85 (dd, J = 7.3, 7.3 Hz, 1H), 6.64 (d, J = 7.8 Hz, 2H), 6.31-6.01 (m, 1H), 4.63 (t, J = 6.6 Hz, 2H), 3.44 (s, 3H), 3.18 (t, J = 6.6 Hz, 2H) |

The examples in Table 4 were synthesized according to procedure of Example 44 using the appropriate electrophiles.

TABLE 4

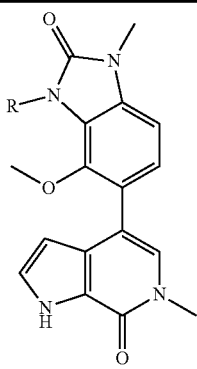

| Ex. No. | Compound Name | R | MS [M + H]+ |
|---|---|---|---|
| 49 | 4-Methoxy-1-methyl-5-(6-methyl-7-oxo-6,7-dihydro-1H-pyrrolo[2,3-c]pyridin-4-yl)-3-(2-phenylethyl)-1,3-dihydro-2H-benzimidazol-2-one | phenylethyl | 429.1 |
| 50 | 4-Methoxy-1-methyl-5-(6-methyl-7-oxo-6,7-dihydro-1H-pyrrolo[2,3-c]pyridin-4-yl)-3-(2-morpholin-4-ylethyl)-1,3-dihydro-2H-benzimidazol-2-one | 2-morpholin-4-ylethyl | 438.2 |
| 53 | 4-[7-Methoxy-3-methyl-6-(6-methyl-7-oxo-6,7-dihydro-1H-pyrrolo[2,3-c]pyridin-4-yl)-2-oxo-2,3-dihydro-1H-benzimidazol-1-yl]butanenitrile | NC-(CH2)3- | 392.1 |
| 54 | 3-[7-Methoxy-3-methyl-6-(6-methyl-7-oxo-6,7-dihydro-1H-pyrrolo[2,3-c]pyridin-4-yl)-2-oxo-2,3-dihydro-1H-benzimidazol-1-yl]propanenitrile | NC-(CH2)2- | 378.1 |

| NMR data for examples 49, 50, 53, 54 | |
|---|---|
| Ex. No. | $^1$H NMR |
| 49 | (400 MHz, DMSO-$d_6$) δ 12.06 (br s, 1H), 7.33-7.25 (m, 4H), 7.24-7.13 (m, 3H), 7.05 (d, J = 8.0 Hz, 1H), 7.00 (d, J = 8.1 Hz, 1H), 6.17-6.09 (m, 1H), 4.25-4.07 (m, 2H), 3.58 (s, 3H), 3.42 (s, 3H), 3.33 (s, 3H), 3.05-2.91 (m, 2H) |
| 50 | (400 MHz, DMSO-$d_6$) δ 12.05 (br s, 1H), 7.27 (dd, J = 2.8, 2.8 Hz, 1H), 7.24 (s, 1H), 7.04 (d, J = 8.0 Hz, 1H), 6.99 (d, J = 8.1 Hz, 1H), 6.22-5.98 (m, 1H), 4.12-3.97 (m, 2H), 3.57 (s, 3H), 3.53-3.46 (m, 4H), 3.38 (s, 3H), 3.33 (s, 3H), 2.61 (dd, J = 6.8, 6.8 Hz, 2H), 2.46-2.28 (m, 4H) |
| 53 | (300 MHz, DMSO-$d_6$) δ 12.05 (br s, 1H), 7.33-7.20 (m, 2H), 7.13-6.92 (m, 2H), 6.12 (d, J = 2.6 Hz, 1H), 4.14-3.91 (m, 2H), 3.57 (s, 3H), 3.40 (s, 3H), 3.34 (s, 3H), 2.59 (dd, J = 7.0, 7.0 Hz, 2H), 2.09-1.90 (m, 2H) |
| 54 | (300 MHz, DMSO-$d_6$) δ 12.04 (br s, 1H), 7.34-7.19 (m, 2H), 7.16-6.98 (m, 2H), 6.19 (dd, J = 2.0, 2.0 Hz, 1H), 4.24 (dd, J = 6.3, 6.3 Hz, 2H), 3.57 (s, 3H), 3.40 (s, 3H), 3.36 (s, 3H), 3.00 (dd, J = 6.4, 6.4 Hz, 2H) |

The examples in Table 5 were synthesized according to procedure of example 4 using the appropriate phenols.

TABLE 5

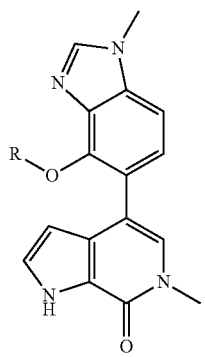

| Ex. No. | Compound Name | R | MS [M + H]+ |
|---|---|---|---|
| 56 | 6-Methyl-4-(1-methyl-4-phenoxy-1H-benzimidazol-5-yl)-1,6-dihydro-7H-pyrrolo[2,3-c]pyridin-7-one | phenyl | 371.1 |
| 57 | 4-[4-(2-Fluorophenoxy)-1-methyl-1H-benzimidazol-5-yl]-6-methyl-1,6-dihydro-7H-pyrrolo[2,3-c]pyridin-7-one | 2-fluorophenyl | 389.1 |
| 58 | 4-[4-(3-Fluorophenoxy)-1-methyl-1H-benzimidazol-5-yl]-6-methyl-1,6-dihydro-7H-pyrrolo[2,3-c]pyridin-7-one | 3-fluorophenyl | 389.0 |
| 59 | 4-[4-(4-Fluorophenoxy)-1-methyl-1H-benzimidazol-5-yl]-6-methyl-1,6-dihydro-7H-pyrrolo[2,3-c]pyridin-7-one | 4-fluorophenyl | 389.1 |

$^1$H NMR data for examples 56-59

| Ex. No. | $^1$H NMR |
|---|---|
| 56 | (300 MHz, DMSO-$d_6$) δ 11.93 (br s, 1H), 8.12 (s, 1H), 7.55 (d, J = 8.4 Hz, 1H), 7.40 (d, J = 8.3 Hz, 1H), 7.24 (d, J = 2.8 Hz, 1H), 7.18-7.04 (m, 3H), 6.84 (dd, J = 7.3, 7.3 Hz, 1H), 6.73-6.58 (m, 2H), 6.16 (d, J = 2.8 Hz, 1H), 3.88 (s, 3H), 3.44 (s, 3H) |
| 57 | (300 MHz, DMSO-$d_6$) δ 11.98 (br s, 1H), 8.13 (s, 1H), 7.56 (d, J = 8.4 Hz, 1H), 7.39 (d, J = 8.3 Hz, 1H), 7.28-7.07 (m, 3H), 7.01-6.73 (m, 2H), 6.64-6.38 (m, 1H), 6.14 (d, J = 2.8 Hz, 1H), 3.88 (s, 3H), 3.47 (s, 3H) |
| 58 | (300 MHz, DMSO-$d_6$) δ 11.99 (br s, 1H), 8.15 (s, 1H), 7.58 (d, J = 8.3 Hz, 1H), 7.40 (d, J = 8.3 Hz, 1H), 7.24 (d, J = 2.7 Hz, 1H), 7.21-7.02 (m, 2H), 6.80-6.62 (m, 1H), 6.57-6.37 (m, 2H), 6.14 (d, J = 2.7 Hz, 1H), 3.88 (s, 3H), 3.46 (s, 3H) |
| 59 | (300 MHz, DMSO-$d_6$) δ 11.97 (br s, 1H), 8.13 (s, 1H), 7.55 (d, J = 8.3 Hz, 1H), 7.39 (d, J = 8.3 Hz, 1H), 7.24 (d, J = 2.8 Hz, 1H), 7.14 (s, 1H), 7.06-6.84 (m, 2H), 6.81-6.56 (m, 2H), 6.14 (d, J = 2.7 Hz, 1H), 3.87 (s, 3H), 3.46 (s, 3H) |

Example 60. 4-(Cyclobutylmethoxy)-1-methyl-5-(6-methyl-7-oxo-6,7-dihydro-1H-pyrrolo[2,3-c]pyridin-4-yl)-3-(2-morpholin-4-ylethyl)-1,3-dihydro-2H-benzimidazol-2-one

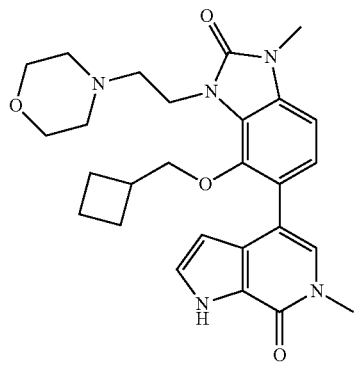 [SMILES: Cn1cc(-c2ccc3c(c2OCC2CCC2)n(CCN2CCOCC2)c(=O)n3C)c2cc[nH]c2c1=O]

Step 1. 4-Bromo-3-fluoro-N-methyl-2-nitroaniline

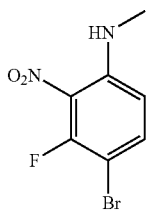

A solution of N-(4-bromo-3-fluoro-2-nitrophenyl)-2,2,2-trifluoroacetamide (3.42 g, 10.3 mmol) and triphenylphosphine (3.79 g, 14.4 mmol) in tetrahydrofuran (31.0 mL) at 0° C. was treated with methanol (1.67 mL, 41.3 mmol) followed by dropwise addition of diisopropyl azodicarboxylate (2.84 mL, 14.4 mmol), and the resultant reaction mixture was stirred at RT for 2 h. The reaction mixture was quenched with water (10 mL), concentrated in vacuo to remove most of the THF. Water (200 mL) was added and the resultant mixture was extracted with ethyl acetate (200 mL). Layers were separated and the organic layer was washed with brine, dried with sodium sulfate, filtered, and concentrated to give the crude product. Purification by flash column chromatography (100% hexanes to 80% dichloromethane/hexanes) gave the desired product (2.46 g, 96%) as an orange solid. LCMS calculated for $C_7H_7BrFN_2O_2$ (M+H)$^+$: m/z=249.0, 251.0; found: 248.9, 250.9.

Step 2. 4-Bromo-3-(cyclobutylmethoxy)-N-methyl-2-nitroaniline

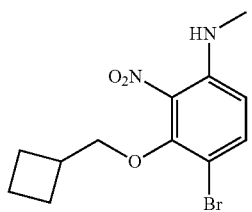 [SMILES: CNc1ccc(Br)c(OCC2CCC2)c1N]

This compound was synthesized according to the procedure of Example 11, Step 1, using 4-bromo-3-fluoro-N-methyl-2-nitroaniline and cyclobutylmethanol as the starting materials. LCMS calculated for $C_{12}H_{16}BrN_2O_3$ (M+H)$^+$: m/z=315.0, 317.0; found: 315.0, 317.0.

Step 3. 4-Bromo-3-(cyclobutylmethoxy)-N$^1$-methyl-benzene-1,2-diamine

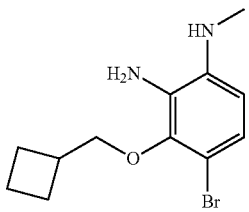

This compound was synthesized according to the procedure of Example 1, Step 3, using 4-bromo-3-(cyclobutylmethoxy)-N-methyl-2-nitroaniline as the starting material. LCMS calculated for $C_{12}H_{18}BrN_2O$ (M+H)$^+$: m/z=285.1, 287.1; found: 285.1, 287.1.

Step 4. 5-Bromo-4-(cyclobutylmethoxy)-1-methyl-1,3-dihydro-2H-benzimidazol-2-one

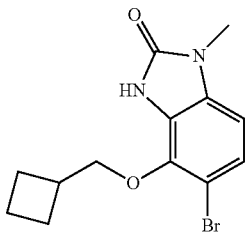 [SMILES: Cn1c(=O)[nH]c2c(OCC3CCC3)c(Br)ccc21]

This compound was synthesized according to the procedure of Example 6, Step 1, using 4-bromo-3-(cyclobutylmethoxy)-N$^1$-methylbenzene-1,2-diamine as the starting material. LCMS calculated for $C_{13}H_{16}BrN_2O_2$ (M+H)$^+$: m/z=311.0, 313.0; found: 311.0, 313.0.

Step 5. 5-Bromo-4-(cyclobutylmethoxy)-1-methyl-3-(2-morpholin-4-ylethyl)-1,3-dihydro-2H-benzimidazol-2-one

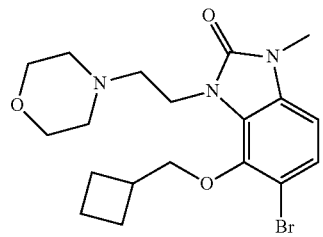 [SMILES: Cn1c(=O)n(CCN2CCOCC2)c2c(OCC3CCC3)c(Br)ccc21]

This compound was synthesized according to the procedure of Example 44, Step 2, using 5-bromo-4-(cyclobutylmethoxy)-1-methyl-1,3-dihydro-2H-benzimidazol-2-one and 4-(2-bromoethyl)morpholine hydrochloride as the starting materials. LCMS calculated for $C_{19}H_{27}BrN_3O_3$ (M+H)$^+$: m/z=424.1, 426.1; found: 424.3, 426.3.

Step 6. 4-(Cyclobutylmethoxy)-1-methyl-5-(6-methyl-7-oxo-6,7-dihydro-1H-pyrrolo[2,3-c]pyridin-4-yl)-3-(2-morpholin-4-ylethyl)-1,3-dihydro-2H-benzimidazol-2-one This compound was synthesized according to the procedure of Example 44, Step 3, using 5-bromo-4-(cyclobutylmethoxy)-1-methyl-3-(2-morpholin-4-ylethyl)-1,3-dihydro-2H-benzimidazol-2-one as the starting material. $^1$H NMR (300 MHz, DMSO-d$_6$) δ 12.01 (br s, 1H), 7.30-7.26 (m, 1H), 7.23 (s, 1H), 7.05 (d, J=8.0 Hz, 1H), 6.99 (d, J=8.0 Hz, 1H), 6.10 (s, 1H), 4.07 (dd, J=6.4, 6.4 Hz, 2H), 3.56 (s, 3H), 3.55-3.41 (m, 6H), 3.33 (s, 3H), 2.63 (dd, J=6.5, 6.5 Hz, 2H), 2.46-2.32 (m, 5H), 1.84-1.60 (m, 3H), 1.60-1.44 (m, 1H), 1.44-1.16 (m, 2H); LCMS calculated for C$_{27}$H$_{34}$N$_5$O$_4$ (M+H)$^+$: m/z=492.3; found: 492.2.

The examples in Table 6 were synthesized according to procedure of Example 60 using the appropriate electrophiles.

TABLE 6

| Ex. No. | Compound Name | R | MS [M + H]$^+$ |
|---|---|---|---|
| 61 | 4-[7-(Cyclobutylmethoxy)-3-methyl-6-(6-methyl-7-oxo-6,7-dihydro-1H-pyrrolo[2,3-c]pyridin-4-yl)-2-oxo-2,3-dihydro-1H-benzimidazol-1-yl]butanenitrile | NC-(CH$_2$)$_3$- | 446.1 |
| 62 | 3-[7-(Cyclobutylmethoxy)-3-methyl-6-(6-methyl-7-oxo-6,7-dihydro-1H-pyrrolo[2,3-c]pyridin-4-yl)-2-oxo-2,3-dihydro-1H-benzimidazol-1-yl]propanenitrile | NC-(CH$_2$)$_2$- | 432.2 |
| 63 | 4-(Cyclobutylmethoxy)-1-methyl-5-(6-methyl-7-oxo-6,7-dihydro-1H-pyrrolo[2,3-c]pyridin-4-yl)-3-(2-phenylethyl)-1,3-dihydro-2H-benzimidazol-2-one | Ph-CH$_2$CH$_2$- | 483.2 |
| 64 | 3-Benzyl-4-(cyclobutylmethoxy)-1-methyl-5-(6-methyl-7-oxo-6,7-dihydro-1H-pyrrolo[2,3-c]pyridin-4-yl)-1,3-dihydro-2H-benzimidazol-2-one | Ph-CH$_2$- | 469.2 |

| $^1$H NMR data for examples 61-64 | |
|---|---|
| Ex. No. | $^1$H NMR |
| 61 | (300 MHz, DMSO-d$_6$) δ 12.02 (br s, 1H), 7.44-7.18 (m, 2H), 7.18-6.79 (m, 2H), 6.11 (s, 1H), 4.22-3.88 (m, 2H), 3.56 (s, 3H), 3.54-3.43 (m, 2H), 2.01 (d, J = 6.5 Hz, 2H), 1.88-1.60 (m, 3H), 1.52 (s, 1H), 1.32 (d, J = 8.2 Hz, 2H) |
| 62 | (300 MHz, DMSO-d$_6$) δ 12.01 (br s, 1H), 7.36-7.19 (m, 2H), 7.10 (d, J = 8.1 Hz, 1H), 7.03 (d, J = 8.1 Hz, 1H), 6.19 (d, J = 2.7 Hz, 1H), 4.23 (dd, J = 6.5, 6.5 Hz, 2H), 3.56 (s, 3H), 3.53 (d, J = 6.7 Hz, 2H), 3.36 (s, 3H), 3.02 (dd, J = 6.5, 6.5 Hz, 2H), 2.46-2.29 (m, 1H), 1.84-1.61 (m, 3H), 1.61-1.46 (m, 1H), 1.46-1.27 (m, 2H) |
| 63 | (400 MHz, DMSO-d$_6$) δ 12.02 (br s, 1H), 7.36-7.23 (m, 4H), 7.23-7.13 (m, 3H), 7.07 (d, J = 8.0 Hz, 1H), 7.00 (d, J = 8.1 Hz, 1H), 6.23-6.02 (m, 1H), 4.34-4.09 (m, 2H), 3.57 (s, 3H), 3.47 (d, J = 6.7 Hz, 2H), 3.32 (s, 3H), 3.09-2.90 (m, 2H), 2.41-2.24 (m, 1H), 1.81-1.56 (m, 3H), 1.56-1.39 (m, 1H), 1.39-1.16 (m, 2H) |
| 64 | (400 MHz, DMSO-d$_6$) δ 12.00 (br s, 1H), 7.38-7.27 (m, 2H), 7.27-7.15 (m, 5H), 7.13-6.98 (m, 2H), 6.21-5.85 (m, 1H), 5.23 (s, 2H), 3.53 (s, 3H), 3.38 (s, 3H), 3.22 (d, J = 6.7 Hz, 2H), 2.30-2.11 (m, 1H), 1.70-1.55 (m, 3H), 1.50-1.35 (m, 1H), 1.19-1.05 (m, 2H) |

Example 65. 4-(Cyclobutylmethoxy)-1-methyl-5-(6-methyl-7-oxo-6,7-dihydro-1H-pyrrolo[2,3-c]pyridin-4-yl)-3-(2-piperidin-4-ylethyl)-1,3-dihydro-2H-benzimidazol-2-one

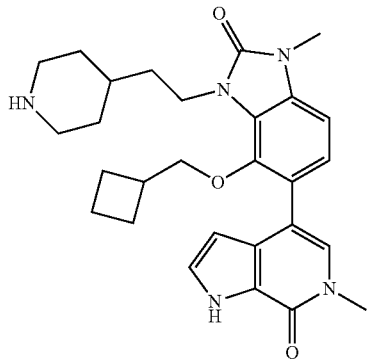 [SMILES: Cn1cc(-c2ccc3c(c2OCC2CCC2)n(CCC2CCNCC2)c(=O)n3C)c2cc[nH]c2c1=O]

Step 1. tert-Butyl 4-{2-[6-bromo-7-(cyclobutylmethoxy)-3-methyl-2-oxo-2,3-dihydro-1H-benzimidazol-1-yl]ethyl}piperidine-1-carboxylate

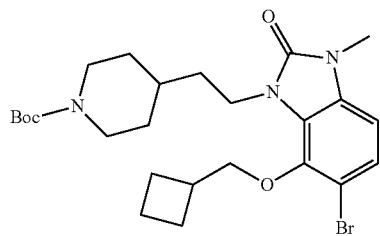 [SMILES: Cn1c(=O)n(CCC2CCN(C(=O)OC(C)(C)C)CC2)c2c(OCC3CCC3)c(Br)ccc21]

This compound was synthesized according to the procedure of Example 44, Step 2, using 5-bromo-4-(cyclobutylmethoxy)-1-methyl-1,3-dihydro-2H-benzimidazol-2-one and tert-butyl 4-(2-bromoethyl)piperidine-1-carboxylate as the starting materials. LCMS calculated for $C_{20}H_{29}BrN_3O_2$ ([M-Boc+H]+H)$^+$: m/z=422.2, 424.2; found: 422.0, 424.0.

Step 2. 4-(Cyclobutylmethoxy)-1-methyl-5-{6-methyl-1-[(4-methylphenyl)sulfonyl]-7-oxo-6,7-dihydro-1H-pyrrolo[2,3-c]pyridin-4-yl}-3-(2-piperidin-4-ylethyl)-1,3-dihydro-2H-benzimidazol-2-one trifluoroacetate

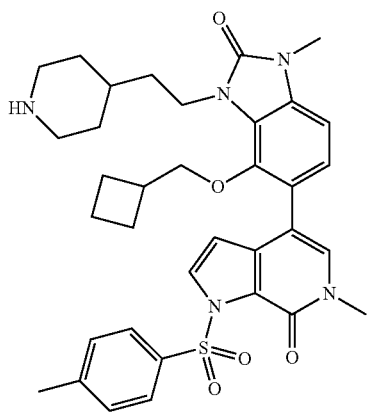 [SMILES: Cc1ccc(S(=O)(=O)n2ccc3c(-c4ccc5c(c4OCC4CCC4)n(CCC4CCNCC4)c(=O)n5C)cn(C)c(=O)c32)cc1]

A solution of 4-(di-tert-butylphosphino)-N,N-dimethylaniline-dichloropalladium (2:1) (1.46 mg, 0.00206 mmol), cesium fluoride (72.8 mg, 0.480 mmol), tert-butyl 4-{2-[6-bromo-7-(cyclobutylmethoxy)-3-methyl-2-oxo-2,3-dihydro-1H-benzimidazol-1-yl]ethyl}piperidine-1-carboxylate (71.6 mg, 0.137 mmol), 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one (58.7 mg, 0.137 mmol) in 1-butanol (0.624 mL) and water (0.15 mL) was degassed with nitrogen for 5 min and the resultant reaction mixture was stirred at 100° C. for 1 h. The reaction mixture was diluted with ethyl acetate and water. Layers were separated and the organic layer was washed with brine, dried with magnesium sulfate, filtered, and concentrated in vacuo to give the crude intermediate which was used without further purification. The crude intermediate was dissolved in a mixture of methylene chloride (2.0 mL) and trifluoroacetic acid (1.0 mL) and the resultant solution was stirred at RT for 3 h, after which time the reaction mixture was purified via preparative LCMS (XBridge C18 column, eluting with a gradient of acetonitrile/water containing 0.1% trifluoroacetic acid, at flow rate of 60 mL/min) to give the desired product (37 mg, 42%). LCMS calculated for $C_{35}H_{42}N_5O_5S$ (M+H)$^+$: m/z=644.3; found: 644.3.

Step 3. 4-(Cyclobutylmethoxy)-1-methyl-5-(6-methyl-7-oxo-6,7-dihydro-1H-pyrrolo[2,3-c]pyridin-4-yl)-3-(2-piperidin-4-ylethyl)-1,3-dihydro-2H-benzimidazol-2-one A 3.0 M solution of sodium hydroxide in water (0.40 L) was added to the solution of 4-(cyclobutylmethoxy)-1-methyl-5-{6-methyl-1-[(4-methylphenyl)sulfonyl]-7-oxo-6,7-dihydro-1H-pyrrolo[2,3-c]pyridin-4-yl}-3-(2-piperidin-4-ylethyl)-1,3-dihydro-2H-benzimidazol-2-one (20.0 mg, 0.031 mmol) in methanol (1.0 mL), and the resultant reaction mixture was stirred at 60° C. for 1 h. The reaction mixture was purified via preparative LCMS (XBridge C18 column, eluting with a gradient of acetonitrile/water 0.1% ammonium hydroxide, at flow rate of 60 mL/min) to give the desired product (1.1 mg, 7%). LCMS calculated for $C_{28}H_{36}N_5O_3$ (M+H)$^+$: m/z=490.3; found: 490.3.

Example 66. 3-(2-(4-Acetylpiperazin-1-yl)ethyl)-4-(cyclobutylmethoxy)-1-methyl-5-(6-methyl-7-oxo-6,7-dihydro-1H-pyrrolo[2,3-c]pyridin-4-yl)-1H-benzo[d]imidazol-2(3H)-one

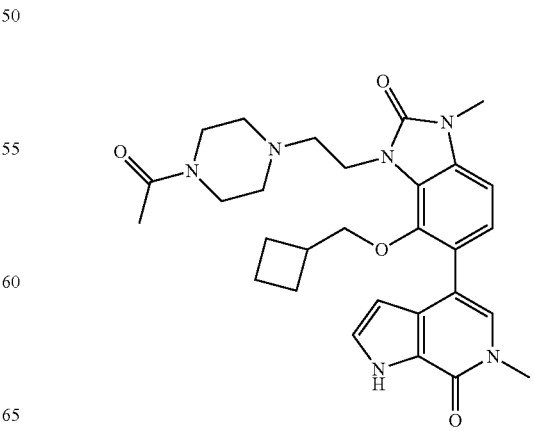

127

Step 1. 5-Bromo-4-(cyclobutylmethoxy)-1-methyl-3-(2-piperazin-1-ylethyl)-1,3-dihydro-2H-benzimidazol-2-one

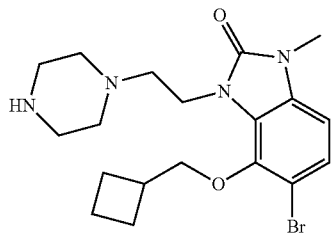 [SMILES: Cn1c(=O)n(CCN2CCNCC2)c2c(OCC3CCC3)c(Br)ccc21]

A solution of 5-bromo-4-(cyclobutylmethoxy)-1-methyl-1,3-dihydro-2H-benzimidazol-2-one (250 mg, 0.803 mmol) in N,N-dimethylformamide (7.96 mL) was treated with cesium carbonate (1.31 g, 4.02 mmol) followed by the addition of tert-butyl 4-(2-bromoethyl)piperazine-1-carboxylate (471 mg, 1.61 mmol), and the resultant reaction mixture was stirred at 60° C. overnight, after which time the LCMS analysis of the reaction mixture indicated complete conversion of the starting materials. The reaction mixture was diluted with ethyl acetate and water. Layers were separated and the organic layer was washed with brine, dried with magnesium sulfate, filtered, and concentrated in vacuo to give the crude intermediate tert-butyl carboxylate, which was used in further step without purification. The crude intermediate tert-butyl carboxylate was dissolved in the mixture of methylene chloride (4.0 mL) and trifluoroacetic acid (3.0 mL) and the resultant reaction mixture was stirred at RT for 2 h. Solvents were removed in vacuo and the resulting residue was diluted with ethyl acetate and saturated sodium bicarbonate solution. Layers were separated and the organic layer was washed with water and brine, dried with magnesium sulfate, filtered, and concentrated in vacuo to give the desired product (289 mg, 85%) that was used in further step without purification. LCMS calculated for $C_{19}H_{28}BrN_4O_2$ (M+H)$^+$: m/z=423.1, 425.1; found: 423.1, 425.1.

Step 2. 3-[2-(4-Acetylpiperazin-1-yl)ethyl]-5-bromo-4-(cyclobutylmethoxy)-1-methyl-1,3-dihydro-2H-benzimidazol-2-one

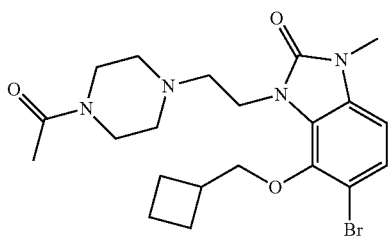 [SMILES: CC(=O)N1CCN(CCn2c(=O)n(C)c3ccc(Br)c(OCC4CCC4)c32)CC1]

A solution of 5-bromo-4-(cyclobutylmethoxy)-1-methyl-3-(2-piperazin-1-ylethyl)-1,3-dihydro-2H-benzimidazol-2-one (40.0 mg, 0.0945 mmol) in methylene chloride (2.0 mL) was treated with N,N-diisopropylethylamine (49.4 µL, 0.283 mmol) followed by the addition of acetyl chloride (10.1 µL, 0.142 mmol), and the resultant reaction mixture was stirred at RT for 1 h. Purification by flash column chromatography

128

(5% MeOH/EtOAc) gave the desired product (46 mg, 94%). LCMS calculated for $C_{21}H_{30}BrN_4O_3$ (M+H)$^+$: m/z=465.1, 467.1; found: 465.1, 467.1.

Step 3. 3-(2-(4-Acetylpiperazin-1-yl)ethyl)-4-(cyclobutylmethoxy)-1-methyl-5-(6-methyl-7-oxo-6,7-dihydro-1H-pyrrolo[2,3-c]pyridin-4-yl)-1H-benzo[d]imidazol-2(3H)-one

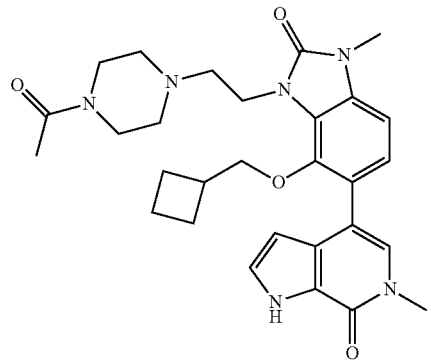 [SMILES: CC(=O)N1CCN(CCn2c(=O)n(C)c3ccc(-c4cn(C)c(=O)c5[nH]ccc45)c(OCC4CCC4)c32)CC1]

This compound was synthesized according to the procedure of Example 44, Step 3, using 3-[2-(4-acetylpiperazin-1-yl)ethyl]-5-bromo-4-(cyclobutylmethoxy)-1-methyl-1,3-dihydro-2H-benzimidazol-2-one as the starting material. $^1$H NMR (300 MHz, DMSO-d$_6$) δ 7.27 (d, J=2.7 Hz, 1H), 7.24 (s, 1H), 7.06 (d, J=8.0 Hz, 1H), 6.99 (d, J=8.1 Hz, 1H), 6.10 (d, J=2.7 Hz, 1H), 4.08 (dd, J=6.2, 6.2 Hz, 2H), 3.56 (s, 3H), 3.51 (d, J=6.6 Hz, 2H), 2.65 (dd, J=6.4, 6.4 Hz, 2H), 2.46-2.40 (m, 2H), 2.40-2.30 (m, 2H), 1.96 (s, 3H), 1.82-1.63 (m, 3H), 1.63-1.45 (m, 1H), 1.42-1.29 (m, 2H); LCMS calculated for $C_{29}H_{37}N_6O_4$ (M+H)$^+$: m/z=533.3; found: 533.3.

Example 67. 4-(Cyclobutylmethoxy)-1-methyl-5-(6-methyl-7-oxo-6,7-dihydro-1H-pyrrolo[2,3-c]pyridin-4-yl)-3-{2-[4-(methylsulfonyl)piperazin-1-yl]ethyl}-1,3-dihydro-2H-benzimidazol-2-one

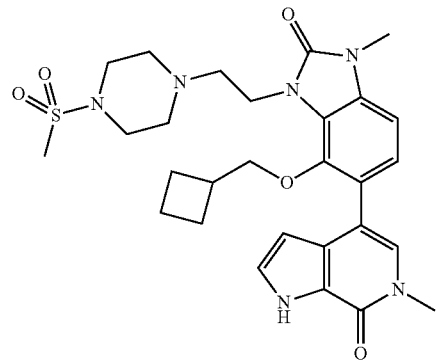 [SMILES: Cn1cc(-c2ccc3c(c2OCC2CCC2)n(CCN2CCN(S(C)(=O)=O)CC2)c(=O)n3C)c2cc[nH]c2c1=O]

This compound was synthesized according to the procedure of Example 66 using methanesulfonyl chloride instead of acetyl chloride. $^1$H NMR (300 MHz, DMSO-d$_6$) δ 12.02 (br s, 1H), 7.28 (d, J=2.7 Hz, 1H), 7.24 (s, 1H), 7.06 (d, J=8.0 Hz, 1H), 6.99 (d, J=8.0 Hz, 1H), 6.11 (d, J=2.7 Hz, 1H), 4.07 (dd, J=6.1, 6.1 Hz, 2H), 3.56 (s, 3H), 3.51 (d, J=6.6 Hz, 2H), 3.17-2.95 (m, 4H), 2.70 (dd, J=6.2, 6.2 Hz, 2H), 2.57-2.51 (m, 2H), 2.44-2.31 (m, 2H), 1.83-1.60 (m, 3H), 1.60-1.44 (m, 1H), 1.44-1.24 (m, 2H); LCMS calculated for $C_{28}H_{37}N_6O_5S$ (M+H)$^+$: m/z=569.3; found: 569.2.

Example 68. 4-(Cyclobutylmethoxy)-1-methyl-5-(6-methyl-7-oxo-6,7-dihydro-1H-pyrrolo[2,3-c]pyridin-4-yl)-3-[2-(4-methylpiperazin-1-yl)ethyl]-1,3-dihydro-2H-benzimidazol-2-one

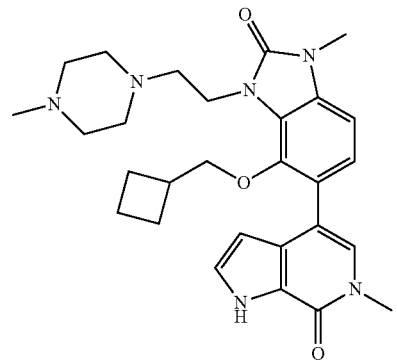

Step 1. 5-Bromo-4-(cyclobutylmethoxy)-1-methyl-3-[2-(4-methylpiperazin-1-yl)ethyl]-1,3-dihydro-2H-benzimidazol-2-one

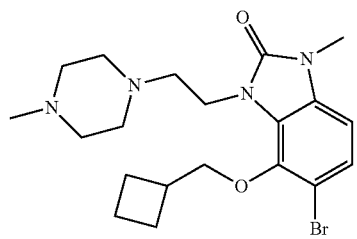 [SMILES: CN1CCN(CCn2c(=O)n(C)c3ccc(Br)c(OCC4CCC4)c32)CC1]

A solution of 5-bromo-4-(cyclobutylmethoxy)-1-methyl-3-(2-piperazin-1-ylethyl)-1,3-dihydro-2H-benzimidazol-2-one (40.0 mg, 0.0945 mmol) in tetrahydrofuran (2.0 mL) was treated with a 1.23M solution of formaldehyde in water (384 µL, 0.474 mmol). The resultant reaction mixture was stirred at RT for 30 min, followed by the addition of sodium cyanoborohydride (17.8 mg, 0.284 mmol). After stirring at RT for 2 h, the reaction mixture was quenched with acetic acid (0.5 mL) and concentrated in vacuo to give the crude product. Purification via preparative LCMS (XBridge C18 column, eluting with a gradient of acetonitrile/water 0.1% ammonium hydroxide, at flow rate of 60 mL/min) gave the desired product (38 mg, 92%). LCMS calculated for $C_{20}H_{30}BrN_4O_2$ (M+H)$^+$: m/z=437.2, 439.2; found: 437.1, 439.1.

Step 2. 4-(Cyclobutylmethoxy)-1-methyl-5-(6-methyl-7-oxo-6,7-dihydro-1H-pyrrolo[2,3-c]pyridin-4-yl)-3-[2-(4-methylpiperazin-1-yl)ethyl]-1,3-dihydro-2H-benzimidazol-2-one This compound was synthesized according to the procedure of Example 44, step 3, using 5-bromo-4-(cyclobutylmethoxy)-1-methyl-3-[2-(4-methylpiperazin-1-yl)ethyl]-1,3-dihydro-2H-benzimidazol-2-one as the starting material. LCMS calculated for $C_{28}H_{37}N_6O_3$ (M+H)$^+$: m/z=505.3; found: 505.3.

Example 69. 5-(6-Methyl-7-oxo-6,7-dihydro-1H-pyrrolo[2,3-c]pyridin-4-yl)-1-(2-morpholin-4-yl-ethyl)-4-phenoxy-1,3-dihydro-2H-benzimidazol-2-one trifluoroacetate

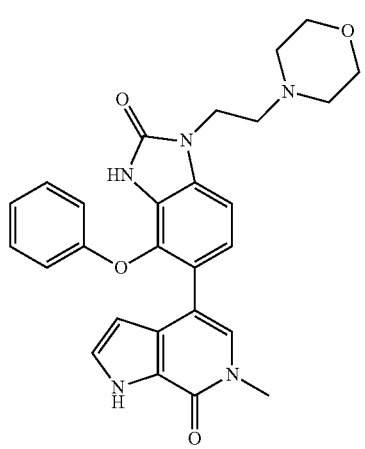 [SMILES: Cn1cc(-c2ccc3c([nH]c(=O)n3CCN3CCOCC3)c2Oc2ccccc2)c2cc[nH]c2c1=O]

Step 1. 1-Bromo-4-fluoro-3-nitro-2-phenoxybenzene

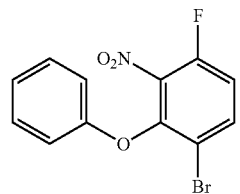 [SMILES: O=[N+]([O-])c1c(F)ccc(Br)c1Oc1ccccc1]

A solution of 1-bromo-2,4-difluoro-3-nitrobenzene (0.128 g, 0.538 mmol) [Combi-Blocks, AN-3334] and cesium carbonate (0.211 g, 0.646 mmol) in dimethyl sulfoxide (0.59 mL) was treated with phenol (0.0609 g, 0.647 mmol) and stirred at 20° C. for 3 h, after which time the reaction mixture was diluted with water and ethyl acetate. Layers were separated and the organic layer was washed with brine, dried with magnesium sulfate, filtered, and concentrated to give a crude oil. Purification by preparative LCMS (XBridge C18 column, eluting with a gradient of acetonitrile/water containing 0.1% trifluoroacetic acid, at flow rate of 60 mL/min) gave the desired product (57 mg, 34%) as a yellow solid.

Step 2. 4-Bromo-N-(2-morpholin-4-ylethyl)-2-nitro-3-phenoxyaniline

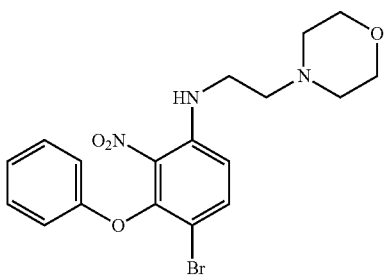 [SMILES: O=[N+]([O-])c1c(NCCN2CCOCC2)ccc(Br)c1Oc1ccccc1]

A solution of 1-bromo-4-fluoro-3-nitro-2-phenoxybenzene (0.057 g, 0.18 mmol) and cesium carbonate (0.0715 g, 0.220 mmol) in dimethyl sulfoxide (0.20 mL, 2.8 mmol) was treated with N-(2-aminoethyl)morpholine (0.0289 mL, 0.220 mmol) and stirred at 20° C. for 24 h, after which time the reaction mixture was diluted with water and ethyl acetate. Layers were separated and the organic layer was washed with brine, dried with magnesium sulfate, filtered, and concentrated in vacuo to give the crude product. Purification by flash column chromatography (100% hexanes to 100% EtOAc) gave the desired product (60 mg, 78%) a brown oil. LCMS calculated for $C_{18}H_{21}BrN_3O_4$ (M+H)$^+$: m/z=422.1, 424.1; found: 422.1, 424.1.

Step 3. 4-Bromo-N1-(2-morpholin-4-ylethyl)-3-phenoxybenzene-1,2-diamine

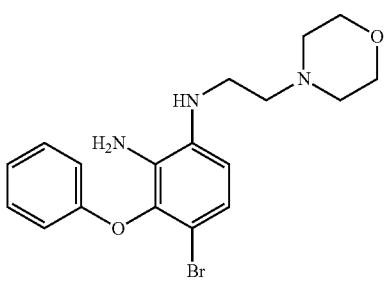 [SMILES: Nc1c(NCCN2CCOCC2)ccc(Br)c1Oc1ccccc1]

This compound was synthesized according to the procedure of Example 1, Step 3, using 4-bromo-N-(2-morpholin-4-ylethyl)-2-nitro-3-phenoxyaniline as the starting material. LCMS calculated for $C_{18}H_{23}BrN_3O_2$ (M+H)$^+$: m/z=392.1, 394.1; found: 392.1, 394.0.

Step 4. 5-Bromo-1-(2-morpholin-4-ylethyl)-4-phenoxy-1,3-dihydro-2H-benzimidazol-2-one

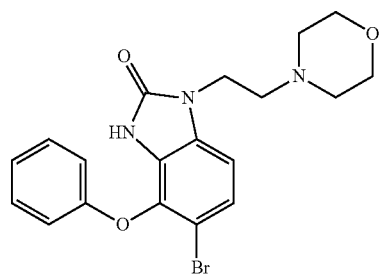 [SMILES: O=c1[nH]c2c(Oc3ccccc3)c(Br)ccc2n1CCN1CCOCC1]

This compound was synthesized according to the procedure of Example 6, Step 1, using 4-bromo-N$^1$-(2-morpholin-4-ylethyl)-3-phenoxybenzene-1,2-diamine as the starting material. LCMS calculated for $C_{19}H_{21}BrN_3O_3$ (M+H)$^+$: m/z=418.1, 420.1; found: 418.0, 420.1.

Step 5. 5-{6-Methyl-1-[(4-methylphenyl)sulfonyl]-7-oxo-6,7-dihydro-1H-pyrrolo[2,3-c]pyridin-4-yl}-1-(2-morpholin-4-ylethyl)-4-phenoxy-1,3-dihydro-2H-benzimidazol-2-one trifluoroacetate

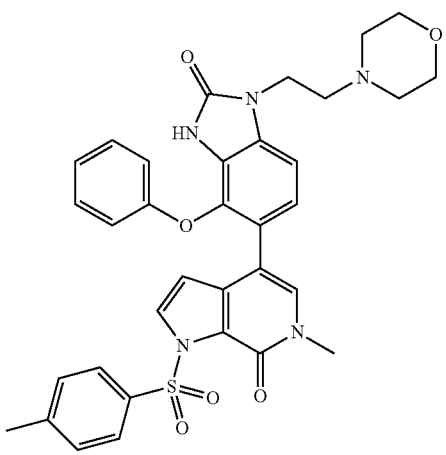 [SMILES: Cc1ccc(S(=O)(=O)n2ccc3c(-c4ccc5c([nH]c(=O)n5CCN5CCOCC5)c4Oc4ccccc4)cn(C)c(=O)c32)cc1]

This compound was synthesized according to the procedure of Example 10, Step 5, using 5-bromo-1-(2-morpholin-4-ylethyl)-4-phenoxy-1,3-dihydro-2H-benzimidazol-2-one as the starting material. Purification by preparative LCMS (XBridge C18 column, eluting with a gradient of acetonitrile/water containing 0.1% trifluoroacetic acid, at flow rate of 60 mL/min) gave the desired product as a TFA salt. LCMS calculated for $C_{34}H_{34}N_5O_6S$ (M+H)$^+$: m/z=640.2; found: 640.3.

Step 6. 5-(6-Methyl-7-oxo-6,7-dihydro-1H-pyrrolo[2,3-c]pyridin-4-yl)-1-(2-morpholin-4-ylethyl)-4-phenoxy-1,3-dihydro-2H-benzimidazol-2-one trifluoroacetate This compound was synthesized according to the procedure of Example 6, Step 2, using 5-{6-methyl-1-[(4-methylphenyl)sulfonyl]-7-oxo-6,7-dihydro-1H-pyrrolo[2,3-c]pyridin-4-yl}-1-(2-morpholin-4-ylethyl)-4-phenoxy-1,3-dihydro-2H-benzimidazol-2-one trifluoroacetate as the starting material. Purification by preparative LCMS (XBridge C18 column, eluting with a gradient of acetonitrile/water containing 0.1% trifluoroacetic acid, at flow rate of 60 mL/min) gave the desired product as a TFA salt. $^1$H NMR (400 MHz, DMSO-d$_6$) δ 11.97 (br s, 1H), 11.43 (br s, 1H), 7.33-7.23 (m, 2H), 7.20 (d, J=8.1 Hz, 1H), 7.14-7.02 (m, 3H), 6.84 (dd, J=7.3, 7.3 Hz, 1H), 6.58 (d, J=7.8 Hz, 2H), 6.24-6.11 (m, 1H), 4.36-4.20 (m, 2H), 4.14-3.94 (m, 2H), 3.83-3.50 (m, 6H), 3.41 (s, 3H), 3.29-3.08 (m, 2H); LCMS calculated for $C_{27}H_{28}N_5O_4$ (M+H)$^+$: m/z=486.2; found: 486.2.

Example 70. 1-{2-[(2R,6S)-2,6-Dimethylmorpholin-4-yl]ethyl}-5-(6-methyl-7-oxo-6,7-dihydro-1H-pyrrolo[2,3-c]pyridin-4-yl)-4-phenoxy-1,3-dihydro-2H-benzimidazol-2-one trifluoroacetate

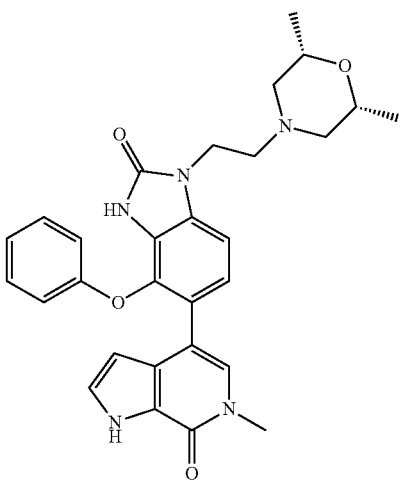 [SMILES: C[C@@H]1CN(CCn2c(=O)[nH]c3c(Oc4ccccc4)c(-c4cn(C)c(=O)c5[nH]ccc45)ccc32)C[C@H](C)O1]

This compound was synthesized according to the procedure of Example 69 using 2-[(2R,6S)-2,6-dimethylmorpholin-4-yl]ethanamine instead of N-(2-aminoethyl)morpholine in step 2. $^1$H NMR (400 MHz, DMSO-d$_6$) δ 11.96 (br s, 1H), 11.41 (s, 1H), 7.35-7.27 (m, 1H), 7.26-7.22 (m, 1H), 7.20 (d, J=8.1 Hz, 1H), 7.13-7.01 (m, 3H), 6.84 (dd, J=7.3, 7.3 Hz, 1H), 6.58 (d, J=7.8 Hz, 2H), 6.17 (dd, J=2.4, 2.4 Hz, 1H), 4.41-4.15 (m, 2H), 3.90-3.74 (m, 2H), 3.74-3.64 (m, 2H), 3.41 (s, 3H), 2.85-2.65 (m, 2H), 1.14 (d, J=6.3 Hz, 6H); LCMS calculated for C$_{29}$H$_{32}$N$_5$O$_4$ (M+H)$^+$: m/z=514.2; found: 514.2.

Example 71. 4-(2-(Benzylamino)-1-{2-[(2R,6S)-2,6-dimethylmorpholin-4-yl]ethyl}-4-phenoxy-1H-benzimidazol-5-yl)-6-methyl-1,6-dihydro-7H-pyrrolo[2,3-c]pyridin-7-one trifluoroacetate

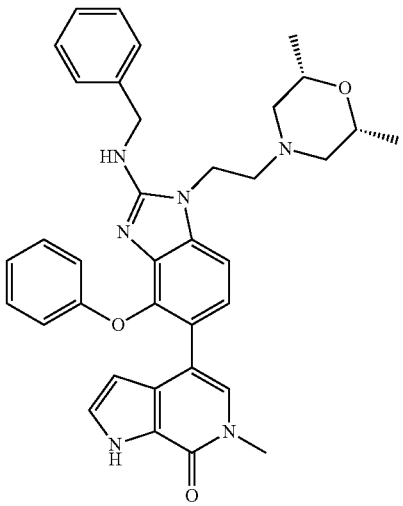 [SMILES: C[C@@H]1CN(CCn2c(NCc3ccccc3)nc3c(Oc4ccccc4)c(-c4cn(C)c(=O)c5[nH]ccc45)ccc32)C[C@H](C)O1]

A solution of 1-{2-[(2R,6S)-2,6-dimethylmorpholin-4-yl]ethyl}-5-{6-methyl-1-[(4-methylphenyl)sulfonyl]-7-oxo-6,7-dihydro-1H-pyrrolo[2,3-c]pyridin-4-yl}-4-phenoxy-1,3-dihydro-2H-benzimidazol-2-one (74.5 mg, 0.112 mmol) (from example 70) in phosphoryl chloride (2.079 mL, 22.31 mmol) was heated at 60° C. overnight, after which time the reaction mixture was concentrated in vacuo and the resultant residue was dissolved in toluene and reconcentrated to give the crude chloride which was used in further step without purification. The solution of crude chloride in N-methylpyrrolidinone (1.0 mL) was treated with benzylamine (122 µL, 1.12 mmol) and heated in the microwave reactor at 150° C. for 20 min. The reaction mixture was then treated with methanol (1.0 mL) and 2.0 M solution of sodium hydroxide in water (200 µL, 0.400 mmol) and stirred at 60° C. for 30 min. The reaction mixture was purified by preparative LCMS (XBridge C18 column, eluting with a gradient of acetonitrile/water containing 0.1% trifluoroacetic acid, at flow rate of 60 mL/min) to give the desired product (5 mg, 7%). $^1$H NMR (400 MHz, DMSO-d$_6$) δ 12.08 (br s, 1H), 11.51 (br s, 1H), 8.26 (dd, J=6.2, 6.2 Hz, 1H), 7.78 (dd, J=2.8, 2.8 Hz, 1H), 7.67 (s, 1H), 7.42-7.26 (m, 6H), 7.19 (d, J=8.1 Hz, 1H), 7.05 (dd, J=7.8, 7.8 Hz, 2H), 6.84 (dd, J=7.4, 7.4 Hz, 1H), 6.51 (d, J=8.6 Hz, 2H), 6.42 (s, 1H), 5.75 (s, 2H), 5.02 (d, J=6.1 Hz, 2H), 4.39-4.16 (m, 2H), 3.88 (s, 3H), 3.86-3.73 (m, 2H), 2.86-2.63 (m, 2H), 1.14 (d, J=6.1 Hz, 6H); LCMS calculated for C$_{36}$H$_{39}$N$_6$O$_3$ (M+H)$^+$: m/z=603.3; found: 603.3.

Example 72. 4-(2-[(Cyclopropylmethyl)amino]-1-{2-[(2R,6S)-2,6-dimethylmorpholin-4-yl]ethyl}-4-phenoxy-1H-benzimidazol-5-yl)-6-methyl-1,6-dihydro-7H-pyrrolo[2,3-c]pyridin-7-one trifluoroacetate

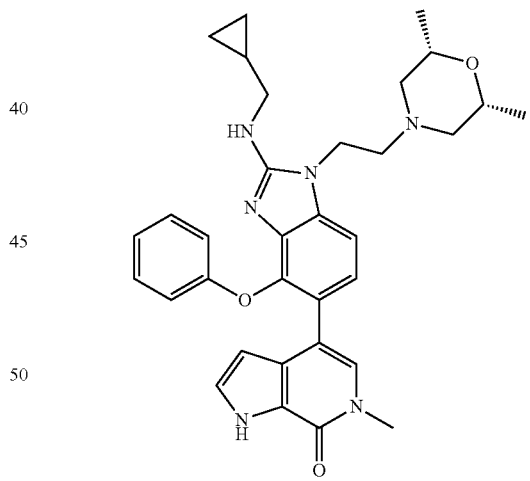

This compound was synthesized according to the procedure of Example 71 using cyclopropylmethylamine instead of benzylamine. $^1$H NMR (400 MHz, DMSO-d$_6$) δ 12.16 (br s, 1H), 11.51 (br s, 1H), 7.81 (dd, J=3.0, 3.0 Hz, 1H), 7.73 (dd, J=5.7, 5.7 Hz, 1H), 7.61 (s, 1H), 7.34 (d, J=8.2 Hz, 1H), 7.20 (d, J=8.1 Hz, 1H), 7.11-7.03 (m, 2H), 6.83 (dd, J=7.3, 7.3 Hz, 1H), 6.53 (dd, J=8.7, 1.0 Hz, 2H), 6.45 (dd, J=2.8, 1.6 Hz, 1H), 5.75 (s, 1H), 4.39-4.17 (m, 2H), 3.82 (s, 3H), 3.67-3.59 (m, 2H), 2.95-2.61 (m, 2H), 1.22-1.13 (m, 6H), 1.13-1.06 (m, 1H), 0.56-0.43 (m, 2H), 0.38-0.27 (m, 2H); LCMS calculated for C$_{33}$H$_{39}$N$_6$O$_3$ (M+H)$^+$: m/z=567.3; found: 567.3.

Example 73. 4-(7-Ethoxy-2,5-dimethylpyrazolo[1,5-a]pyrimidin-6-yl)-6-methyl-1,6-dihydro-7H-pyrrolo[2,3-c]pyridin-7-one

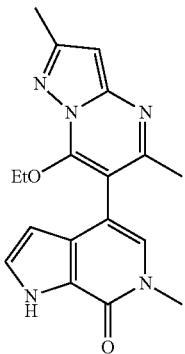 [SMILES: CCOc1c(-c2cn(C)c(=O)c3[nH]ccc23)c(C)nc2cc(C)nn12]

Step 1. Ethyl 2-bromo-3-oxobutanoate

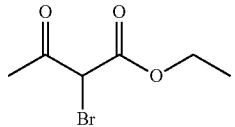

3-Oxobutanoic acid ethyl ester (1.26 mL, 10.0 mmol) was added dropwise to a suspension of N-bromosuccinimide (1.78 g, 10.0 mmol) and p-toluenesulfonic acid (10.0 mg, 0.0581 mmol) in methylene chloride (30.0 mL) at 0° C., and the resultant reaction mixture was stirred at 0° C. for 3 h, then warmed to RT and stirred at that temperature for 1 h. The reaction mixture was concentrated in vacuo and the resultant oily solid was treated with hexanes and the resultant suspension was filtered. The solid was washed with additional hexanes and the filtrate was concentrated in vacuo to give a crude oil. Purification by flash column chromatography (100% hexanes to 30% Et$_2$O/hexanes) gave the desired product (1.20 g, 57%) as an oil.

Step 2.
6-Bromo-2,5-dimethylpyrazolo[1,5-a]pyrimidin-7-ol

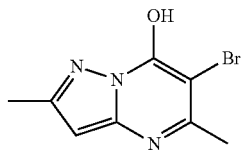

A mixture of 3-methyl-1H-pyrazol-5-amine (0.186 g, 1.92 mmol) and acetic acid (3.71 mL, 65.2 mmol) was slightly heated until complete dissolution and the resultant solution was cooled to RT and mixed with ethyl 2-bromo-3-oxobutanoate (1.20 g, 5.74 mmol). The resultant reaction mixture was stirred at RT for 16 h, after which time the reaction mixture was diluted with diethyl ether, cooled to 0° C. and stirred at that temperature for 30 min. The white solid precipitate was separated by filtration and washed with cold diethyl ether and dried to give the desired product (363 mg, 78%) as a white solid. LCMS calculated for C$_8$H$_9$BrN$_3$O (M+H)$^+$: m/z=242.0, 244.0; found: 241.9, 244.0.

Step 3. 6-Bromo-7-chloro-2,5-dimethylpyrazolo[1,5-a]pyrimidine

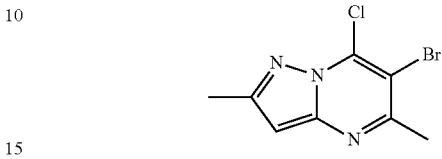

Pyridine (0.179 mL, 2.22 mmol) was added dropwise to a solution of 6-bromo-2,5-dimethylpyrazolo[1,5-a]pyrimidin-7(4H)-one (0.179 g, 0.739 mmol) in phosphoryl chloride (1.85 mL, 19.8 mmol) and 1,2-dichloroethane (1.85 mL). The resultant reaction mixture was stirred at RT for 15 min, then warmed to 80° C. and stirred at that temperature for 15 h. The reaction mixture was concentrated in vacuo to yield a crude residue which was diluted with dichloromethane and the resultant solution was added dropwise to a saturated solution of sodium bicarbonate (40 mL) at 0° C. Additional dichloromethane (50 mL) was added, layers were separated and the organic layer was dried with sodium sulfate, filtered, and concentrated in vacuo to give a crude residue. Purification by flash column chromatography (100% hexanes to 30% EtOAc/hexanes) gave the desired product (171 mg, 89%) as a white solid. LCMS calculated for C$_8$H$_8$BrClN$_3$ (M+H)$^+$: m/z=260.0, 262.0; found: 259.9, 261.9.

Step 4. 6-Bromo-7-(2,4-difluorophenoxy)-2,5-dimethylpyrazolo[1,5-a]pyrimidine

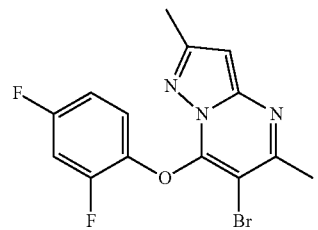 [SMILES: Cc1cc2nc(C)c(Br)c(Oc3ccc(F)cc3F)n2n1]

A solution of 2,4-difluorophenol (0.156 mL, 0.960 mmol) in tetrahydrofuran (3.0 mL) was treated with sodium hydride (0.0242 g, 0.960 mmol) at 0° C. The resultant reaction mixture was warmed to RT and stirred at that temperature for 30 min. The reaction mixture was then cooled to 0° C., treated with 6-bromo-7-chloro-2,5-dimethylpyrazolo[1,5-a]pyrimidine (0.125 g, 0.480 mmol), warmed to RT and stirred at RT for 14 h. The reaction mixture was cooled to 0° C., quenched with saturated ammonium chloride solution, and diluted with ethyl acetate. Layers were separated and the organic layer was washed with water and brine, dried with sodium sulfate, filtered, and concentrated to give a crude residue. Purification by flash column chromatography (100% hexanes to 30% Et$_2$O/hexanes) gave the desired product (162 mg, 95%) as a white solid. LCMS calculated for C$_{14}$H$_{11}$BrF$_2$N$_3$O (M+H)$^+$: m/z=354.0, 356.0; found: 353.9, 356.0.

Step 5. 4-[7-(2,4-Difluorophenoxy)-2,5-dimethyl-pyrazolo[1,5-a]pyrimidin-6-yl]-6-methyl-1-[(4-methylphenyl)sulfonyl]-1,6-dihydro-7H-pyrrolo[2,3-c]pyridin-7-one

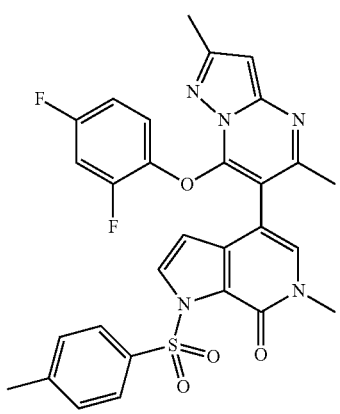

This compound was synthesized according to the procedure of Example 10, Step 5, using 6-bromo-7-(2,4-difluorophenoxy)-2,5-dimethylpyrazolo[1,5-a]pyrimidine and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{29}H_{24}F_2N_5O_4S$ (M+H)$^+$: m/z=576.1; found: 576.1.

Step 6. 4-(7-Ethoxy-2,5-dimethylpyrazolo[1,5-a]pyrimidin-6-yl)-6-methyl-1,6-dihydro-7H-pyrrolo[2,3-c]pyridin-7-one A suspension of 4-[7-(2,4-difluorophenoxy)-2,5-dimethylpyrazolo[1,5-a]pyrimidin-6-yl]-6-methyl-1-[(4-methylphenyl)sulfonyl]-1,6-dihydro-7H-pyrrolo[2,3-c]pyridin-7-one (29.1 mg, 50.6 μmol) in ethanol (1.0 mL) was treated with a 3.0 M solution of sodium hydroxide in water (0.254 mL, 0.762 mmol), then warmed to 55° C. and stirred at that temperature for 30 min. The reaction mixture was purified via preparative LCMS (XBridge C18 column, eluting with a gradient of acetonitrile/water 0.1% ammonium hydroxide, at flow rate of 60 mL/min) to give the desired product (6 mg, 14%). $^1$H NMR (300 MHz, DMSO-d$_6$) δ 12.15 (br s, 1H), 7.28 (d, J=2.8 Hz, 1H), 7.24 (s, 1H), 6.39 (s, 1H), 6.03 (d, J=2.7 Hz, 1H), 4.45 (q, J=7.0 Hz, 2H), 3.55 (s, 3H), 2.42 (s, 3H), 2.24 (s, 3H), 1.07 (t, J=7.1 Hz, 3H); LCMS calculated for $C_{18}H_{20}N_5O_2$ (M+H)$^+$: m/z=338.2; found: 338.1.

Example 75. 8-(2,4-Difluorophenoxy)-7-(6-methyl-7-oxo-6,7-dihydro-1H-pyrazolo[3,4-c]pyridin-4-yl)quinoxalin-2(1H)-one

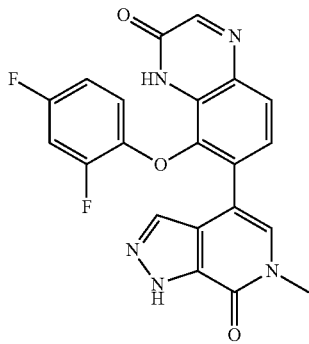 [SMILES: Cn1cc(-c2ccc3ncc(=O)[nH]c3c2Oc2ccc(F)cc2F)c2cn[nH]c2c1=O]

Step 1. N-[4-Bromo-3-(2,4-difluorophenoxy)-2-nitrophenyl]-2,2,2-trifluoroacetamide

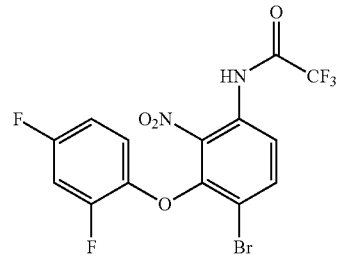 [SMILES: O=C(Nc1ccc(Br)c(Oc2ccc(F)cc2F)c1[N+](=O)[O-])C(F)(F)F]

This compound was synthesized according to the procedure of Example 4, Step 1, using 4-bromo-3-(2,4-difluorophenoxy)-2-nitroaniline as the starting material.

Step 2. Methyl {[4-bromo-3-(2,4-difluorophenoxy)-2-nitrophenyl]amino}acetate

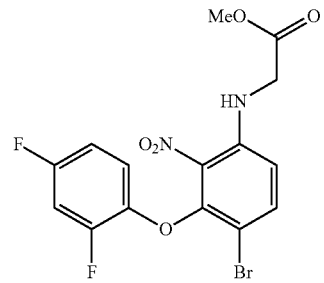 [SMILES: COC(=O)CNc1ccc(Br)c(Oc2ccc(F)cc2F)c1[N+](=O)[O-]]

A solution of 2-hydroxyacetic acid methyl ester (0.0742 mL, 0.961 mmol) in tetrahydrofuran (2.42 mL) was treated with triphenylphosphine (0.176 g, 0.673 mmol), cooled to 0° C., followed by dropwise addition of with diisopropyl azodicarboxylate (0.142 mL, 0.721 mmol). The reaction mixture was stirred at 0° C. for 15 min, treated with N-[4-bromo-3-(2,4-difluorophenoxy)-2-nitrophenyl]-2,2,2-trifluoroacetamide (0.212 g, 0.481 mmol), warmed to RT and stirred at RT for 16 h. The reaction mixture was diluted with ethyl acetate and water. Layers were separated and the aqueous layer was re-extracted with ethyl acetate. The combined organic layers were washed with brine, dried with sodium sulfate, filtered, and concentrated in vacuo to give the intermediate trifluoroacetamide. This crude intermediate trifluoroacetamide was dissolved in methanol (2.42 mL), the resultant solution was treated with ammonium hydroxide (0.187 mL, 4.81 mmol) and then stirred at RT for 15 min. The reaction mixture was diluted with water (50 mL) and extracted with dichloromethane (2×50 mL). The combined organic layers were washed with brine, dried with sodium sulfate, filtered, and concentrated in vacuo to give the crude product. Purification by flash column chromatography (100% hexanes to 20% CH$_2$Cl$_2$/hexanes) gave the desired product (123 mg, 61%) as a yellow solid. LCMS calculated for $C_{15}H_{12}BrF_2N_2O_5$ (M+H)$^+$: m/z=417.0, 419.0; found: 416.9, 418.9.

Step 3. Methyl {[3-(2,4-difluorophenoxy)-4-(6-methyl-7-oxo-1-{[2-(trimethylsilyl)ethoxy]methyl}-6,7-dihydro-1H-pyrazolo[3,4-c]pyridin-4-yl)-2-nitrophenyl]amino}acetate

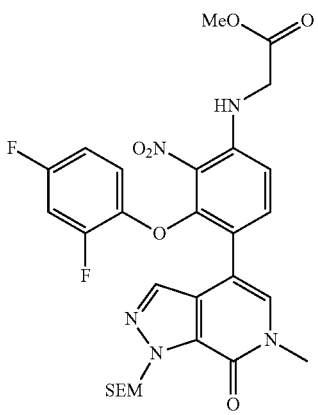 [SMILES: COC(=O)CNc1ccc(-c2cn(C)c(=O)c3c2cnn3COCC[Si](C)(C)C)c(Oc2ccc(F)cc2F)c1[N+](=O)[O-]]

This compound was synthesized according to the procedure of Example 10, Step 5, using methyl {[4-bromo-3-(2,4-difluorophenoxy)-2-nitrophenyl]amino}acetate and 6-methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one as the starting materials. LCMS calculated for $C_{28}H_{32}F_2N_5O_7Si$ $(M+H)^+$: m/z=616.2; found: 616.2.

Step 4. 8-(2,4-Difluorophenoxy)-7-(6-methyl-7-oxo-1-{[2-(trimethylsilyl)ethoxy]methyl}-6,7-dihydro-1H-pyrazolo[3,4-e]pyridin-4-yl)-3,4-dihydroquinoxalin-2(1H)-one

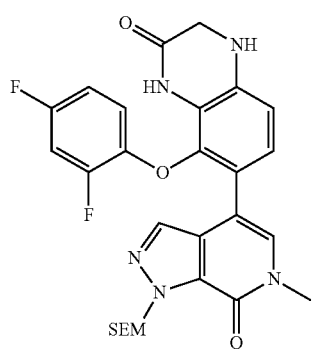 [SMILES: Cn1cc(-c2ccc3c(c2Oc2ccc(F)cc2F)NC(=O)CN3)c2cnn(COCC[Si](C)(C)C)c2c1=O]

A suspension of methyl {[3-(2,4-difluorophenoxy)-4-(6-methyl-7-oxo-1-{[2-(trimethylsilyl)ethoxy]methyl}-6,7-dihydro-1H-pyrazolo[3,4-c]pyridin-4-yl)-2-nitrophenyl]amino}acetate (0.048 g, 0.078 mmol) in ethyl acetate (0.452 mL) and methanol (0.452 mL) was cooled to 0° C. and then treated with saturated ammonium chloride solution (0.0679 mL, 1.01 mmol) at that temperature. Zinc (0.0408 g, 0.624 mmol) was added to the reaction mixture in two portions over 5 min and the reaction mixture was stirred at RT for 16 h. The reaction mixture was diluted with dichloromethane and filtered through a pad of Celite. The solids were washed with additional dichloromethane and the filtrate was concentrated in vacuo to yield a crude residue. The residue was dissolved in dichloromethane and the organic phase was washed with saturated sodium bicarbonate solution, dried with sodium sulfate, filtered, and concentrated in vacuo to give the crude product. Purification via preparative LCMS (XBridge C18 column, eluting with a gradient of acetonitrile/water 0.1% ammonium hydroxide, at flow rate of 60 mL/min) gave the desired product (10.5 mg, 24%) along with a small amount of the oxidized product, 8-(2,4-difluorophenoxy)-7-(6-methyl-7-oxo-1-{[2-(trimethylsilyl)ethoxy]methyl}-6,7-dihydro-1H-pyrazolo[3,4-c]pyridin-4-yl)quinoxalin-2(1H)-one. This mixture was used in the next step without separation. LCMS calculated for $C_{27}H_{30}F_2N_5O_4Si$ $(M+H)^+$: m/z=554.2; found: 554.1.

Step 5. 8-(2,4-Difluorophenoxy)-7-(6-methyl-7-oxo-6,7-dihydro-1H-pyrazolo[3,4-c]pyridin-4-yl)quinoxalin-2(1H)-one Trifluoroacetic acid (0.40 mL, 5.19 mmol) was added dropwise at RT to a solution of 8-(2,4-difluorophenoxy)-7-(6-methyl-7-oxo-1-{[2-(trimethylsilyl)ethoxy]methyl}-6,7-dihydro-1H-pyrazolo[3,4-c]pyridine-4-yl)-3,4-dihydroquinoxalin-2(1H)-one (10.5 mg, 0.0190 mmol, mixture of oxidized (quinoxalin) and reduced (dihydroquinoxalin) forms from previous step) in methylene chloride (0.40 mL), and the reaction mixture was stirred at RT for 1 h. The reaction mixture was purified via preparative LCMS (XBridge C18 column, eluting with a gradient of acetonitrile/water 0.1% ammonium hydroxide, at flow rate of 60 mL/min) to give the desired product (4 mg, 50%). $^1$H NMR (500 MHz, DMSO-$d_6$) δ 14.05 (br s, 1H), 12.50 (br s, 1H), 8.19 (s, 1H), 7.79 (d, J=8.4 Hz, 2H), 7.42 (d, J=8.3 Hz, 1H), 7.35 (s, 1H), 7.16-6.99 (m, 1H), 6.70-6.56 (m, 1H), 6.55-6.34 (m, 1H), 3.48 (s, 3H); LCMS calculated for $C_{11}H_{14}F_2N_5O_3$ $(M+H)^+$: m/z=422.1; found: 422.0.

Example 76. 4-[4-(Cyclopropylmethoxy)-1-methyl-1H-indazol-5-yl]-6-methyl-1,6-dihydro-7H-pyrrolo[2,3-c]pyridin-7-one

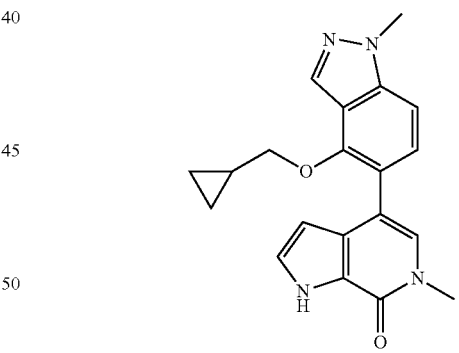

Step 1. 3-Bromo-6-fluoro-2-methoxybenzaldehyde

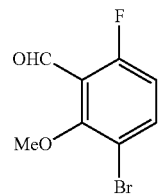 [SMILES: COc1c(Br)ccc(F)c1C=O]

1.6 M Solution of n-butyllithium in hexanes (3.35 mL, 5.36 mmol) was added dropwise to a solution of N,N-diisopropylamine (0.960 mL, 6.85 mmol) in tetrahydrofuran (10 mL) at −78° C. and the resultant reaction mixture was stirred at −78° C. for 10 min. A solution of 1-bromo-4-fluoro-2-methoxybenzene (1.0 g, 4.9 mmol) in tetrahydrofuran (2 mL) was added to the reaction mixture dropwise at −78° C. and the reaction mixture was stirred at −78° C. for 1 h. N,N-dimethylformamide (0.412 mL, 5.32 mmol) was added to the reaction mixture dropwise at −78° C. and the reaction mixture was stirred at −78° C. for 1 h. Reaction mixture was quenched with saturated ammonium chloride, warmed to 20° C., and diluted with ether and 1M aqueous solution of HCl. Layers were separated and the aqueous layer was and re-extracted with ether. The combined organic layers were washed with brine, dried with magnesium sulfate, filtered, and concentrated in vacuo to give a crude residue. Purification by flash column chromatography (100% hexanes to 30% EtOAc/hexanes) gave the desired product (727 mg, 64%) as a yellow solid. LCMS calculated for $C_8H_7BrFO_2$ (M+H)$^+$: m/z=233.0, 235.0; found: 233.0, 234.8.

Step 2. 5-Bromo-4-methoxy-1H-indazole

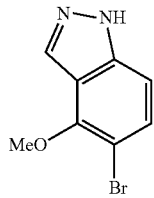

A solution of 3-bromo-6-fluoro-2-methoxybenzaldehyde (0.727 g, 3.12 mmol) and methoxylamine hydrochloride (0.260 g, 3.12 mmol) in 1,2-dimethoxyethane (4 mL) was treated with potassium carbonate (0.472 g, 3.42 mmol) and stirred at 20° C. for 5 h. The reaction mixture was filtered and the filtrate was concentrated in vacuo to give a residue. This residue was dissolved in 1,2-dimethoxyethane (4 mL), the resultant solution was treated with hydrazine (4 mL), warmed to 100° C. and stirred at that temperature for 15 h. The reaction mixture was diluted with ethyl acetate and water. Layers were separated and the organic layer was separated, washed with brine, dried with magnesium sulfate, filtered, and concentrated in vacuo to give a crude residue. This residue was triturated with ether to give the desired product (185 mg, 26%) as a gray solid. LCMS calculated for $C_8H_8BrN_2O$ (M+H)$^+$: m/z=227.0, 229.0; found: 226.9, 229.0.

Step 3. 5-Bromo-4-methoxy-1-methyl-1H-indazole

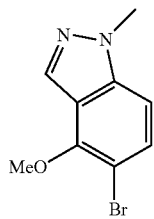

A solution of 5-bromo-4-methoxy-1H-indazole (0.125 g, 0.550 mmol) in N,N-dimethylformamide (2.20 mL) was treated with sodium hydride (0.0166 g, 0.659 mmol) at 20° C. and then stirred at 20° C. for 30 min. The resultant reaction mixture was treated with methyl iodide (0.0410 mL, 0.658 mmol) and stirred at 20° C. for 1 h. The reaction mixture was diluted with water and ethyl acetate. Layers were separated and the organic layer was washed with brine, dried with sodium sulfate, filtered, and concentrated in vacuo to give the crude product. Purification by flash column chromatography (100% hexanes to 100% EtOAc) gave the desired product (87 mg, 66%) as a white solid. LCMS calculated for $C_9H_{10}BrN_2O$ (M+H)$^+$: m/z=241.0, 243.0; found: 240.9, 242.9.

Step 4. 5-Bromo-1-methyl-1H-indazol-4-ol

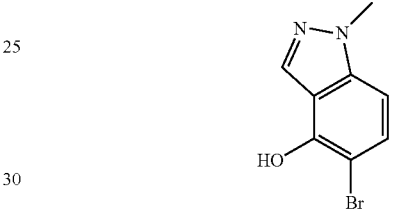

A solution of 5-bromo-4-methoxy-1-methyl-1H-indazole (86.1 mg, 0.357 mmol) in methylene chloride (1.74 mL) was treated with boron tribromide (0.0405 mL, 0.428 mmol) at 0° C. The reaction mixture was warmed to RT and stirred at RT for 16 h, after which time the reaction mixture was cooled to 0° C., treated with additional boron tribromide (0.0405 mL, 0.428 mmol), warmed to RT and stirred at RT for 1.5 h. The reaction mixture was cooled to 0° C., treated with more boron tribromide (0.0405 mL, 0.428 mmol), and stirred for 2 h. The reaction mixture was then cooled to 0° C. and quenched carefully with saturated sodium bicarbonate (30 mL) and extracted with dichloromethane (2×30 mL). The combined organic layers were washed with brine, dried over sodium sulfate, filtered and concentrated in vacuo to yield a crude mixture. This mixture was re-subjected to the initial reaction conditions. The crude mixture was suspended in 1,2-dichloroethane (1.74 mL), cooled to 0° C., treated with boron tribromide (0.0810 mL, 0.857 mmol), warmed to RT and stirred at RT for 2 h. The reaction mixture was cooled to 0° C. and quenched carefully with saturated solution of sodium bicarbonate (30 mL) and extracted with dichloromethane (2×30 mL). The combined organic layers were washed with brine, dried over sodium sulfate, filtered and concentrated in vacuo to give the crude product. This material was diluted with methanol (2.0 mL), treated with ammonium hydroxide (0.278 mL, 7.14 mmol), and stirred for 15 min. The resultant suspension was diluted with saturated ammonium chloride (30 mL) and extracted with dichloromethane (2×30 mL). The combined organic layers were washed with brine, dried over sodium sulfate, filtered and concentrated to give the desired product (73 mg, 90%) as a yellow solid. LCMS calculated for $C_8H_8BrN_2O$ (M+H)$^+$: m/z=227.0, 229.0; found: 226.9, 228.9.

Step 5. 5-Bromo-4-(cyclopropylmethoxy)-1-methyl-1H-indazole

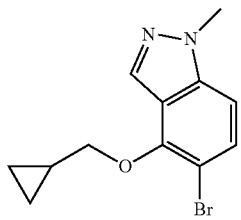 [SMILES: Cn1ncc2c(OCC3CC3)c(Br)ccc21]

A solution of 5-bromo-1-methyl-1H-indazol-4-ol (73.7 mg, 0.324 mmol) and cyclopropyl carbinol (0.0386 mL, 0.489 mmol) in tetrahydrofuran (2.80 mL) was treated with triphenylphosphine (0.102 g, 0.390 mmol), cooled to 0° C., followed by dropwise addition of diisopropyl azodicarboxylate (0.0767 mL, 0.390 mmol). Reaction mixture was warmed to RT and stirred at RT for 16 h. The reaction mixture was poured into saturated sodium bicarbonate solution and extracted with ethyl acetate. Layers were separated and the organic layer was washed with brine, dried over sodium sulfate, filtered and concentrated in vacuo to give the crude product. Purification by flash column chromatography (100% hexanes to 100% $CH_2Cl_2$) gave the desired product (72 mg, 78%) as a yellow solid. LCMS calculated for $C_{12}H_{14}BrN_2O$ $(M+H)^+$: m/z=281.0, 283.0; found: 281.0, 283.0.

Step 6. 4-[4-(Cyclopropylmethoxy)-1-methyl-1H-indazol-5-yl]-6-methyl-1-[(4-methylphenyl)sulfonyl]-1,6-dihydro-7H-pyrrolo[2,3-c]pyridin-7-one

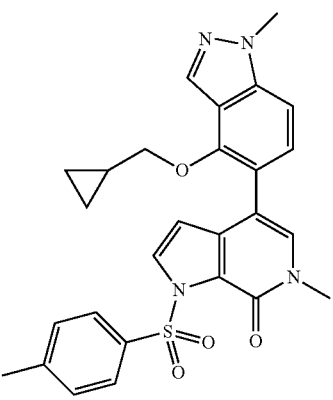

This compound was synthesized according to the procedure of Example 10, Step 5, using 5-bromo-4-(cyclopropylmethoxy)-1-methyl-1H-indazole and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{27}H_{27}N_4O_4S$ $(M+H)^+$: m/z=503.2; found: 503.1.

Step 7. 4-[4-(Cyclopropylmethoxy)-1-methyl-1H-indazol-5-yl]-6-methyl-1,6-dihydro-7H-pyrrolo[2,3-c]pyridin-7-one This compound was synthesized according to the procedure of Example 8, Step 2, using 4-[4-(cyclopropylmethoxy)-1-methyl-1H-indazol-5-yl]-6-methyl-1-[(4-methylphenyl)sulfonyl]-1,6-dihydro-7H-pyrrolo[2,3-c]pyridin-7-one as the starting material. $^1$H NMR (500 MHz, DMSO-$d_6$) δ 11.96 (br s, 1H), 8.19 (s, 1H), 7.41-7.28 (m, 2H), 7.28-7.17 (m, 2H), 6.09 (d, J=2.7 Hz, 1H), 4.03 (s, 3H), 3.98 (d, J=6.8 Hz, 2H), 3.56 (s, 3H), 1.08-0.90 (m, 1H), 0.43-0.23 (m, 2H), 0.21-0.03 (m, 2H); LCMS calculated for $C_{20}H_{21}N_4O_2$ $(M+H)^+$: m/z=349.2; found: 349.1.

Example 77. 4-[4-(Cyclopropylmethoxy)-1-methyl-1H-indazol-5-yl]-6-methyl-1,6-dihydro-7H-pyrazolo[3,4-c]pyridin-7-one

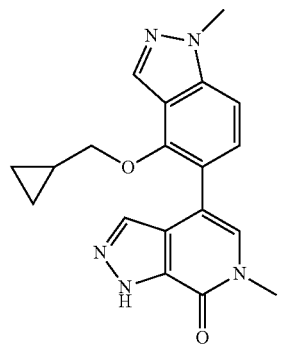 [SMILES: Cn1cc(-c2ccc3c(cnn3C)c2OCC2CC2)c2cn[nH]c2c1=O]

Step 1. 4-(4-(cyclopropylmethoxy)-1-methyl-1H-indazol-5-yl)-6-methyl-1-((2-(trimethylsilyl)ethoxy)methyl)-1H-pyrazolo[3,4-c]pyridin-7(6H)-one

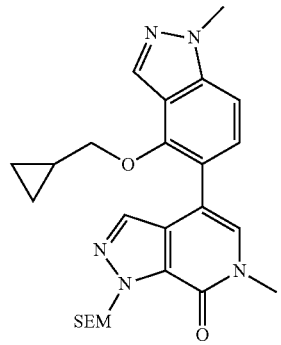 [SMILES: Cn1cc(-c2ccc3c(cnn3C)c2OCC2CC2)c2cnn(COCC[Si](C)(C)C)c2c1=O]

This compound was synthesized according to the procedure of Example 10, Step 5, using 5-bromo-4-(cyclopropylmethoxy)-1-methyl-1H-indazole and 6-methyl-4-(4,4,5,5-tetramethyl-1,3,2-dioxaborolan-2-yl)-1-{[2-(trimethylsilyl)ethoxy]methyl}-1,6-dihydro-7H-pyrazolo[3,4-c]pyridin-7-one as the starting materials. LCMS calculated for $C_{25}H_{34}N_5O_3Si$ $(M+H)^+$: m/z=480.2; found: 480.1.

Step 2. 4-[4-(Cyclopropylmethoxy)-1-methyl-1H-indazol-5-yl]-6-methyl-1,6-dihydro-7H-pyrazolo[3,4-c]pyridin-7-one

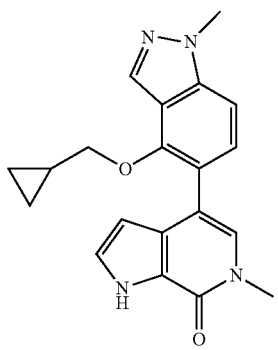 [SMILES: Cn1cc(-c2ccc3c(cnn3C)c2OCC2CC2)c2cc[nH]c2c1=O]

Trifluoroacetic acid (0.564 mL) was added dropwise to a solution of 4-[4-(cyclopropylmethoxy)-1-methyl-1H-indazol-5-yl]-6-methyl-1-{[2-(trimethylsilyl)ethoxy]methyl}-1,6-dihydro-7H-pyrazolo[3,4-c]pyridin-7-one (0.0549 g, 0.114 mmol) in methylene chloride (0.564 mL) and the resultant reaction mixture was stirred at RT for 30 min. The reaction mixture was concentrated in vacuo to yield a crude residue. The crude residue was dissolved in methanol (1.00 mL), followed by dropwise addition of 15.0 M solution of ammonium hydroxide in water (0.250 mL, 3.76 mmol). The resultant reaction mixture was stirred at RT for 30 min. The reaction mixture was purified via preparative LCMS (XBridge C18 column, eluting with a gradient of acetonitrile/water 0.1% ammonium hydroxide, at flow rate of 60 mL/min) to give the desired product (26.8 mg, 67%). $^1$H NMR (500 MHz, DMSO-d$_6$) δ 14.00 (br s, 1H), 8.23 (s, 1H), 7.72 (s, 1H), 7.38 (d, J=8.5 Hz, 1H), 7.33 (d, J=8.5 Hz, 1H), 7.28 (s, 1H), 4.05 (d, J=6.8 Hz, 2H), 4.03 (s, 3H), 3.58 (s, 3H), 1.23-0.81 (m, 1H), 0.51-0.26 (m, 2H), 0.25-0.01 (m, 2H); LCMS calculated for C$_{19}$H$_{20}$N$_5$O$_2$ (M+H)$^+$: m/z=350.2; found: 350.1.

Example 78. 4-[4-(2,4-Difluorophenoxy)-7-(1-hydroxyethyl)-1-methyl-1H-benzimidazol-5-yl]-6-methyl-1,6-dihydro-7H-pyrazolo[3,4-c]pyridin-7-one

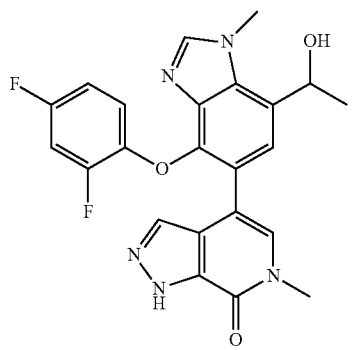 [SMILES: CC(O)c1cc(-c2cn(C)c(=O)c3[nH]ncc23)c(Oc2ccc(F)cc2F)c2ncn(C)c12]

Step 1. 4-[5-Bromo-2-(2,4-difluorophenoxy)-4-(methylamino)-3-nitrophenyl]-6-methyl-1-{[2-(trimethylsilyl)ethoxy]methyl}-1,6-dihydro-7H-pyrazolo[3,4-c]pyridin-7-one

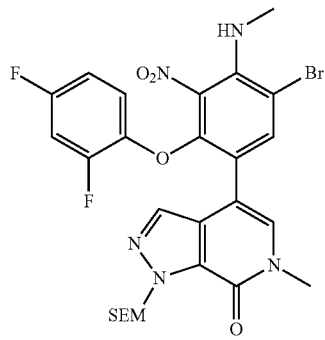

A solution of 4-[2-(2,4-difluorophenoxy)-4-(methylamino)-3-nitrophenyl]-6-methyl-1-{[2-(trimethylsilyl)ethoxy]methyl}-1,6-dihydro-7H-pyrazolo[3,4-c]pyridin-7-one (0.433 g, 0.776 mmol) in N,N-dimethylformamide (5.0 mL) was cooled to 0° C. Two portions of N-bromosuccinimide (0.159 g, 0.893 mmol) were added with a 5 min interval to the above solution at 0° C., and the resultant reaction mixture was stirred at 0° C. for 30 min, after which time the reaction mixture was diluted with water and ethyl acetate. Layers were separated and the organic layer was washed with saturated sodium bicarbonate, dried with sodium sulfate, filtered, and concentrated to give a crude residue. Purification by flash column chromatography (100% hexanes to 50% EtOAc/hexanes [EtOAc contained 5% MeOH]) gave the desired product (444 mg, 90%) as a yellow solid. LCMS calculated for C$_{26}$H$_{29}$BrF$_2$N$_5$O$_5$Si (M+H)$^+$: m/z=636.1, 638.1; found: 636.0, 638.1.

Step 2. 4-[3-Amino-5-bromo-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one

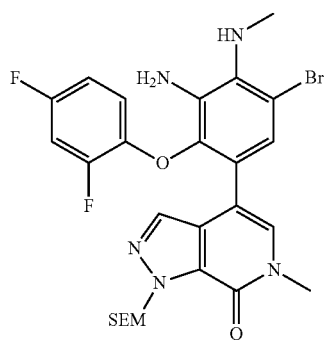 [SMILES: CNc1c(Br)cc(-c2cn(C)c(=O)c3c2cnn3COCC[Si](C)(C)C)c(Oc2ccc(F)cc2F)c1[N+](=O)[O-]]

A suspension of 4-[5-bromo-2-(2,4-difluorophenoxy)-4-(methylamino)-3-nitrophenyl]-6-methyl-1-{[2-(trimethylsilyl)ethoxy]methyl}-1,6-dihydro-7H-pyrazolo[3,4-c]pyridin-7-one (0.209 g, 0.328 mmol) in tetrahydrofuran (1.38 mL) was treated with iron (0.183 g, 3.28 mmol), followed by the addition of acetic acid (1.38 mL, 24.3 mmol). The resultant reaction mixture was warmed to 60° C. and stirred at 60° C. for 1.5 h. The reaction mixture was treated with iron (0.0917 g, 1.64 mmol) and stirred at 60° C. for 14 h, after which time the reaction mixture was filtered through the pad of Celite and washed with ethyl acetate. The filtrate was concentrated in vacuo to give a crude residue. The crude residue was diluted with saturated solution of sodium bicarbonate and ethyl acetate. Layers were separated and the organic layer was washed with brine, dried with sodium sulfate, filtered, and concentrated in vacuo to give a crude residue. Purification by flash column chromatography (100% hexanes to 40% EtOAc/hexanes) gave the desired product (104 mg, 52%) as a white solid. LCMS calculated for $C_{26}H_{31}BrF_2N_5O_3Si$ (M+H)$^+$: m/z=606.1, 608.1; found: 606.0, 608.0.

Step 3. 4-[7-Bromo-4-(2,4-difluorophenoxy)-1-methyl-1H-benzimidazol-5-yl]-6-methyl-1-{[2-(trimethylsilyl)ethoxy]methyl}-1,6-dihydro-7H-pyrazolo[3,4-c]pyridin-7-one

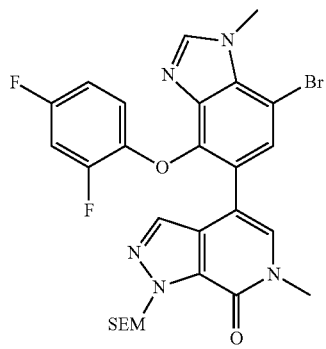 [SMILES: Cn1cc(-c2cc(Br)c3c(ncn3C)c2Oc2ccc(F)cc2F)c2cnn(COCC[Si](C)(C)C)c2c1=O]

This compound was synthesized according to the procedure of Examples 30 and 31, Step 6, using 4-[3-amino-5-bromo-2-(2,4-difluorophenoxy)-4-(methylamino)phenyl]-6-methyl-1-{[2-(trimethylsilyl)ethoxy]methyl}-1,6-dihydro-7H-pyrazolo[3,4-c]pyridin-7-one as the starting material. LCMS calculated for $C_{27}H_{29}BrF_2N_5O_3Si$ (M+H)$^+$: m/z=616.1, 618.1; found: 615.9, 618.0.

Step 4. 4-[4-(2,4-Difluorophenoxy)-1-methyl-7-vinyl-1H-benzimidazol-5-yl]-6-methyl-1-{[2-(trimethylsilyl)ethoxy]methyl}-1,6-dihydro-7H-pyrazolo[3,4-c]pyridin-7-one

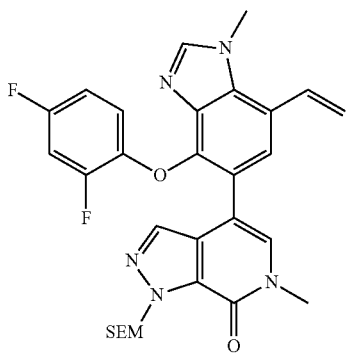 [SMILES: C=Cc1cc(-c2cn(C)c(=O)c3c2cnn3COCC[Si](C)(C)C)c(Oc2ccc(F)cc2F)c2ncn(C)c12]

A mixture of 4-[7-bromo-4-(2,4-difluorophenoxy)-1-methyl-1H-benzimidazol-5-yl]-6-methyl-1-{[2-(trimethyl silyl)ethoxy]methyl}-1,6-dihydro-7H-pyrazolo[3,4-c]pyridin-7-one (0.0990 g, 0.160 mmol), 4,4,5,5-tetramethyl-2-vinyl-1,3,2-dioxaborolane (0.0408 mL, 0.241 mmol), [1,1'-Bis(diphenylphosphino)ferrocene]dichloropalladium(II), complex with dichloromethane (1:1) (0.0131 g, 0.0160 mmol) and potassium carbonate (0.0555 g, 0.401 mmol) in 1,4-dioxane (1.0 mL, 12.8 mmol) and water (0.580 mL, 32.2 mmol) was degassed with nitrogen for 10 min, warmed to 80° C. and stirred at 80° C. for 2 h. The reaction mixture was diluted with water and ethyl acetate. Layers were separated and the organic layer was washed with brine, dried with sodium sulfate, filtered, and concentrated in vacuo to give a crude residue. Purification by flash column chromatography (100% hexanes to 100% EtOAc [EtOAc contained 5% MeOH]) gave the desired product (77 mg, 85%) as a white foam. LCMS calculated for $C_{29}H_{32}F_2N_5O_3Si$ (M+H)$^+$: m/z=564.2; found: 564.1.

Step 5. 4-(2,4-Difluorophenoxy)-1-methyl-5-(6-methyl-7-oxo-1-{[2-(trimethylsilyl)ethoxy]methyl}-6,7-dihydro-1H-pyrazolo[3,4-c]pyridin-4-yl)-1H-benzimidazole-7-carbaldehyde

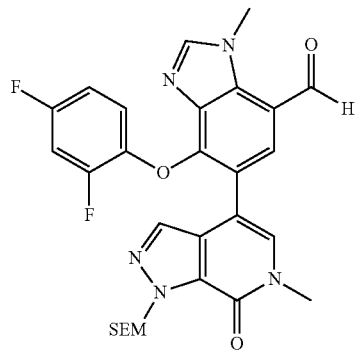 [SMILES: Cn1cc(-c2cc(C=O)c3c(ncn3C)c2Oc2ccc(F)cc2F)c2cnn(COCC[Si](C)(C)C)c2c1=O]

A mixture of 4-[4-(2,4-difluorophenoxy)-1-methyl-7-vinyl-1H-benzimidazol-5-yl]-6-methyl-1-{[2-(trimethyl silyl)ethoxy]methyl}-1,6-dihydro-7H-pyrazolo[3,4-c]pyridin-7-one (0.076 g, 0.13 mmol) and sodium metaperiodate (0.0865 g, 0.404 mmol) in water (0.23 mL) and tetrahydrofuran (3.10 mL) was treated with 0.16M solution of osmium tetraoxide in water (0.172 mL, 0.0270 mmol). The resultant reaction mixture was stirred at 60° C. for 30 min. The reaction mixture was diluted with water and ethyl acetate. Layers were separated and the organic layer was washed with brine, dried with sodium sulfate, filtered, and concentrated in vacuo to give a crude residue. Purification by flash column chromatography (100% hexanes to 100% EtOAc [EtOAc contained 5% MeOH]) gave the desired product (50.6 mg, 66%). LCMS calculated for $C_{28}H_{30}F_2N_5O_4Si$ (M+H)$^+$: m/z=566.2; found: 566.1.

149

Step 6. 4-[4-(2,4-Difluorophenoxy)-7-(1-hydroxy-ethyl)-1-methyl-1H-benzimidazol-5-yl]-6-methyl-1-{[2-(trimethylsilyl)ethoxy]methyl}-1,6-dihydro-7H-pyrazolo[3,4-c]pyridin-7-one

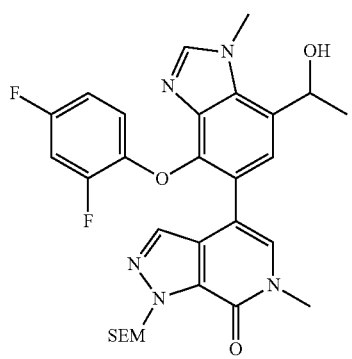 [SMILES: CC(O)c1cc(-c2cn(C)c(=O)c3c2cnn3COCC[Si](C)(C)C)c(Oc2ccc(F)cc2F)c2ncn(C)c12]

A 3.0 M solution of methylmagnesium iodide in diethyl ether (21.1 μL, 0.0634 mmol) was added to a solution of 4-(2,4-difluorophenoxy)-1-methyl-5-(6-methyl-7-oxo-1-{[2-(trimethylsilyl)ethoxy]methyl}-6,7-dihydro-1H-pyrazolo[3,4-c]pyridin-4-yl)-1H-benzimidazole-7-carbaldehyde (0.0478 g, 0.0845 mmol) in tetrahydrofuran (0.734 mL) at 0° C. The resultant reaction mixture was stirred at 0° C. for 1 h, after which time an additional amount of 3.0 M solution of methylmagnesium iodide in diethyl ether (42.2 μL, 0.127 mmol) was added to the reaction mixture and stirring was continued at 0° C. for 30 min. The reaction mixture was quenched at 0° C. with methanol, diluted with methanol, and purified via preparative LCMS (XBridge C18 column, eluting with a gradient of acetonitrile/water 0.1% ammonium hydroxide, at flow rate of 60 mL/min) to give the desired product (25.2 mg, 51%). LCMS calculated for $C_{29}H_{34}F_2N_5O_4Si$ (M+H)$^+$: m/z=582.2; found: 582.2.

Step 7. 4-[4-(2,4-Difluorophenoxy)-7-(1-hydroxy-ethyl)-1-methyl-1H-benzimidazol-5-yl]-6-methyl-1,6-dihydro-7H-pyrazolo[3,4-c]pyridin-7-one This compound was synthesized according to the procedure of Example 77, Step 2, using 4-[4-(2,4-difluorophenoxy)-7-(1-hydroxyethyl)-1-methyl-1H-benzimidazol-5-yl]-6-methyl-1-{[2-(trimethylsilyl)ethoxy]methyl}-1,6-dihydro-7H-pyrazolo[3,4-c]pyridin-7-one as the starting material. $^1$H NMR (500 MHz, DMSO-d6) δ 14.04 (br s, 1H), 8.12 (s, 1H), 7.76 (s, 1H), 7.45 (s, 1H), 7.29-7.17 (m, 2H), 6.83-6.63 (m, 1H), 6.63-6.41 (m, 1H), 5.45 (q, J=6.3 Hz, 1H), 4.11 (s, 3H), 3.53 (s, 3H), 1.56 (d, J=6.3 Hz, 3H); LCMS calculated for $C_{23}H_{20}F_2N_5O_3$ (M+H)$^+$: m/z=452.2; found: 452.1.

150

Example 79. 4-(2,4-Difluorophenoxy)-5-(6-methyl-7-oxo-6,7-dihydro-1H-pyrrolo[2,3-c]pyridin-4-yl)-7-{[(2-morpholin-4-ylethyl)amino]methyl}-1,3-dihydro-2H-benzimidazol-2-one

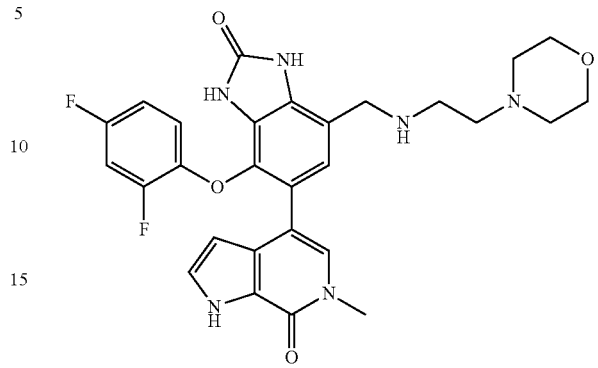

Step 1. 4-[4-Amino-5-bromo-2-(2,4-difluorophenoxy)-3-nitrophenyl]-6-methyl-1-[(4-methylphenyl)sulfonyl]-1,6-dihydro-7H-pyrrolo[2,3-c]pyridin-7-one

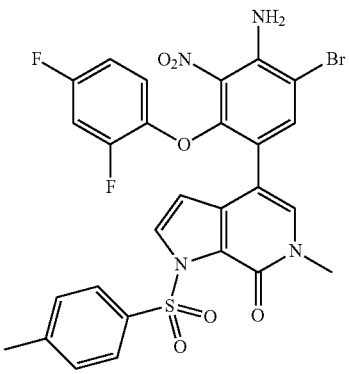

This compound was synthesized according to the procedure of Example 78, Step 1, using 4-[4-amino-2-(2,4-difluorophenoxy)-3-nitrophenyl]-6-methyl-1-[(4-methylphenyl)sulfonyl]-1,6-dihydro-7H-pyrrolo[2,3-c]pyridin-7-one as the starting material. LCMS calculated for $C_{27}H_{20}BrF_2N_4O_6S$ (M+H)$^+$: m/z=645.0, 647.0; found: 644.9, 646.9.

Step 2. 4-[4-Amino-2-(2,4-difluorophenoxy)-3-nitro-5-vinylphenyl]-6-methyl-1-[(4-methylphenyl)sulfonyl]-1,6-dihydro-7H-pyrrolo[2,3-c]pyridin-7-one

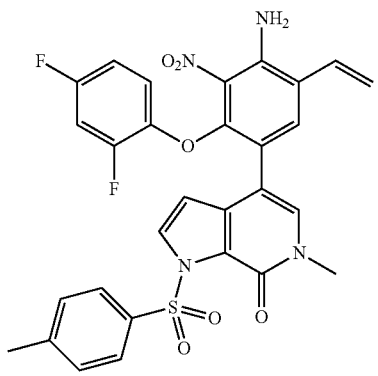 [SMILES: C=Cc1cc(-c2cn(C)c(=O)c3c2ccn3S(=O)(=O)c2ccc(C)cc2)c(Oc2ccc(F)cc2F)c([N+](=O)[O-])c1N]

This compound was synthesized according to the procedure of Example 78, Step 4, using 4-[4-amino-5-bromo-2-(2,4-difluorophenoxy)-3-nitrophenyl]-6-methyl-1-[(4-methylphenyl)sulfonyl]-1,6-dihydro-7H-pyrrolo[2,3-c]pyridin-7-one as the starting material. LCMS calculated for $C_{29}H_{23}F_2N_4O_6S$ (M+H)$^+$: m/z=593.1; found: 593.0.

Step 3. 4-[3,4-Diamino-2-(2,4-difluorophenoxy)-5-vinylphenyl]-6-methyl-1-[(4-methylphenyl)sulfonyl]-1,6-dihydro-7H-pyrrolo[2,3-c]pyridin-7-one

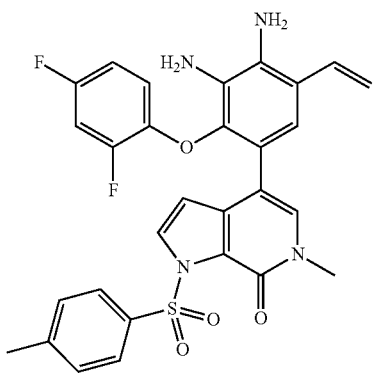

This compound was synthesized according to the procedure of Example 1, Step 3, using 4-[4-amino-2-(2,4-difluorophenoxy)-3-nitro-5-vinylphenyl]-6-methyl-1-[(4-methylphenyl)sulfonyl]-1,6-dihydro-7H-pyrrolo[2,3-c]pyridin-7-one as the starting material. LCMS calculated for $C_{29}H_{25}F_2N_4O_4S$ (M+H)$^+$: m/z=563.2; found: 563.1.

Step 4. 4-(2,4-Difluorophenoxy)-5-{6-methyl-1-[(4-methylphenyl)sulfonyl]-7-oxo-6,7-dihydro-1H-pyrrolo[2,3-c]pyridin-4-yl}-7-vinyl-1,3-dihydro-2H-benzimidazol-2-one

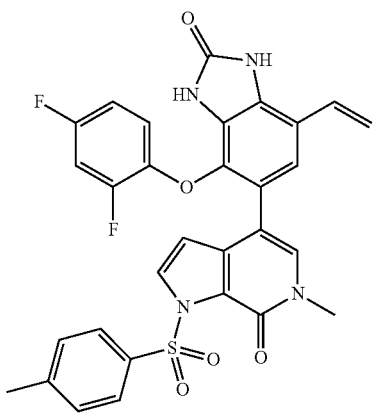 [SMILES: C=Cc1cc(-c2cn(C)c(=O)c3c2ccn3S(=O)(=O)c2ccc(C)cc2)c(Oc2ccc(F)cc2F)c2[nH]c(=O)[nH]c12]

This compound was synthesized according to the procedure of Example 6, Step 1, using 4-[3,4-diamino-2-(2,4-difluorophenoxy)-5-vinylphenyl]-6-methyl-1-[(4-methylphenyl)sulfonyl]-1,6-dihydro-7H-pyrrolo[2,3-c]pyridin-7-one as the starting material. LCMS calculated for $C_{30}H_{23}F_2N_4O_5S$ (M+H)$^+$: m/z=589.1; found: 589.1.

Step 5. 7-(2,4-Difluorophenoxy)-6-{6-methyl-1-[(4-methylphenyl)sulfonyl]-7-oxo-6,7-dihydro-1H-pyrrolo[2,3-c]pyridin-4-yl}-2-oxo-2,3-dihydro-1H-benzimidazole-4-carbaldehyde

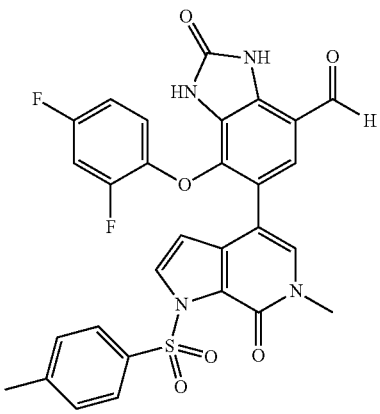 [SMILES: Cc1ccc(S(=O)(=O)n2ccc3c(-c4cc(C=O)c5[nH]c(=O)[nH]c5c4Oc4ccc(F)cc4F)cn(C)c(=O)c32)cc1]

This compound was synthesized according to the procedure of Example 78, Step 5, using 4-(2,4-difluorophenoxy)-5-{6-methyl-1-[(4-methylphenyl)sulfonyl]-7-oxo-6,7-dihydro-1H-pyrrolo[2,3-c]pyridin-4-yl}-7-vinyl-1,3-dihydro-2H-benzimidazol-2-one as the starting material. LCMS calculated for $C_{29}H_{21}F_2N_4O_6S$ (M+H)$^+$: m/z=591.1; found: 591.0.

Step 6. 4-(2,4-Difluorophenoxy)-5-{6-methyl-1-[(4-methylphenyl)sulfonyl]-7-oxo-6,7-dihydro-1H-pyrrolo[2,3-c]pyridin-4-yl}-7-{[(2-morpholin-4-ylethyl)amino]methyl}-1,3-dihydro-2H-benzimidazol-2-one

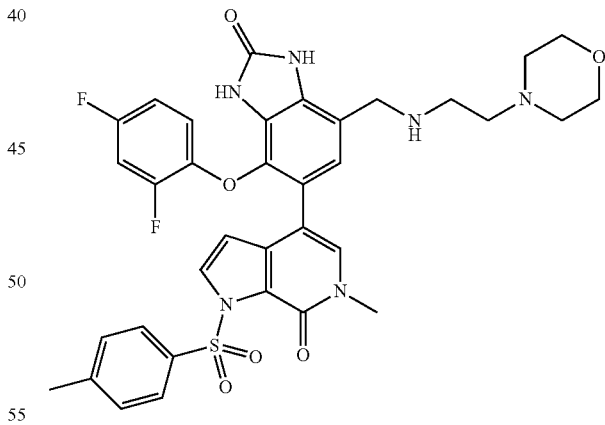

A suspension of 7-(2,4-difluorophenoxy)-6-{6-methyl-1-[(4-methylphenyl)sulfonyl]-7-oxo-6,7-dihydro-1H-pyrrolo[2,3-c]pyridin-4-yl}-2-oxo-2,3-dihydro-1H-benzimidazole-4-carbaldehyde (25.0 mg, 0.0423 mmol) and N-(2-aminoethyl)morpholine (0.0111 mL, 0.0847 mmol) in methanol (0.40 mL) and methylene chloride (0.40 mL) was heated to 60° C. and stirred at 60° C. for 1 h. The reaction mixture was cooled to 0° C., treated with sodium cyanoborohydride (0.0106 g, 0.169 mmol), warmed to RT and stirred for at RT 15 h. The reaction mixture was concentrated in vacuo and the residue was dissolved in methanol (0.50 mL), treated with sodium cyanoborohydride (0.00532 g, 0.0847 mmol), and stirred at 60° C. for 3 h. The reaction mixture was diluted with acetonitrile, methanol and a few drops of water and purified via preparative LCMS (XBridge C18 column, eluting with a gradient of acetonitrile/water 0.1% ammonium hydroxide, at flow rate of 60 mL/min) to give the desired product (11.9 mg, 40%). LCMS calculated for $C_{35}H_{35}F_2N_6O_6S$ (M+H)$^+$: m/z=705.2; found: 705.2.

Step 7. 4-(2,4-Difluorophenoxy)-5-(6-methyl-7-oxo-6,7-dihydro-1H-pyrrolo[2,3-c]pyridin-4-yl)-7{[(2-morpholin-4-ylethyl)amino]methyl}-1,3-dihydro-2H-benzimidazol-2-one This compound was synthesized according to the procedure of Example 6, Step 2, using 4-(2,4-difluorophenoxy)-5-{6-methyl-1-[(4-methylphenyl)sulfonyl]-7-oxo-6,7-dihydro-1H-pyrrolo[2,3-c]pyridin-4-yl}-7-{[(2-morpholin-4-ylethyl)amino]methyl}-1,3-dihydro-2H-benzimidazol-2-one as the starting material. $^1$H NMR (500 MHz, DMSO-d$_6$) δ 11.90 (br s, 1H), 10.95 (br s, 1H), 7.19 (d, J=2.3 Hz, 1H), 7.18-7.10 (m, 1H), 7.06 (s, 1H), 7.02 (s, 1H), 6.69 (dd, J=7.9, 7.9 Hz, 1H), 6.49-6.33 (m, 1H), 6.11 (d, J=2.5 Hz, 1H), 3.80 (s, 2H), 3.66-3.51 (m, 4H), 3.43 (s, 3H), 2.65 (t, J=6.1 Hz, 2H), 2.40 (t, J=6.1 Hz, 2H), 2.37-2.21 (m, 4H); LCMS calculated for $C_{28}H_{29}F_2N_6O_4$ (M+H)$^+$: m/z=551.2; found: 551.2.

Example 80. 7-[(Benzylamino)methyl]-4-(2,4-difluorophenoxy)-5-(6-methyl-7-oxo-6,7-dihydro-1H-pyrrolo[2,3-c]pyridin-4-yl)-1,3-dihydro-2H-benzimidazol-2-one

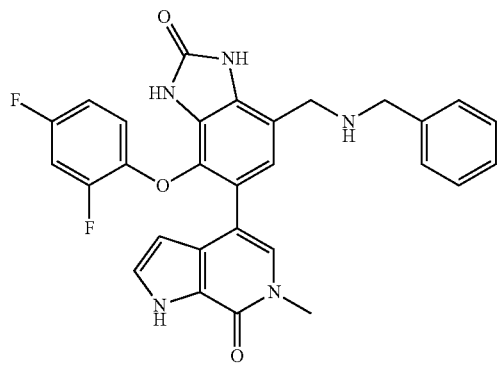 [SMILES: Cn1cc(-c2cc(CNCc3ccccc3)c3[nH]c(=O)[nH]c3c2Oc2ccc(F)cc2F)c2cc[nH]c2c1=O]

This compound was synthesized according to the procedure of Example 79 using benzyl amine in Step 6 instead of N-(2-aminoethyl)morpholine. $^1$H NMR (300 MHz, DMSO-d$_6$) δ 11.91 (br s, 1H), 10.97 (br s, 1H), 7.42-7.00 (m, 7H), 6.81-6.58 (m, 1H), 6.52-6.31 (m, 1H), 6.14 (br s, 1H), 3.82 (s, 2H), 3.73 (s, 2H), 3.43 (s, 3H); LCMS calculated for $C_{29}H_{24}F_2N_5O_3$ (M+H)$^+$: m/z=528.2; found: 528.1.

Example 81. 7-{[(Cyclopropylmethyl)amino]methyl}-4-(2,4-difluorophenoxy)-5-(6-methyl-7-oxo-6,7-dihydro-1H-pyrrolo[2,3-c]pyridin-4-yl)-1,3-dihydro-2H-benzimidazol-2-one

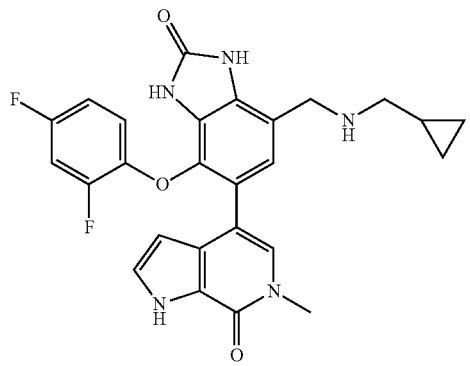 [SMILES: Cn1cc(-c2cc(CNCC3CC3)c3[nH]c(=O)[nH]c3c2Oc2ccc(F)cc2F)c2cc[nH]c2c1=O]

This compound was synthesized according to the procedure of Example 79 using 1-cyclopropylmethanamine hydrochloride in Step 6 instead of N-(2-aminoethyl)morpholine. $^1$H NMR (400 MHz, DMSO-d$_6$) δ 11.94 (br s, 1H), 11.00 (br s, 1H), 7.24-7.11 (m, 2H), 7.08 (d, J=1.4 Hz, 2H), 6.79-6.62 (m, 1H), 6.51-6.32 (m, 1H), 6.12 (d, J=2.4 Hz, 1H), 3.80 (s, 2H), 3.43 (s, 3H), 2.39 (d, J=6.7 Hz, 2H), 1.01-0.76 (m, 1H), 0.50-0.28 (m, 2H), 0.24-0.10 (m, 2H); LCMS calculated for $C_{26}H_{24}F_2N_5O_3$ (M+H)$^+$: m/z=492.2; found: 492.1.

Example 82. 4-[4-(2,4-Difluorophenoxy)-1-methyl-1H-benzimidazol-5-yl]-1,6-dihydro-7H-pyrrolo[2,3-c]pyridin-7-one

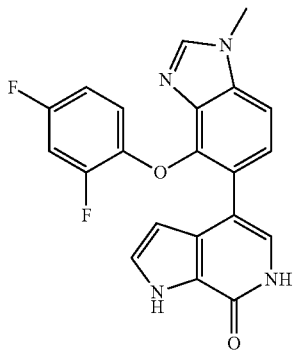 [SMILES: Cn1cnc2c(Oc3ccc(F)cc3F)c(-c3c[nH]c(=O)c4[nH]ccc34)ccc21]

Step 1. N-[4-Bromo-3-(2,4-difluorophenoxy)-2-nitrophenyl]-2,2,2-trifluoroacetamide

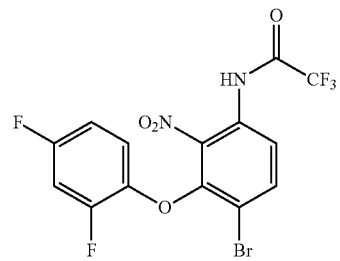 [SMILES: O=C(Nc1ccc(Br)c(Oc2ccc(F)cc2F)c1[N+](=O)[O-])C(F)(F)F]

This compound was synthesized according to the procedure of Example 32, Step 1, using 4-bromo-3-(2,4-difluorophenoxy)-2-nitroaniline as the starting material.

Step 2. 4-Bromo-3-(2,4-difluorophenoxy)-N-methyl-2-nitroaniline

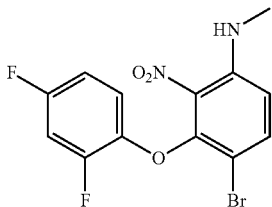

This compound was synthesized according to the procedure of Example 4, Step 2, using N-[4-bromo-3-(2,4-difluorophenyl]-2-nitrophenyl]-2,2,2-trifluoroacetamide as the starting material. LCMS calculated for $C_{13}H_{10}BrF_2N_2O_3$ (M+H)$^+$: m/z=359.0, 361.0; found: 359.0, 361.0.

Step 3. 4-Bromo-3-(2,4-difluorophenoxy)-N-methyl-2-nitroaniline

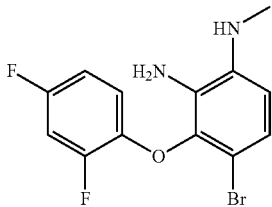 [SMILES: CNc1ccc(Br)c(Oc2ccc(F)cc2F)c1N]

This compound was synthesized according to the procedure of Example 1, Step 3, using 4-bromo-3-(2,4-difluorophenoxy)-N-methyl-2-nitroaniline as the starting material. LCMS calculated for $C_{13}H_{12}BrF_2N_2O$ (M+H)$^+$: m/z=329.0, 331.0; found: 329.0, 330.9.

Step 4. 4-Bromo-3-(2,4-difluorophenoxy)-N-methyl-2-nitroaniline

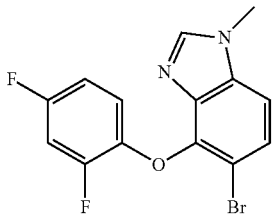 [SMILES: Cn1cnc2c(Oc3ccc(F)cc3F)c(Br)ccc21]

This compound was synthesized according to the procedure of Examples 30 and 31, Step 6, using 4-bromo-3-(2,4-difluorophenoxy)-M-methylbenzene-1,2-diamine as the starting material. LCMS calculated for $C_{14}H_{10}BrF_2N_2O$ (M+H)$^+$: m/z=339.0, 341.0; found: 338.9, 340.9.

Step 5. 4-[4-(2,4-Difluorophenoxy)-1-methyl-1H-benzimidazol-5-yl]-1-[(4-methylphenyl)sulfonyl]-1,6-dihydro-7H-pyrrolo[2,3-c]pyridin-7-one

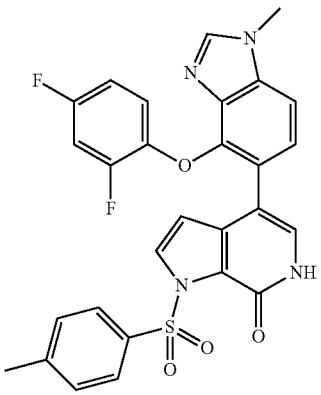 [SMILES: Cc1ccc(S(=O)(=O)n2ccc3c(-c4ccc5c(ncn5C)c4Oc4ccc(F)cc4F)c[nH]c(=O)c32)cc1]

A suspension of 5-bromo-4-(2,4-difluorophenoxy)-1-methyl-1H-benzimidazole (0.300 g, 0.885 mmol) and potassium acetate (0.260 g, 2.65 mmol) in ethanol (6.63 mL) was degassed with nitrogen for 5 min, treated with tetrahydroxydiborane (0.238 g, 2.65 mmol), dicyclohexyl(2',4',6'-triisopropylbiphenyl-2-yl)phosphine (0.0056 g, 0.012 mmol), and dicyclohexyl(2',4',6'-triisopropylbiphenyl-2-yl)phosphine-(2'-aminobiphenyl-2-yl)(chloro)palladium (1:1) (0.0035 g, 0.0044 mmol). The resultant reaction mixture was degassed with nitrogen for another 5 min, warmed to 80° C. and stirred at that temperature for 17 h, after which time the reaction mixture was cooled to RT, degassed with nitrogen for 5 min, treated with previously degassed 1.8M solution of potassium carbonate in water (1.47 mL, 2.65 mmol), followed by addition of 4-bromo-1-[(4-methylphenyl)sulfonyl]-1,6-dihydro-7H-pyrrolo[2,3-c]pyridin-7-one (0.108 g, 0.295 mmol) and dicyclohexyl(2',4',6'-triisopropylbiphenyl-2-yl)phosphine-(2'-aminobiphenyl-2-yl)(chloro)palladium (1:1) (0.0046 g, 0.0059 mmol). The resultant reaction mixture was degassed with nitrogen for another 5 min, and heated at 90° C. for 2 h. The reaction mixture was diluted with saturated sodium bicarbonate solution and ethyl acetate. The precipitate was collected by filtration, layers of filtrate were separated and the organic layer was dried with sodium sulfate, filtered, and concentrated to give a crude residue. This crude residue was combined with the previously collected solid precipitate and purified by flash column chromatography (100% $CH_2Cl_2$ to 12% MeOH/$CH_2Cl_2$) gave the desired product (84.8 mg, 53%) as a yellow solid. LCMS calculated for $C_{28}H_{21}F_2N_4O_4S$ (M+H)$^+$: m/z=547.1; found: 547.0.

Step 6. 4-[4-(2,4-Difluorophenoxy)-1-methyl-1H-benzimidazol-5-yl]-1,6-dihydro-7H-pyrrolo[2,3-c]pyridin-7-one This compound was synthesized according to the procedure of Example 8, Step 2, using 4-[4-(2,4-difluorophenoxy)-1-methyl-1H-benzimidazol-5-yl]-1-[(4-methylphenyl)sulfonyl]-1,6-dihydro-7H-pyrrolo[2,3-c]pyridin-7-one as the starting material. $^1$H NMR (400 MHz, DMSO-$d_6$) δ 12.01 (br s, 1H), 10.97 (d, J=5.7 Hz, 1H), 8.12 (s, 1H), 7.55 (d, J=8.4 Hz, 1H), 7.39 (d, J=8.3 Hz, 1H), 7.34-7.17 (m, 2H), 6.82 (d, J=5.7 Hz, 1H), 6.80-6.66 (m, 1H), 6.66-6.47 (m, 1H), 6.15 (s, 1H), 3.87 (s, 3H); LCMS calculated for C$_{21}$H$_{15}$F$_2$N$_4$O$_2$ (M+H)$^+$: m/z=393.1; found: 393.1.

Example 83. 4-[4-(2,4-Difluorophenoxy)-1-methyl-1H-benzimidazol-5-yl]-6-ethyl-1,6-dihydro-7H-pyrrolo[2,3-c]pyridin-7-one

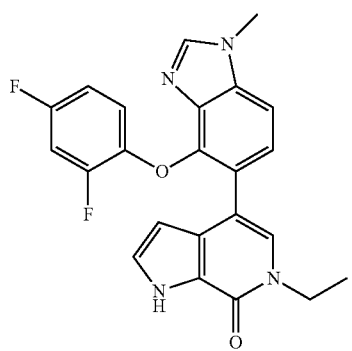 [SMILES: CCn1cc(-c2ccc3c(ncn3C)c2Oc2ccc(F)cc2F)c2cc[nH]c2c1=O]

Step 1. 4-[4-(2,4-Difluorophenoxy)-1-methyl-1H-benzimidazol-5-yl]-6-ethyl-1-[(4-methylphenyl)sulfonyl]-1,6-dihydro-7H-pyrrolo[2,3-c]pyridin-7-one

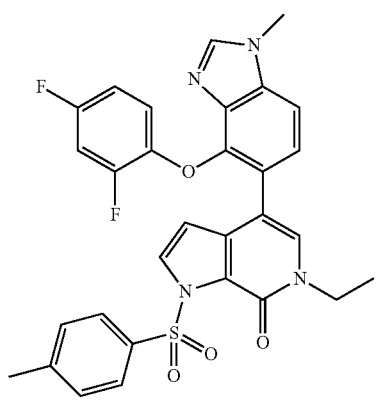 [SMILES: CCn1cc(-c2ccc3c(ncn3C)c2Oc2ccc(F)cc2F)c2ccn(S(=O)(=O)c3ccc(C)cc3)c2c1=O]

A suspension of 4-[4-(2,4-difluorophenoxy)-1-methyl-1H-benzimidazol-5-yl]-1-[(4-methylphenyl)sulfonyl]-1,6-dihydro-7H-pyrrolo[2,3-c]pyridin-7-one (33.2 mg, 0.0607 mmol) in tetrahydrofuran (1.0 mL) at 0° C. was treated with 1.0 M solution of potassium tert-butoxide in THF (0.0850 mL, 0.0850 mmol) and the resultant reaction mixture was stirred at 0° C. for 30 min, after which time the reaction mixture was treated with iodoethane (0.00680 mL, 0.0850 mmol), warmed to RT and stirred at RT for 19 h. The reaction mixture was quenched with saturated ammonium chloride solution, diluted with water, and extracted with ethyl acetate. Layers were separated and the organic layer was washed with brine, dried with sodium sulfate, filtered, and concentrated in vacuo to give a crude residue. Purification via preparative LCMS (XBridge C18 column, eluting with a gradient of acetonitrile/water 0.1% ammonium hydroxide, at flow rate of 60 mL/min) gave the desired product (15.4 mg, 44%). LCMS calculated for C$_{30}$H$_{25}$F$_2$N$_4$O$_4$S (M+H)$^+$: m/z=575.2; found: 575.1.

Step 2. 4-[4-(2,4-Difluorophenoxy)-1-methyl-1H-benzimidazol-5-yl]-6-ethyl-1,6-dihydro-7H-pyrrolo[2,3-c]pyridin-7-one This compound was synthesized according to the procedure of Example 8, Step 2, using 4-[4-(2,4-difluorophenoxy)-1-methyl-1H-benzimidazol-5-yl]-6-ethyl-1-[(4-methylphenyl)sulfonyl]-1,6-dihydro-7H-pyrrolo[2,3-c]pyridin-7-one as the starting material. $^1$H NMR (400 MHz, DMSO-d$_6$) δ 11.99 (br s, 1H), 8.14 (s, 1H), 7.56 (d, J=8.4 Hz, 1H), 7.40 (d, J=8.3 Hz, 1H), 7.31-7.19 (m, 2H), 7.15 (s, 1H), 6.80-6.68 (m, 1H), 6.65-6.47 (m, 1H), 6.12 (d, J=2.8 Hz, 1H), 3.96 (q, J=7.1 Hz, 2H), 3.88 (s, 3H), 1.16 (t, J=7.1 Hz, 3H); LCMS calculated for C$_{23}$K$_9$F$_2$N$_4$O$_2$ (M+H)$^+$: m/z=421.1; found: 421.0.

Example 84. 6-Benzyl-4-[4-(2,4-difluorophenoxy)-1-methyl-1H-benzimidazol-5-yl]-1,6-dihydro-7H-pyrrolo[2,3-c]pyridin-7-one trifluoroacetate

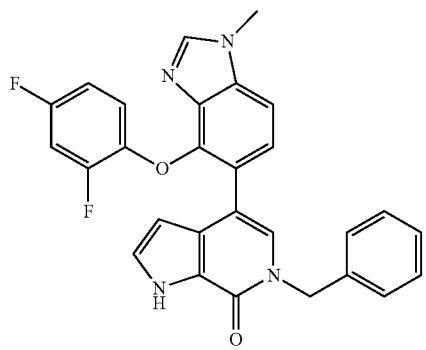 [SMILES: Cn1cnc2c(Oc3ccc(F)cc3F)c(-c3cn(Cc4ccccc4)c(=O)c4[nH]ccc34)ccc21]

This compound was synthesized according to the procedure of Example 83 using benzyl bromide in Step 1 instead of iodoethane. $^1$H NMR (500 MHz, DMSO-d$_6$) δ 12.04 (s, 1H), 8.51 (br s, 1H), 7.67 (d, J=8.4 Hz, 1H), 7.47 (d, J=8.4 Hz, 1H), 7.34-7.03 (m, 8H), 6.78-6.58 (m, 1H), 6.59-6.40 (m, 1H), 6.32-5.92 (m, 1H), 5.16 (s, 2H), 3.93 (s, 3H); LCMS calculated for C$_{28}$H$_{21}$F$_2$N$_4$O$_2$ (M+H)$^+$: m/z=483.2; found: 483.1.

Example 85. {4-[4-(2,4-Difluorophenoxy)-1-methyl-1H-benzimidazol-5-yl]-7-oxo-1,7-dihydro-6H-pyrrolo[2,3-c]pyridin-6-yl}acetonitrile trifluoroacetate

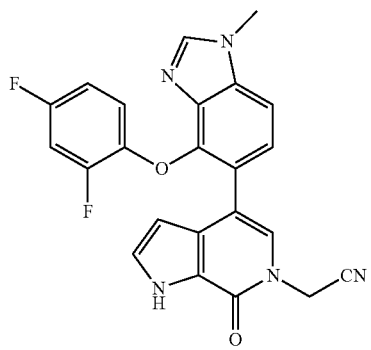 [SMILES: Cn1cnc2c(Oc3ccc(F)cc3F)c(-c3cn(CC#N)c(=O)c4[nH]ccc34)ccc21]

Step 1. {4-Bromo-1-[(4-methylphenyl)sulfonyl]-7-oxo-1,7-dihydro-6H-pyrrolo[2,3-c]pyridin-6-yl}acetonitrile

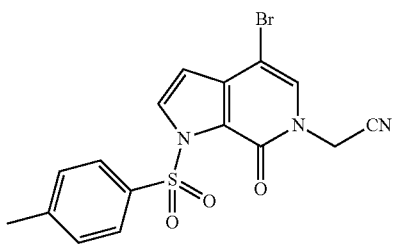 [SMILES: Cc1ccc(S(=O)(=O)n2ccc3c(Br)cn(CC#N)c(=O)c32)cc1]

This compound was synthesized according to the procedure of Example 83, Step 1, using 4-bromo-1-[(4-methylphenyl)sulfonyl]-1H-pyrrolo[2,3-c]pyridin-7-ol and bromoacetonitrile as the starting materials. LCMS calculated for $C_{16}H_{13}BrN_3O_3S$ (M+H)$^+$: m/z=406.0, 408.0; found: 405.9, 407.9.

Step 2. {4-[4-(2,4-Difluorophenoxy)-1-methyl-1H-benzimidazol-5-yl]-1-[(4-methylphenyl)sulfonyl]-7-oxo-1,7-dihydro-6H-pyrrolo[2,3-c]pyridin-6-yl}acetonitrile

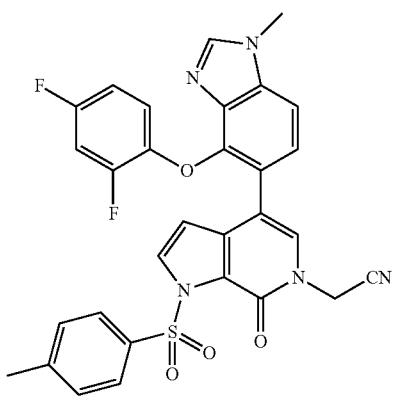 [SMILES: Cc1ccc(S(=O)(=O)n2ccc3c(-c4ccc5c(ncn5C)c4Oc4ccc(F)cc4F)cn(CC#N)c(=O)c32)cc1]

This compound was synthesized according to the procedure of Example 82, Step 5, using {4-bromo-1-[(4-methylphenyl)sulfonyl]-7-oxo-1,7-dihydro-6H-pyrrolo[2,3-c]pyridin-6-yl}acetonitrile instead of 4-bromo-1-[(4-methylphenyl)sulfonyl]-1,6-dihydro-7H-pyrrolo[2,3-c]pyridin-7-one. LCMS calculated for $C_{30}H_{22}F_2N_5O_4S$ (M+H)$^+$: m/z=586.1; found: 586.0.

Step 3. {4-[4-(2,4-Difluorophenoxy)-1-methyl-1H-benzimidazol-5-yl]-7-oxo-1,7-dihydro-6H-pyrrolo[2,3-c]pyridin-6-yl}acetonitrile trifluoroacetate A 1.0 M solution of tetra-n-butylammonium fluoride in THF (0.330 mL, 0.330 mmol) was added dropwise to a solution of {4-[4-(2,4-difluorophenoxy)-1-methyl-1H-benz-imidazol-5-yl]-1-[(4-methylphenyl)sulfonyl]-7-oxo-1,7-dihydro-6H-pyrrolo[2,3-c]pyridine-6-yl}acetonitrile (38.6 mg, 0.0659 mmol) in tetrahydrofuran (1.00 mL), and the resultant reaction mixture was stirred at RT for 30 min. The reaction mixture was purified via preparative LCMS (XBridge C18 column, eluting with a gradient of acetonitrile/water containing 0.1% trifluoroacetic acid, at flow rate of 60 mL/min) to give the desired product (13.8 mg, 38%) as a white solid. $^1$H NMR (400 MHz, DMSO-$d_6$) δ 12.28 (s, 1H), 8.51 (br s, 1H), 7.67 (d, J=8.4 Hz, 1H), 7.45 (d, J=8.4 Hz, 1H), 7.39-7.27 (m, 2H), 7.26-7.11 (m, 1H), 6.82-6.67 (m, 1H), 6.67-6.49 (m, 1H), 6.19-6.06 (m, 1H), 5.10 (s, 2H), 3.94 (s, 3H); LCMS calculated for $C_{23}H_{16}F_2N_5O_2$ (M+H)$^+$: m/z=432.0; found: 432.0.

Example 86. 4-(4-Chlorophenoxy)-1-methyl-5-(6-methyl-7-oxo-6,7-dihydro-1H-pyrrolo[2,3-c]pyridin-4-yl)-1,3-dihydro-2H-benzimidazol-2-one

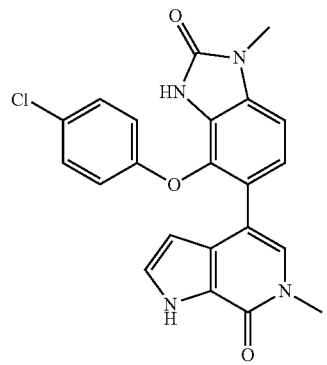 [SMILES: Cn1cc(-c2ccc3c([nH]c(=O)n3C)c2Oc2ccc(Cl)cc2)c2cc[nH]c2c1=O]

Step 1. 4-[2-Fluoro-4-(methylamino)-3-nitrophenyl]-6-methyl-1-{[2-(trimethylsilyl)ethoxy]methyl}-1,6-dihydro-7H-pyrrolo[2,3-c]pyridin-7-one

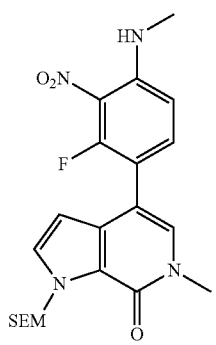 [SMILES: CNc1ccc(-c2cn(C)c(=O)c3c2ccn3COCC[Si](C)(C)C)c(F)c1[N+](=O)[O-]]

This compound was synthesized according to the procedure of Example 10, Step 5, using 4-bromo-3-fluoro-N-methyl-2-nitroaniline and 6-methyl-4-(4,4,5,5-tetramethyl-1,3,2-dioxaborolan-2-yl)-1-{[2-(trimethylsilyl)ethoxy]methyl}-1,6-dihydro-7H-pyrrolo[2,3-c]pyridin-7-one as the starting materials. LCMS calculated for $C_{21}H_{28}FN_4O_4Si$ (M+H)$^+$: m/z=447.2; found: 447.1.

Step 2. 4-[2-(4-Chlorophenoxy)-4-(methylamino)-3-nitrophenyl]-6-methyl-1-{[2-(trimethylsilyl)ethoxy]methyl}-1,6-dihydro-7H-pyrrolo[2,3-c]pyridin-7-one

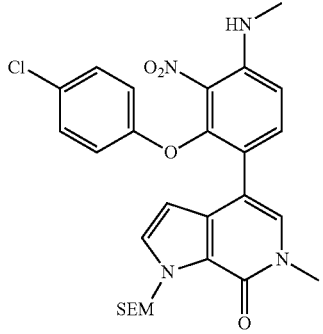 [SMILES: CNc1ccc(-c2cn(C)c(=O)c3c2ccn3COCC[Si](C)(C)C)c(Oc2ccc(Cl)cc2)c1[N+](=O)[O-]]

This compound was synthesized according to the procedure of Example 1, Step 1, using 4-[2-fluoro-4-(methylamino)-3-nitrophenyl]-6-methyl-1-{[2-(trimethylsilyl)ethoxy]methyl}-1,6-dihydro-7H-pyrrolo[2,3-c]pyridin-7-one and p-chlorophenol as the starting materials. LCMS calculated for $C_{27}H_{32}ClN_4O_5Si$ $(M+H)^+$: m/z=555.2; found: 555.1.

Step 3. 4-[3-Amino-2-(4-chlorophenoxy)-4-(methylamino)phenyl]-6-methyl-1-{[2-(trimethylsilyl)ethoxy]methyl}-1,6-dihydro-7H-pyrrolo[2,3-c]pyridin-7-one

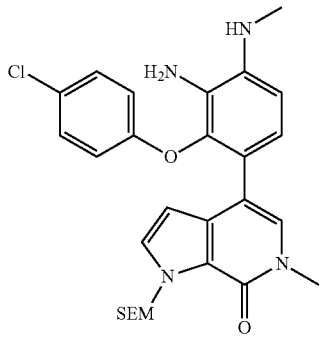 [SMILES: CNc1ccc(-c2cn(C)c(=O)c3c2ccn3COCC[Si](C)(C)C)c(Oc2ccc(Cl)cc2)c1N]

This compound was synthesized according to the procedure of Example 1, Step 3, using 4-[2-(4-chlorophenoxy)-4-(methylamino)-3-nitrophenyl]-6-methyl-1-{[2-(trimethylsilyl)ethoxy]methyl}-1,6-dihydro-7H-pyrrolo[2,3-c]pyridin-7-one as the starting material. LCMS calculated for $C_{27}H_{34}ClN_4O_3Si$ $(M+H)^+$: m/z=525.2; found: 525.1.

Step 4. 4-(4-chlorophenoxy)-1-methyl-5-(6-methyl-7-oxo-1-{[2-(trimethylsilyl)ethoxy]methyl}-6,7-dihydro-1H-pyrrolo[2,3-c]pyridin-4-yl)-1,3-dihydro-2H-benzimidazol-2-one

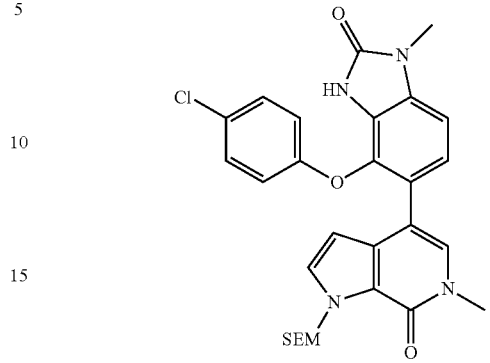

This compound was synthesized according to the procedure of Example 6, Step 1, using 4-[3-amino-2-(4-chlorophenoxy)-4-(methylamino)phenyl]-6-methyl-1-{[2-(trimethylsilyl)ethoxy]methyl}-1,6-dihydro-7H-pyrrolo[2,3-c]pyridin-7-one as the starting material. LCMS calculated for $C_{28}H_{32}ClN_4O_4Si$ $(M+H)^+$: m/z=551.2; found: 551.1.

Step 5. 4-(4-Chlorophenoxy)-1-methyl-5-(6-methyl-7-oxo-6,7-dihydro-1H-pyrrolo[2,3-c]pyridin-4-yl)-1,3-dihydro-2H-benzimidazol-2-one Trifluoroacetic acid (1.50 mL) was added dropwise to a solution of 4-(4-chlorophenoxy)-1-methyl-5-(6-methyl-7-oxo-1-{[2-(trimethyl silyl)ethoxy]methyl}-6,7-dihydro-1H-pyrrolo[2,3-c]pyridin-4-yl)-1,3-dihydro-2H-benzimidazol-2-one (0.057 g, 0.103 mmol) in methylene chloride (0.50 mL), and the resultant reaction mixture was stirred at RT for 3 h, after which time the reaction mixture was concentrated in vacuo to give a residue. This residue was dissolved in methanol (0.50 mL), treated with ethylenediamine (0.131 mL, 1.95 mmol) dropwise, and the resultant solution was stirred at RT for 16 h. The reaction mixture was purified via preparative LCMS (XBridge C18 column, eluting with a gradient of acetonitrile/water 0.1% ammonium hydroxide, at flow rate of 60 mL/min) to give the desired product (24.6 mg, 60%). $^1$H NMR (400 MHz, DMSO-$d_6$) δ 11.96 (br s, 1H), 11.20 (br s, 1H), 7.23 (dd, J=2.7, 2.7 Hz, 1H), 7.21-6.99 (m, 5H), 6.70-6.48 (m, 2H), 6.25-6.06 (m, 1H), 3.43 (s, 3H), 3.33 (s, 3H); LCMS calculated for $C_{22}H_{18}ClN_4O_3$ $(M+H)^+$: m/z=421.1; found: 421.1.

Example 87. 4-(3-Chlorophenoxy)-1-methyl-5-(6-methyl-7-oxo-6,7-dihydro-1H-pyrrolo[2,3-c]pyridin-4-yl)-1,3-dihydro-2H-benzimidazol-2-one

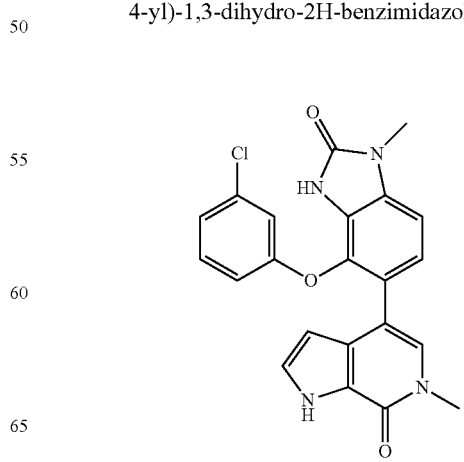

This compound was synthesized according to the procedure of Example 86 using 3-chlorophenol in Step 2 instead of p-chlorophenol. $^1$H NMR (400 MHz, DMSO-d$_6$) δ 11.97 (br s, 1H), 11.24 (s, 1H), 7.24 (dd, J=2.8, 2.8 Hz, 1H), 7.22-7.05 (m, 4H), 6.94-6.86 (m, 1H), 6.62 (dd, J=2.2, 2.2 Hz, 1H), 6.60-6.47 (m, 1H), 6.32-6.02 (m, 1H), 3.43 (s, 3H), 3.34 (s, 3H); LCMS calculated for C$_{22}$H$_{18}$ClN$_4$O$_3$ (M+H)$^+$: m/z=421.1; found: 421.0.

Example 88. 4-(Cyclohexylmethoxy)-1-methyl-5-(6-methyl-7-oxo-6,7-dihydro-1H-pyrrolo[2,3-c]pyridin-4-yl)-1,3-dihydro-2H-benzimidazol-2-one

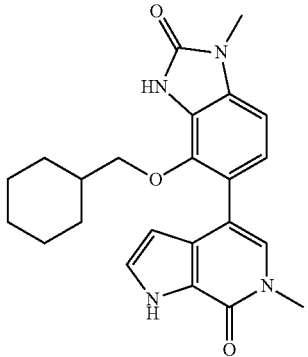 [SMILES: Cn1cc(-c2ccc3c([nH]c(=O)n3C)c2OCC2CCCCC2)c2cc[nH]c2c1=O]

Step 1. 4-Bromo-3-(cyclohexylmethoxy)-N-methyl-2-nitroaniline

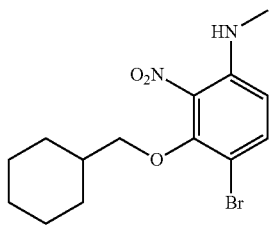 [SMILES: CNc1ccc(Br)c(OCC2CCCCC2)c1[N+](=O)[O-]]

This compound was synthesized according to the procedure of Example 11, Step 1, using 4-bromo-3-fluoro-N-methyl-2-nitroaniline and cyclohexanemethanol as the starting materials. LCMS calculated for C$_{14}$H$_{20}$BrN$_2$O$_3$ (M+H)$^+$: m/z=343.1, 345.1; found: 343.0, 345.1.

Step 2. 4-[2-(Cyclohexylmethoxy)-4-(methylamino)-3-nitrophenyl]-6-methyl-1-[(4-methylphenyl)sulfonyl]-1,6-dihydro-7H-pyrrolo[2,3-c]pyridin-7-one

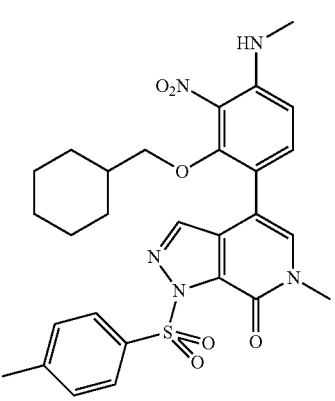

This compound was synthesized according to the procedure of Example 10, Step 5, using 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one and 4-bromo-3-(cyclohexylmethoxy)-N-methyl-2-nitroaniline as the starting materials. LCMS calculated for C$_{29}$H$_{33}$N$_4$O$_6$S (M+H)$^+$: m/z=565.2; found: 565.1.

Step 4. 4-[3-Amino-2-(cyclohexylmethoxy)-4-(methylamino)phenyl]-6-methyl-1-[(4-methylphenyl)sulfonyl]-1,6-dihydro-7H-pyrrolo[2,3-c]pyridin-7-one

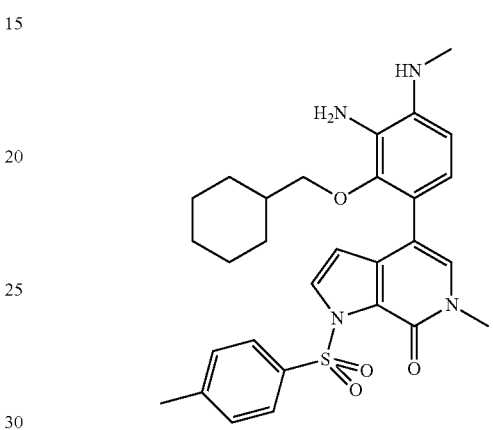

This compound was synthesized according to the procedure of Example 1, Step 3, using 4-[2-(cyclohexylmethoxy)-4-(methylamino)-3-nitrophenyl]-6-methyl-1-[(4-methylphenyl)sulfonyl]-1,6-dihydro-7H-pyrrolo[2,3-c]pyridin-7-one as the starting material. LCMS calculated for C$_{29}$H$_{35}$N$_4$O$_4$S (M+H)$^+$: m/z=535.2; found: 535.2.

Step 5. 4-(Cyclohexylmethoxy)-1-methyl-5-(6-methyl-7-oxo-6,7-dihydro-1H-pyrrolo[2,3-c]pyridin-4-yl)-1,3-dihydro-2H-benzimidazol-2-one

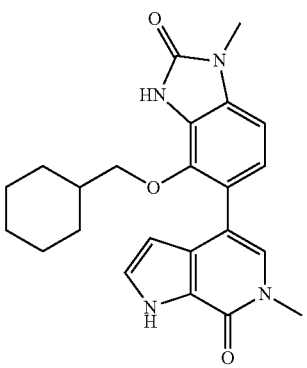 [SMILES: Cn1cc(-c2ccc3c([nH]c(=O)n3C)c2OCC2CCCCC2)c2cc[nH]c2c1=O]

This compound was synthesized according to the procedure of Example 1, Step 4, using 4-[3-amino-2-(cyclohexylmethoxy)-4-(methylamino)phenyl]-6-methyl-1-[(4-methylphenyl)sulfonyl]-1,6-dihydro-7H-pyrrolo[2,3-c]pyridin-7-one as the starting material. $^1$H NMR (400 MHz, DMSO-d$_6$) δ 11.98 (br s, 1H), 11.06 (s, 1H), 7.25 (dd, J=2.7, 2.7 Hz, 1H), 7.18 (s, 1H), 7.02 (d, J=8.0 Hz, 1H), 6.91 (d, J=8.1 Hz, 1H), 6.09 (dd, J=2.3, 2.3 Hz, 1H), 3.54 (s, 3H), 3.44 (d, J=5.9 Hz, 2H), 3.29 (s, 3H), 1.56-1.33 (m, 6H), 1.12-0.80 (m, 3H), 0.75-0.49 (m, 2H); LCMS calculated for $C_{23}H_{27}N_4O_3$ (M+H)$^+$: m/z=407.2; found: 407.1.

Example 94. 6-(6-Methyl-7-oxo-6,7-dihydro-1H-pyrrolo[2,3-c]pyridin-4-yl)-5-phenoxy-2H-1,4-benzoxazin-3(4H)-one

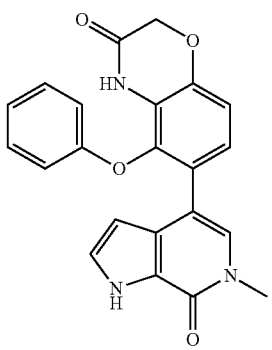 [SMILES: Cn1cc(-c2ccc3c(c2Oc2ccccc2)NC(=O)CO3)c2cc[nH]c2c1=O]

Step 1. 1-Fluoro-3-methoxy-2-nitrobenzene

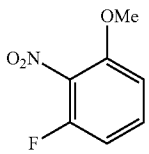 [SMILES: COc1cccc(F)c1[N+](=O)[O-]]

This compound was synthesized according to the procedure of Example 76, Step 5, using 3-fluoro-2-nitrophenol [Combi-Blocks, OR-7136] and methanol as the starting materials.

Step 2.
1-Bromo-2-fluoro-4-methoxy-3-nitrobenzene

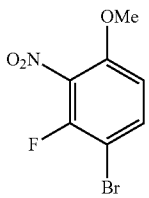 [SMILES: COc1ccc(Br)c(F)c1[N+](=O)[O-]]

Bromine (1.55 mL, 30.1 mmol) was added dropwise to a solution of 1-fluoro-3-methoxy-2-nitrobenzene (1.29 g, 7.53 mmol) in acetic acid (15.1 mL). The reaction mixture was warmed to 55° C. and stirred at 55° C. for 17 h, after which time the reaction mixture was concentrated in vacuo to give a crude solid. The crude solid was diluted with saturated sodium bicarbonate solution and extracted with ethyl acetate. Layers were separated and the organic layer was washed with saturated sodium bicarbonate solution, dried with sodium sulfate, filtered, and concentrated in vacuo to give the desired product (1.87 g, 99%) as a yellow solid that was used in further step without purification.

Step 3.
1-Bromo-4-methoxy-3-nitro-2-phenoxybenzene

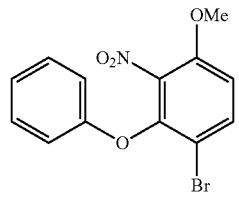 [SMILES: COc1ccc(Br)c(Oc2ccccc2)c1[N+](=O)[O-]]

This compound was synthesized according to the procedure of Example 1, Step 1, using 1-bromo-2-fluoro-4-methoxy-3-nitrobenzene and phenol as the starting materials.

Step 4.
1-Bromo-4-methoxy-3-nitro-2-phenoxybenzene

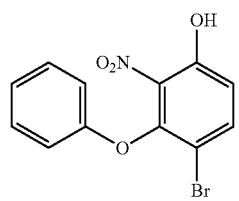 [SMILES: O=[N+]([O-])c1c(O)ccc(Br)c1Oc1ccccc1]

A solution of 1-bromo-4-methoxy-3-nitro-2-phenoxybenzene (0.709 g, 2.19 mmol) in methylene chloride (8.76 mL) at −78° C. was treated with 1.0 M solution of boron tribromide in dichloromethane (4.37 mL, 4.37 mmol) and stirred at RT for 30 min, after which time the reaction mixture was quenched with saturated sodium bicarbonate solution and extracted with dichloromethane (2×). The combined organic layers were washed with brine, dried with sodium sulfate, filtered, and concentrated in vacuo to give the desired product (673 mg g, 99%) as a yellow solid that was used in further step without purification.

Step 5. 2-Amino-4-bromo-3-phenoxyphenol

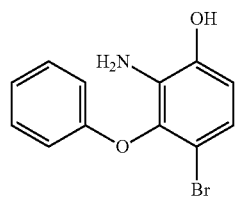 [SMILES: Nc1c(O)ccc(Br)c1Oc1ccccc1]

A solution of 4-bromo-2-nitro-3-phenoxyphenol (0.468 g, 1.51 mmol) in ethanol (11.2 mL, 192 mmol) was degassed with nitrogen and treated with a slurry of Raney Nickel 2800 in water (0.468 ml). The reaction mixture was degassed again with nitrogen and hydrogenated with a balloon of hydrogen for 30 min. The reaction suspension was diluted with dichloromethane and methanol and filtered through a pad of Celite. The pad of Celite was washed with ethyl acetate and dichloromethane and the filtrate was concentrated in vacuo to give brown oil. Purification by flash column chromatography (100% CH$_2$Cl$_2$ to 30% CH$_3$CN/ CH$_2$Cl$_2$ [CH$_3$CN contained 5% MeOH]) gave the desired product (346 mg, 82%) as a tan solid. LCMS calculated for C$_{12}$H$_{11}$BrNO$_2$ (M+H)$^+$: m/z=280.0, 282.0; found: 280.0, 282.0.

Step 6.
6-Bromo-5-phenoxy-2H-1,4-benzoxazin-3(4H)-one

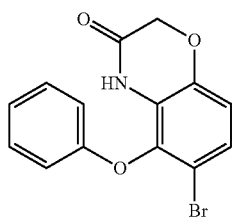 [SMILES: O=C1COc2ccc(Br)c(Oc3ccccc3)c2N1]

A solution of 2-amino-4-bromo-3-phenoxyphenol (0.060 g, 0.214 mmol) in acetonitrile (3.88 mL) and water (1.21 mL) was treated with potassium carbonate (0.118 g, 0.857 mmol), followed by the addition of bromoacetyl bromide (0.0279 mL, 0.321 mmol), and the resultant reaction mixture was stirred at RT for 30 min, after which time additional bromoacetyl bromide (0.0186 mL, 0.214 mmol) was added dropwise and the reaction mixture was stirred at RT for 1 h, then warmed to 75° C. and stirred at that temperature for 30 min. The reaction mixture was concentrated and diluted with ethyl acetate and water. Layers were separated and the organic layer was washed with brine, dried with sodium sulfate, filtered, and concentrated in vacuo the yield a crude product. Purification by flash column chromatography (100% hexanes to 50% EtOAc/hexanes) gave the desired product (59.5 mg, 87%) as a white solid. LCMS calculated for C$_{14}$H$_{11}$BrNO$_3$ (M+H)$^+$: m/z=320.0, 322.0; found: 319.9, 321.9.

Step 7. 6-{6-Methyl-1-[(4-methylphenyl)sulfonyl]- 7-oxo-6,7-dihydro-1H-pyrrolo[2,3-c]pyridin-4-yl}- 5-phenoxy-2H-1,4-benzoxazin-3(4H)-one

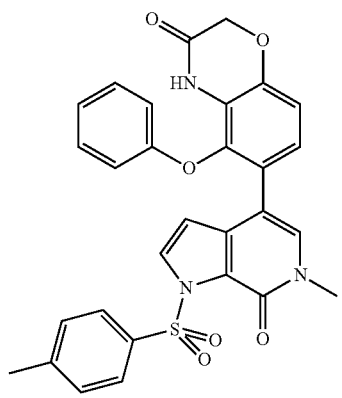

This compound was synthesized according to the procedure of Example 10, Step 5, using 6-bromo-5-phenoxy-2H- 1,4-benzoxazin-3(4H)-one and 6-methyl-1-[(4-methylphenyl)sulfonyl]-4-(4,4,5,5-tetramethyl-1,3,2-dioxaborolan-2- yl)-1,6-dihydro-7H-pyrrolo[2,3-c]pyridin-7-one as the starting materials. LCMS calculated for C$_{29}$H$_{24}$N$_3$O$_6$S (M+H)$^+$: m/z=542.1; found: 542.0.

Step 8. 6-(6-Methyl-7-oxo-6,7-dihydro-1H-pyrrolo [2,3-c]pyridin-4-yl)-5-phenoxy-2H-1,4-benzoxazin-3 (4H)-one This compound was synthesized according to the procedure of Example 8, Step 2, using 6-{6-methyl-1-[(4-methylphenyl)sulfonyl]-7-oxo-6,7-dihydro-1H-pyrrolo[2,3-c] pyridin-4-yl}-5-phenoxy-2H-1,4-benzoxazin-3 (4H)-one as the starting material. $^1$H NMR (500 MHz, DMSO-d$_6$) δ 11.89 (br s, 1H), 10.58 (br s, 1H), 7.23 (d, J=2.7 Hz, 1H), 7.10-7.04 (m, 3H), 7.03 (s, 1H), 6.99 (d, J=8.4 Hz, 1H), 6.81 (dd, J=7.3, 7.3 Hz, 1H), 6.68-6.49 (m, 2H), 6.17 (d, J=2.8 Hz, 1H), 4.64 (s, 2H), 3.38 (s, 3H); LCMS calculated for C$_{22}$H$_{18}$N$_3$O$_4$ (M+H)$^+$: m/z=388.1; found: 388.1.

Example 95. 2,2-Dimethyl-6-(6-methyl-7-oxo-6,7- dihydro-1H-pyrrolo[2,3-c]pyridin-4-yl)-5-phenoxy- 2H-1,4-benzoxazin-3(4H)-one

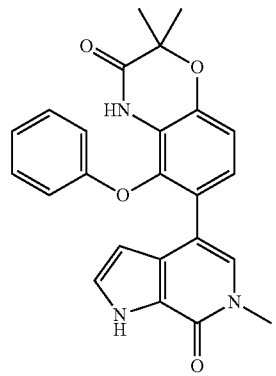 [SMILES: Cn1cc(-c2ccc3c(c2Oc2ccccc2)NC(=O)C(C)(C)O3)c2cc[nH]c2c1=O]

This compound was synthesized according to the procedure of Example 94 using 2-bromo-2-methylpropanoyl bromide, in Step 6 instead of bromoacetyl bromide. $^1$H NMR (500 MHz, DMSO-d$_6$) δ 11.89 (br s, 1H), 10.49 (br s, 1H), 7.23 (d, J=2.6 Hz, 1H), 7.14-7.02 (m, 4H), 6.98 (d, J=8.4 Hz, 1H), 6.82 (dd, J=7.3, 7.3 Hz, 1H), 6.55 (d, J=8.0 Hz, 2H), 6.19 (d, J=2.6 Hz, 1H), 3.38 (s, 3H), 1.44 (s, 6H); LCMS calculated for C$_{24}$H$_{22}$N$_3$O$_4$ (M+H)$^+$: m/z=416.2; found: 416.1.

Example 96. 6-Methyl-4-(4-phenoxy-1,3-benzox- azol-5-yl)-1,6-dihydro-7H-pyrrolo[2,3-c]pyridin-7- one

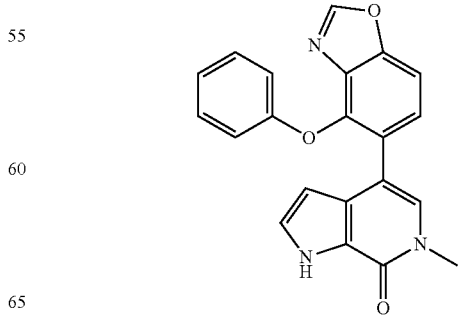

Step 1. 5-Bromo-4-phenoxy-1,3-benzoxazole

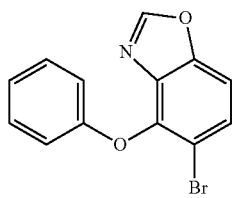 [SMILES: Brc1ccc2ocnc2c1Oc1ccccc1]

A solution of 2-amino-4-bromo-3-phenoxyphenol (0.075 g, 0.268 mmol) in ethyl orthoformate (0.405 mL, 2.43 mmol) was heated at 100° C. for 2.5 h. after which time the reaction mixture was cooled to RT and concentrated in vacuo to a crude residue. Purification by flash column chromatography (100% hexanes to 50% EtOAc/hexanes) gave the desired product (75.1 mg, 97%) as a white solid. LCMS calculated for $C_{13}H_9BrNO_2$ (M+H)$^+$: m/z=290.0, 292.0; found: 289.9, 291.9.

Step 2. 6-Methyl-1-[(4-methylphenyl)sulfonyl]-4-(4-phenoxy-1,3-benzoxazol-5-yl)-1,6-dihydro-7H-pyrrolo[2,3-c]pyridin-7-one

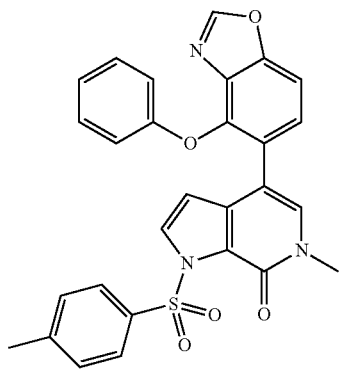

This compound was synthesized according to the procedure of Example 10, Step 5, using 5-bromo-4-phenoxy-1,3-benzoxazole and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{28}H_{22}N_3O_5S$ (M+H)$^+$: m/z=512.1; found: 512.0.

Step 3. 6-Methyl-4-(4-phenoxy-1,3-benzoxazol-5-yl)-1,6-dihydro-7H-pyrrolo[2,3-c]pyridin-7-one This compound was synthesized according to the procedure of Example 85, Step 3, using 6-methyl-1-[(4-methylphenyl)sulfonyl]-4-(4-phenoxy-1,3-benzoxazol-5-yl)-1,6-dihydro-7H-pyrrolo[2,3-c]pyridin-7-one as the starting material. $^1$H NMR (500 MHz, DMSO-d$_6$) δ 11.99 (br s, 1H), 8.68 (s, 1H), 7.74 (d, J=8.4 Hz, 1H), 7.57 (d, J=8.4 Hz, 1H), 7.24 (dd, J=2.7, 2.7 Hz, 1H), 7.21-7.09 (m, 3H), 6.91 (dd, J=7.3, 7.3 Hz, 1H), 6.71 (d, J=8.0 Hz, 2H), 6.17 (dd, J=2.2, 2.2 Hz, 1H), 3.46 (s, 3H); LCMS calculated for $C_{21}H_{16}N_3O_3$ (M+H)$^+$: m/z=358.1; found: 358.1.

Example 97. 1-Methyl-5-(6-methyl-7-oxo-6,7-dihydro-1H-pyrrolo[2,3-c]pyridin-4-yl)-4-(phenylthio)-1,3-dihydro-2H-benzimidazol-2-one

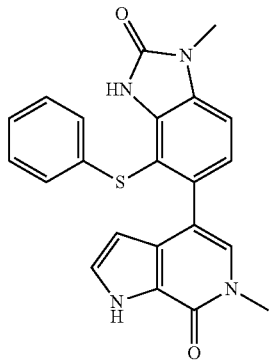 [SMILES: Cn1cc(-c2ccc3c([nH]c(=O)n3C)c2Sc2ccccc2)c2cc[nH]c2c1=O]

Step 1. 4-Bromo-N-methyl-2-nitro-3-(phenylthio)aniline

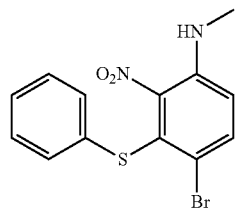 [SMILES: CNc1ccc(Br)c(Sc2ccccc2)c1[N+](=O)[O-]]

A solution of 4-bromo-3-fluoro-N-methyl-2-nitroaniline (0.30 g, 1.20 mmol) in N,N-dimethylformamide (2.45 mL) was treated with cesium carbonate (0.472 g, 1.45 mmol) and benzenethiol (0.149 mL, 1.45 mmol). The resultant reaction mixture was warmed to 80° C. and stirred at 80° C. for 30 min, after which time the reaction mixture was diluted with ethyl acetate and water. Layers were separated and the organic layer was washed with 10% solution of $K_2CO_3$ and brine, dried with sodium sulfate, filtered, and concentrated in vacuo to give the crude product. Purification by flash column chromatography (100% hexanes to 40% EtOAc/hexanes) gave the desired product (396 mg, 97%) as an orange solid. LCMS calculated for $C_{13}H_{12}BrN_2O_2S$ (M+H)$^+$: m/z=339.0, 341.0; found: 338.9, 340.9.

Step 2. 4-Bromo-N1-methyl-3-(phenylthio)benzene-1,2-diamine

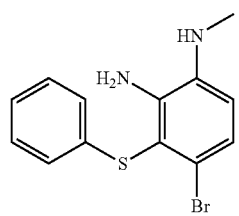 [SMILES: CNc1ccc(Br)c(Sc2ccccc2)c1N]

This compound was synthesized according to the procedure of Example 1, Step 3, using 4-bromo-N-methyl-2-nitro- 3-(phenylthio)aniline as the starting material. LCMS calculated for $C_{13}H_{14}BrN_2S$ (M+H)⁺: m/z=309.0, 311.0; found: 309.0, 310.9.

Step 3. 5-Bromo-1-methyl-4-(phenylthio)-1,3-dihydro-2H-benzimidazol-2-one

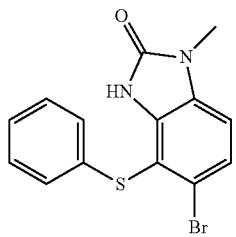 [SMILES: Cn1c(=O)[nH]c2c(Sc3ccccc3)c(Br)ccc21]

This compound was synthesized according to the procedure of Example 6, Step 1, using 4-bromo-N1-methyl-3-(phenylthio)benzene-1,2-diamine as the starting material. LCMS calculated for $C_{14}H_{12}BrN_2OS$ (M+H)⁺: m/z=335.0, 337.0; found: 334.9, 336.9.

Step 4. 1-Methyl-5-{6-methyl-1-[(4-methylphenyl)sulfonyl]-7-oxo-6,7-dihydro-1H-pyrrolo[2,3-c]pyridin-4-yl}-4-(phenylthio)-1,3-dihydro-2H-benzimidazol-2-one

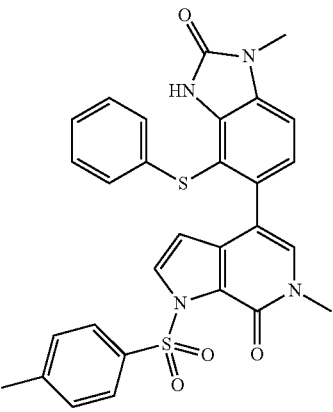

This compound was synthesized according to the procedure of Example 10, Step 5, using 5-bromo-1-methyl-4-(phenylthio)-1,3-dihydro-2H-benzimidazol-2-one and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{29}H_{25}N_4O_4S_2$ (M+H)⁺: m/z=557.1; found: 557.0.

Step 5. 1-Methyl-5-(6-methyl-7-oxo-6,7-dihydro-1H-pyrrolo[2,3-c]pyridin-4-yl)-4-(phenylthio)-1,3-dihydro-2H-benzimidazol-2-one This compound was synthesized according to the procedure of Example 8, Step 2, using 1-methyl-5-{6-methyl-1-[(4-methylphenyl)sulfonyl]-7-oxo-6,7-dihydro-1H-pyrrolo[2,3-c]pyridin-4-yl}-4-(phenylthio)-1,3-dihydro-2H-benzimidazol-2-one as the starting material. ¹H NMR (500 MHz, DMSO-d₆) δ 11.95 (br s, 1H), 11.10 (br s, 1H), 7.26 (d, J=8.0 Hz, 1H), 7.20 (s, 1H), 7.18-7.11 (m, 3H), 7.04 (dd, J=7.4, 7.4 Hz, 1H), 6.88 (s, 1H), 6.82 (d, J=7.4 Hz, 2H), 5.92 (d, J=2.3 Hz, 1H), 3.40 (s, 3H), 3.33 (s, 3H); LCMS calculated for $C_{22}H_{19}N_4O_2S$ (M+H)⁺: m/z=403.1; found: 403.1.

Example 98. 4-(Ethylthio)-1-methyl-5-(6-methyl-7-oxo-6,7-dihydro-1H-pyrrolo[2,3-c]pyridin-4-yl)-1,3-dihydro-2H-benzimidazol-2-one

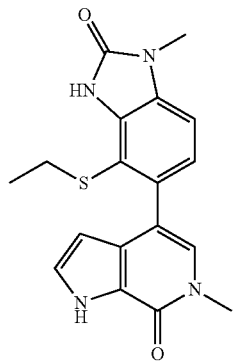 [SMILES: CCSc1c(-c2cn(C)c(=O)c3[nH]ccc23)ccc2c1[nH]c(=O)n2C]

Step 1.
4-Bromo-3-(ethylthio)-N-methyl-2-nitroaniline

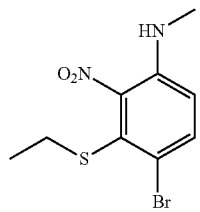

This compound was synthesized according to the procedure of Example 11, Step 1, using 4-bromo-3-fluoro-N-methyl-2-nitroaniline and ethanethiol as the starting materials. LCMS calculated for $C_9H_{12}BrN_2O_2S$ (M+H)⁺: m/z=291.0, 293.0; found: 290.9, 292.9.

Step 2.
4-Bromo-3-(ethylthio)-N1-methylbenzene-1,2-diamine

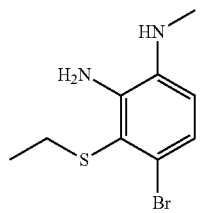

This compound was synthesized according to the procedure of Example 1, Step 3, using 4-bromo-3-(ethylthio)-N-methyl-2-nitroaniline as the starting material. LCMS calculated for $C_9H_{14}BrN_2S$ (M+H)⁺: m/z=261.0, 263.9; found: 261.0, 263.9.

Step 3. 5-Bromo-4-(ethylthio)-1-methyl-1,3-dihydro-2H-benzimidazol-2-one

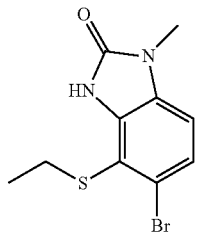

This compound was synthesized according to the procedure of Example 6, Step 1, using 4-bromo-3-(ethylthio)-N1-methylbenzene-1,2-diamine as the starting material. LCMS calculated for $C_{10}H_{12}BrN_2OS$ (M+H)⁺: m/z=287.0, 289.0; found: 286.9, 288.9.

Step 4. 4-(Ethylthio)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one

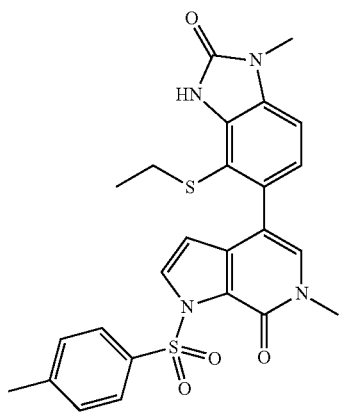

This compound was synthesized according to the procedure of Example 10, Step 5, using 5-bromo-4-(ethylthio)-1-methyl-1,3-dihydro-2H-benzimidazol-2-one and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{25}H_{25}N_4O_4S_2$ (M+H)⁺: m/z=509.1; found: 509.1.

Step 5. 4-(Ethylthio)-1-methyl-5-(6-methyl-7-oxo-6,7-dihydro-1H-pyrrolo[2,3-c]pyridin-4-yl)-1,3-dihydro-2H-benzimidazol-2-one This compound was synthesized according to the procedure of Example 8, Step 2, using 4-(ethylthio)-1-methyl-5-{6-methyl-1-[(4-methylphenyl)sulfonyl]-7-oxo-6,7-dihydro-1H-pyrrolo[2,3-c]pyridin-4-yl}-1,3-dihydro-2H-benzimidazol-2-one as the starting material. ¹H NMR (500 MHz, DMSO-d₆) δ 11.96 (br s, 1H), 11.03 (br s, 1H), 7.21 (s, 1H), 7.12 (d, J=8.0 Hz, 1H), 7.09-6.97 (m, 2H), 5.96-5.80 (m, 1H), 3.54 (s, 3H), 3.31 (s, 3H), 2.52 (q, J=7.4 Hz, 2H), 0.84 (t, J=7.3 Hz, 3H); LCMS calculated for $C_{18}H_{19}N_4O_2S$ (M+H)⁺: m/z=355.1; found: 355.1.

Example 99. 4-(Ethylsulfonyl)-1-methyl-5-(6-methyl-7-oxo-6,7-dihydro-1H-pyrrolo[2,3-c]pyridin-4-yl)-1,3-dihydro-2H-benzimidazol-2-one A suspension of 4-(ethylthio)-1-methyl-5-(6-methyl-7-oxo-6,7-dihydro-1H-pyrrolo[2,3-c]pyridin-4-yl)-1,3-dihydro-2H-benzimidazol-2-one (0.0424 g, 0.120 mmol) in methylene chloride (11.4 mL, 178 mmol) at 0° C. was treated with m-chloroperbenzoic acid (0.0938 g, 0.419 mmol) (77% MCPBA) and stirred at room temperature for 17 h. The reaction mixture was concentrated in vacuo and the crude residue was dissolved in ethyl acetate. The resultant solution was washed with 10% solution of $Na_2S_2O_3$, saturated sodium bicarbonate solution, and brine, dried with sodium sulfate, filtered, and concentrated in vacuo to give a crude residue. Purification by preparative LCMS (XBridge C18 column, eluting with a gradient of acetonitrile/water 0.1% ammonium hydroxide, at flow rate of 60 mL/min) to give the desired product (7.2 mg, 16%) as a white solid. ¹H NMR (300 MHz, DMSO-d₆) δ 12.08 (br s, 1H), 10.50 (br s, 1H), 7.45 (d, J=8.0 Hz, 1H), 7.23 (d, J=2.5 Hz, 1H), 7.19-6.99 (m, 2H), 5.84 (s, 1H), 3.52 (s, 3H), 3.36 (s, 3H), 3.16-2.75 (m, 2H), 0.97 (t, J=7.3 Hz, 3H); LCMS calculated for $C_{18}H_{19}N_4O_4S$ (M+H)⁺: m/z=387.1; found: 387.1.

Example 100. 4-Methyl-6-(6-methyl-7-oxo-6,7-dihydro-1H-pyrrolo[2,3-c]pyridin-4-yl)-5-phenoxy-2H-1,4-benzoxazin-3(4H)-one

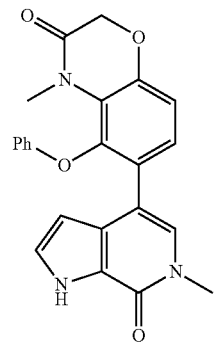

Step 1. 6-Bromo-4-methyl-5-phenoxy-2H-1,4-benzoxazin-3(4H)-one

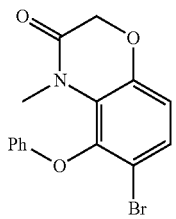 [SMILES: CN1C(=O)COc2ccc(Br)c(Oc3ccccc3)c21]

This compound was synthesized according to the procedure of Example 83, Step 1, using 6-bromo-5-phenoxy-2H-1,4-benzoxazin-3(4H)-one and methyl iodide as the starting materials. LCMS calculated for $C_{18}H_{13}BrNO_3$ (M+H)$^+$: m/z=334.0, 336.0; found: 333.9, 335.9.

Step 2. 4-Methyl-6-{6-methyl-1-[(4-methylphenyl)sulfonyl]-7-oxo-6,7-dihydro-1H-pyrrolo[2,3-c]pyridin-4-yl}-5-phenoxy-2H-1,4-benzoxazin-3(4H)-one

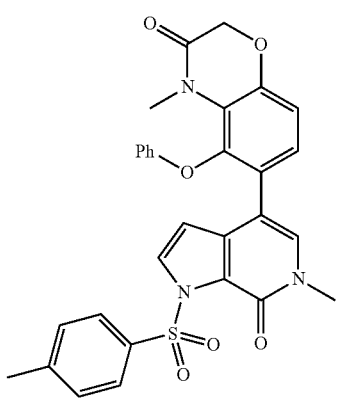

This compound was synthesized according to the procedure of Example 10, Step 5, using 6-bromo-4-methyl-5-phenoxy-2H-1,4-benzoxazin-3(4H)-one and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{30}H_{26}N_3O_6S$ (M+H)$^+$: m/z=556.2; found: 556.0.

Step 3. 4-Methyl-6-(6-methyl-7-oxo-6,7-dihydro-1H-pyrrolo[2,3-c]pyridin-4-yl)-5-phenoxy-2H-1,4-benzoxazin-3(4H)-one This compound was synthesized according to the procedure of Example 8, Step 2, using 4-methyl-6-{6-methyl-1-[(4-methylphenyl)sulfonyl]-7-oxo-6,7-dihydro-1H-pyrrolo[2,3-c]pyridin-4-yl}-5-phenoxy-2H-1,4-benzoxazin-3(4H)-one as the starting material. $^1$H NMR (500 MHz, DMSO-$d_6$) δ 11.90 (br s, 1H), 7.28-7.15 (m, 2H), 7.14-7.02 (m, 4H), 6.84 (dd, J=7.3, 7.3 Hz, 1H), 6.57 (d, J=7.9 Hz, 2H), 6.22 (d, J=2.7 Hz, 1H), 4.66 (s, 2H), 3.40 (s, 3H), 3.26 (s, 3H); LCMS calculated for $C_{23}H_{20}N_3O_4$ (M+H)$^+$: m/z=402.1; found: 402.1.

Example 101. 4-Benzyl-6-(6-methyl-7-oxo-6,7-dihydro-1H-pyrrolo[2,3-c]pyridin-4-yl)-5-phenoxy-2H-1,4-benzoxazin-3(4H)-one

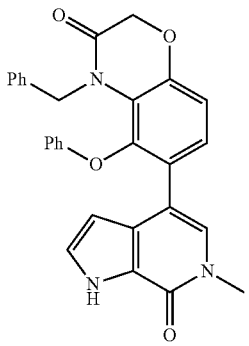 [SMILES: Cn1cc(-c2ccc3c(c2Oc2ccccc2)N(Cc2ccccc2)C(=O)CO3)c2cc[nH]c2c1=O]

This compound was synthesized according to the procedure of Example 100 using benzyl bromide in step 1 instead of methyl iodide. $^1$H NMR (400 MHz, DMSO-$d_6$) δ 11.87 (br s, 1H), 7.38-7.26 (m, 2H), 7.26-7.02 (m, 8H), 6.92 (s, 1H), 6.85 (dd, J=7.3, 7.3 Hz, 1H), 6.58-6.40 (m, 2H), 5.72 (d, J=1.9 Hz, 1H), 5.14 (s, 2H), 4.78 (s, 2H), 3.36 (s, 3H); LCMS calculated for $C_{29}H_{24}N_3O_4$ (M+H)$^+$: m/z=478.2; found: 478.2.

Example 102. 6-(6-Methyl-7-oxo-6,7-dihydro-1H-pyrrolo[2,3-c]pyridin-4-yl)-4-(2-morpholin-4-yl-ethyl)-5-phenoxy-2H-1,4-benzoxazin-3(4H)-one trifluoroacetate

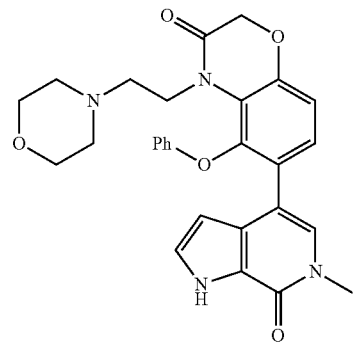 [SMILES: Cn1cc(-c2ccc3c(c2Oc2ccccc2)N(CCN2CCOCC2)C(=O)CO3)c2cc[nH]c2c1=O]

This compound was synthesized according to the procedure of Example 100 using 4-(2-bromoethyl)morpholine hydrochloride in step 1 instead of methyl iodide. $^1$H NMR (400 MHz, DMSO-$d_6$) δ 11.96 (br s, 1H), 7.30-7.23 (m, 2H), 7.16 (d, J=8.4 Hz, 1H), 7.10 (dd, J=8.6, 7.4 Hz, 2H), 7.05 (s, 1H), 6.86 (dd, J=7.4, 7.4 Hz, 1H), 6.60 (d, J=7.8 Hz, 2H), 6.30-6.18 (m, 1H), 4.74 (s, 2H), 4.33-4.13 (m, 4H), 4.13-3.82 (m, 4H), 3.81-3.54 (m, 2H), 3.39 (s, 3H), 3.18-2.90 (m, 2H); LCMS calculated for $C_{28}H_{29}N_4O_5$ (M+H)$^+$: m/z=501.2; found: 501.1.

Example 103. 4-[2-(Aminomethyl)-4-phenoxy-1,3-benzoxazol-5-yl]-6-methyl-1,6-dihydro-7H-pyrrolo[2,3-c]pyridin-7-one

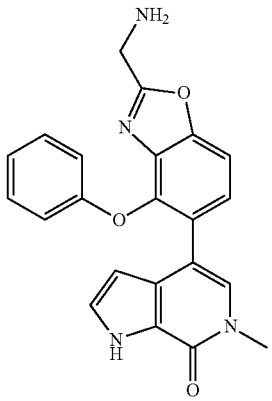 [SMILES: Cn1cc(-c2ccc3oc(CN)nc3c2Oc2ccccc2)c2cc[nH]c2c1=O]

Step 1. tert-Butyl {2-[(3-bromo-6-hydroxy-2-phenoxyphenyl)amino]-2-oxoethyl}carbamate

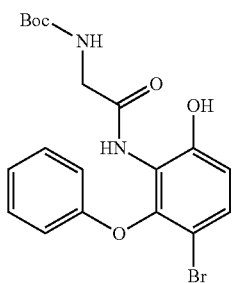 [SMILES: CC(C)(C)OC(=O)NCC(=O)Nc1c(O)ccc(Br)c1Oc1ccccc1]

A solution of N-α-(tert-butoxycarbonyl)glycine (0.172 g, 0.982 mmol) in N,N-dimethylformamide (3.57 mL) was treated with N,N-carbonyldiimidazole (0.174 g, 1.07 mmol), stirred at RT for 30 min, treated with 2-amino-4-bromo-3-phenoxyphenol (0.250 g, 0.892 mmol) and stirred at RT for 1 h and then at 60° C. for 16 h. The reaction mixture was diluted with ethyl acetate and washed with water, 0.1M solution of HCl, saturated sodium bicarbonate solution, and brine, dried with sodium sulfate, filtered, and concentrated in vacuo to give a crude residue. Purification by flash column chromatography (100% hexanes to 30% EtOAc/hexanes) gave the desired product (376 mg, 96%) as a tan foam. LCMS calculated for $C_{19}H_{21}BrN_2O_5Na$ (M+Na)$^+$: m/z=459.1, 461.1; found: 459.0, 461.0.

Step 2. tert-Butyl [(5-bromo-4-phenoxy-1,3-benzoxazol-2-yl)methyl]carbamate

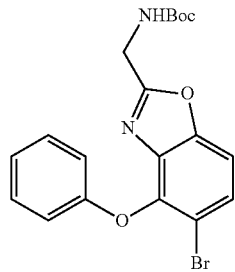 [SMILES: CC(C)(C)OC(=O)NCc1nc2c(Oc3ccccc3)c(Br)ccc2o1]

A mixture of tert-butyl {2-[(3-bromo-6-hydroxy-2-phenoxyphenyl)amino]-2-oxoethyl}carbamate (0.298 g, 0.681 mmol), triphenylphosphine (0.393 g, 1.50 mmol), and freshly activated 4 A molecular sieves (2.72 g, 4 g/mmol) at 0° C. was treated with tetrahydrofuran (10.2 mL) and stirred at 0° C. for 1 h, followed by dropwise addition of diisopropyl azodicarboxylate (0.295 mL, 1.50 mmol) at this temperature. The resultant reaction mixture was warmed to RT and stirred at RT for 16 h, after which time the reaction mixture was filtered through a pad of Celite and washed with ethyl acetate. The filtrate was concentrated in vacuo to yield a crude residue that was purified by flash column chromatography (100% hexanes to 40% EtOAc/hexanes) to give the desired product (207 mg, 72%) as a tan solid. LCMS calculated for $C_{19}H_{19}BrN_2O_4Na$ (M+Na)$^+$: m/z=441.0, 443.0; found: 441.0, 443.0.

Step 3. tert-Butyl [(5-bromo-4-phenoxy-1,3-benzoxazol-2-yl)methyl]carbamate

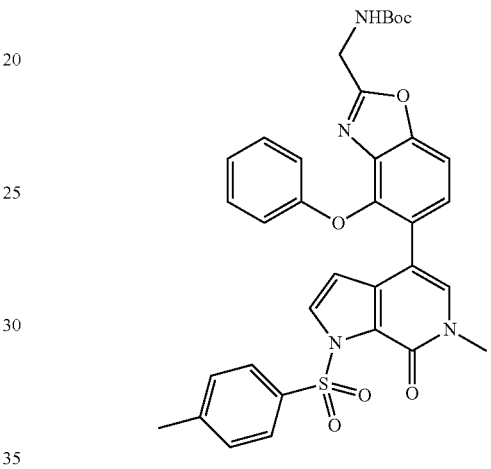

This compound was synthesized according to the procedure of Example 10, Step 5, using tert-butyl [(5-bromo-4-phenoxy-1,3-benzoxazol-2-yl)methyl]carbamate and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{34}H_{33}N_4O_7S$ (M+H)$^+$: m/z=641.2; found: 641.1.

Step 4. 4-[2-(Aminomethyl)-4-phenoxy-1,3-benzoxazol-5-yl]-6-methyl-1-[(4-methylphenyl)sulfonyl]-1,6-dihydro-7H-pyrrolo[2,3-c]pyridin-7-one

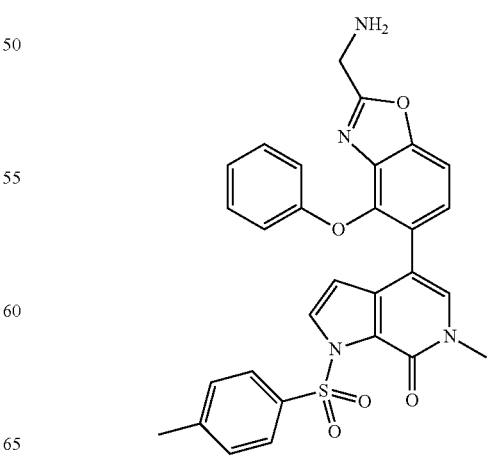

Trifluoroacetic acid (2.20 mL) was added dropwise to a solution of tert-butyl [(5-{6-methyl-1-[(4-methylphenyl)sulfonyl]-7-oxo-6,7-dihydro-1H-pyrrolo[2,3-c]pyridin-4-yl}-4-phenoxy-1,3-benzoxazol-2-yl)methyl]carbamate (0.282 g, 0.440 mmol) in methylene chloride (2.20 mL) and the resultant reaction mixture was stirred at RT for 30 min. The reaction mixture was concentrated in vacuo to a residue that was dissolved in small amount of dichloromethane and added dropwise to a saturated solution of sodium bicarbonate at 0° C. The aqueous solution was extracted with dichloromethane to give the desired product (231 mg, 97%) which was used immediately without further purification. LCMS calculated for $C_{29}H_{25}N_4O_5S$ $(M+H)^+$: m/z=541.2; found: 541.1.

Step 5. 4-[2-(Aminomethyl)-4-phenoxy-1,3-benzoxazol-5-yl]-6-methyl-1,6-dihydro-7H-pyrrolo[2,3-c]pyridin-7-one This compound was synthesized according to the procedure of Example 85, Step 3, using 4-[2-(aminomethyl)-4-phenoxy-1,3-benzoxazol-5-yl]-6-methyl-1-[(4-methylphenyl)sulfonyl]-1,6-dihydro-7H-pyrrolo[2,3-c]pyridin-7-one as the starting material. $^1$H NMR (500 MHz, DMSO-$d_6$) δ 11.97 (br s, 1H), 7.68 (d, J=8.4 Hz, 1H), 7.49 (d, J=8.4 Hz, 1H), 7.24 (d, J=2.7 Hz, 1H), 7.19-7.03 (m, 2H), 6.88 (dd, J=7.3, 7.3 Hz, 1H), 6.65 (d, J=7.8 Hz, 2H), 6.16 (d, J=2.7 Hz, 1H), 3.91 (s, 2H), 3.44 (s, 3H); LCMS calculated for $C_{22}H_{19}N_4O_3$ $(M+H)^+$: m/z=387.1; found: 387.1.

Example 104. N-{[5-(6-Methyl-7-oxo-6,7-dihydro-1H-pyrrolo[2,3-c]pyridin-4-yl)-4-phenoxy-1,3-benzoxazol-2-yl]methyl}acetamide

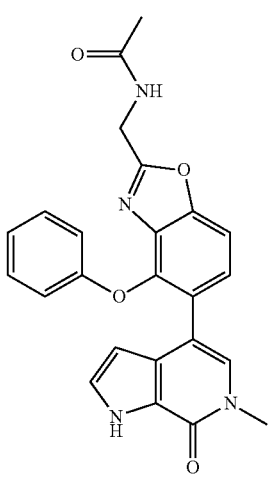 [SMILES: CC(=O)NCc1nc2c(Oc3ccccc3)c(-c3cn(C)c(=O)c4[nH]ccc34)ccc2o1]

Step 1. N-[(5-{6-Methyl-1-[(4-methylphenyl)sulfonyl]-7-oxo-6,7-dihydro-1H-pyrrolo[2,3-c]pyridin-4-yl}-4-phenoxy-1,3-benzoxazol-2-yl)methyl]acetamide

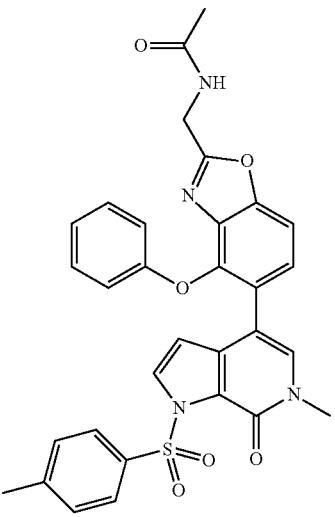

This compound was synthesized according to the procedure of Example 66, Step 2, using 4-[2-(aminomethyl)-4-phenoxy-1,3-benzoxazol-5-yl]-6-methyl-1-[(4-methylphenyl)sulfonyl]-1,6-dihydro-7H-pyrrolo[2,3-c]pyridin-7-one as the starting material. LCMS calculated for $C_{31}H_{27}N_4O_6S$ $(M+H)^+$: m/z=583.2; found: 583.2.

Step 2. N-{[5-(6-Methyl-7-oxo-6,7-dihydro-1H-pyrrolo[2,3-c]pyridin-4-yl)-4-phenoxy-1,3-benzoxazol-2-yl]methyl}acetamide This compound was synthesized according to the procedure of Example 85, Step 3, using N-[(5-{6-methyl-1-[(4-methylphenyl)sulfonyl]-7-oxo-6,7-dihydro-1H-pyrrolo[2,3-c]pyridin-4-yl}-4-phenoxy-1,3-benzoxazol-2-yl)methyl]acetamide as the starting material. $^1$H NMR (300 MHz, DMSO-$d_6$) δ 12.00 (br s, 1H), 8.67 (dd, J=5.7, 5.7 Hz, 1H), 7.71 (d, J=8.4 Hz, 1H), 7.51 (d, J=8.5 Hz, 1H), 7.35-7.23 (m, 1H), 7.21-7.02 (m, 3H), 6.88 (dd, J=7.3, 7.3 Hz, 1H), 6.65 (d, J=7.8 Hz, 2H), 6.16 (s, 1H), 4.50 (d, J=5.8 Hz, 2H), 3.44 (s, 3H), 1.87 (s, 3H); LCMS calculated for $C_{24}H_{21}N_4O_4$ $(M+H)^+$: m/z=429.2; found: 429.1.

The examples in Table 7 were synthesized according to procedure of Example 104 using the appropriate acid chlorides or sulfonyl chlorides.

TABLE 7

| Ex. No. | Compound Name | R | MS [M + H]+ |
|---|---|---|---|
| 105 | N-{[5-(6-Methyl-7-oxo-6,7-dihydro-1H-pyrrolo[2,3-c]pyridin-4-yl)-4-phenoxy-1,3-benzoxazol-2-yl]methyl}methanesulfonamide | methanesulfonyl | 465.1 |
| 106 | N-{[5-(6-methyl-7-oxo-6,7-dihydro-1H-pyrrolo[2,3-c]pyridin-4-yl)-4-phenoxy-1,3-benzoxazol-2-yl]methyl}benzamide | benzoyl | 491.1 |
| 107 | N-{[5-(6-Methyl-7-oxo-6,7-dihydro-1H-pyrrolo[2,3-c]pyridin-4-yl)-4-phenoxy-1,3-benzoxazol-2-yl]methyl}-2-phenylacetamide | phenylacetyl | 505.2 |
| 108 | N-{[5-(6-Methyl-7-oxo-6,7-dihydro-1H-pyrrolo[2,3-c]pyridin-4-yl)-4-phenoxy-1,3-benzoxazol-2-yl]methyl}cyclopropanecarboxamide | cyclopropanecarbonyl | 455.1 |
| 109 | 2-Cyclopentyl-N-{[5-(6-methyl-7-oxo-6,7-dihydro-1H-pyrrolo[2,3-c]pyridin-4-yl)-4-phenoxy-1,3-benzoxazol-2-yl]methyl}acetamide | cyclopentylacetyl | 497.2 |

| | 1H NMR data for examples 105-109 |
|---|---|
| Ex. No. | 1H NMR |
| 105 | (500 MHz, DMSO-$d_6$) δ 11.98 (br s, 1H), 7.93 (br s, 1H), 7.73 (d, J = 8.4 Hz, 1H), 7.54 (d, J = 8.5 Hz, 1H), 7.24 (dd, J = 2.7, 2.7 Hz, 1H), 7.21-7.08 (m, 3H), 6.90 (dd, J = 7.3, 7.3 Hz, 1H), 6.69 (d, J = 7.8 Hz, 2H), 6.34-6.05 (m, 1H), 4.48 (s, 2H), 3.45 (s, 3H), 2.87 (s, 3H) |
| 106 | (300 MHz, DMSO-$d_6$) δ 12.00 (br s, 1H), 10.01-9.02 (m, 1H), 7.88 (d, J = 7.1 Hz, 2H), 7.71 (d, J = 8.5 Hz, 1H), 7.65-7.36 (m, 4H), 7.24 (s, 1H), 7.20-7.02 (m, 3H), 6.87 (dd, J = 7.1, 7.1 Hz, 1H), 6.65 (d, J = 8.0 Hz, 2H), 6.15 (s, 1H), 4.72 (d, J = 5.3 Hz, 2H), 3.44 (s, 3H) |
| 107 | (300 MHz, DMSO-$d_6$) δ 8.89 (br s, 1H), 7.70 (d, J = 8.4 Hz, 1H), 7.51 (d, J = 8.4 Hz, 1H), 7.37-7.07 (m, 10H), 6.89 (dd, J = 7.3, 7.3 Hz, 1H), 6.66 (d, J = 7.8 Hz, 2H), 6.16 (d, J = 2.8 Hz, 1H), 4.54 (s, 2H), 3.49 (s, 2H), 3.44 (s, 3H) |
| 108 | (500 MHz, DMSO-$d_6$) δ 11.97 (br s, 1H), 8.84 (dd, J = 5.8, 5.8 Hz, 1H), 7.71 (d, J = 8.4 Hz, 1H), 7.51 (d, J = 8.4 Hz, 1H), 7.24 (d, J = 2.8 Hz, 1H), 7.20-7.07 (m, 3H), 6.88 (dd, J = 7.3, 7.3 Hz, 1H), 6.79-6.59 (m, 2H), 6.16 (d, J = 2.8 Hz, 1H), 4.55 (d, J = 5.8 Hz, 2H), 3.44 (s, 3H), 1.73-1.56 (m, 1H), 0.82-0.60 (m, 4H) |

TABLE 7-continued

| | |
|---|---|
| 109 | (400 MHz, DMSO-d$_6$) δ 12.02 (br s, 1H), 8.60 (dd, J = 5.7, 5.7 Hz, 1H), 7.69 (d, J = 8.4 Hz, 1H), 7.51 (d, J = 8.4 Hz, 1H), 7.25 (d, J = 2.7 Hz, 1H), 7.22-7.06 (m, 3H), 6.88 (dd, J = 7.3, 7.3 Hz, 1H), 6.65 (d, J = 7.9 Hz, 2H), 6.16 (d, J = 2.7 Hz, 1H), 4.50 (d, J = 5.7 Hz, 2H), 3.44 (s, 3H), 2.20-2.05 (m, 3H), 1.66 (d, J = 6.2 Hz, 2H), 1.53 (d, J = 7.0 Hz, 2H), 1.50-1.33 (m, 2H), 1.09 (dd, J = 12.2, 7.3 Hz, 2H) |

Example 110. 6-Methyl-4-(5-phenoxy-3-phenyl-3,4-dihydro-2H-1,4-benzoxazin-6-yl)-1,6-dihydro-7H-pyrrolo[2,3-c]pyridin-7-one

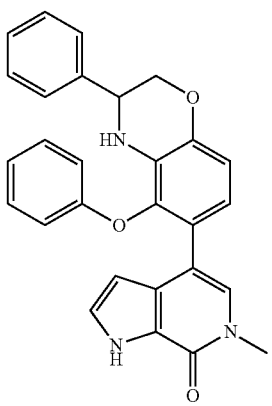 [SMILES: Cn1cc(-c2ccc3c(c2Oc2ccccc2)NC(c2ccccc2)CO3)c2cc[nH]c2c1=O]

Step 1. 2-(4-Bromo-2-nitro-3-phenoxyphenoxy)-1-phenylethanone

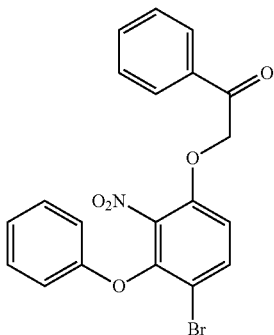 [SMILES: O=C(COc1ccc(Br)c(Oc2ccccc2)c1[N+](=O)[O-])c1ccccc1]

This compound was synthesized according to the procedure of Example 76, Step 5, using 4-bromo-2-nitro-3-phenoxyphenol and 2-hydroxy-1-phenylethanone as the starting materials. LCMS calculated for C$_{20}$H$_{15}$BrNO$_5$ (M+H)$^+$: m/z=428.0, 430.0; found: 427.9, 429.9.

Step 2. 6-Bromo-5-phenoxy-3-phenyl-2H-1,4-benzoxazine

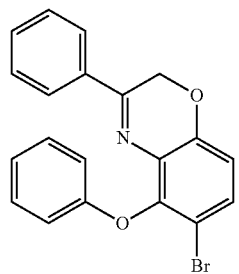 [SMILES: Brc1ccc2c(c1Oc1ccccc1)N=C(c1ccccc1)CO2]

This compound was synthesized according to the procedure of Example 78, Step 2, using 2-(4-bromo-2-nitro-3-phenoxyphenoxy)-1-phenylethanone as the starting material. LCMS calculated for C$_{20}$H$_{15}$BrNO$_2$ (M+H)$^+$: m/z=380.0, 382.0; found: 380.0, 382.0.

Step 3. 6-Bromo-5-phenoxy-3-phenyl-3,4-dihydro-2H-1,4-benzoxazine

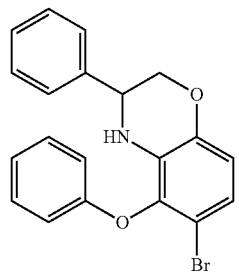 [SMILES: Brc1ccc2c(c1Oc1ccccc1)NC(c1ccccc1)CO2]

A suspension of 6-bromo-5-phenoxy-3-phenyl-2H-1,4-benzoxazine (0.0692 g, 0.182 mmol) in ethanol (1.20 mL) and water (0.240 mL) was treated with sodium tetrahydroborate (13.8 mg, 0.364 mmol) and stirred at 90° C. for 2 h. The reaction mixture was diluted with water and ethyl acetate. Layers were separated and the organic layer was washed with brine, dried with sodium sulfate, filtered, and concentrated in vacuo to give the crude product. Purification by flash column chromatography (100% hexanes to 30% EtOAc/hexanes) gave the desired product (67.3 mg, 97%) as a colorless oil. LCMS calculated for C$_{20}$H$_{17}$BrNO$_2$ (M+H)$^+$: m/z=382.0, 384.0; found: 382.0, 384.0.

Step 4. 6-Bromo-5-phenoxy-3-phenyl-3,4-dihydro-2H-1,4-benzoxazine

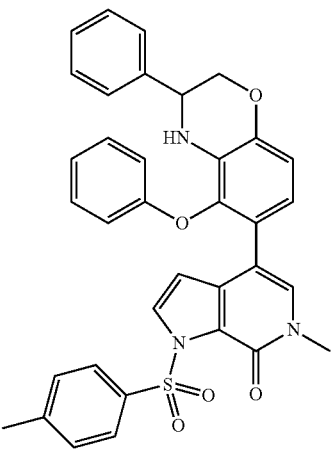

This compound was synthesized according to the procedure of Example 10, Step 5, using 6-bromo-5-phenoxy-3-phenyl-3,4-dihydro-2H-1,4-benzoxazine and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{35}H_{30}N_3O_5S$ (M+H)$^+$: m/z=604.2; found: 604.0.

Step 5. 6-Methyl-4-(5-phenoxy-3-phenyl-3,4-dihydro-2H-1,4-benzoxazin-6-yl)-1,6-dihydro-7H-pyrrolo[2,3-c]pyridin-7-one This compound was synthesized according to the procedure of Example 6, Step 2, using 6-methyl-1-[(4-methylphenyl)sulfonyl]-4-(5-phenoxy-3-phenyl-3,4-dihydro-2H-1,4-benzoxazin-6-yl)-1,6-dihydro-7H-pyrrolo[2,3-c]pyridin-7-one as the starting material. $^1$H NMR (500 MHz, DMSO-d$_6$) δ 11.86 (br s, 1H), 7.38-7.18 (m, 6H), 7.10 (dd, J=7.8, 7.8 Hz, 2H), 7.03 (s, 1H), 6.89-6.72 (m, 2H), 6.68 (d, J=8.2 Hz, 3H), 6.23 (s, 1H), 5.77 (s, 1H), 4.68-4.47 (m, 1H), 4.40-4.16 (m, 1H), 4.13-3.92 (m, 1H), 3.39 (s, 3H); LCMS calculated for $C_{28}H_{24}N_3O_3$ (M+H)$^+$: m/z=450.2; found: 450.2.

Example 111. N-{[1-Methyl-5-(6-methyl-7-oxo-6,7-dihydro-1H-pyrrolo[2,3-c]pyridin-4-yl)-4-phenoxy-1H-benzimidazol-2-yl]methyl}cyclobutanecarboxamide

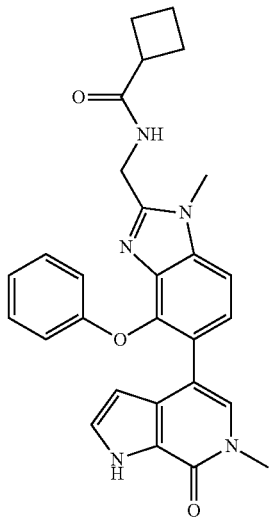 [SMILES: Cn1cc(-c2ccc3c(nc(CNC(=O)C4CCC4)n3C)c2Oc2ccccc2)c2cc[nH]c2c1=O]

Step 1. 4-Bromo-N-methyl-2-nitro-3-phenoxyaniline

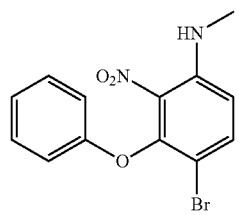 [SMILES: CNc1ccc(Br)c(Oc2ccccc2)c1[N+](=O)[O-]]

This compound was synthesized according to the procedure of Example 1, Step 1, using 4-bromo-3-fluoro-N-methyl-2-nitroaniline and phenol as the starting materials. LCMS calculated for $C_{13}H_{12}BrN_2O_3$ (M+H)$^+$: m/z=323.0, 325.0; found: 322.9, 325.0.

Step 2. 4-Bromo-N1-methyl-3-phenoxybenzene-1,2-diamine

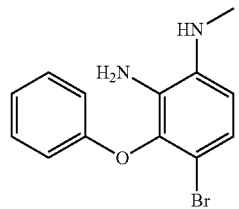

This compound was synthesized according to the procedure of Example 1, Step 3, using 4-bromo-N-methyl-2-nitro-3-phenoxyaniline as the starting material. LCMS calculated for $C_{13}H_{14}BrN_2O$ (M+H)$^+$: m/z=293.0, 295.0; found: 293.0, 295.0.

Step 3. tert-Butyl [(5-bromo-1-methyl-4-phenoxy-1H-benzimidazol-2-yl)methyl]carbamate

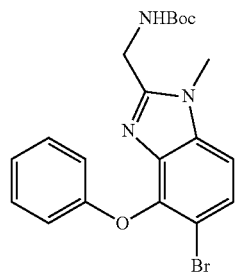 [SMILES: Cn1c(CNC(=O)OC(C)(C)C)nc2c(Oc3ccccc3)c(Br)ccc21]

Phosphoryl chloride (0.0864 mL, 0.927 mmol) was added dropwise at −15° C. to a solution of N-α-(tert-butoxycarbonyl)glycine (0.150 g, 0.856 mmol) and 4-bromo-N$^1$-methyl-3-phenoxybenzene-1,2-diamine (0.209 g, 0.713 mmol) in pyridine (2.85 mL). The reaction mixture was warmed to RT and stirred at RT for 1 h, after which time the reaction mixture was concentrated in vacuo to give a crude residue. The residue was dissolved in ethyl acetate and the solution was washed with saturated solution of sodium bicarbonate and brine, dried with sodium sulfate, filtered, and concentrated in vacuo to give a crude residue. This residue was dissolved in acetic acid (5.00 mL) and heated at 70° C. for 30 min. The reaction mixture was concentrated to give a crude residue, which was diluted with saturated sodium bicarbonate solution and ethyl acetate. Layers were separated and the organic layer was washed with brine, dried with sodium sulfate, filtered, and concentrated in vacuo to give the crude product. Purification by flash column chromatography (100% hexanes to 80% EtOAc/hexanes [EtOAc contained 5% MeOH]) gave the desired product (149 mg, 48%). LCMS calculated for $C_{20}H_{23}BrN_3O_3$ (M+H)$^+$: m/z=432.1, 434.1; found: 432.1, 434.1.

Step 4. tert-Butyl [(5-bromo-1-methyl-4-phenoxy-1H-benzimidazol-2-yl)methyl]carbamate

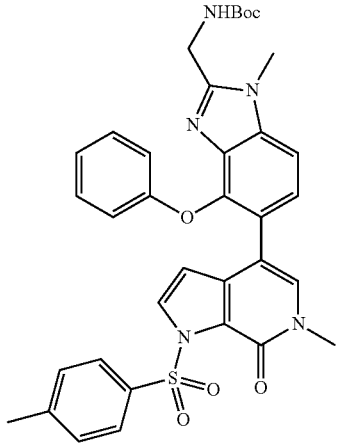

This compound was synthesized according to the procedure of Example 10, Step 5, using tert-butyl [(5-bromo-1-methyl-4-phenoxy-1H-benzimidazol-2-yl)methyl]carbamate and 6-methyl-1-[(4-methylphenyl)sulfonyl]-4-(4,4,5,5-tetramethyl-1,3,2-dioxaborolan-2-yl)-1,6-dihydro-7H-pyrrolo[2,3-c]pyridin-7-one as the starting materials. LCMS calculated for $C_{35}H_{36}N_5O_6S$ (M+H)$^+$: m/z=654.2; found: 654.3.

Step 5. 4-[2-(Aminomethyl)-1-methyl-4-phenoxy-1H-benzimidazol-5-yl]-6-methyl-1-[(4-methylphenyl)sulfonyl]-1,6-dihydro-7H-pyrrolo[2,3-c]pyridin-7-one

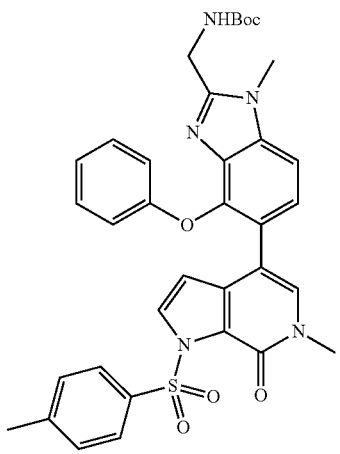

This compound was synthesized according to the procedure of Example 103, Step 4, using tert-butyl [(1-methyl-5-{6-methyl-1-[(4-methylphenyl)sulfonyl]-7-oxo-6,7-dihydro-1H-pyrrolo[2,3-c]pyridin-4-yl}-4-phenoxy-1H-benzimidazol-2-yl)methyl]carbamate as the starting material. LCMS calculated for $C_{30}H_{28}N_5O_4S$ (M+H)$^+$: m/z=554.2; found: 554.2.

Step 6. N-[(1-Methyl-5-{6-methyl-1-[(4-methylphenyl)sulfonyl]-7-oxo-6,7-dihydro-1H-pyrrolo[2,3-c]pyridin-4-yl}-4-phenoxy-1H-benzimidazol-2-yl)methyl]cyclobutanecarboxamide

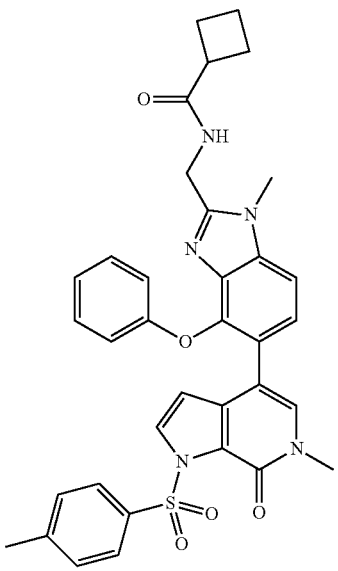

This compound was synthesized according to the procedure of Example 66, Step 2, using 4-[2-(aminomethyl)-1-methyl-4-phenoxy-1H-benzimidazol-5-yl]-6-methyl-1-[(4-methylphenyl)sulfonyl]-1,6-dihydro-7H-pyrrolo[2,3-c]pyridin-7-one and cyclobutanecarboxylic acid chloride as the starting materials. LCMS calculated for $C_{35}H_{34}N_5O_5S$ (M+H)$^+$: m/z=636.2; found: 636.2.

Step 7. N-{[1-Methyl-5-(6-methyl-7-oxo-6,7-dihydro-1H-pyrrolo[2,3-c]pyridin-4-yl)-4-phenoxy-1H-benzimidazol-2-yl]methyl}cyclobutanecarboxamide This compound was synthesized according to the procedure of Example 6, Step 2, using N-[(1-methyl-5-{6-methyl-1-[(4-methylphenyl)sulfonyl]-7-oxo-6,7-dihydro-1H-pyrrolo[2,3-c]pyridin-4-yl}-4-phenoxy-1H-benzimidazol-2-yl)methyl]cyclobutanecarboxamide as the starting material. $^1$H NMR (500 MHz, DMSO-d$_6$) δ 11.92 (br s, 1H), 8.29 (dd, J=5.6, 5.6 Hz, 1H), 7.52 (d, J=8.4 Hz, 1H), 7.37 (d, J=8.3 Hz, 1H), 7.23 (dd, J=2.8, 2.8 Hz, 1H), 7.18-7.03 (m, 3H), 6.82 (dd, J=7.3, 7.3 Hz, 1H), 6.59 (dd, J=8.7, 1.0 Hz, 2H), 6.29-6.08 (m, 1H), 4.48 (d, J=5.7 Hz, 2H), 3.81 (s, 3H), 3.42 (s, 3H), 3.15-2.88 (m, 1H), 2.17-2.04 (m, 2H), 2.03-1.92 (m, 2H), 1.91-1.78 (m, 1H), 1.78-1.66 (m, 1H); LCMS calculated for $C_{28}H_{28}N_5O_3$ (M+H)$^+$: m/z=482.2; found: 482.2.

Example 112. N-{[1-Methyl-5-(6-methyl-7-oxo-6,7-dihydro-1H-pyrrolo[2,3-c]pyridin-4-yl)-4-phenoxy-1H-benzimidazol-2-yl]methyl}cyclopropanecarboxamide

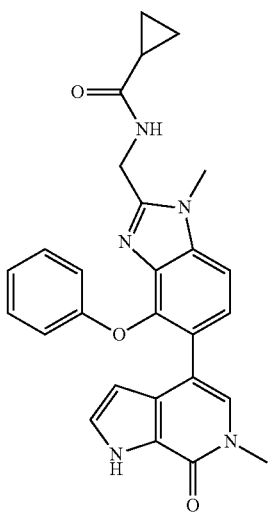 [SMILES: Cn1cc(-c2ccc3c(nc(CNC(=O)C4CC4)n3C)c2Oc2ccccc2)c2cc[nH]c2c1=O]

This compound was synthesized according to the procedure of Example 111 using cyclopropanecarbonyl chloride in step 6 instead of cyclobutanecarboxylic acid chloride. $^1$H NMR (500 MHz, DMSO-$d_6$) δ 11.92 (br s, 1H), 8.71 (dd, J=5.6, 5.6 Hz, 1H), 7.53 (d, J=8.4 Hz, 1H), 7.37 (d, J=8.3 Hz, 1H), 7.23 (dd, J=2.7, 2.7 Hz, 1H), 7.18-7.02 (m, 3H), 6.82 (dd, J=7.3, 7.3 Hz, 1H), 6.60 (dd, J=8.7, 0.9 Hz, 2H), 6.26-6.11 (m, 1H), 4.52 (d, J=5.7 Hz, 2H), 3.82 (s, 3H), 3.42 (s, 3H), 1.72-1.45 (m, 1H), 0.84-0.45 (m, 4H); LCMS calculated for $C_{27}H_{26}N_5O_3$ (M+H)$^+$: m/z=468.2; found: 468.2.

Example A1: BRD4 AlphaScreen™ Assay

BRD4-BD1 and BRD4-BD2 assays were conducted in white 384-well polystyrene plate in a final volume of 20 μL for BD1 and 40 μL for BD2. Inhibitors were first serially diluted in DMSO and added to the plate wells before the addition of other reaction components. The final concentration of DMSO in the assay was 1.25% (BD1) and 0.83% (BD2). The assays were carried out at room temperature for 75 min. in the assay buffer (50 mM HEPES, pH 7.4, 100 mM NaCl, 0.05% CHAPS, 0.01% BSA), containing 50 nM Biotin-labeled tetra-acetylated histone H4 peptide (H4Ac4), 3.8 nM (BRD4-BD1, BPS Bioscience #31040) or 20 nM (BRD4-BD2, BPS Bioscience #31041). The reaction followed by the addition of 20 μL of assay buffer supplemented with Streptavidin donor beads (PerkinElmer 6760002) and GSH Acceptor beads (PerkinElmer-AL109C) at 4 μg/mL under reduced light. After plate sealing, the plate was incubated in the dark at room temperature for 75 min. before reading on a PHERAstar FS plate reader (BMG Labtech). IC$_{50}$ determination was performed by fitting the curve of percent control activity versus the log of the inhibitor concentration using the GraphPad Prism 5.0 software.

IC$_{50}$ data for the Examples is presented in Table 8 as determined by Assay A1.

TABLE 8

| Example # | BRD4 BD-1 enzyme IC$_{50}$ (nM)* | BRD4 BD-2 enzyme IC$_{50}$ (nM)* |
|---|---|---|
| 1 | + | + |
| 2 | + | + |
| 3 | + | + |
| 4 | + | + |
| 5 | + | + |
| 6 | + | + |
| 7 | + | + |
| 8 | + | + |
| 9 | + | + |
| 10 | + | + |
| 11 | + | + |
| 12 | + | + |
| 13 | + | + |
| 14 | + | + |
| 15 | + | + |
| 16 | + | + |
| 17 | + | + |
| 18 | + | + |
| 19 | + | + |
| 20 | + | + |
| 21 | + | + |
| 22 | + | + |
| 23 | + | + |
| 24 | + | + |
| 25 | + | + |
| 26 | + | + |
| 27 | ++ | + |
| 28 | ++ | + |
| 29 | + | + |
| 30 | + | + |
| 31 | + | + |
| 32 | ++ | + |
| 33 | + | + |
| 34 | + | + |
| 35 | + | + |
| 36 | + | + |
| 37 | + | + |
| 38 | + | + |
| 39 | + | + |
| 40 | + | + |
| 41 | + | + |
| 42 | + | + |
| 43 | + | + |
| 44 | + | + |
| 45 | + | + |
| 46 | + | + |
| 47 | + | + |
| 48 | + | + |
| 49 | ++ | + |
| 50 | ++ | + |
| 51 | + | + |
| 52 | + | + |
| 53 | ++ | + |
| 54 | ++ | + |
| 55 | + | + |
| 56 | + | + |
| 57 | + | + |
| 58 | + | + |
| 59 | + | + |
| 60 | + | + |
| 61 | + | + |
| 62 | + | + |
| 63 | + | + |
| 64 | + | + |
| 65 | + | + |
| 66 | + | + |
| 67 | + | + |
| 68 | + | + |
| 69 | + | + |
| 70 | + | + |
| 71 | +++ | +++ |
| 72 | ++ | + |
| 73 | +++ | ++ |
| 74 | + | + |
| 75 | + | + |
| 76 | + | + |

TABLE 8-continued

| Example # | BRD4 BD-1 enzyme IC$_{50}$ (nM)* | BRD4 BD-2 enzyme IC$_{50}$ (nM)* |
|---|---|---|
| 77 | + | + |
| 78 | + | + |
| 79 | ++ | + |
| 80 | + | + |
| 81 | ++ | + |
| 82 | ++ | ++ |
| 83 | ++ | + |
| 84 | +++ | ++ |
| 85 | +++ | ++ |
| 86 | + | + |
| 87 | + | + |
| 88 | + | + |
| 89 | + | + |
| 90 | + | + |
| 91 | + | + |
| 92 | + | + |
| 93 | + | + |
| 94 | + | + |
| 95 | + | + |
| 96 | + | + |
| 97 | + | + |
| 98 | + | + |
| 99 | +++ | ++ |
| 100 | ++ | + |
| 101 | ++ | ++ |
| 102 | ++ | + |
| 103 | + | + |
| 104 | + | + |
| 105 | + | + |
| 106 | + | + |
| 107 | + | + |
| 108 | + | + |
| 109 | + | + |
| 110 | ++ | + |
| 111 | + | + |
| 112 | + | + |
| 113 | + | + |

*column symbols:
+ refers to ≤100 nM
++ refers to >100 nM to 1000 nM
+++ refers to >1000 nM to 10000 nM
NT = not tested

Example B1: KMS.12.BM Cell Viability Assay

KMS.12.BM cell line (human myeloma) was purchased from JCRB (Osaka, Japan) and maintained in RPMI with 10% FBS culture medium. To measure the cytotoxic activity of the compounds through ATP quantitation, the KMS.12.BM cells are plated in the RPMI culture medium at 5000 cells/well/per 100 µL into a 96-well polystyrene clear black tissue culture plate (Greiner-bio-one through VWR, NJ), in the presence or absence of a concentration range of test compounds. After 3 days, 100 mL Cell Titer-GLO Luminescent (Promega, Madison, Wis.) cell culture agent is added to each well for 10 minutes at room temperature to stabilize the luminescent signal. This determines the number of viable cells in culture based on quantitation of the ATP present, which signals the presence of metabolically active cells. Luminescence is measured with the Top Count 384 (Packard Bioscience through Perkin Elmer, Boston, Mass.). Compound inhibition is determined relative to cells cultured with no drug and the IC$_{50}$ is reported as the compound concentration required for 50% cell death. IC$_{50}$ data for the Examples is presented in Table 9 as determined by Assay B1.

TABLE 9

| Example # | KMS cellular IC50 (nM)* |
|---|---|
| 1 | + |
| 2 | + |
| 3 | + |
| 4 | + |
| 5 | + |
| 6 | + |
| 7 | + |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | + |
| 24 | + |
| 25 | + |
| 26 | + |
| 27 | + |
| 28 | + |
| 29 | + |
| 30 | + |
| 31 | + |
| 32 | + |
| 33 | + |
| 34 | + |
| 35 | + |
| 36 | + |
| 37 | + |
| 38 | + |
| 39 | + |
| 40 | + |
| 41 | + |
| 42 | + |
| 43 | + |
| 44 | + |
| 45 | + |
| 46 | + |
| 47 | + |
| 48 | + |
| 49 | + |
| 50 | NT |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | ++ |
| 66 | + |
| 67 | + |
| 68 | + |
| 69 | + |
| 70 | + |
| 71 | NT |
| 72 | ++ |
| 73 | NT |
| 74 | + |
| 75 | + |
| 76 | + |
| 77 | + |
| 78 | + |

TABLE 9-continued

| Example # | KMS cellular IC50 (nM)* |
|---|---|
| 79 | ++ |
| 80 | + |
| 81 | + |
| 82 | NT |
| 83 | + |
| 84 | NT |
| 85 | NT |
| 86 | + |
| 87 | + |
| 88 | + |
| 89 | + |
| 90 | + |
| 91 | + |
| 92 | + |
| 93 | + |
| 94 | + |
| 95 | + |
| 96 | + |
| 97 | + |
| 98 | + |
| 99 | NT |
| 100 | + |
| 101 | NT |
| 102 | NT |
| 103 | + |
| 104 | + |
| 105 | + |
| 106 | + |
| 107 | + |
| 108 | + |
| 109 | + |
| 110 | NT |
| 111 | + |
| 112 | + |
| 113 | + |

*column symbols:
+ refers to ≤1000 nM
++ refers to >1000 nM to 10000 nM
NT = not tested

Example C1: KMS.12.BM C-myc ELISA Assay

KMS.12.BM cell line (human myeloma) was purchased from JCRB (Osaka, Japan) and maintained in RPMI with 10% FBS culture medium. To measure the C-myc inhibitory activity of the compounds, the KMS.12.BM cells are plated in the RPMI culture medium at 75000 cells/well/per 200 µL into a 96-well flat bottom polystyrene tissue culture plate (Corning through VWR, NJ), in the presence or absence of a concentration range of test compounds. After 2 hours, cell are pelleted and lysed with Cell Extraction Buffer (BioSource, Carlsbad, Calif.) in the presence of protease inhibitors (Life Technologies, Grand Island, N.Y. and Sigma, St Louis, Mo.). Clarified lyses are tested in a C-myc commercial ELISA (Life Technologies, Grand Island, N.Y.). Compound inhibition is determined relative to cells cultured with no drug and the $IC_{50}$ is reported as the compound concentration required for 50% C-myc inhibition. $IC_{50}$ data for the Examples is presented in Table 10 as determined by Assay C1.

TABLE 10

| Example # | KMS C-myc $IC_{50}$ (nM)* |
|---|---|
| 1 | + |
| 2 | + |
| 3 | + |
| 4 | + |
| 5 | + |
| 6 | + |
| 7 | ++ |
| 8 | + |
| 9 | + |
| 10 | + |
| 11 | + |
| 12 | + |
| 13 | + |
| 14 | + |
| 15 | + |
| 16 | + |
| 17 | + |
| 18 | + |
| 19 | + |
| 20 | + |
| 21 | + |
| 22 | + |
| 23 | NT |
| 24 | + |
| 25 | + |
| 26 | + |
| 27 | + |
| 28 | ++ |
| 29 | + |
| 30 | + |
| 31 | + |
| 32 | + |
| 33 | NT |
| 34 | + |
| 35 | NT |
| 36 | + |
| 37 | + |
| 38 | + |
| 39 | + |
| 40 | + |
| 41 | + |
| 42 | + |
| 43 | + |
| 44 | NT |
| 45 | + |
| 46 | + |
| 47 | + |
| 48 | + |
| 49 | NT |
| 50 | NT |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | NT |
| 64 | + |
| 65 | NT |
| 66 | + |
| 67 | NT |
| 68 | + |
| 69 | + |
| 70 | + |
| 71 | NT |
| 72 | NT |
| 73 | NT |
| 74 | + |
| 75 | + |
| 76 | + |
| 77 | + |
| 78 | + |
| 79 | NT |
| 80 | NT |
| 81 | NT |
| 82 | NT |
| 83 | NT |

TABLE 10-continued

| Example # | KMS C-myc IC$_{50}$ (nM)* |
|---|---|
| 84 | NT |
| 85 | NT |
| 86 | + |
| 87 | + |
| 88 | + |
| 89 | + |
| 90 | + |
| 91 | + |
| 92 | + |
| 93 | + |
| 94 | + |
| 95 | NT |
| 96 | + |
| 97 | NT |
| 98 | NT |
| 99 | NT |
| 100 | NT |
| 101 | NT |
| 102 | NT |
| 103 | + |
| 104 | + |
| 105 | + |
| 106 | ++ |
| 107 | + |
| 108 | + |
| 109 | ++ |
| 110 | NT |
| 111 | NT |
| 112 | NT |
| 113 | + |

*column symbols:
+ refers to ≤1000 nM
++ refers to >1000 nM to 10000 nM
NT = not tested Various modifications of the invention, in addition to those described herein, will be apparent to those skilled in the art from the foregoing description. Such modifications are also intended to fall within the scope of the appended claims. Each reference, including all patent, patent applications, and publications, cited in the present application is incorporated herein by reference in its entirety.

What is claimed is:

1. A method of inhibiting bromodomain and extra-terminal protein activity in a patient suffering from cancer, comprising administering to a patient in need of such treatment a therapeutically effective amount of a compound of Formula I:

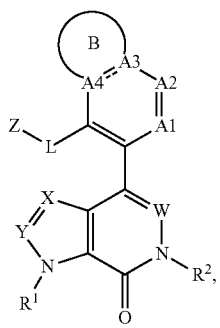

or a pharmaceutically acceptable salt thereof,
wherein:
====== represents a single or double bond;
ring B is phenyl, 5-6 membered heteroaryl, $C_{5-6}$ cycloalkyl, or 5-6 membered heterocycloalkyl, each optionally substituted by 1, 2, 3, or 4 $R^B$;

L is absent, $-(CR^aR^b)_p-$, $-(CR^aR^b)_n-O-(CR^aR^b)_m-$, $-(CR^aR^b)_n-S-(CR^aR^b)_m-$, $-(CR^aR^b)_n-S(=O)-(CR^aR^b)_m-$, $-(CR^aR^b)_n-S(=O)_2-(CR^aR^b)_m-$, $-(CR^aR^b)_n-C(=O)-(CR^aR^b)_m-$, $-(CR^aR^b)_n-C(=O)O-(CR^aR^b)_m-$, $-(CR^aR^b)_n-OC(=O)-(CR^aR^b)_m-$, $-(CR^aR^b)_n-NR^c-(CR^aR^b)_m-$, $-(CR^aR^b)_n-C(=O)NR^c-(CR^aR^b)_m-$, $-(CR^aR^b)_n-NR^cC(=O)-(CR^aR^b)_m-$, or $-(CR^aR^b)_n-NR^cC(=O)NR^d-(CR^aR^b)_m-$;

A1 is $CR^3$ or N;
A2 is $CR^4$ or N;
A3 is C or N;
A4 is C or N;
wherein when one of A3 and A4 is N, then the other of A3 and A4 is C;
W is $CR^5$;
X is $CR^6$;
Y is $CR^7$ or N;

(i) Z is $C_{6-10}$ aryl, $C_{3-10}$ cycloalkyl, 5-10 membered heteroaryl, or 4-10 membered heterocycloalkyl, each of which is optionally substituted by 1, 2, 3, 4, or 5 $R^Z$; and $R^3$ and $R^4$ are each independently selected from H, halo, CN, NO$_2$, $C_{1-6}$ alkyl, $C_{1-6}$ haloalkyl, $C_{1-6}$ hydroxyalkyl, $C_{1-6}$ aminoalkyl, $C_{1-6}$ alkylamino-$C_{1-6}$ alkyl, di-$C_{1-6}$-alkylamino-$C_{1-6}$ alkyl, $C_{2-6}$ alkenyl, and $C_{2-6}$ alkynyl, wherein said $C_{1-6}$ alkylamino-$C_{1-6}$ alkyl and di-$C_{1-6}$-alkylamino-$C_{1-6}$ alkyl are each optionally substituted with 1 or 2 substituents independently selected from $C_{6-10}$ aryl, $C_{3-10}$ cycloalkyl, 5-10 membered heteroaryl, and 4-10 membered heterocycloalkyl; or (ii) Z is $C_{1-6}$ alkyl optionally substituted by 1, 2, 3, 4, or 5 $R^Z$; $R^3$ is selected from H, halo, CN, NO$_2$, $C_{1-6}$ alkyl, $C_{1-6}$ haloalkyl, $C_{1-6}$ hydroxyalkyl, $C_{1-6}$ aminoalkyl, $C_{1-6}$ alkylamino-$C_{1-6}$ alkyl, di-$C_{1-6}$-alkylamino-$C_{1-6}$ alkyl, $C_{2-6}$ alkenyl, and $C_{2-6}$ alkynyl; and $R^4$ is selected from H, halo, CN, NO$_2$, $C_{1-6}$ alkyl, $C_{1-6}$ haloalkyl, $C_{1-6}$ hydroxyalkyl, $C_{1-6}$ aminoalkyl, $C_{1-6}$ alkylamino-$C_{1-6}$ alkyl, di-$C_{1-6}$-alkylamino-$C_{1-6}$ alkyl, $C_{2-6}$ alkenyl, and $C_{2-6}$ alkynyl, wherein said $C_{1-6}$ alkylamino-$C_{1-6}$ alkyl and di-$C_{1-6}$-alkylamino-$C_{1-6}$ alkyl are each optionally substituted with 1 or 2 substituents independently selected from $C_{6-10}$ aryl, $C_{3-10}$ cycloalkyl, 5-10 membered heteroaryl, and 4-10 membered heterocycloalkyl;

$R^1$ is H or $C_{1-4}$ alkyl;
$R^2$ is H, $C_{1-4}$ alkyl, $C_{1-4}$ haloalkyl, $C_{1-4}$ hydroxyalkyl, $C_{1-4}$ cyanoalkyl, or $C_{6-10}$ aryl-$C_{1-6}$ alkyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, NO$_2$, $OR^{a2}$, $SR^{a2}$, $C(O)R^{b2}$, $C(O)NR^{c2}R^{d2}$, $C(O)OR^{a2}$, OC(O)$R^{b2}$, OC(O)NR$^{c2}$R$^{d2}$, NR$^{c2}$R$^{d2}$, NR$^{c2}$C(O)R$^{b2}$, NR$^{c2}$C(O)OR$^{a2}$, NR$^{c2}$C(O)NR$^{c2}$R$^{d2}$, C(=NR$^{e2}$)R$^{b2}$, C(=NR$^{e2}$)NR$^{c2}$R$^{d2}$, NR$^{c2}$C(=NR$^{e2}$)NR$^{c2}$R$^{d2}$, NR$^{c2}$S(O)R$^{b2}$, NR$^{c2}$S(O)$_2$R$^{b2}$, NR$^{c2}$S(O)$_2$NR$^{c2}$R$^{d2}$, S(O)R$^{b2}$, S(O)NR$^{c2}$R$^{d2}$, S(O)$_2$R$^{b2}$, and S(O)$_2$NR$^{c2}$R$^{d2}$;

each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, C(=NR$^{e3}$)R$^{b3}$, C(=NR$^{e3}$)NR$^{c3}$R$^{d3}$, NR$^{c3}$C(=NR$^{e3}$)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$, and wherein said phenyl, $C_{3-7}$ cycloalkyl, 5-6 membered heteroaryl, and 4-7 membered heterocycloalkyl are each independently substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a3}$, SR$^{a3}$, C(O)R$^{b3}$, C(O)NR$^{c3}$R$^{d3}$, C(O)OR$^{a3}$, OC(O)R$^{b3}$, OC(O)NR$^{c3}$R$^{d3}$, C(=NR$^{e3}$)NR$^{c3}$R$^{d3}$, NR$^{c3}$C(=NR$^{e3}$)NR$^{c3}$R$^{d3}$, NR$^{c3}$R$^{d3}$, NR$^{c3}$C(O)R$^{b3}$, NR$^{c3}$C(O)OR$^{a3}$, NR$^{c3}$C(O)NR$^{c3}$R$^{d3}$, NR$^{c3}$S(O)R$^{b3}$, NR$^{c3}$S(O)$_2$R$^{b3}$, NR$^{c3}$S(O)$_2$NR$^{c3}$R$^{d3}$, S(O)R$^{b3}$, S(O)NR$^{c3}$R$^{d3}$, S(O)$_2$R$^{b3}$, and S(O)$_2$NR$^{c3}$R$^{d3}$;

each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$ NR$^{c4}$R$^{d4}$;

each $R^a$ and $R^b$ is independently selected from H, halo, OH, methyl, and ethyl;

each $R^c$ and $R^d$ is independently selected from H, $C_{1-4}$ alkyl, $C_{1-4}$ haloalkyl, $C_{1-4}$ hydroxyalkyl, and cyclopropyl;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, and $R^{d4}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl is optionally substituted with 1, 2, 3, 4, or 5 substituents independently selected from $C_{1-4}$ alkyl, $C_{1-4}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any $R^{c1}$ and $R^{d1}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any $R^{c2}$ and $R^{d2}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any $R^{c3}$ and $R^{d3}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$ $NRcsC(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

or any $R^{c4}$ and $R^{d4}$ together with the N atom to which they are attached form a 4-, 5-, 6-, or 7-membered heterocycloalkyl group optionally substituted with 1, 2, or 3 substituents independently selected from $C_{1-6}$ alkyl, $C_{3-7}$ cycloalkyl, 4-7 membered heterocycloalkyl, $C_{6-10}$ aryl, 5-6 membered heteroaryl, $C_{1-6}$ haloalkyl, halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$, wherein said $C_{1-6}$ alkyl, $C_{3-7}$ cycloalkyl, 4-7 membered heterocycloalkyl, $C_{6-10}$ aryl, and 5-6 membered heteroaryl are optionally substituted by 1, 2, or 3 substituents independently selected from halo, CN, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $NR^{c5}R^{d5}$, $NR^{c5}C(O)R^{b5}$, $NR^{c5}C(O)NR^{c5}R^{d5}$, $NR^{c5}C(O)OR^{a5}$, $C(=NR^{e5})NR^{c5}R^{d5}$, $NR^{c5}C(=NR^{e5})NR^{c5}R^{d5}$, $S(O)R^{b5}$, $S(O)NR^{c5}R^{d5}$, $S(O)_2R^{b5}$, $NR^{c5}S(O)_2R^{b5}$, $NR^{c5}S(O)_2NR^{c5}R^{d5}$, and $S(O)_2NR^{c5}R^{d5}$;

each $R^{e1}$, $R^{e2}$, $R^{e3}$, and $R^{e4}$ is independently selected from H, $C_{1-4}$ alkyl, CN, $OR^{a5}$, $SR^{b5}$, $S(O)_2R^{b5}$, $C(O)R^{b5}$, $S(O)_2NR^{c5}R^{d5}$, and $C(O)NR^{c5}R^{d5}$;

each $R^{a5}$, $R^{b5}$, $R^{c5}$, and $R^{d5}$ is independently selected from H, $C_{1-4}$ alkyl, $C_{1-4}$ haloalkyl, $C_{2-4}$ alkenyl, and $C_{2-4}$ alkynyl, wherein said $C_{1-4}$ alkyl, $C_{2-4}$ alkenyl, and $C_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group is optionally substituted by 1 or 2 oxo groups.

2. The method of claim 1, wherein the cancer is adenocarcinoma, adult T-cell leukemia/lymphoma, bladder cancer, blastoma, bone cancer, breast cancer, brain cancer, carcinoma, myeloid sarcoma, cervical cancer, colorectal cancer, esophageal cancer, gastrointestinal cancer, glioblastoma multiforme, glioma, gallbladder cancer, gastric cancer, head and neck cancer, Hodgkin's lymphoma, non-Hodgkin's lymphoma, intestinal cancer, kidney cancer, laryngeal cancer, leukemia, lung cancer, lymphoma, liver cancer, small cell lung cancer, non-small cell lung cancer, mesothelioma, multiple myeloma, ocular cancer, optic nerve tumor, oral cancer, ovarian cancer, pituitary tumor, primary central nervous system lymphoma, prostate cancer, pancreatic cancer, pharyngeal cancer, renal cell carcinoma, rectal cancer, sarcoma, skin cancer, spinal tumor, small intestine cancer, stomach cancer, T-cell lymphoma, testicular cancer, thyroid cancer, throat cancer, urogenital cancer, urothelial carcinoma, uterine cancer, vaginal cancer, or Wilms' tumor.

3. The method of claim 1, wherein A1 is $CR^3$.

4. The method of claim 1, wherein A2 is $CR^4$.

5. The method of claim 1, wherein A2 is N.

6. The method of claim 1, wherein A3 is C.

7. The method of claim 1, wherein A4 is C.

8. The method of claim 1, wherein A4 is N.

9. The method of claim 1, wherein L is $-(CR^aR^b)_p-$, $-(CR^aR^b)_n-O-(CR^aR^b)_m-$, $-(CR^aR^b)_n-S-(CR^aR^b)_m-$, or $-(CR^aR^b)_n-S(=O)_2-(CR^aR^b)_m-$.

10. The method of claim 1, wherein L is $-(CR^aR^b)_n-O-(CR^aR^b)_m-$.

11. The method of claim 1, wherein L is $-CH_2-O-$.

12. The method of claim 1, wherein L is O, S, or $S(=O)_2$.

13. The method of claim 1, wherein L is O.

14. The method of claim 1, wherein $R^1$ is H.

15. The method of claim 1, wherein $R^2$ is $C_{1-4}$ alkyl, $C_{1-4}$ cyanoalkyl, or $C_{6-10}$ aryl-$C_{1-6}$ alkyl.

16. The method of claim 1, wherein $R^2$ is $C_{1-4}$ alkyl.

17. The method of claim 1, wherein $R^2$ is methyl, cyanomethyl, or benzyl.

18. The method of claim 1, wherein $R^2$ is methyl.

19. The method of claim 1, wherein Y is $CR^7$.

20. The method of claim 1, wherein Y is N.

21. The method of claim 1, wherein Z is $C_{1-4}$ alkyl, $C_{6-10}$ aryl, $C_{3-10}$ cycloalkyl, or 4-10 membered heterocycloalkyl, each of which is optionally substituted by 1, 2, 3, 4, or 5 $R^Z$.

22. The method of claim 1, wherein Z is $C_{6-10}$ aryl or $C_{3-10}$ cycloalkyl, each of which is optionally substituted by 1, 2, 3, 4, or 5 $R^Z$.

23. The method of claim 1, wherein Z is phenyl optionally substituted by 1, 2, 3, 4, or 5 $R^Z$.

24. The method of claim 1, wherein Z is $C_{1-4}$ alkyl.

25. The method of claim 1, wherein Z is $C_{3-7}$ cycloalkyl optionally substituted by 1, 2, 3, 4, or 5 $R^Z$.

26. The method of claim 1, wherein Z is cyclopropyl, cyclobutyl, cyclopentyl, or cyclohexyl, each of which is optionally substituted by 1, 2, 3, 4, or 5 $R^Z$.

27. The method of claim 1, wherein Z is 4-10 membered heterocycloalkyl optionally substituted by 1, 2, 3, 4, or 5 $R^Z$.

28. The method of claim 1, wherein Z is tetrahydropyranyl.

29. The method of claim 1, wherein each $R^Z$ is independently selected from halo, $C_{1-6}$ alkyl, $C_{2-6}$ alkenyl, $C_{2-6}$ alkynyl, $C_{1-6}$ haloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $C(=NR^{e4})R^{b4}$, $C(=NR^{e4})NR^{c4}R^{d4}$, $NR^{c4}C(=NR^{e4})NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$.

30. The method of claim 1, wherein each $R^Z$ is independently selected from F, Cl, and Br.

31. The method of claim 1, wherein $R^4$ is H, $C_{1-6}$ hydroxyalkyl, or $C_{1-6}$ alkylamino-$C_{1-6}$ alkyl, wherein said $C_{1-6}$ alkylamino-$C_{1-6}$ alkyl is optionally substituted with 1 or 2 substituents independently selected from $C_{6-10}$ aryl, $C_{3-10}$ cycloalkyl, 5-10 membered heteroaryl, and 4-10 membered heterocycloalkyl.

32. The method of claim 1, wherein $R^4$ is H.

33. The method of claim 1, wherein $R^4$ is 1-hydroxyethyl.

34. The method of claim 1, wherein $R^4$ is $C_{1-6}$ alkylamino-$C_{1-6}$ alkyl substituted with 2-(morpholin-N-yl)ethyl, benzyl, or cyclopropylmethyl.

35. The method of claim 1, wherein the compound is a compound of Formula II:

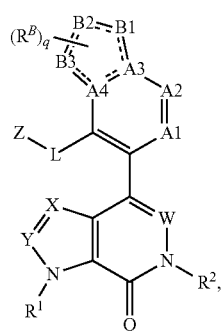

II or a pharmaceutically acceptable salt thereof, wherein:
the 5-membered ring formed by A3, A4, B1, B2, and B3 is (1) 5-membered heteroaryl wherein B1, B2, and B3 are each independently selected from CH, N, NH, O, and S, (2) $C_5$-cycloalkyl wherein B1, B2, and B3 are each independently selected from CH, $CH_2$, and C(O), or (3) 5-membered heterocycloalkyl wherein B1, B2, and B3 are each independently selected from CH, $CH_2$, C(O), N, NH, O, S, S(O), and $S(O)_2$; and
q is 0, 1, 2 or 3.

36. The method of claim 35, wherein B1, B2, and B3 are each independently selected from CH, C(O), N, O, and NH.

37. The method of claim 35, wherein B1, B2, and B3 are each independently selected from CH, C(O), N, and NH.

38. The method of claim 35, wherein B1 is N, NH, CH, or O.

39. The method of claim 35, wherein B1 is NH.

40. The method of claim 35, wherein B2 is N, C(O), or CH.

41. The method of claim 35, wherein B3 is N, NH, or CH.

42. The method of claim 35, wherein B3 is N or NH.

43. The method of claim 35, wherein the compound is a compound of Formula IIa:

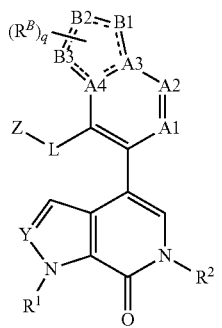

IIa or a pharmaceutically acceptable salt thereof.

44. The method of claim 35, wherein the compound is a compound of Formula IIb:

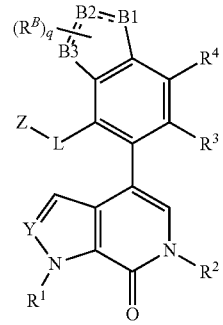

IIb or a pharmaceutically acceptable salt thereof.

45. The method of claim 35, wherein the compound is a compound of Formula IIc:

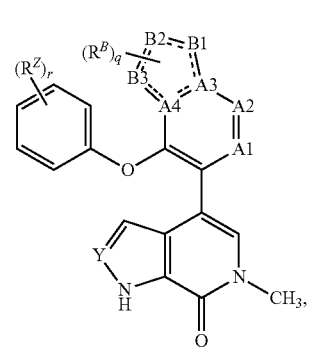

IIc or a pharmaceutically acceptable salt thereof, wherein r is 0, 1, 2, 3, 4, or 5.

46. The method of claim 45, wherein r is 0, 1, 2, or 3.

47. The method of claim 35, wherein the compound is a compound of Formula IId, Formula IIe, Formula IIf, or Formula IIf-1:

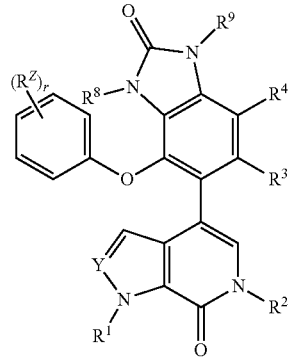

IId

-continued

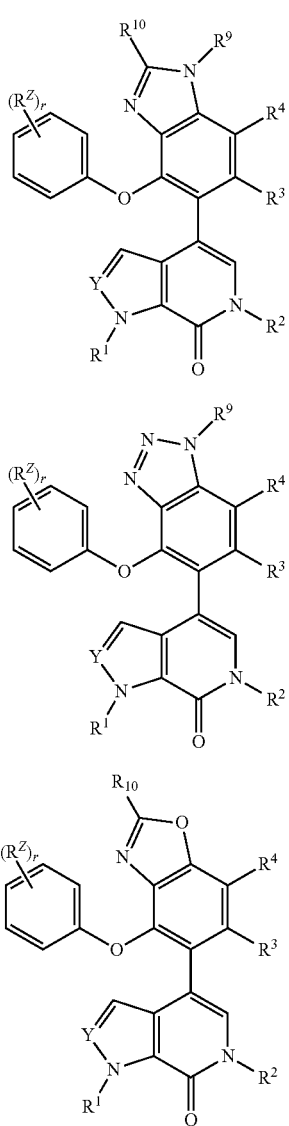

or a pharmaceutically acceptable salt thereof,
wherein:
r is 0, 1, 2, 3, 4, or 5; and
each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, phenyl, $C_{3-7}$ cycloalkyl, 5-6 membered heteroaryl, 4-7 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$, and wherein said phenyl, $C_{3-7}$ cycloalkyl, 5-6 membered heteroaryl, and 4-7 membered heterocycloalkyl are each independently substituted by 1, 2, or 3 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

48. The method of claim 35, wherein the compound is a compound of Formula IId, Formula IIe, or Formula IIf:

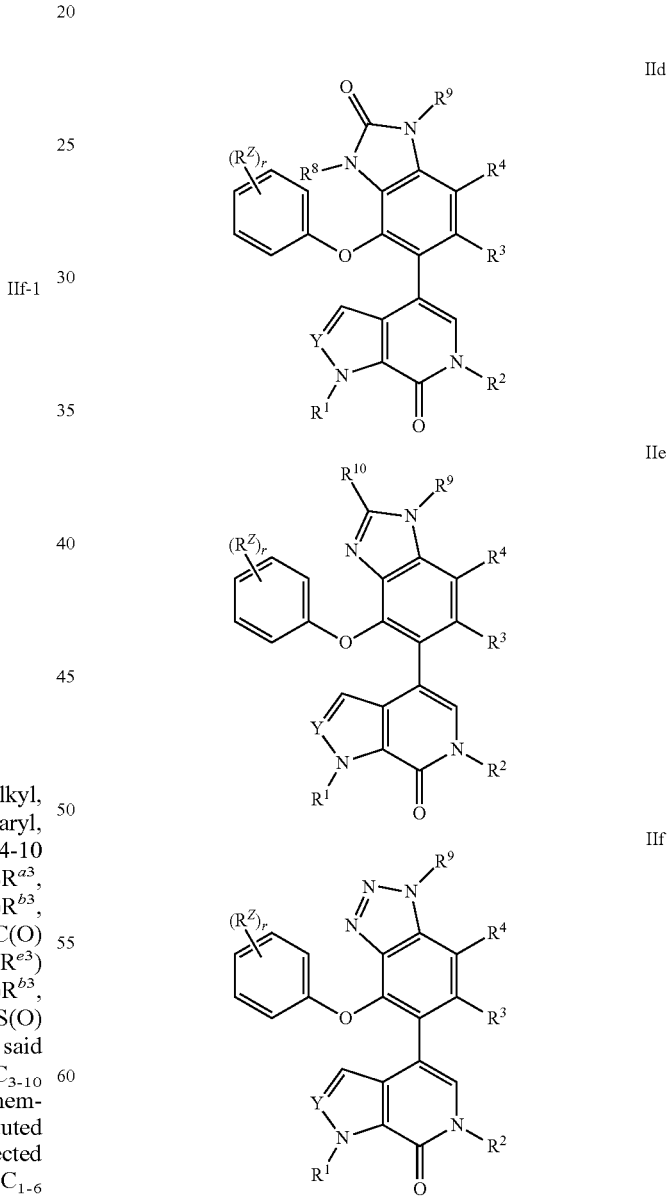

or a pharmaceutically acceptable salt thereof, wherein:

r is 0, 1, 2, 3, 4, or 5; and $R^8$, $R^9$, and $R^{10}$ are each independently selected from H, $C_{1-6}$ alkyl, $C_{6-10}$ aryl, $C_{3-10}$ cycloalkyl, 5-10 membered heteroaryl, and 4-10 membered heterocycloalkyl, wherein said $C_{1-6}$ alkyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $NR^{c3}R^{d3}$, $NR^{c3}C(O)R^{b3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$.

49. The method of claim 1, wherein the compound is a compound of Formula III:

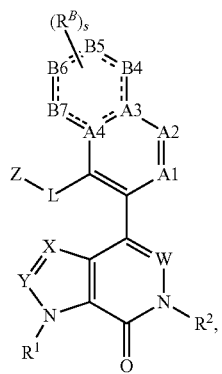

III or a pharmaceutically acceptable salt thereof,
wherein:

the 6-membered ring formed by A3, A4, B4, B5, B6, and B7 is (1) phenyl, (2) 6-membered heteroaryl wherein B4, B5, B6, and B7 are each independently selected from CH and N, (3) $C_6$-cycloalkyl wherein B4, B5, B6, and B7 are each independently selected from CH, $CH_2$, and C(O), or (4) 6-membered heterocycloalkyl wherein B4, B5, B6, and B7 are each independently selected from CH, $CH_2$, C(O), N, NH, O, S, S(O), and $S(O)_2$; and s is 0, 1, 2, 3, or 4.

50. The method of claim 49, wherein the 6-membered ring formed by A3, A4, B4, B5, B6, and B7 is 6-membered heterocycloalkyl wherein B4, B5, B6, and B7 are each independently selected from CH, $CH_2$, C(O), N, NH, O, S, S(O), and $S(O)_2$.

51. The method of claim 49, wherein B4 is selected from O or N.

52. The method of claim 49, wherein B5 is selected from CH or $CH_2$.

53. The method of claim 49, wherein B6 is selected from CH or C(O).

54. The method of claim 49, wherein B7 is selected from N or NH.

55. The method of claim 49, wherein the compound is a compound of Formula IIIa:

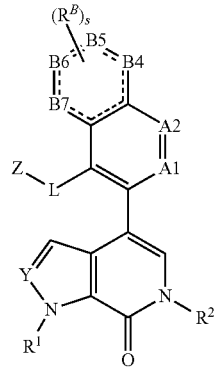

IIIa or a pharmaceutically acceptable salt thereof.

56. The method of claim 1, wherein the compound is selected from:
4-(2,4-Difluorophenoxy)-5-(6-methyl-7-oxo-6,7-dihydro-1H-pyrrolo[2,3-c]pyridin-4-yl)-1,3-dihydro-2H-benzimidazol-2-one;
4-[4-(2,4-Difluorophenoxy)-1H-benzimidazol-5-yl]-6-methyl-1,6-dihydro-7H-pyrrolo[2,3-c]pyridin-7-one; and
4-[4-(2,4-Difluorophenoxy)-2-methyl-1H-benzimidazol-5-yl]-6-methyl-1,6-dihydro-7H-pyrrolo[2,3-c]pyridin-7-one;
4-[4-(2,4-Difluorophenoxy)-1-methyl-1H-benzimidazol-5-yl]-6-methyl-1,6-dihydro-7H-pyrrolo[2,3-c]pyridin-7-one;
4-[4-(2,4-Difluorophenoxy)-1,2-dimethyl-1H-benzimidazol-5-yl]-6-methyl-1,6-dihydro-7H-pyrrolo[2,3-c]pyridin-7-one;
4-(2, 4-Difluorophenoxy)-1-methyl-5-(6-methyl-7-oxo-6,7-dihydro-1H-pyrrolo[2,3-c]pyridin-4-yl)-1,3-dihydro-2H-benzimidazol-2-one;
4-(2, 4-Difluorophenoxy)-1,3-dimethyl-5-(6-methyl-7-oxo-6,7-dihydro-1H-pyrrolo[2,3-c]pyridin-4-yl)-1,3-dihydro-2H-benzimidazol-2-one;
4-[4-(2,4-Difluorophenoxy)-1H-1,2,3-benzotriazol-5-yl]-6-methyl-1,6-dihydro-7H-pyrrolo[2,3-c]pyridin-7-one;
4-[4-(2,4-Difluorophenoxy)-1-methyl-1H-1,2,3-benzotriazol-5-yl]-6-methyl-1,6-dihydro-7H-pyrrolo[2,3-c]pyridin-7-one;
4-[4-(2,4-Difluorophenoxy)-1H-1,2,3-benzotriazol-5-yl]-6-methyl-1,6-dihydro-7H-pyrazolo[3,4-c]pyridin-7-one;
4-(Cyclopropylmethoxy)-5-(6-methyl-7-oxo-6,7-dihydro-1H-pyrrolo[2,3-c]pyridin-4-yl)-1,3-dihydro-2H-benzimidazol-2-one;
4-[4-(Cyclopropylmethoxy)-1H-benzimidazol-5-yl]-6-methyl-1,6-dihydro-7H-pyrrolo[2,3-c]pyridin-7-one; and
4-[4-(Cyclopropylmethoxy)-2-methyl-1H-benzimidazol-5-yl]-6-methyl-1,6-dihydro-7H-pyrrolo[2,3-c]pyridin-7-one, or a pharmaceutically acceptable salt thereof.

57. The method of claim 1, wherein the compound is selected from:
4-[4-(2,4-Difluorophenoxy)-1H-benzimidazol-5-yl]-6-methyl-1,6-dihydro-7H-pyrazolo[3,4-c]pyridin-7-one;
4-[4-(2,4-Difluorophenoxy)-2-methyl-1H-benzimidazol-5-yl]-6-methyl-1,6-dihydro-7H-pyrazolo[3,4-c]pyridin-7-one;

4-[4-(2,4-Difluorophenoxy)-2-oxo-2,3-dihydro-1H-benzimidazol-5-yl]-6-methyl-1,6-dihydro-7H-pyrazolo[3,4-c]pyridin-7-one;
4-[4-(2,4-Difluorophenoxy)-1-(2-morpholin-4-ylethyl)-1H-benzimidazol-5-yl]-6-methyl-1,6-dihydro-7H-pyrazolo[3,4-c]pyridin-7-one;
4-[4-(2,4-Difluorophenoxy)-1-methyl-1H-benzimidazol-5-yl]-6-methyl-1,6-dihydro-7H-pyrazolo[3,4-c]pyridin-7-one;
4-[4-(2,4-Difluorophenoxy)-1,2-dimethyl-1H-benzimidazol-5-yl]-6-methyl-1,6-dihydro-7H-pyrazolo[3,4-c]pyridin-7-one;
4-[4-(2,4-Difluorophenoxy)-1-methyl-1H-1,2,3-benzotriazol-5-yl]-6-methyl-1,6-dihydro-7H-pyrazolo[3,4-c]pyridin-7-one;
4-[4-(2,4-Difluorophenoxy)-1-methyl-2-oxo-2,3-dihydro-1H-benzimidazol-5-yl]-6-methyl-1,6-dihydro-7H-pyrazolo[3,4-c]pyridin-7-one;
5-(6-Methyl-7-oxo-6,7-dihydro-1H-pyrrolo[2,3-c]pyridin-4-yl)-4-phenoxy-1,3-dihydro-2H-benzimidazol-2-one;
4-[(4,4-Difluorocyclohexyl)oxy]-5-(6-methyl-7-oxo-6,7-dihydro-1H-pyrrolo[2,3-c]pyridin-4-yl)-1,3-dihydro-2H-benzimidazol-2-one;
4-(4-Fluorophenoxy)-5-(6-methyl-7-oxo-6,7-dihydro-1H-pyrrolo[2,3-c]pyridin-4-yl)-1,3-dihydro-2H-benzimidazol-2-one;
4-(3-Fluorophenoxy)-5-(6-methyl-7-oxo-6,7-dihydro-1H-pyrrolo[2,3-c]pyridin-4-yl)-1,3-dihydro-2H-benzimidazol-2-one;
5-(6-Methyl-7-oxo-6,7-dihydro-1H-pyrrolo[2,3-c]pyridin-4-yl)-4-(tetrahydro-2H-pyran-3-yloxy)-1,3-dihydro-2H-benzimidazol-2-one;
4-(Benzyloxy)-1-methyl-5-(6-methyl-7-oxo-6,7-dihydro-1H-pyrrolo[2,3-c]pyridin-4-yl)-1,3-dihydro-2H-benzimidazol-2-one;
4-[(2,4-Difluorobenzyl)oxy]-1-methyl-5-(6-methyl-7-oxo-6,7-dihydro-1H-pyrrolo[2,3-c]pyridin-4-yl)-1,3-dihydro-2H-benzimidazol-2-one;
1-Methyl-5-(6-methyl-7-oxo-6,7-dihydro-1H-pyrrolo[2,3-c]pyridin-4-yl)-4-(tetrahydro-2H-pyran-4-yloxy)-1,3-dihydro-2H-benzimidazol-2-one;
4-[7-(2,4-Difluorophenoxy)-1-(2-morpholin-4-yl-2-oxoethyl)-1H-benzimidazol-6-yl]-6-methyl-1,6-dihydro-7H-pyrrolo[2,3-c]pyridin-7-one;
4-[4-(2,4-difluorophenoxy)-1-(2-morpholin-4-yl-2-oxoethyl)-1H-benzimidazol-5-yl]-6-methyl-1,6-dihydro-7H-pyrrolo[2,3-c]pyridin-7-one;
4-Methoxy-1-methyl-5-(6-methyl-7-oxo-6,7-dihydro-1H-pyrrolo[2,3-c]pyridin-4-yl)-1,3-dihydro-2H-benzimidazol-2-one;
2-[7-(2,4-Difluorophenoxy)-6-(6-methyl-7-oxo-6,7-dihydro-1H-pyrrolo[2,3-c]pyridin-4-yl)-1H-benzimidazol-1-yl]-N,N-dimethylacetamide;
2-[4-(2,4-difluorophenoxy)-5-(6-methyl-7-oxo-6,7-dihydro-1H-pyrrolo[2,3-c]pyridin-4-yl)-1H-benzimidazol-1-yl]-N,N-dimethylacetamide;
2-[7-(2,4-Difluorophenoxy)-6-(6-methyl-7-oxo-6,7-dihydro-1H-pyrrolo[2,3-c]pyridin-4-yl)-1H-benzimidazol-1-yl]-N-methylacetamide;
2-[4-(2,4-difluorophenoxy)-5-(6-methyl-7-oxo-6,7-dihydro-1H-pyrrolo[2,3-c]pyridin-4-yl)-1H-benzimidazol-1-yl]-N-methylacetamide;
4-(Cyclobutylmethoxy)-1-methyl-5-(6-methyl-7-oxo-6,7-dihydro-1H-pyrrolo[2,3-c]pyridin-4-yl)-1,3-dihydro-2H-benzimidazol-2-one;
1-Methyl-5-(6-methyl-7-oxo-6,7-dihydro-1H-pyrrolo[2,3-c]pyridin-4-yl)-4-phenoxy-1,3-dihydro-2H-benzimidazol-2-one;
4-(2-Fluorophenoxy)-1-methyl-5-(6-methyl-7-oxo-6,7-dihydro-H-pyrrolo[2,3-c]pyridin-4-yl)-1,3-dihydro-2H-benzimidazol-2-one;
4-(3-Fluorophenoxy)-1-methyl-5-(6-methyl-7-oxo-6,7-dihydro-1H-pyrrolo[2,3-c]pyridin-4-yl)-1,3-dihydro-2H-benzimidazol-2-one;
4-(4-Fluorophenoxy)-1-methyl-5-(6-methyl-7-oxo-6,7-dihydro-1H-pyrrolo[2,3-c]pyridin-4-yl)-1,3-dihydro-2H-benzimidazol-2-one;
6-Methyl-4-[1-(2-morpholin-4-ylethyl)-7-phenoxy-1H-benzimidazol-6-yl]-1,6-dihydro-7H-pyrrolo[2,3-c]pyridin-7-one;
6-methyl-4-[1-(2-morpholin-4-ylethyl)-4-phenoxy-1H-benzimidazol-5-yl]-1,6-dihydro-7H-pyrrolo[2,3-c]pyridin-7-one;
3-Benzyl-4-methoxy-1-methyl-5-(6-methyl-7-oxo-6,7-dihydro-1H-pyrrolo[2,3-c]pyridin-4-yl)-1,3-dihydro-2H-benzimidazol-2-one;
4-(1-Benzyl-7-phenoxy-1H-benzimidazol-6-yl)-6-methyl-1,6-dihydro-7H-pyrrolo[2,3-c]pyridin-7-one;
4-(1-Benzyl-4-phenoxy-1H-benzimidazol-5-yl)-6-methyl-1,6-dihydro-7H-pyrrolo[2,3-c]pyridin-7-one;
6-Methyl-4-[7-phenoxy-1-(2-phenylethyl)-1H-benzimidazol-6-yl]-1,6-dihydro-7H-pyrrolo[2,3-c]pyridin-7-one;
6-Methyl-4-[4-phenoxy-1-(2-phenylethyl)-1H-benzimidazol-5-yl]-1,6-dihydro-7H-pyrrolo[2,3-c]pyridin-7-one;
4-Methoxy-1-methyl-5-(6-methyl-7-oxo-6,7-dihydro-1H-pyrrolo[2,3-c]pyridin-4-yl)-3-(2-phenylethyl)-1,3-dihydro-2H-benzimidazol-2-one;
4-Methoxy-1-methyl-5-(6-methyl-7-oxo-6,7-dihydro-1H-pyrrolo[2,3-c]pyridin-4-yl)-3-(2-morpholin-4-ylethyl)-1,3-dihydro-2H-benzimidazol-2-one;
4-[6-(6-Methyl-7-oxo-6,7-dihydro-1H-pyrrolo[2,3-c]pyridin-4-yl)-7-phenoxy-1H-benzimidazol-1-yl]butanenitrile;
4-[5-(6-Methyl-7-oxo-6,7-dihydro-1H-pyrrolo[2,3-c]pyridin-4-yl)-4-phenoxy-1H-benzimidazol-1-yl]butanenitrile;
4-[7-Methoxy-3-methyl-6-(6-methyl-7-oxo-6,7-dihydro-1H-pyrrolo[2,3-c]pyridin-4-yl)-2-oxo-2,3-dihydro-1H-benzimidazol-1-yl]butanenitrile;
3-[7-Methoxy-3-methyl-6-(6-methyl-7-oxo-6,7-dihydro-1H-pyrrolo[2,3-c]pyridin-4-yl)-2-oxo-2,3-dihydro-1H-benzimidazol-1-yl]propanenitrile;
3-[6-(6-Methyl-7-oxo-6,7-dihydro-1H-pyrrolo[2,3-c]pyridin-4-yl)-7-phenoxy-1H-benzimidazol-1-yl]propanenitrile;
6-Methyl-4-(1-methyl-4-phenoxy-1H-benzimidazol-5-yl)-1,6-dihydro-7H-pyrrolo[2,3-c]pyridin-7-one;
4-[4-(2-Fluorophenoxy)-1-methyl-1H-benzimidazol-5-yl]-6-methyl-1,6-dihydro-7H-pyrrolo[2,3-c]pyridin-7-one;
4-[4-(3-Fluorophenoxy)-1-methyl-1H-benzimidazol-5-yl]-6-methyl-1,6-dihydro-7H-pyrrolo[2,3-c]pyridin-7-one;
4-[4-(4-Fluorophenoxy)-1-methyl-1H-benzimidazol-5-yl]-6-methyl-1,6-dihydro-7H-pyrrolo[2,3-c]pyridin-7-one;
4-(Cyclobutylmethoxy)-1-methyl-5-(6-methyl-7-oxo-6,7-dihydro-1H-pyrrolo[2,3-c]pyridin-4-yl)-3-(2-morpholin-4-ylethyl)-1,3-dihydro-2H-benzimidazol-2-one;

4-[7-(Cyclobutylmethoxy)-3-methyl-6-(6-methyl-7-oxo-6,7-dihydro-1H-pyrrolo[2,3-c]pyridin-4-yl)-2-oxo-2,3-dihydro-1H-benzimidazol-1-yl]butanenitrile;

3-[7-(Cyclobutylmethoxy)-3-methyl-6-(6-methyl-7-oxo-6,7-dihydro-1H-pyrrolo[2,3-c]pyridin-4-yl)-2-oxo-2,3-dihydro-1H-benzimidazol-1-yl]propanenitrile;

4-(Cyclobutylmethoxy)-1-methyl-5-(6-methyl-7-oxo-6,7-dihydro-1H-pyrrolo[2,3-c]pyridin-4-yl)-3-(2-phenylethyl)-1,3-dihydro-2H-benzimidazol-2-one;

3-Benzyl-4-(cyclobutylmethoxy)-1-methyl-5-(6-methyl-7-oxo-6,7-dihydro-1H-pyrrolo[2,3-c]pyridin-4-yl)-1,3-dihydro-2H-benzimidazol-2-one;

4-(Cyclobutylmethoxy)-1-methyl-5-(6-methyl-7-oxo-6,7-dihydro-1H-pyrrolo[2,3-c]pyridin-4-yl)-3-(2-piperidin-4-ylethyl)-1,3-dihydro-2H-benzimidazol-2-one;

3-(2-(4-Acetylpiperazin-1-yl)ethyl)-4-(cyclobutylmethoxy)-1-methyl-5-(6-methyl-7-oxo-6,7-dihydro-1H-pyrrolo[2,3-c]pyridin-4-yl)-1H-benzo[d]imidazol-2(3H)-one;

4-(Cyclobutylmethoxy)-1-methyl-5-(6-methyl-7-oxo-6,7-dihydro-1H-pyrrolo[2,3-c]pyridin-4-yl)-3-{2-[4-(methylsulfonyl)piperazin-1-yl]ethyl}-1,3-dihydro-2H-benzimidazol-2-one;

4-(Cyclobutylmethoxy)-1-methyl-5-(6-methyl-7-oxo-6,7-dihydro-1H-pyrrolo[2,3-c]pyridin-4-yl)-3-[2-(4-methylpiperazin-1-yl)ethyl]-1,3-dihydro-2H-benzimidazol-2-one;

5-(6-Methyl-7-oxo-6,7-dihydro-1H-pyrrolo[2,3-c]pyridin-4-yl)-1-(2-morpholin-4-ylethyl)-4-phenoxy-1,3-dihydro-2H-benzimidazol-2-one;

1-{2-[(2R,6S)-2,6-Dimethylmorpholin-4-yl]ethyl}-5-(6-methyl-7-oxo-6,7-dihydro-1H-pyrrolo[2,3-c]pyridin-4-yl)-4-phenoxy-1,3-dihydro-2H-benzimidazol-2-one;

4-(2-(Benzylamino)-1-{2-[(2R,6S)-2,6-dimethylmorpholin-4-yl]ethyl}-4-phenoxy-1H-benzimidazol-5-yl)-6-methyl-1,6-dihydro-7H-pyrrolo[2,3-c]pyridin-7-one;

4-(2-[(Cyclopropylmethyl)amino]-1-{2-[(2R,6S)-2,6-dimethylmorpholin-4-yl]ethyl}-4-phenoxy-1H-benzimidazol-5-yl)-6-methyl-1,6-dihydro-7H-pyrrolo[2,3-c]pyridin-7-one;

4-(Cyclopropylmethoxy)-1-methyl-5-(6-methyl-7-oxo-6,7-dihydro-1H-pyrrolo[2,3-c]pyridin-4-yl)-1,3-dihydro-2H-benzimidazol-2-one;

8-(2,4-Difluorophenoxy)-7-(6-methyl-7-oxo-6,7-dihydro-1H-pyrazolo[3,4-c]pyridin-4-yl)quinoxalin-2(1H)-one;

4-[4-(Cyclopropylmethoxy)-1-methyl-1H-indazol-5-yl]-6-methyl-1,6-dihydro-7H-pyrrolo[2,3-c]pyridin-7-one;

4-[4-(Cyclopropylmethoxy)-1-methyl-1H-indazol-5-yl]-6-methyl-1,6-dihydro-7H-pyrazolo[3,4-c]pyridin-7-one;

4-[4-(2,4-Difluorophenoxy)-7-(1-hydroxyethyl)-1-methyl-1H-benzimidazol-5-yl]-6-methyl-1,6-dihydro-7H-pyrazolo[3,4-c]pyridin-7-one;

4-(2,4-Difluorophenoxy)-5-(6-methyl-7-oxo-6,7-dihydro-1H-pyrrolo[2,3-c]pyridin-4-yl)-7-{[(2-morpholin-4-ylethyl)amino]methyl}-1,3-dihydro-2H-benzimidazol-2-one;

7-[(Benzylamino)methyl]-4-(2, 4-difluorophenoxy)-5-(6-methyl-7-oxo-6,7-dihydro-1H-pyrrolo[2,3-c]pyridin-4-yl)-1,3-dihydro-2H-benzimidazol-2-one;

7-{[(Cyclopropylmethyl)amino]methyl)}-4-(2,4-difluorophenoxy)-5-(6-methyl-7-oxo-6,7-dihydro-1H-pyrrolo[2,3-c]pyridin-4-yl)-1,3-dihydro-2H-benzimidazol-2-one;

4-[4-(2,4-Difluorophenoxy)-1-methyl-1H-benzimidazol-5-yl]-1,6-dihydro-7H-pyrrolo[2,3-c]pyridin-7-one;

4-[4-(2,4-Difluorophenoxy)-1-methyl-1H-benzimidazol-5-yl]-6-ethyl-1,6-dihydro-7H-pyrrolo[2,3-c]pyridin-7-one;

6-Benzyl-4-[4-(2,4-difluorophenoxy)-1-methyl-1H-benzimidazol-5-yl]-1,6-dihydro-7H-pyrrolo[2,3-c]pyridin-7-one;

{4-[4-(2,4-Difluorophenoxy)-1-methyl-1H-benzimidazol-5-yl]-7-oxo-1,7-dihydro-6H-pyrrolo[2,3-c]pyridin-6-yl}acetonitrile;

4-(4-Chlorophenoxy)-1-methyl-5-(6-methyl-7-oxo-6,7-dihydro-1H-pyrrolo[2,3-c]pyridin-4-yl)-1,3-dihydro-2H-benzimidazol-2-one;

4-(3-Chlorophenoxy)-1-methyl-5-(6-methyl-7-oxo-6,7-dihydro-1H-pyrrolo[2,3-c]pyridin-4-yl)-1,3-dihydro-2H-benzimidazol-2-one;

4-(Cyclohexylmethoxy)-1-methyl-5-(6-methyl-7-oxo-6,7-dihydro-1H-pyrrolo[2,3-c]pyridin-4-yl)-1,3-dihydro-2H-benzimidazol-2-one;

4-(Cyclobutyloxy)-1-methyl-5-(6-methyl-7-oxo-6,7-dihydro-1H-pyrrolo[2,3-c]pyridin-4-yl)-1,3-dihydro-2H-benzimidazol-2-one;

4-(Cyclohexyloxy)-1-methyl-5-(6-methyl-7-oxo-6,7-dihydro-1H-pyrrolo[2,3-c]pyridin-4-yl)-1,3-dihydro-2H-benzimidazol-2-one;

1-Methyl-5-(6-methyl-7-oxo-6,7-dihydro-1H-pyrrolo[2,3-c]pyridin-4-yl)-4-(tetrahydro-2H-pyran-3-yloxy)-1,3-dihydro-2H-benzimidazol-2-one;

4-(Cyclopentylmethoxy)-1-methyl-5-(6-methyl-7-oxo-6,7-dihydro-1H-pyrrolo[2,3-c]pyridin-4-yl)-1,3-dihydro-2H-benzimidazol-2-one;

4-(Cyclopentyloxy)-1-methyl-5-(6-methyl-7-oxo-6,7-dihydro-1H-pyrrolo[2,3-c]pyridin-4-yl)-1,3-dihydro-2H-benzimidazol-2-one;

6-(6-Methyl-7-oxo-6,7-dihydro-1H-pyrrolo[2,3-c]pyridin-4-yl)-5-phenoxy-2H-1,4-benzoxazin-3(4H)-one;

2,2-Dimethyl-6-(6-methyl-7-oxo-6,7-dihydro-1H-pyrrolo[2,3-c]pyridin-4-yl)-5-phenoxy-2H-1,4-benzoxazin-3(4H)-one;

6-Methyl-4-(4-phenoxy-1,33-benzoxazol-5-yl)-1,6-dihydro-7H-pyrrolo[2,3-c]pyridin-7-one;

1-Methyl-5-(6-methyl-7-oxo-6,7-dihydro-1H-pyrrolo[2,3-c]pyridin-4-yl)-4-(phenylthio)-1,3-dihydro-2H-benzimidazol-2-one;

4-(Ethylthio)-1-methyl-5-(6-methyl-7-oxo-6,7-dihydro-1H-pyrrolo[2,3-c]pyridin-4-yl)-1,3-dihydro-2H-benzimidazol-2-one;

4-(Ethylsulfonyl)-1-methyl-5-(6-methyl-7-oxo-6,7-dihydro-1H-pyrrolo[2,3-c]pyridin-4-yl)-1,3-dihydro-2H-benzimidazol-2-one;

4-Methyl-6-(6-methyl-7-oxo-6,7-dihydro-1H-pyrrolo[2,3-c]pyridin-4-yl)-5-phenoxy-2H-1,4-benzoxazin-3(4H)-one;

4-Benzyl-6-(6-methyl-7-oxo-6,7-dihydro-1H-pyrrolo[2,3-c]pyridin-4-yl)-5-phenoxy-2H-1,4-benzoxazin-3(4H)-one;

6-(6-Methyl-7-oxo-6,7-dihydro-1H-pyrrolo[2,3-c]pyridin-4-yl)-4-(2-morpholin-4-ylethyl)-5-phenoxy-2H-1,4-benzoxazin-3(4H)-one;

4-[2-(Aminomethyl)-4-phenoxy-1,3-benzoxazol-5-yl]-6-methyl-1, 6-dihydro-7H-pyrrolo[2,3-c]pyridin-7-one;

N-{[5-(6-Methyl-7-oxo-6,7-dihydro-1H-pyrrolo[2,3-c]pyridin-4-yl)-4-phenoxy-1,3-benzoxazol-2-yl]methyl}acetamide;

N-{[5-(6-Methyl-7-oxo-6,7-dihydro-1H-pyrrolo[2,3-c]pyridin-4-yl)-4-phenoxy-1,3-benzoxazol-2-yl]methyl}methanesulfonamide'

N-{[5-(6-methyl-7-oxo-6,7-dihydro-1H-pyrrolo[2,3-c]
pyridin-4-yl)-4-phenoxy-1,3-benzoxazol-2-yl]
methyl}benzamide;
N-{[5-(6-Methyl-7-oxo-6,7-dihydro-1H-pyrrolo[2,3-c]
pyridin-4-yl)-4-phenoxy-1,3-benzoxazol-2-yl]
methyl}-2-phenylacetamide;
N-{[5-(6-Methyl-7-oxo-6,7-dihydro-1H-pyrrolo[2,3-c]
pyridin-4-yl)-4-phenoxy-1,3-benzoxazol-2-yl]
methyl}cyclopropanecarboxamide;
2-Cyclopentyl-N-{[5-(6-methyl-7-oxo-6,7-dihydro-1H-
pyrrolo[2,3-c]pyridin-4-yl)-4-phenoxy-1,3-benzox-
azol-2-yl]methyl}acetamide;
6-Methyl-4-(5-phenoxy-3-phenyl-3,4-dihydro-2H-1,4-
benzoxazin-6-yl)-1, 6-dihydro-7H-pyrrolo[2,3-c]pyri-
din-7-one;
N-{[1-Methyl-5-(6-methyl-7-oxo-6,7-dihydro-1H-pyr-
rolo[2,3-c]pyridin-4-yl)-4-phenoxy-1H-benzimidazol-
2-yl]methyl}cyclobutanecarboxamide;
N-{[1-Methyl-5-(6-methyl-7-oxo-6,7-dihydro-1H-pyr-
rolo[2,3-c]pyridin-4-yl)-4-phenoxy-1H-benzimidazol-
2-yl]methyl}cyclopropanecarboxamide;
3-[5-(6-Methyl-7-oxo-6,7-dihydro-1H-pyrrolo[2,3-c]
pyridin-4-yl)-4-phenoxy-1H-benzimidazol-1-yl]pro-
panenitrile; and
4-(7-Ethoxy-2, 5-dimethylpyrazolo[1,5-a]pyrimidin-6-
yl)-6-methyl-1,6-dihydro-7H-pyrrolo[2,3-c]pyridin-7-
one,
or a pharmaceutically acceptable salt thereof.

58. A method of inhibiting bromodomain and extra-terminal protein activity in a patient suffering from cancer, comprising administering to a patient in need of such treatment a therapeutically effective amount of a compound of Formula I:

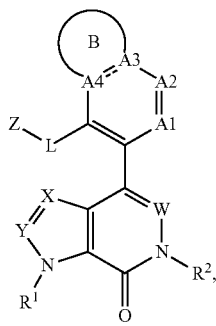

I or a pharmaceutically acceptable salt thereof,
wherein:
══════ represents a single or double bond;
ring B is phenyl, 5-6 membered heteroaryl, $C_{5-6}$ cycloalkyl, or 5-6 membered heterocycloalkyl, each optionally substituted by 1, 2, 3, or 4 $R^B$;
L is absent, $-(CR^aR^b)_p-$, $-(CR^aR^b)_n-O-(CR^aR^b)_m-$, $-(CR^aR^b)_n-S-(CR^aR^b)_m-$, $-(CR^aR^b)_n-S(=O)-(CR^aR^b)_m-$, $-(CR^aR^b)_n-S(=O)_2-(CR^aR^b)_m-$, $-(CR^aR^b)_n-C(=O)-(CR^aR^b)_m-$, $-(CR^aR^b)_n-C(=O)O-(CR^aR^b)_m-$, $-(CR^aR^b)_n-OC(=O)-(CR^aR^b)_m-$, $-(CR^aR^b)_n-NR^c-(CR^aR^b)_m-$, $-(CR^aR^b)_n-C(=O)NR^c-(CR^aR^b)_m-$, $-(CR^aR^b)_n-NR^cC(=O)-(CR^aR^b)_m-$, or $-(CR^aR^b)_n-NR^cC(=O)NR^d-(CR^aR^b)_m-$;
A1 is $CR^3$ or N;
A2 is $CR^4$ or N;
A3 is C or N;
A4 is C or N;
wherein when one of A3 and A4 is N, then the other of A3 and A4 is C;
W is $CR^5$;
X is $CR^6$;
Y is $CR^7$ or N;
Z is $C_{6-10}$ aryl, $C_{3-10}$ cycloalkyl, 5-10 membered heteroaryl, or 4-10 membered heterocycloalkyl, each of which is optionally substituted by 1, 2, 3, 4, or 5 $R^Z$;
$R^1$ is H or $C_{1-4}$ alkyl;
$R^2$ is $C_{1-4}$ alkyl, $C_{1-4}$ haloalkyl, or $C_{1-4}$ hydroxyalkyl;
$R^3$ and $R^4$ are each independently selected from H, halo, CN, $NO_2$, $C_{1-6}$ alkyl, $C_{1-6}$ haloalkyl, $C_{2-6}$ alkenyl, and $C_{2-6}$ alkynyl;
$R^5$ is H, halo, $C_{1-6}$ alkyl, or $C_{1-6}$ haloalkyl;
$R^6$ is H, $C_{1-6}$ alkyl, $C_{1-6}$ haloalkyl, $C_{2-6}$ alkenyl, $C_{2-6}$ alkynyl, $C(O)R^{b1}$, $C(O)NR^{c1}R^{d1}$, $C(O)OR^{a1}$, $S(O)R^{b1}$, $S(O)NR^{c1}R^{d1}$, $S(O)_2R^{b1}$, or $S(O)_2NR^{c1}R^{d1}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $C(=NR^{e1})R^{b1}$, $C(=NR^{e1})NR^{c1}R^{d1}$, $NR^{c1}C(=NR^{e1})NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;
$R^7$ is H, $C_{1-6}$ alkyl, $C_{1-6}$ haloalkyl, $C_{2-6}$ alkenyl, $C_{2-6}$ alkynyl, $C(O)R^{b2}$, $C(O)NR^{c2}R^{d2}$, $C(O)OR^{a2}$, $S(O)R^{b2}$, $S(O)NR^{c2}R^{d2}$, $S(O)_2R^{b2}$, or $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, 4, or 5 substituents independently selected from halo, $C_{1-4}$ haloalkyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $C(=NR^{e2})R^{b2}$, $C(=NR^{e2})NR^{c2}R^{d2}$, $NR^{c2}C(=NR^{e2})NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;
each $R^B$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $C(=NR^{e3})R^{b3}$, $C(=NR^{e3})NR^{c3}R^{d3}$, $NR^{c3}C(=NR^{e3})NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$; wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted with 1, 2, 3, 4, or 5 substituents independently selected from halo, $C_{1-6}$ alkyl, $C_{2-6}$ alkenyl, $C_{2-6}$ alkynyl, $C_{1-6}$ haloalkyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;
each $R^Z$ is independently selected from halo, $C_{1-6}$ alkyl, $C_{2-6}$ alkenyl, $C_{2-6}$ alkynyl, $C_{1-6}$ haloalkyl, $C_{6-10}$ aryl, $C_{3-10}$ cycloalkyl, 5-10 membered heteroaryl, 4-10 membered heterocycloalkyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, OC(O)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, C(=NR$^{e4}$)R$^{b4}$, C(=NR$^{e4}$)NR$^{c4}$R$^{d4}$, NR$^{c4}$C(=NR$^{e4}$)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$; wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heteroaryl, and 4-10 membered heterocycloalkyl are each optionally substituted with 1, 2, 3, 4, or 5 substituents independently selected from halo, C$_{1-6}$ alkyl, C$_{2-6}$ alkenyl, C$_{2-6}$ alkynyl, C$_{1-6}$ haloalkyl, CN, NO$_2$, OR$^{a4}$, SR$^{a4}$, C(O)R$^{b4}$, C(O)NR$^{c4}$R$^{d4}$, C(O)OR$^{a4}$, OC(O)R$^{b4}$, OC(O)NR$^{c4}$R$^{d4}$, C(=NR$^{e4}$)NR$^{c4}$R$^{d4}$, NR$^{c4}$C(=NR$^{e4}$)NR$^{c4}$R$^{d4}$, NR$^{c4}$R$^{d4}$, NR$^{c4}$C(O)R$^{b4}$, NR$^{c4}$C(O)OR$^{a4}$, NR$^{c4}$C(O)NR$^{c4}$R$^{d4}$, NR$^{c4}$S(O)R$^{b4}$, NR$^{c4}$S(O)$_2$R$^{b4}$, NR$^{c4}$S(O)$_2$NR$^{c4}$R$^{d4}$, S(O)R$^{b4}$, S(O)NR$^{c4}$R$^{d4}$, S(O)$_2$R$^{b4}$, and S(O)$_2$NR$^{c4}$R$^{d4}$;

each R$^a$ and R$^b$ is independently selected from H, halo, OH, methyl, and ethyl;

each R$^c$ and R$^d$ is independently selected from H, C$_{1-4}$ alkyl, C$_{1-4}$ haloalkyl, C$_{1-4}$ hydroxyalkyl, and cyclopropyl;

each R$^{a1}$, R$^{b1}$, R$^{c1}$, R$^{d1}$, R$^{a2}$, R$^{b2}$, R$^{c2}$, R$^{d2}$, R$^{a3}$, R$^{b3}$, R$^{c3}$, R$^{d3}$, R$^{a4}$, R$^{b4}$, R$^{c4}$, and R$^{d4}$ is independently selected from H, C$_{1-6}$ alkyl, C$_{1-4}$ haloalkyl, C$_{2-6}$ alkenyl, C$_{2-6}$ alkynyl, C$_{6-10}$ aryl, C$_{3-10}$ cycloalkyl, 5-10 membered heteroaryl, 4-10 membered heterocycloalkyl, C$_{6-10}$ aryl-C$_{1-6}$ alkyl, C$_{3-10}$ cycloalky-C$_{1-6}$ alkyl, (5-10 membered heteroaryl)-C$_{1-6}$ alkyl, and (4-10 membered heterocycloalkyl)-C$_{1-6}$ alkyl, wherein said C$_{1-6}$ alkyl, C$_{2-6}$ alkenyl, C$_{2-6}$ alkynyl, C$_{6-10}$ aryl, C$_{3-10}$ cycloalkyl, 5-10 membered heterocycloalkyl, C$_{6-10}$ aryl-C$_{1-6}$ alkyl, C$_{3-10}$ cycloalky-C$_{1-6}$ alkyl, (5-10 membered heteroaryl)-C$_{1-6}$ alkyl, and (4-10 membered heterocycloalkyl)-C$_{1-6}$ alkyl is optionally substituted with 1, 2, 3, 4, or 5 substituents independently selected from C$_{1-4}$ alkyl, C$_{1-4}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c1}$ and R$^{d1}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c2}$ and R$^{d2}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c3}$ and R$^{d3}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

or any R$^{c4}$ and R$^{d4}$ together with the N atom to which they are attached form a 4-, 5-, 6-, or 7-membered heterocycloalkyl group optionally substituted with 1, 2, or 3 substituents independently selected from C$_{1-6}$ alkyl, C$_{3-7}$ cycloalkyl, 4-7 membered heterocycloalkyl, C$_{6-10}$ aryl, 5-6 membered heteroaryl, C$_{1-6}$ haloalkyl, halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$, wherein said C$_{1-6}$ alkyl, C$_{3-7}$ cycloalkyl, 4-7 membered heterocycloalkyl, C$_{6-10}$ aryl, and 5-6 membered heteroaryl are optionally substituted by 1, 2, or 3 substituents independently selected from halo, CN, OR$^{a5}$, SR$^{a5}$, C(O)R$^{b5}$, C(O)NR$^{c5}$R$^{d5}$, C(O)OR$^{a5}$, OC(O)R$^{b5}$, OC(O)NR$^{c5}$R$^{d5}$, NR$^{c5}$R$^{d5}$, NR$^{c5}$C(O)R$^{b5}$, NR$^{c5}$C(O)NR$^{c5}$R$^{d5}$, NR$^{c5}$C(O)OR$^{a5}$, C(=NR$^{e5}$)NR$^{c5}$R$^{d5}$, NR$^{c5}$C(=NR$^{e5}$)NR$^{c5}$R$^{d5}$, S(O)R$^{b5}$, S(O)NR$^{c5}$R$^{d5}$, S(O)$_2$R$^{b5}$, NR$^{c5}$S(O)$_2$R$^{b5}$, NR$^{c5}$S(O)$_2$NR$^{c5}$R$^{d5}$, and S(O)$_2$NR$^{c5}$R$^{d5}$;

each R$^{e1}$, R$^{e2}$, R$^{e3}$, and R$^{e4}$ is independently selected from H, C$_{1-4}$ alkyl, CN, OR$^{a5}$, SR$^{b5}$, S(O)$_2$R$^{b5}$, C(O)R$^{b5}$, S(O)$_2$NR$^{c5}$R$^{d5}$, and C(O)NR$^{c5}$R$^{d5}$;

each R$^{a5}$, R$^{b5}$, R$^{c5}$, and R$^{d5}$ is independently selected from H, C$_{1-4}$ alkyl, C$_{1-4}$ haloalkyl, C$_{2-4}$ alkenyl, and C$_{2-4}$ alkynyl, wherein said C$_{1-4}$ alkyl, C$_{2-4}$ alkenyl, and C$_{2-4}$ alkynyl, is optionally substituted with 1, 2, or 3 substituents independently selected from OH, CN, amino, halo, $C_{1-4}$ alkyl, $C_{1-4}$ alkoxy, $C_{1-4}$ alkylthio, $C_{1-4}$ alkylamino, di($C_{1-4}$ alkyl)amino, $C_{1-4}$ haloalkyl, and $C_{1-4}$ haloalkoxy;

each $R^{e5}$ is independently selected from H, $C_{1-4}$ alkyl, and CN;

n is 0, 1, or 2;

m is 0, 1, or 2; and p is 1, 2, 3, or 4;

wherein any aforementioned heterocycloalkyl group is optionally substituted by 1 or 2 oxo groups.

* * * * *

UNITED STATES PATENT AND TRADEMARK OFFICE
CERTIFICATE OF CORRECTION

PATENT NO. : 9,918,990 B2
APPLICATION NO. : 15/186697
DATED : March 20, 2018
INVENTOR(S) : Eddy W. Yue, Andrew P. Combs and Brent Douty Page 1 of 2

It is certified that error appears in the above-identified patent and that said Letters Patent is hereby corrected as shown below:

In the Claims

Column 198, Line 6, Claim 1, delete "cycloalky-" and insert -- cycloalkyl- --;

Column 198, Line 11, Claim 1, delete "cycloalky-" and insert -- cycloalkyl- --;

Column 199, Lines 13-14, Claim 1, delete "$NR^{c5}R^{d5}$ $NRcsC(O)R^{b5}$," and insert -- $NR^{c5}R^{d5}$, $NR^{c5}C(O)R^{b5}$, --;

Column 206, Line 27, Claim 56, after "7-one;" delete "and";

Column 206, Line 37, Claim 56, delete "4-(2, 4-Difluorophenoxy)-" and insert -- 4-(2,4-Difluorophenoxy)- --;

Column 206, Line 40, Claim 56, delete "4-(2, 4-Difluorophenoxy)-" and insert -- 4-(2,4-Difluorophenoxy)- --;

Column 207, Line 46, Claim 57, delete "[2, 3-c]" and insert -- [2,3-c] --;

Column 207, Line 49, Claim 57, delete "[2, 3-c]" and insert -- [2,3-c] --;

Column 208, Line 5, Claim 57, delete "H-pyrrolo" and insert -- 1H-pyrrolo --;

Column 208, Line 14, Claim 57, delete "6-yl]-1, 6-dihydro-" and insert -- 6-yl]-1,6-dihydro- --;

Column 208, Line 27, Claim 57, delete "6-yl]-1, 6-dihydro-" and insert -- 6-yl]-1,6-dihydro- --;

Column 208, Line 30, Claim 57, delete "5-yl]-1, 6-dihydro-" and insert -- 5-yl]-1,6-dihydro- --;

Column 208, Line 38, Claim 57, delete "[2, 3-c]" and insert -- [2,3-c] --;

Signed and Sealed this
Seventeenth Day of March, 2020

Andrei Iancu
*Director of the United States Patent and Trademark Office*

CERTIFICATE OF CORRECTION (continued)
U.S. Pat. No. 9,918,990 B2

Column 208, Line 41, Claim 57, delete "[2, 3-c]" and insert -- [2,3-c] --;

Column 208, Line 50, Claim 57, delete "[2, 3-c]" and insert -- [2,3-c] --;

Column 209, Line 28, Claim 57, delete "[2, 3-c]" and insert -- [2,3-c] --;

Column 210, Line 36, Claim 57, delete "-3 (4H)-" and insert -- -3(4H)- --;

Column 210, Lines 38-39, Claim 57, delete "-3 (4H)-" and insert -- -3(4H)- --;

Column 210, Line 40, Claim 57, delete "-1,33-" and insert -- -1,3- --;

Column 210, Lines 52-53, Claim 57, delete "3 (4H)-" and insert -- 3(4H)- --;

Column 210, Lines 55-56, Claim 57, delete "3 (4H)-" and insert -- 3(4H)- --;

Column 210, Line 59, Claim 57, delete "3 (4H)-" and insert -- 3(4H)- --;

Column 210, Line 61, Claim 57, delete "1, 6-" and insert -- 1,6- --;

Column 210, Line 67, Claim 57, delete "methanesulfonamide'" and insert -- methanesulfonamide; --;

Column 211, Line 15, Claim 57, delete "-1, 6-" and insert -- -1,6- --;

Column 211, Line 26, Claim 57, delete "-2, 5-" and insert -- -2,5- --;

Column 213, Line 28, Claim 58, delete "cycloalky-" and insert -- cycloalkyl- --;

Column 213, Line 33, Claim 58, delete "cycloalky-" and insert -- cycloalkyl- --.